United States Patent
Romero et al.

(10) Patent No.: US 11,155,557 B2
(45) Date of Patent: Oct. 26, 2021

(54) PYRAZOLOPYRIMIDINE COMPOUNDS AND METHODS OF USE THEREOF

(71) Applicant: Genentech, Inc., South San Francisco, CA (US)

(72) Inventors: F. Anthony Romero, Brisbane, CA (US); Mark Zak, South San Francisco, CA (US); Guiling Zhao, South San Francisco, CA (US); Paul Gibbons, South San Francisco, CA (US); Wei Li, Beijing (CN); Yun-Xing Cheng, Beijing (CN); Po-Wai Yuen, Beijing (CN); Limin Cheng, Beijing (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/452,058

(22) Filed: Jun. 25, 2019

(65) Prior Publication Data

US 2019/0345165 A1 Nov. 14, 2019

Related U.S. Application Data

(63) Continuation of application No. PCT/EP2017/084569, filed on Dec. 22, 2017.

(30) Foreign Application Priority Data

Dec. 29, 2016 (WO) ................. PCT/CN2016/112932

(51) Int. Cl.
  *C07D 487/04* (2006.01)
  *C07D 498/10* (2006.01)

(52) U.S. Cl.
  CPC ......... *C07D 487/04* (2013.01); *C07D 498/10* (2013.01)

(58) Field of Classification Search
  CPC ........................... C07D 487/04; A61K 31/519
  USPC ....................................... 544/281; 514/259.3
  See application file for complete search history.

(56) References Cited

U.S. PATENT DOCUMENTS

2015/0152117 A1    6/2015  Gibbons et al.

FOREIGN PATENT DOCUMENTS

| CL | 2016002877 | 6/2017 |
| CL | 2018003754 | 2/2019 |
| JP | 2012-532112 | 12/2012 |
| RU | 2434013 | 11/2011 |
| WO | 2011/003065 A2 | 1/2011 |
| WO | 2015/177326 A1 | 11/2015 |
| WO | 2017/089390 A1 | 6/2017 |
| WO | 2017/140825 A1 | 8/2017 |
| WO | 2018/122212 A1 | 7/2018 |

OTHER PUBLICATIONS

"International Preliminary Report on Patentability—PCT/EP2017/084569":1-9 (dated Jul. 11, 2019).
"International Search Report—PCT/EP2017/084569":1-5 (dated Apr. 4, 2018).
"RU Patent Application No. 2019123319 Search Report" (National Phase of PCT/EP2017/084569),:1-2 (dated Dec. 20, 2019).

*Primary Examiner* — Jeffrey H Murray
(74) *Attorney, Agent, or Firm* — Robert C. Hall

(57) ABSTRACT

Compounds of Formula (IA), or a pharmaceutically acceptable salt thereof, and methods of use as Janus kinase inhibitors are described herein.

19 Claims, No Drawings

PYRAZOLOPYRIMIDINE COMPOUNDS AND METHODS OF USE THEREOF

CROSS-REFERENCE TO RELATED APPLICATION

This application is a continuation of International Application No. PCT/EP2017/084569 filed on Dec. 22, 2017, which claims the benefit of priority to International Application No. PCT/CN2016/112932, filed Dec. 29, 2016, the disclosures of which are incorporated herein by reference.

FIELD OF THE INVENTION

The field of the invention pertains to small molecule inhibitors of a Janus kinase, such as JAK1, as well as compositions containing these compounds, and methods of use including, but not limited to, diagnosis or treatment of patients suffering from a condition responsive to the inhibition of a JAK kinase.

BACKGROUND OF INVENTION

Cytokine pathways mediate a broad range of biological functions, including many aspects of inflammation and immunity. Janus kinases (JAK), including JAK1, JAK2, JAK3, and TYK2, are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2, and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence. Exemplary therapeutic benefits of the inhibition of JAK enzymes are discussed, for example, in International Application No. WO 2013/014567.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFN-gamma), and IL-2 and IL-6 cytokine receptor complexes (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). JAK1 knockout mice die perinatally due to defects in LIF receptor signaling (Kisseleva et al., 2002, Gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4 and IL-6 pathways. A humanized monoclonal antibody targeting the IL-6 pathway (Tocilizumab) was approved by the European Commission for the treatment of moderate-to-severe rheumatoid arthritis (Scheinecker et al., 2009, Nat. Rev. Drug Discov. 8:273-274).

CD4 T cells play an important role in asthma pathogenesis through the production of TH2 cytokines within the lung, including IL-4, IL-9 and IL-13 (Cohn et al., 2004, Annu. Rev. Immunol. 22:789-815). IL-4 and IL-13 induce increased mucus production, recruitment of eosinophils to the lung, and increased production of IgE (Kasaian et al., 2008, Biochem. Pharmacol. 76(2): 147-155). IL-9 leads to mast cell activation, which exacerbates the asthma symptoms (Kearley et al., 2011, Am. J. Resp. Crit. Care Med., 183(7): 865-875). The IL-4Rα chain activates JAK1 and binds to either IL-4 or IL-13 when combined with the common gamma chain or the IL-13Rα1 chain respectively (Pernis et al., 2002, J. Clin. Invest. 109(10): 1279-1283). The common gamma chain can also combine with IL-9Rα to bind to IL-9, and IL-9Rα activates JAK1 as well (Demoulin et al., 1996, Mol. Cell Biol. 16(9):4710-4716). While the common gamma chain activates JAK3, it has been shown that JAK1 is dominant over JAK3, and inhibition of JAK1 is sufficient to inactivate signaling through the common gamma chain despite JAK3 activity (Haan et al., 2011, Chem. Biol. 18(3):314-323). Inhibition of IL-4, IL-13, and IL-9 signaling by blocking the JAK/STAT signaling pathway can alleviate asthmatic symptoms in pre-clinical lung inflammation models (Mathew et al., 2001, J. Exp. Med. 193(9): 1087-1096; Kudlacz et. al., 2008, Eur. J. Pharmacol. 582(1-3): 154-161).

Biochemical and genetic studies have shown an association between JAK2 and single-chain (e.g., EPO), IL-3 and interferon gamma cytokine receptor families (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders in humans.

JAK3 associates exclusively with the gamma common cytokine receptor chain, which is present in the IL-2, IL-4, IL-7, IL-9, IL-15, and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, Gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and IL-23 cytokines (Ustekinumab) was approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

There exists a need in the art for additional or alternative treatments of conditions mediated by JAK kinases, such as those described above.

SUMMARY OF INVENTION

Provided herein are pyrazolopyridmine-containing compounds that inhibit one or more JAK kinases.

Accordingly, one aspect of the invention includes a compound having the general structure (IA):

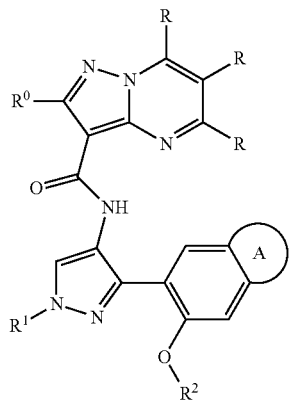

(IA)

or a pharmaceutically acceptable salt thereof;
wherein:

A is a fused ring selected from the group consisting of a 6-membered aromatic group; a 5-membered or 6-membered heterocyclic group; and a 5-membered or 6-membered cycloalkyl group; wherein fused ring A is optionally substituted by 1-5 $R^n$;

R is independently selected from the group consisting of hydrogen; halogen; cyano; —$NH_2$; $C_1$-$C_3$ alkyl, optionally substituted with halogen; $C_2$-$C_3$ alkenyl; $C_2$-$C_3$ alkynyl; and —$OR^t$;

$R^0$ is selected from the group consisting of hydrogen, halogen, cyano, $C_1$-$C_3$alkyl, $C_2$-$C_3$alkenyl, $C_2$-$C_3$alkynyl, —$NH_2$, and —$OR^t$;

$R^1$ is selected from the group consisting of hydrogen, $C_2$-$C_6$alkenyl, $C_2$-$C_6$alkynyl, —($C_0$-$C_3$alkyl)CN, —($C_0$-$C_4$alkyl)$OR^a$, —($C_0$-$C_3$alkyl)$R^a$, —($C_0$-$C_3$alkyl)$SR^a$, —($C_0$-$C_6$alkyl)$NR^aR^b$, —($C_0$-$C_3$alkyl)$OCF_3$, —($C_0$-$C_3$alkyl)$CF_3$, —($C_0$-$C_3$alkyl)$NO_2$, —($C_0$-$C_6$alkyl)C(O)$R^a$, —($C_0$-$C_6$alkyl)C(O)$OR^a$, —($C_0$-$C_3$alkyl)C(O)$NR^aR^b$, —($C_0$-$C_3$alkyl)$NR^aC(O)R^b$, —($C_0$-$C_3$alkyl)S(O)$_{1-2}R^a$, —($C_0$-$C_3$alkyl)$NR^aS(O)_{1-2}R^b$, —($C_0$-$C_3$alkyl)S(O)$_{1-2}NR^aR^b$, —($C_0$-$C_6$alkyl)(5-6-membered heteroaryl group), or —($C_0$-$C_6$alkyl)phenyl, wherein when $R^1$ is not hydrogen, $R^1$ is optionally substituted by one or more groups independently selected from the group consisting of halogen, $C_1$-$C_6$alkyl, oxo, —$CF_3$, —($C_0$-$C_3$alkyl)$OR^c$, and —($C_0$-$C_3$alkyl)$NR^cR^d$;

$R^2$ is —$C(R^3)_3$, wherein $R^3$ is independently selected from the group consisting of hydrogen and halogen;

$R^a$ is independently hydrogen, hydroxy, $C_1$-$C_6$alkyl, $C_3$-$C_6$ cycloalkyl group, 3-10 membered heterocyclic group, —C(O)$R^c$, —C(O)$OR^c$, —C(O)$NR^cR^d$, —$NR^cC(O)R^d$, —S(O)$_{1-2}R^c$, —$NR^cS(O)_{1-2}R^d$ or —S(O)$_{1-2}NR^cR^d$, wherein any $C_3$-$C_6$ cycloalkyl group, and 3-10 membered heterocyclic group of $R^a$ is optionally substituted with one or more groups $R^e$;

$R^b$ is independently hydrogen or $C_1$-$C_3$alkyl, wherein said alkyl is optionally substituted by one or more groups independently selected from the group consisting of halogen and oxo;

$R^c$ and $R^d$ are independently selected from the group consisting of hydrogen, 3-6 membered heterocyclic group, $C_3$-$C_6$ cycloalkyl group, and $C_1$-$C_3$alkyl, wherein any 3-6 membered heterocyclic group, $C_3$-$C_6$ cycloalkyl group, and $C_1$-$C_3$alkyl of $R^c$ and $R^d$ is optionally substituted by one or more groups independently selected from the group consisting of halogen and oxo; or $R^c$ and $R^d$ are taken together with the atom to which they are attached to form a 3-6-membered heterocyclic group, optionally substituted by one or more groups independently selected from the group consisting of halogen, oxo, —$CF_3$, and $C_1$-$C_3$alkyl;

each $R^e$ is independently selected from the group consisting of oxo, —$OR^f$, —$NR^fR^g$, —C(O)$OR^f$, —C(O)$R^f$, halogen, 3-10 membered heterocyclic group, $C_3$-$C_6$ cycloalkyl group, and $C_1$-$C_6$alkyl, wherein any $C_3$-$C_6$ cycloalkyl group and $C_1$-$C_6$alkyl of $R^e$ is optionally substituted by one or more groups independently selected from the group consisting of —$OR^f$, —$NR^fR^g$, —C(O)$OR^f$, —C(O)$NR^fR^g$, halogen, 3-10 membered heterocyclic group, oxo, and cyano, and wherein any 3-10 membered heterocyclic group of $R^e$ and any 3-10 membered heterocyclic group substituted on a $C_3$-$C_6$ cycloalkyl group or $C_1$-$C_6$alkyl of $R^e$ is optionally substituted by one or more groups independently selected from the group consisting of halogen, oxo, cyano, —$CF_3$, —$NR^hR^k$, 3-6 membered heterocyclic group, and $C_1$-$C_3$alkyl that is optionally substituted by one or more groups independently selected from the group consisting of halogen, oxo, —$OR^f$, and —$NR^hR^k$;

$R^f$ and $R^g$ are each independently selected from the group consisting of hydrogen, $C_1$-$C_6$alkyl, 3-6 membered heterocyclic group, and $C_3$-$C_6$ cycloalkyl group, wherein any $C_1$-$C_6$alkyl, 3-6 membered heterocyclic group, and $C_3$-$C_6$ cycloalkyl group of $R^f$ and $R^g$ is optionally substituted by one or more $R^m$;

$R^h$ and $R^k$ are each independently selected from the group consisting of hydrogen and $C_1$-$C_6$alkyl that is optionally substituted by one or more groups independently selected from the group consisting of halogen, cyano, 3-6 membered heterocyclic group, and oxo; or $R^h$ and $R^k$ are taken together with the atom to which they are attached to form a 3-6-membered heterocyclic group that is optionally substituted by one or more groups independently selected from the group consisting of halogen, cyano, oxo, —$CF_3$ and $C_1$-$C_3$alkyl that is optionally substituted by one or more groups independently selected from the group consisting of halogen and oxo;

each $R^m$ is independently selected from the group consisting of halogen, cyano, oxo, $C_3$-$C_6$cycloalkyl group, hydroxy, and $NR^hR^k$, wherein any $C_3$-$C_6$cycloalkyl group of $R^m$ is optionally substituted with one or more groups independently selected from the group consisting of halogen, oxo, cyano, and $C_1$-$C_3$alkyl;

each $R^n$ is independently $C_1$-$C_6$ alkyl, $C_2$-$C_6$ alkenyl, $C_2$-$C_6$ alkynyl, oxo, halogen, —($C_0$-$C_3$ alkyl)CN, —($C_0$-$C_6$ alkyl)$OR^o$, —($C_0$-$C_3$ alkyl)$SR^o$, —($C_0$-$C_6$ alkyl)$NR^oR^p$, —($C_0$-$C_3$ alkyl)$OCF_3$, —($C_0$-$C_3$ alkyl)$CF_3$, —($C_0$-$C_3$ alkyl)$NO_2$, —($C_0$-$C_6$ alkyl)C(O)$R^o$, —($C_0$-$C_6$ alkyl)C(O)$OR^o$, —($C_0$-$C_6$ alkyl)C(O)$NR^oR^p$, —($C_0$-$C_3$ alkyl)$NR^oC(O)R^p$, —($C_0$-$C_3$ alkyl)S(O)$_{1-2}R^o$, —($C_0$-$C_3$ alkyl)$NR^oS(O)_{1-2}R^p$, —($C_0$-$C_3$ alkyl)S(O)$_{1-2}NR^oR^p$, —($C_0$-$C_3$ alkyl)($C_3$-$C_6$ cycloalkyl), —($C_0$-$C_6$ alkyl)(3-6-membered heterocyclic group), —($C_0$-$C_3$ alkyl)C(O)(3-6-membered heterocyclic group), or —($C_0$-$C_3$ alkyl)phenyl, wherein each $R^n$ is independently optionally substituted by halogen, $C_1$-$C_3$ alkyl, oxo, —$CF_3$, —($C_0$-$C_3$ alkyl)$OR^r$, —($C_0$-$C_3$ alkyl)$NR^rR^s$; or two $R^n$ are taken together to form —O(CH$_2$)$_{1-3}$O— or —(CH$_2$)$_{1-3}$—O—(CH$_2$)$_{1-3}$—;

$R^o$ is independently hydrogen, $C_1$-$C_6$ alkyl, $C_2$-$C_6$alkenyl, $C_2$-$C_6$alkynyl, $C_3$-$C_6$ cycloalkyl group, 3-6 membered heterocyclic group, —($C_3$-$C_6$ cycloalkyl group)$C_1$-$C_6$alkyl, -(3-6-membered heterocyclic group)$C_1$-$C_6$alkyl, —C(O)($C_3$-$C_6$ cycloalkyl group), —C(O)(3-6-membered heterocyclic group), —C(O)R$^r$, —C(O)OR$^r$, —NR'R$^s$, —C(O)NR'R$^s$, —NR'C(O)R$^s$, —S(O)$_{1-2}$R$^r$, —NR'S(O)$_{1-2}$R$^s$ or —S(O)$_{1-2}$NR'R$^s$, wherein said alkyl, cycloalkyl group, and heterocyclic group are independently optionally substituted by oxo, C$_1$-C$_3$ alkyl, —OR$^r$, NR'R$^s$, —C(O)OR$^r$, or halogen;

R$^p$ is independently hydrogen or C$_1$-C$_3$ alkyl, wherein said alkyl is independently optionally substituted by halogen or oxo;

or R$^o$ and R$^p$ are taken together with the atom to which they are attached to form a 3-6-membered heterocyclic group, optionally substituted by halogen, oxo, or C$_1$-C$_3$ alkyl optionally substituted by halogen;

R$^r$ and R$^s$ are independently hydrogen or C$_1$-C$_6$ alkyl optionally substituted by halogen or oxo; or R$^r$ and R$^s$ are taken together with the atom to which they are attached to form a 3-6-membered heterocyclic group, optionally substituted by halogen, oxo, or C$_1$-C$_3$ alkyl optionally substituted by halogen; and R$^t$ is hydrogen, C$_1$-C$_6$ alkyl, C$_2$-C$_6$ alkenyl, C$_2$-C$_6$ alkynyl, or —(C$_0$-C$_3$ alkyl)phenyl.

Another aspect of the invention is a pharmaceutical composition comprising a compound having the general structure (IA), or a pharmaceutically acceptable salt thereof, and a pharmaceutically acceptable carrier, diluent or excipient.

Yet another aspect of the invention is a use of a compound having the general structure (IA), or a pharmaceutically acceptable salt thereof, in therapy.

Yet another aspect of the invention is a method of preventing, treating or lessening the severity of a disease or condition responsive to the inhibition of a Janus kinase activity in a patient, comprising administering to the patient a therapeutically effective amount of a compound having the general structure (IA), or a pharmaceutically acceptable salt thereof.

DETAILED DESCRIPTION OF
EMBODIMENT(S) OF THE INVENTION

Definitions

"Halogen" or "halo" refers to F, Cl, Br, or I. These may be referred to as fluoro, chloro, bromo, and iodo. Additionally, terms such as "haloalkyl," are meant to include mono-haloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms (C$_1$-C$_{18}$). In other examples, the alkyl radical is C$_0$-C$_6$, C$_0$-C$_5$, C$_0$-C$_3$, C$_1$-C$_{12}$, C$_1$-C$_{10}$, C$_1$-C$_8$, C$_1$-C$_6$, C$_1$-C$_5$, C$_1$-C$_4$, or C$_1$-C$_3$. C$_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, and 1-octyl. In some embodiments, substituents for "optionally substituted alkyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl, and heterocyclic portions thereof may be optionally substituted, such as by one to four instances of substituents selected from this same list.

The term "alkenyl" refers to linear or branched-chain monovalent hydrocarbon radical with at least one site of unsaturation, i.e., a carbon-carbon double bond, wherein the alkenyl radical may be optionally substituted, and includes radicals having "cis" and "trans" orientations, or alternatively, "E" and "Z" orientations. In one example, the alkenyl radical is two to eighteen carbon atoms (C$_2$-C$_{18}$). In other examples, the alkenyl radical is C$_2$-C$_{12}$, C$_2$-C$_{10}$, C$_2$-C$_8$, C$_2$-C$_6$, or C$_2$-C$_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl. In some embodiments, substituents for "optionally substituted alkenyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl, and heterocyclic portions thereof may be optionally substituted, such as by one to four instances of substituents selected from this same list.

The term "alkynyl" refers to a linear or branched monovalent hydrocarbon radical with at least one site of unsaturation, i.e., a carbon-carbon, triple bond, wherein the alkynyl radical may be optionally substituted. In one example, the alkynyl radical is two to eighteen carbon atoms (C$_2$-C$_{18}$). In other examples, the alkynyl radical is C$_2$-C$_{12}$, C$_2$-C$_{10}$, C$_2$-C$_8$, C$_2$-C$_6$, or C$_2$-C$_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl, and but-3-ynyl. In some embodiments, substituents for "optionally substituted alkynyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl, and heterocyclic portions thereof may be optionally substituted, such as by one to four instances of substituents selected from this same list.

"Alkylene" refers to a saturated, branched, or straight chain hydrocarbon group having two monovalent radical centers derived by the removal of two hydrogen atoms from the same or two different carbon atoms of a parent alkane. In one example, the divalent alkylene group is one to eighteen carbon atoms (C$_1$-C$_{18}$). In other examples, the divalent alkylene group is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. The group $C_0$ alkylene refers to a bond. Example alkylene groups include methylene (—$CH_2$—), 1,1-ethyl (—CH($CH_3$)—), (1,2-ethyl (—$CH_2CH_2$—), 1,1-propyl (—CH($CH_2CH_3$)—), 2,2-propyl (—C($CH_3$)$_2$—), 1,2-propyl (—CH($CH_3$)$CH_2$—), 1,3-propyl (—$CH_2CH_2CH_2$—), 1,1-dimethyleth-1,2-yl (—C($CH_3$)$_2CH_2$—), 1,4-butyl (—$CH_2CH_2CH_2CH_2$—), and the like.

The term "heteroalkyl" refers to a straight or branched chain monovalent hydrocarbon radical, consisting of the stated number of carbon atoms, or, if none are stated, up to 18 carbon atoms, and from one to five heteroatoms selected from the group consisting of O, N, Si, and S, and wherein the nitrogen and sulfur atoms can optionally be oxidized and the nitrogen heteroatom can optionally be quaternized. In some embodiments, the heteroatom is selected from O, N, and S, wherein the nitrogen and sulfur atoms can optionally be oxidized and the nitrogen heteroatom can optionally be quaternized. The heteroatom(s) can be placed at any interior position of the heteroalkyl group, including the position at which the alkyl group is attached to the remainder of the molecule (e.g., —O—$CH_2$—$CH_3$). Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —Si($CH_3$)$_3$, and —$CH_2$—CH=N—$OCH_3$. Up to two heteroatoms can be consecutive, such as, for example, —$CH_2$—NH—$OCH_3$ and —$CH_2$—O—Si($CH_3$)$_3$. Heteroalkyl groups can be optionally substituted. In some embodiments, substituents for "optionally substituted heteroalkyls" include one to four instances of F, Cl, Br, I, OH, SH, CN, $NH_2$, $NHCH_3$, N($CH_3$)$_2$, $NO_2$, $N_3$, C(O)$CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl, and heterocyclic portions thereof may be optionally substituted, such as by one to four instances of substituents selected from this same list.

"Amino" means primary (i.e., —$NH_2$), secondary (i.e., —NRH), tertiary (i.e., —NRR), and quaternary (i.e., —N(+)RRR) amines, that are optionally substituted, in which each R is the same or different and selected from alkyl, cycloalkyl, aryl, and heterocyclyl, wherein the alkyl, cycloalkyl, aryl, and heterocyclyl groups are as defined herein. Particular secondary and tertiary amines are alkylamine, dialkylamine, arylamine, diarylamine, aralkylamine, and diaralkylamine, wherein the alkyl and aryl portions can be optionally substituted. Particular secondary and tertiary amines are methylamine, ethylamine, propylamine, isopropylamine, phenylamine, benzylamine, dimethylamine, diethylamine, dipropylamine, and diisopropylamine. In some embodiments, R groups of a quarternary amine are each independently optionally substituted alkyl groups.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four, or five substituents, for example, 1-2, 1-3 or 1-4 substituents, such as chosen from groups specified herein (see "optionally substituted" definition), such as F, Cl, Br, I, OH, SH, CN, $NH_2$, $NHCH_3$, N($CH_3$)$_2$, $NO_2$, $N_3$, C(O)$CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl, and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl, and the like; 3- or 4-trifluoromethylphenyl; a mono- or dicarboxyphenyl or (protected carboxy)phenyl group such 4-carboxyphenyl, a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. In some embodiments, a substituent of an aryl, such as phenyl, comprises an amide. For example, an aryl (e.g., phenyl) substituent may be —($CH_2$)$_{0-4}$CONR'R", wherein R' and R" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R".

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$, or $C_5$-$C_{10}$. In other examples, the cycloalkyl group, as a monocycle, is $C_3$-$C_8$, $C_3$-$C_6$, or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane, and bicyclo[3.2.2]nonane. Examples of spiro cycloalkyl include, spiro[2.2]pentane, spiro[2.3] hexane, spiro[2.4]heptane, spiro[2.5]octane, and spiro[4.5] decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, isopropyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list. In some embodiments, a substituent of a cycloalkyl comprises an amide. For example, a cycloalkyl substituent may be —$(CH_2)_{0-4}$CONR'R", wherein R' and R" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R".

"Guanidine" or "guanidinyl" means the group —NH—C (NH)—NHR in which R is hydrogen, alkyl, cycloalkyl, aryl or heterocyclyl, wherein the alkyl, cycloalkyl, aryl and heterocyclyl groups are as defined herein. A particular guanidine is the group —NH—C(NH)—$NH_2$.

"Heterocyclic group", "heterocyclic", "heterocycle", "heterocyclyl", or "heterocyclo" are used interchangeably and refer to any mono-, bi-, tricyclic or spiro, saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen.

In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6, 7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list. In some embodiments, a substituent of a heterocyclic group, such as a heteroaryl or heterocycloalkyl, comprises an amide. For example, a heterocyclic (e.g., heteroaryl or heterocycloalkyl) substituent may be —$(CH_2)_{0-4}$CONR'R", wherein R' and R" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R".

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) $13^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. In some embodiments, a substituent of a heteroaryl comprises an amide. For example, a heteroaryl substituent may be —$(CH_2)_{0-4}$CONR'R", wherein R' and R" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R".

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, n-butoxy, isobutoxy, tert-butoxy, mono-, di- and tri-fluoromethoxy and cyclopropoxy.

"Acyl" means a carbonyl containing substituent represented by the formula —C(O)—R in which R is hydrogen, alkyl, cycloalkyl, aryl or heterocyclyl, wherein the alkyl, cycloalkyl, aryl and heterocyclyl are as defined herein. Acyl groups include alkanoyl (e.g., acetyl), aroyl (e.g., benzoyl), and heteroaroyl (e.g., pyridinoyl).

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

Optional substituents for alkyl radicals, alone or as part of another substituent (e.g., alkoxy), as well as alkylenyl, alkenyl, alkynyl, heteroalkyl, heterocycloalkyl, and cycloalkyl, also each alone or as part of another substituent, can be a variety of groups, such as those described herein, as well as selected from the group consisting of halogen; oxo; CN; NO; $N_3$; —OR'; perfluoro-$C_1$-$C_4$ alkoxy; unsubstituted $C_3$-$C_7$ cycloalkyl; $C_3$-$C_7$ cycloalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl (e.g., phenyl); $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; NR'R"; SR'; SiR'R"R"'; OC(O)R'; C(O)R'; $CO_2R'$; CONR'R"; OC(O)NR'R"; NR"C(O)R'; NR"C(O)NR'R"; NR"C(O)$_2R'$; S(O)$_2R'$; S(O)$_2$NR'R"; NR'S(O)$_2$R"; NR"'S(O)$_2$NR'R"; amidinyl; guanidinyl; (CH2)1-4 OR'; (CH2)1-4 NR'R"; $(CH_2)_{1-4}$—SR'; —$(CH_2)_{1-4}$—SiR'R"R"'; —$(CH_2)_{1-4}$—OC(O)R'; —$(CH_2)_{1-4}$—C(O)R'; —$(CH_2)_{1-4}$—CO$_2$R'; and —$(CH_2)_{1-4}$CONR'R", or combinations thereof, in a number ranging from zero to (2 m'+1), where m' is the total number of carbon atoms in such radical. R', R" and R"' each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R". For example, —NR'R" is meant to include 1-pyrrolidinyl and 4-morpholinyl.

Similarly, optional substituents for the aryl and heteroaryl groups are varied. In some embodiments, substituents for aryl and heteroaryl groups are selected from the group consisting of halogen; CN; NO; $N_3$; —OR'; perfluoro-$C_1$-$C_4$ alkoxy; unsubstituted $C_3$-$C_7$ cycloalkyl; $C_3$-$C_7$ cycloalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl (e.g., phenyl); $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo, or NR'R"; —NR'R"; —SR'; —SiR'R"R"'; —OC(O)R'; —C(O)R'; —CO$_2$R'; —CONR'R"; —OC(O)NR'R"; —NR"C(O) R'; —NR"'C(O) NR'R"; —NR"C(O)$_2$R'; —S(O)$_2$R'; —S(O)$_2$NR'R"; —NR'S (O)$_2$R"; —NR"'S(O)$_2$NR'R"; amidinyl; guanidinyl; —$(CH_2)_{1-4}$—OR'; —$(CH_2)_{1-4}$—NR'R"; —$(CH_2)_{1-4}$—SR'; —$(CH_2)_{1-4}$—SiR'R"R"'; —$(CH_2)_{1-4}$—OC(O)R'; —$(CH_2)_{1-4}$—C(O)R'; —$(CH_2)_{1-4}$—CO$_2$R'; and —$(CH_2)_{1-4}$ CONR'R", or combinations thereof, in a number ranging from zero to (2 m'+1), where m' is the total number of carbon atoms in such radical. R', R" and R"' each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R". For example, —NR'R" is meant to include 1-pyrrolidinyl and 4-morpholinyl.

The term "oxo" refers to =O or (=O)$_2$.

The terms "cyano" or "nitrile" refers to —C≡N or —CN.

As used herein a wavy line "〜" that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment. In some embodiments, a functional group, e.g., a cyclic structure, may be spiro bonded to another functional group, e.g., another cyclic structure. In such embodiments, the atom that is the point of attachment between the two cyclic structures in the spiro structure (i.e., the atoms shared between the two cyclic structures) will be marked with an arrow together with an asterisk.

In certain embodiments, divalent groups are described generically without specific bonding configurations. It is understood that the generic description is meant to include both bonding configurations, unless specified otherwise. For example, in the group $R^1$—$R^2$—$R^3$, if the group $R^2$ is described as —CH$_2$C(O)—, then it is understood that this group can be bonded both as $R^1$—CH$_2$C(O)—$R^3$, and as $R^1$—C(O)CH$_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the present invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid, and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid, and the like.

"Pharmaceutically acceptable base addition salts" include those derived from inorganic bases such as sodium, potassium, lithium, ammonium, calcium, magnesium, iron, zinc, copper, manganese, aluminum salts, and the like. Particular base addition salts are the ammonium, potassium, sodium, calcium, and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins, and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers, and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the present invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the present invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS, or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl) methylsilyl)ethyl, p-toluenesulfonylethyl, 4-nitrobenzylsulfonylethyl, allyl, cinnamyl, 1-(trimethylsilylmethyl) prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, $3^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., tert-butyldimethylsilyl ether (TBS), tert-butyldiphenylsilyl ether (TBDPS)) groups. Further examples of these groups are found in T. W. Greene and P. G. M. Wuts, "Protecting Groups in Organic Synthesis, $3^{rd}$ ed., John Wiley & Sons, Inc., 1999. The term "protected hydroxy" refers to a hydroxy group substituted with one of the above hydroxy-protecting groups.

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound according to the present invention, to a patient, the patient is typically in need thereof.

The term "Janus kinase" refers to JAK1, JAK2, JAK3 and TYK2 protein kinases. In some embodiments, a Janus kinase may be further defined as one of JAK1, JAK2, JAK3 or TYK2. In any embodiment, any one of JAK1, JAK2, JAK3 and TYK2 may be specifically excluded as a Janus kinase.

In some embodiments, a Janus kinase is JAK1. In some embodiments, a Janus kinase is a combination of JAK1 and JAK2.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., JAK1 activity) compared to normal.

In some embodiments, a compound according to the present invention, including compounds of Formula IA, or a compound of Table 1 or of Examples 1-154, is selective for inhibition of JAK1 over JAK3 and TYK2. In some embodiments, a compound according to the present invention, including compounds of Formula IA, or a compound of Table 1 or of Examples 1-154, is selective for inhibition of JAK1 over JAK2, JAK3, or TYK2, or any combination of JAK2, JAK3, or TYK2. In some embodiments, a compound according to the present invention, including compounds of Formula IA, or a compound of Table 1 or of Examples 1-154, is selective for inhibition of JAK1 and JAK2 over JAK3 and TYK2. In some embodiments, a compound according to the present invention, including compounds of Formula IA, or a compound of Table 1 or of Examples 1-154, is selective for inhibition of JAK1 over JAK3. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of a particular Janus kinase (e.g., JAK1) activity compared to another particular Janus kinase (e.g., JAK1) activity, or is at least a 2-, 3-, 4-, 5-, 10-, 25-, 50-, 100-, 250-, or 500-fold better inhibitor of a particular Janus kinase (e.g., JAK1) activity compared to another particular Janus kinase (e.g., JAK1) activity.

"Therapeutically effective amount" means an amount of a compound of the present invention, such as a compound of Formula IA, or a compound of Table 1 or of Examples 1-154 that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., asthma). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, such as a compound of Formula IA, or a compound of Table 1 or of Examples 1-154, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula IA, or a compound of Table 1 or of Examples 1-154, encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Nonlimiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

"Package insert" is used to refer to instructions customarily included in commercial packages of therapeutic products that contain information about the indications, usage, dosage, administration, contraindications or warnings concerning the use of such therapeutic products.

The terms "compound(s) of this invention," and "compound(s) of the present invention" and the like, unless otherwise indicated, include compounds of Formula IA, or a compound of Table 1 or of Examples 1-154, and stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

Unless otherwise stated, structures depicted herein are also meant to include compounds that differ only in the presence of one or more isotopically enriched atoms. Exemplary isotopes that can be incorporated into compounds of the present invention, such as a compound of Formula IA, or a compound of Table 1 or of Examples 1-154, include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds of Formula IA, or a compound of Table 1 or of Examples 1-154, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Reaction Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Inhibitors of Janus Kinases

Accordingly, one aspect of the invention includes a compound of Formula (IA):

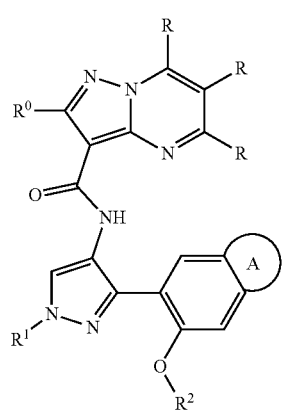

(IA)

or a pharmaceutically acceptable salt thereof.

In some embodiments, A is a fused ring selected from the group consisting of a 6-membered aromatic group; a 5-membered or 6-membered heterocyclic group; and a 5-membered or 6-membered cycloalkyl group; wherein fused ring A is optionally substituted by 1-5 R".

In some embodiments, A is the 6-membered aromatic group.

In some embodiments, A is the 5-membered cycloalkyl group.

In some embodiments, A is the 5-membered heterocyclic group.

In some embodiments, A is a 5-membered heteroaryl group.

In some embodiments, A is the 6-membered heterocyclic group.

In some embodiments, A is a 6-membered heteroaryl group.

In some embodiments, A is a fused ring selected from the group consisting of phenyl, morpholinyl, thiophenyl, thiomorpholinyl, tetrahydrofuranyl, tetrahydro-2H-pyranyl, 1H-pyrazolyl, cyclopentanyl, pyridinyl, 1H-imidazolyl, isothiazolyl, oxathiinyl, and dioxinyl each of which is optionally substituted with 1-5 R".

In some embodiments, A is a fused ring such that the compound of Formula (IA) has any of the following general structures of Formula (IB) through (IV):

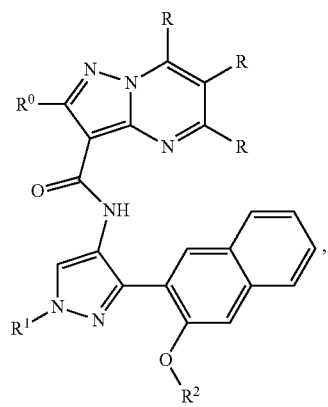

(IB)

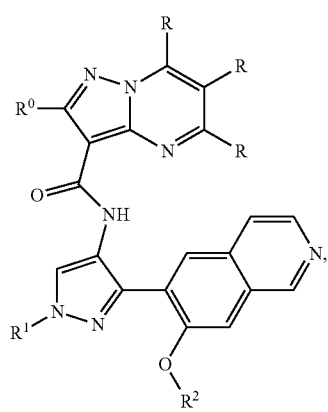

(IC)

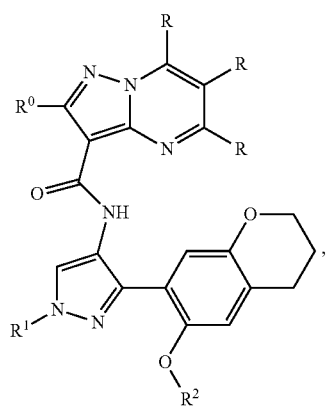

(ID)

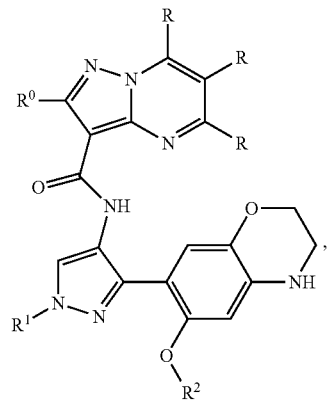

(IE)

-continued
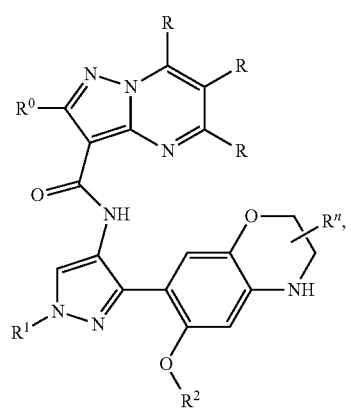
(IF)
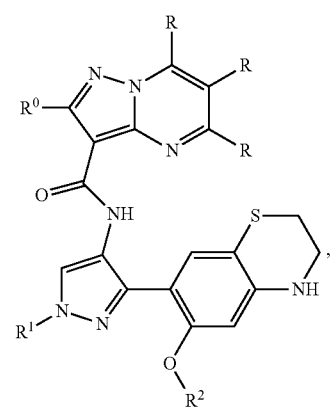
(IG)
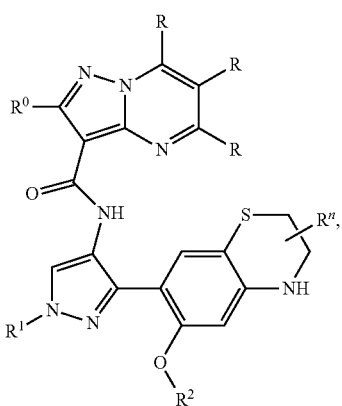
(IH)
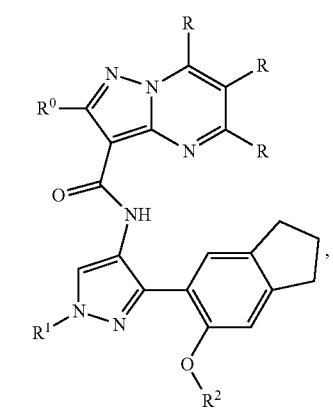
(II)
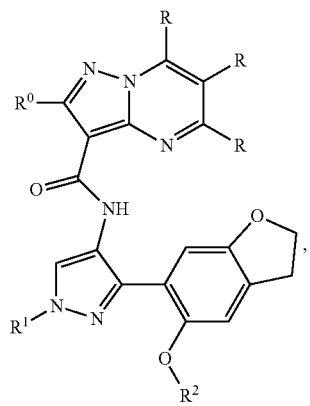
(IJ)
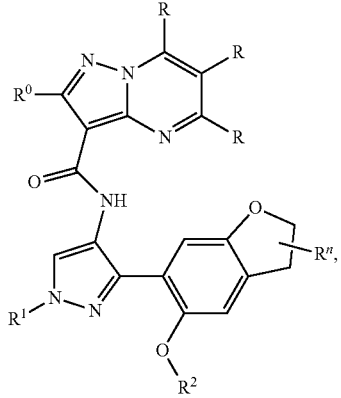
(IK)
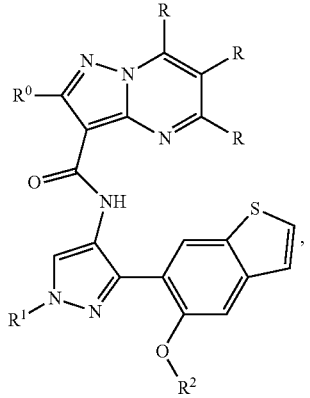
(IL)
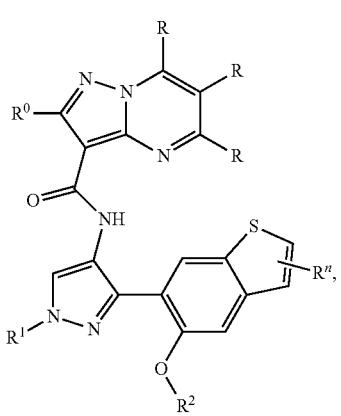
(IM)

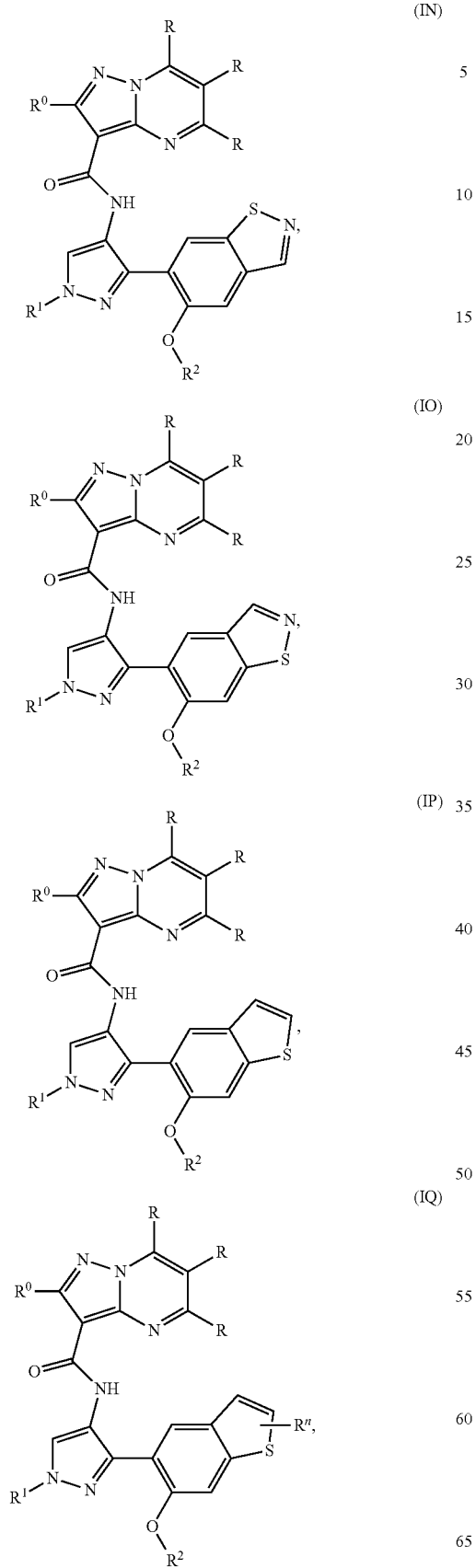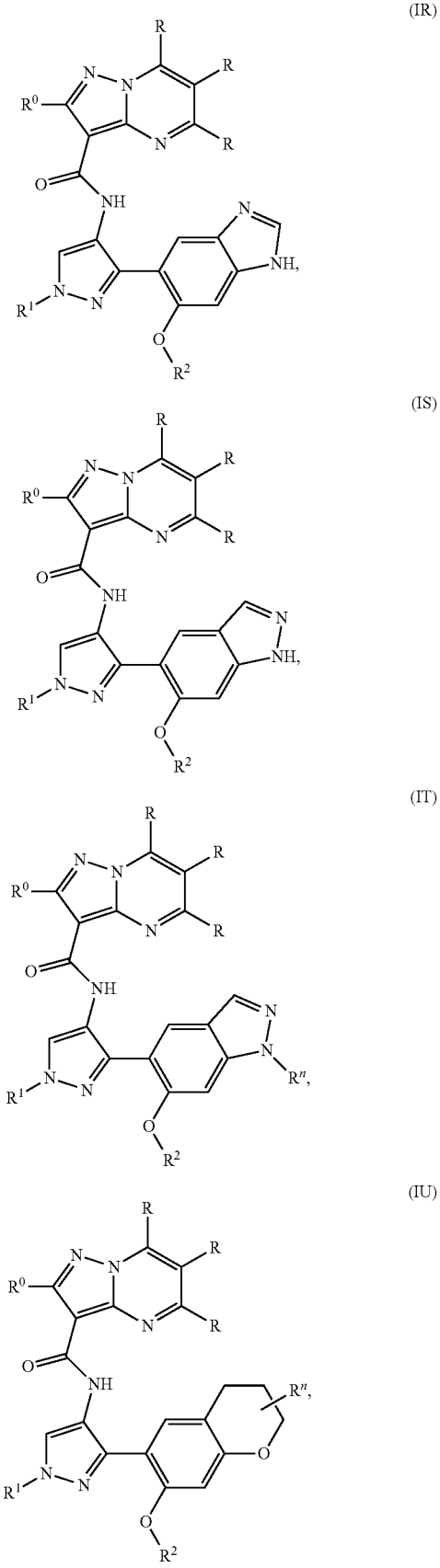

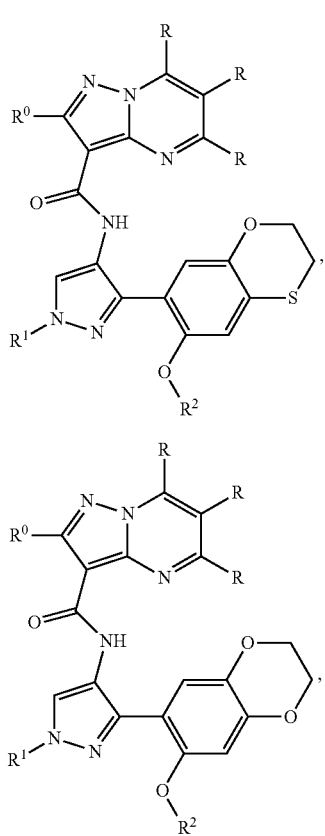

or a pharmaceutically acceptable salt of any of the above.

In some embodiments, A is substituted with 1-5 R″, wherein each R″ is independently $C_1$-$C_6$ alkyl, $C_2$-$C_6$ alkenyl, $C_2$-$C_6$ alkynyl, oxo, halogen, —($C_0$-$C_3$ alkyl)CN, —($C_0$-$C_6$ alkyl)OR°, —($C_0$-$C_3$ alkyl)SR°, —($C_0$-$C_6$ alkyl)NR°R$^p$, —($C_0$-$C_3$ alkyl)OCF$_3$, —($C_0$-$C_3$ alkyl)CF$_3$, —($C_0$-$C_3$ alkyl)NO$_2$, —($C_0$-$C_6$ alkyl)C(O)R°, —($C_0$-$C_6$ alkyl)C(O)OR°, —($C_0$-$C_6$ alkyl)C(O)NR°R$^p$, —($C_0$-$C_3$ alkyl)NR°C(O)R$^p$, —($C_0$-$C_3$ alkyl)S(O)$_{1-2}$R°, —($C_0$-$C_3$ alkyl)NR°S(O)$_{1-2}$R$^p$, —($C_0$-$C_3$ alkyl)S(O)$_{1-2}$NR°R$^p$, —($C_0$-$C_3$ alkyl)($C_3$-$C_6$ cycloalkyl), —($C_0$-$C_6$ alkyl)(3-6-membered heterocyclic group), —($C_0$-$C_3$ alkyl)C(O)(3-6-membered heterocyclic group), or —($C_0$-$C_3$ alkyl)phenyl, wherein each R″ is independently optionally substituted by halogen, $C_1$-$C_3$ alkyl, oxo, —CF$_3$, —($C_0$-$C_3$ alkyl)OR$^r$, —($C_0$-$C_3$ alkyl)NR$^r$R$^s$; or two R″ are taken together to form —O(CH$_2$)$_{1-3}$O— or —(CH$_2$)$_{1-3}$—O—(CH$_2$)$_{1-3}$—.

In some embodiments, R° is independently hydrogen, $C_1$-$C_6$ alkyl, $C_2$-$C_6$alkenyl, $C_2$-$C_6$alkynyl, $C_3$-$C_6$ cycloalkyl group, 3-6 membered heterocyclic group, —($C_3$-$C_6$ cycloalkyl group)$C_1$-$C_6$alkyl, -(3-6-membered heterocyclic group) $C_1$-$C_6$alkyl, —C(O)($C_3$-$C_6$ cycloalkyl group), —C(O)(3-6-membered heterocyclic group), —C(O)R$^r$, —C(O)OR$^r$, —NR$^r$R$^s$, —C(O)NR$^r$R$^s$, —NR$^r$C(O)R$^s$, —S(O)$_{1-2}$R$^r$, —NR$^r$S(O)$_{1-2}$R$^s$ or —S(O)$_{1-2}$NR$^r$R$^s$, wherein said alkyl, cycloalkyl group, and heterocyclic group are independently optionally substituted by oxo, $C_1$-$C_3$ alkyl, —OR$^r$, NR$^r$R$^s$, —C(O)OR$^r$, or halogen.

In some embodiments, R$^p$ is independently hydrogen or $C_1$-$C_3$ alkyl, wherein said alkyl is independently optionally substituted by halogen or oxo.

In some embodiments, R° and R$^p$ are taken together with the atom to which they are attached to form a 3-6-membered heterocyclic group, optionally substituted by halogen, oxo, or $C_1$-$C_3$ alkyl optionally substituted by halogen.

In some embodiments, R$^r$ and R$^s$ are independently hydrogen or $C_1$-$C_6$ alkyl optionally substituted by halogen or oxo; or R$^r$ and R$^s$ are taken together with the atom to which they are attached to form a 3-6-membered heterocyclic group, optionally substituted by halogen, oxo, or $C_1$-$C_3$ alkyl optionally substituted by halogen.

In some embodiments, A is substituted with 1-5 R″, wherein each R″ is independently selected from the group consisting of: oxo; cyano; $C_1$-$C_6$ alkyl; —($C_0$-$C_6$ alkyl)C(O)R°, wherein R° is selected from the group consisting of hydrogen, $C_1$-$C_6$ alkyl, or a 6-membered heterocyclic group, optionally substituted with —($C_0$-$C_3$ alkyl)C(O)OR$^r$, wherein R$^r$ is $C_1$-$C_6$ alkyl; —($C_1$-$C_6$ alkyl)OR°, wherein R° is hydrogen or $C_1$-$C_6$ alkyl; —($C_0$-$C_6$ alkyl)C(O)OR°, wherein R° is hydrogen or $C_1$-$C_6$ alkyl; —($C_0$-$C_6$ alkyl)NR°R$^p$, wherein each R° and R$^p$ is independently hydrogen or $C_1$-$C_3$ alkyl; and —($C_0$-$C_6$ alkyl)C(O)NR°R$^p$, wherein each R° and R$^p$ is independently hydrogen or $C_1$-$C_3$ alkyl.

In some embodiments, A is the 6-membered aromatic group, i.e., a fused phenyl ring.

In some embodiments, A is the 5-membered cycloalkyl group, i.e., a fused cyclopenthyl ring.

In some embodiments, A is the 5-membered heterocyclic group, and more particularly a 5-membered heterocyclic group containing a nitrogen atom, a sulfur atom, an oxygen atom, or any combination thereof, wherein the 5-membered heterocyclic group is substituted with 1-5 R″, wherein R″ is $C_1$-$C_6$ alkyl, optionally substituted with hydroxy.

In some embodiments, A is a 5-membered heteroaryl group, and more particularly a 5-membered heterocyclic group containing a nitrogen atom, a sulfur atom, or both a nitrogen atom and a sulfur atom, wherein the 5-membered heteroaryl group is substituted with 1-5 R″, wherein R″ is selected from the group consisting of: cyano; unsubstituted $C_1$-$C_6$ alkyl; —($C_0$-$C_6$ alkyl)C(O)OR°, wherein R° is hydrogen or $C_1$-$C_6$ alkyl; —($C_0$-$C_6$ alkyl)C(O)R°, wherein R° is selected from the group consisting of hydrogen, $C_1$-$C_6$ alkyl, or a 6-membered heterocyclic group, optionally substituted with —($C_0$-$C_3$ alkyl)C(O)OR$^r$, wherein R$^r$ is $C_1$-$C_6$ alkyl; and —($C_0$-$C_6$ alkyl)C(O)NR°R$^p$, wherein each R° and R$^p$ is independently hydrogen or $C_1$-$C_3$ alkyl.

In some embodiments, A is the 6-membered heterocyclic group, and more particularly a 5-membered heterocyclic group containing a nitrogen atom, a sulfur atom, an oxygen atom, or any combination thereof, wherein the 6-membered heterocyclic group is substituted with 1-5 R″, wherein R″ is selected from the group consisting of: oxo; unsubstituted $C_1$-$C_6$ alkyl; and —($C_1$-$C_6$ alkyl)NR°R$^p$, wherein each R° and R$^p$ are hydrogen; or two R″ are taken together to form —(CH$_2$)$_{1-3}$—O—(CH$_2$)$_{1-3}$—.

In some embodiments, A is a 6-membered heteroaryl group, and more particularly a 6-membered heteroaryl group containing a nitrogen atom.

In some embodiments, A is substituted with 1-5R″, such as one R″ group, or 2 R″ groups.

In some embodiments, R″ is selected from the group consisting of —CH$_3$, =O, —CH$_2$OH, —CH$_2$NH$_2$, —CN,

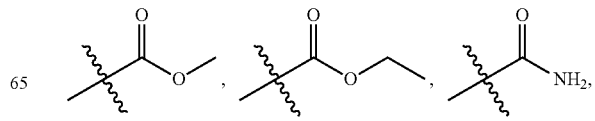

-continued

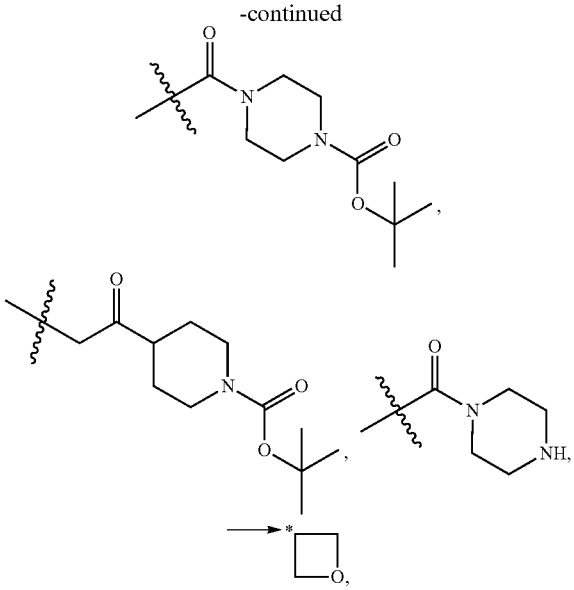

and any combination thereof.

In some embodiments, R is independently selected from the group consisting of hydrogen; halogen; cyano; —NH$_2$; C$_1$-C$_3$ alkyl, optionally substituted with halogen; C$_2$-C$_3$ alkenyl; C$_2$-C$_3$ alkynyl; and —OR$^t$. In some embodiments, R$^t$ is hydrogen, C$_1$-C$_6$ alkyl, C$_2$-C$_6$ alkenyl, C$_2$-C$_6$ alkynyl, or —(C$_0$-C$_3$ alkyl)phenyl.

In some embodiments, each R is independently selected from the group consisting of: hydrogen; —NH$_2$; and C$_1$-C$_3$ alkyl, optionally substituted with halogen.

In some embodiments, each R is independently selected from the group consisting of: hydrogen, —NH$_2$, —CH$_3$, CHF$_2$, and halogen.

In some embodiments, each R is hydrogen.

In some embodiments, R$^0$ is selected from the group consisting of hydrogen, halogen, cyano, C$_1$-C$_3$alkyl, C$_2$-C$_3$alkenyl, C$_2$-C$_3$alkynyl, —NH$_2$, and —OR$^t$. In some embodiments, R$^t$ is hydrogen, C$_1$-C$_6$ alkyl, C$_2$-C$_6$ alkenyl, C$_2$-C$_6$ alkynyl, or —(C$_0$-C$_3$ alkyl)phenyl.

In some embodiments, R$^0$ is hydrogen or —NH$_2$.

In some embodiments, R$^0$ is hydrogen.

In some embodiments, R$^1$ is selected from the group consisting of hydrogen, C$_2$-C$_6$alkenyl, C$_2$-C$_6$alkynyl, —(C$_0$-C$_3$alkyl)CN, —(C$_0$-C$_4$alkyl)OR$^a$, —(C$_0$-C$_3$alkyl)R$^a$, —(C$_0$-C$_3$alkyl)SR$^a$, —(C$_0$-C$_6$alkyl)NR$^a$R$^b$, —(C$_0$-C$_3$alkyl)OCF$_3$, —(C$_0$-C$_3$alkyl)CF$_3$, —(C$_0$-C$_3$alkyl)NO$_2$, —(C$_0$-C$_6$alkyl)C(O)R$^a$, —(C$_0$-C$_6$alkyl)C(O)OR$^a$, —(C$_0$-C$_3$alkyl)C(O)NR$^a$R$^b$, —(C$_0$-C$_3$alkyl)NR$^a$C(O)R$^b$, —(C$_0$-C$_3$alkyl)S(O)$_{1-2}$R$^a$, —(C$_0$-C$_3$alkyl)NR$^a$S(O)$_{1-2}$R$^b$, —(C$_0$-C$_3$alkyl)S(O)$_{1-2}$NR$^a$R$^b$, —(C$_0$-C$_6$alkyl)(5-6-membered heteroaryl group), or —(C$_0$-C$_6$alkyl)phenyl, wherein when R$^1$ is not hydrogen, R$^1$ is optionally substituted by one or more groups independently selected from the group consisting of halogen, C$_1$-C$_6$alkyl, oxo, —CF$_3$, —(C$_0$-C$_3$alkyl)OR$^c$, and —(C$_0$-C$_3$alkyl)NR$^c$R$^d$.

In some embodiments, R$^a$ is independently hydrogen, hydroxy, C$_1$-C$_6$alkyl, C$_3$-C$_6$ cycloalkyl group, 3-10 membered heterocyclic group, —C(O)R$^c$, —C(O)OR$^c$, —C(O)NR$^c$R$^d$, —NR$^c$C(O)R$^d$, —S(O)$_{1-2}$R$^c$, —NR$^c$S(O)$_{1-2}$R$^d$ or —S(O)$_{1-2}$NR$^c$R$^d$, wherein any C$_3$-C$_6$ cycloalkyl group, and 3-10 membered heterocyclic group of R$^a$ is optionally substituted with one or more groups R$^e$.

In some embodiments, R$^b$ is independently hydrogen or C$_1$-C$_3$alkyl, wherein said alkyl is optionally substituted by one or more groups independently selected from the group consisting of halogen and oxo.

In some embodiments, R$^c$ and R$^d$ are independently selected from the group consisting of hydrogen, 3-6 membered heterocyclic group, C$_3$-C$_6$ cycloalkyl group, and C$_1$-C$_3$alkyl, wherein any 3-6 membered heterocyclic group, C$_3$-C$_6$ cycloalkyl group, and C$_1$-C$_3$alkyl of R$^c$ and R$^d$ is optionally substituted by one or more groups independently selected from the group consisting of halogen and oxo; or R$^c$ and R$^d$ are taken together with the atom to which they are attached to form a 3-6-membered heterocyclic group, optionally substituted by one or more groups independently selected from the group consisting of halogen, oxo, —CF$_3$, and C$_1$-C$_3$alkyl.

In some embodiments, each R$^e$ is independently selected from the group consisting of oxo, —OR$^f$, —NR$^f$R$^g$, —C(O)OR$^f$, —C(O)R$^f$, halogen, 3-10 membered heterocyclic group, C$_3$-C$_6$ cycloalkyl group, and C$_1$-C$_6$alkyl, wherein any C$_3$-C$_6$ cycloalkyl group and C$_1$-C$_6$alkyl of R$^e$ is optionally substituted by one or more groups independently selected from the group consisting of —OR$^f$, —NR$^f$R$^g$, —C(O)OR$^f$, —C(O)NR$^f$R$^g$, halogen, 3-10 membered heterocyclic group, oxo, and cyano, and wherein any 3-10 membered heterocyclic group of R$^e$ and any 3-10 membered heterocyclic group substituted on a C$_3$-C$_6$ cycloalkyl group or C$_1$-C$_6$alkyl of R$^e$ is optionally substituted by one or more groups independently selected from the group consisting of halogen, oxo, cyano, —CF$_3$, —NR$^h$R$^k$, 3-6 membered heterocyclic group, and C$_1$-C$_3$alkyl that is optionally substituted by one or more groups independently selected from the group consisting of halogen, oxo, —OR$^f$, and —NR$^h$R$^k$.

In some embodiments, R$^f$ and R$^g$ are each independently selected from the group consisting of hydrogen, C$_1$-C$_6$alkyl, 3-6 membered heterocyclic group, and C$_3$-C$_6$ cycloalkyl group, wherein any C$_1$-C$_6$alkyl, 3-6 membered heterocyclic group, and C$_3$-C$_6$ cycloalkyl group of R$^f$ and R$^g$ is optionally substituted by one or more R$^m$.

In some embodiments, R$^h$ and R$^k$ are each independently selected from the group consisting of hydrogen and C$_1$-C$_6$alkyl that is optionally substituted by one or more groups independently selected from the group consisting of halogen, cyano, 3-6 membered heterocyclic group, and oxo; or R$^h$ and R$^k$ are taken together with the atom to which they are attached to form a 3-6-membered heterocyclic group that is optionally substituted by one or more groups independently selected from the group consisting of halogen, cyano, oxo, —CF$_3$ and C$_1$-C$_3$alkyl that is optionally substituted by one or more groups independently selected from the group consisting of halogen and oxo.

In some embodiments, each R$^m$ is independently selected from the group consisting of halogen, cyano, oxo, C$_3$-C$_6$cycloalkyl group, hydroxy, and NR$^h$R$^k$, wherein any C$_3$-C$_6$cycloalkyl group of R$^m$ is optionally substituted with one or more groups independently selected from the group consisting of halogen, oxo, cyano, and C$_1$-C$_3$alkyl.

In some embodiments, R$^1$ is hydrogen or —(C$_0$-C$_3$alkyl)R$^a$ wherein R$^a$ is C$_1$-C$_6$alkyl, which is optionally substituted.

In some embodiments, R$^1$ is —(C$_0$-C$_3$alkyl)R$^a$ wherein R$^a$ is one of: a 3-10 membered heterocyclic group, optionally substituted with one or more R$^e$, wherein R$^e$ is selected from among C$_1$-C$_6$ alkyl, —OR$_f$, and oxo; or a C$_1$-C$_6$ alkyl, substituted with a 5-membered heterocyclic group or a 6-membered heterocyclic group, wherein the 5-membered heterocyclic group or the 6-membered heterocyclic group is optionally substituted with one or more of a $C_1$-$C_6$ alkyl, hydroxyl, or oxo.

In some embodiments, $R^1$ is —($C_0$-$C_3$alkyl)$R^a$ wherein $R^a$ is one of: a 5-membered heterocyclic group or a 6-membered heterocyclic group, wherein the 5-membered heterocyclic group or the 6-membered heterocyclic group is optionally substituted with one or more $R^e$, wherein $R^e$ is selected from among $C_1$-$C_6$alkyl, —$OR_f$, and oxo; or a $C_1$-$C_6$alkyl, substituted with a 5-membered heterocyclic group or a 6-membered heterocyclic group, wherein the 5-membered heterocyclic group or the 6-membered heterocyclic group is optionally substituted with one or more of a $C_1$-$C_6$ alkyl, hydroxyl, or oxo.

In some embodiments, $R^1$ is —($C_0$-$C_3$alkyl)$R^a$ wherein $R^a$ is a 5-membered heterocyclic group or a 6-membered heterocyclic group, wherein the 5-membered heterocyclic group or the 6-membered heterocyclic group is optionally substituted with one or more $R^e$, wherein $R^e$ is selected from among $C_1$-$C_6$alkyl, —$OR_f$, and oxo.

In some embodiments, $R^1$ is —($C_0$-$C_3$alkyl)$R^a$ wherein $R^a$ is a $C_1$-$C_6$alkyl, substituted with a 5-membered heterocyclic group or a 6-membered heterocyclic group, wherein the 5-membered heterocyclic group or the 6-membered heterocyclic group is optionally substituted with one or more of a $C_1$-$C_6$ alkyl, hydroxyl, or oxo.

In some embodiments, $R^1$ is —($C_0$-$C_3$alkyl)CN.

In some embodiments, $R^1$ is —($C_0$-$C_3$alkyl)C(O)NR$^a$R$^b$, wherein R$^a$ and R$^b$ are each independently hydrogen or $C_1$-$C_6$ alkyl.

In some embodiments, $R^1$ is —($C_0$-$C_3$alkyl)C(O)NR$^a$R$^b$, wherein R$^a$ and R$^b$ are each independently hydrogen, methyl, or ethyl.

In some embodiments, $R^1$ is —($C_0$-$C_4$alkyl)OR$^a$, wherein R$^a$ is hydrogen.

In some embodiments, $R^1$ is —($C_1$-$C_6$alkyl)C(O)OR$^a$, wherein R$^a$ is $C_1$-$C_6$ alkyl.

In some embodiments, $R^1$ is —($C_1$-$C_6$alkyl)C(O)R$^a$, wherein R$^a$ is selected from the group consisting of hydroxy, a 5-membered heterocyclic group, and a 6-membered heterocyclic group.

In some embodiments, $R^1$ is —($C_1$-$C_3$alkyl)C(O)R$^a$, wherein R$^a$ is selected from the group consisting of hydroxy, and a 6-membered heterocyclic group.

In some embodiments, $R^1$ is —($C_1$-$C_6$alkyl)C(O)R$^a$, wherein R$^a$ is a 4-membered heterocyclic group, a 5-membered heterocyclic group or a 6-membered heterocyclic group, the 5-membered heterocyclic group or a 6-membered heterocyclic group optionally substituted with R$^e$, wherein R$^e$ is selected from the group consisting of hydroxy; halogen; oxo; a 5-membered or 6-membered heterocyclic group; $C_1$-$C_6$ alkyl, optionally substituted with a 5-membered or 6-membered heterocyclic group or with —C(O)NR$^f$R$^g$, wherein each of R$^f$ and R$^g$ is independently selected from the group consisting of hydrogen and $C_1$-$C_6$ alkyl; —NR$^f$R$^g$, wherein each of R$^f$ and R$^g$ is independently selected from the group consisting of hydrogen and $C_1$-$C_6$ alkyl, which may be optionally substituted with a cyano or a cyclopropyl moiety; —C(O)R$^f$, wherein R$^f$ is hydrogen or $C_1$-$C_6$ alkyl; and —C(O)OR$^f$, wherein R$^f$ is $C_1$-$C_6$ alkyl.

In some embodiments, $R^1$ is —($C_1$-$C_3$alkyl)C(O)R$^a$, wherein R$^a$ is a 6-membered heterocyclic group, the 6-membered heterocyclic group optionally substituted with R$^e$, wherein R$^e$ is selected from the group consisting of hydroxy; oxo; a 6-membered heterocyclic group; a $C_1$-$C_3$ alkyl, optionally substituted with 6-membered heterocyclic group or with —C(O)NR$^f$R$^g$, wherein each of R$^f$ and R$^g$ is independently selected from the group consisting of hydrogen and $C_1$-$C_6$ alkyl; —NR$^f$R$^g$ wherein each of R$^f$ and R$^g$ is independently selected from the group consisting of hydrogen and $C_1$-$C_6$ alkyl, which may be optionally substituted with a cyano or a cyclopropyl moiety; —C(O)R$^f$ wherein R$^f$ is hydrogen or $C_1$-$C_6$ alkyl; and —C(O)OR$^f$ wherein R$^f$ is hydrogen or $C_1$-$C_6$ alkyl.

In some embodiments, the R$^e$ group is the —NR$^f$R$^g$, and each of R$^f$ and R$^g$ is independently selected from the group consisting of hydrogen and $C_1$-$C_6$ alkyl, which may be optionally substituted with a cyano or a cyclopropyl moiety.

In some embodiments, the R$^e$ group is the —NR$^f$R$^g$, and each of R$^f$ and R$^g$ is independently selected from the group consisting of hydrogen and $C_1$-$C_3$ alkyl, which may be optionally substituted with a cyano or a cyclopropyl moiety.

In some embodiments, the R$^e$ group is the —C(O)OR$^f$ and the R$^f$ group is selected from the group consisting of hydrogen and $C_1$-$C_4$ alkyl.

In some embodiments, the R$^e$ group is $C_1$-$C_3$ alkyl substituted with a 6-membered heterocyclic group.

In some embodiments, the R$^e$ group is $C_1$-$C_3$ alkyl substituted with —C(O)NR$^f$R$^g$, wherein each of R$^f$ and R$^g$ is independently selected from the group consisting of hydrogen and $C_1$-$C_3$ alkyl.

In some embodiments, $R^1$ is —($C_1$-$C_6$alkyl)NR$^a$R$^b$, wherein R$^a$ is selected from the group consisting of hydrogen, $C_1$-$C_6$ alkyl, and a 5-membered or 6-membered heterocyclic group, and R$^b$ is hydrogen or $C_1$-$C_3$alkyl.

In some embodiments, $R^1$ is —($C_1$-$C_3$alkyl)NR$^a$R$^b$, wherein R$^a$ is selected from the group consisting of hydrogen, $C_1$-$C_3$ alkyl, and a 5-membered heterocyclic group, and R$^b$ is hydrogen or $C_1$-$C_3$alkyl.

In some embodiments, $R^1$ is a $C_4$-$C_6$ membered heterocyclic group, optionally substituted with one or more of a $C_1$-$C_6$ alkyl and oxo.

In some embodiments, $R^1$ is a 4-membered heterocyclic group or a 6-membered heterocyclic group, wherein the 4-membered heterocyclic group or the 6-membered heterocyclic group is optionally substituted with a $C_1$-$C_3$ alkyl.

In some embodiments, $R^1$ is selected form the group consisting of hydrogen, methyl, ethyl, —CH$_2$CN,

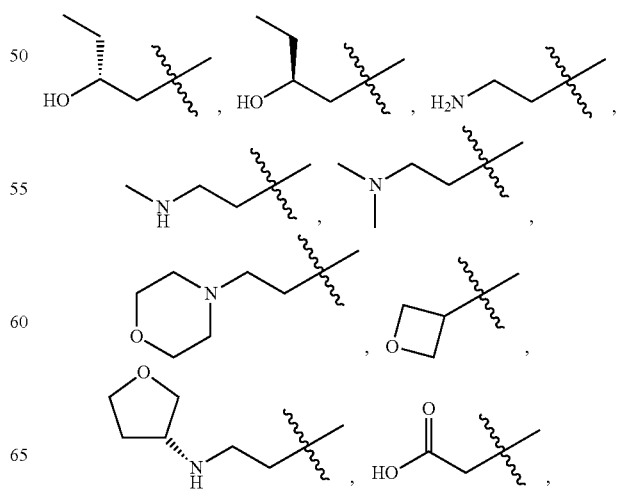

-continued
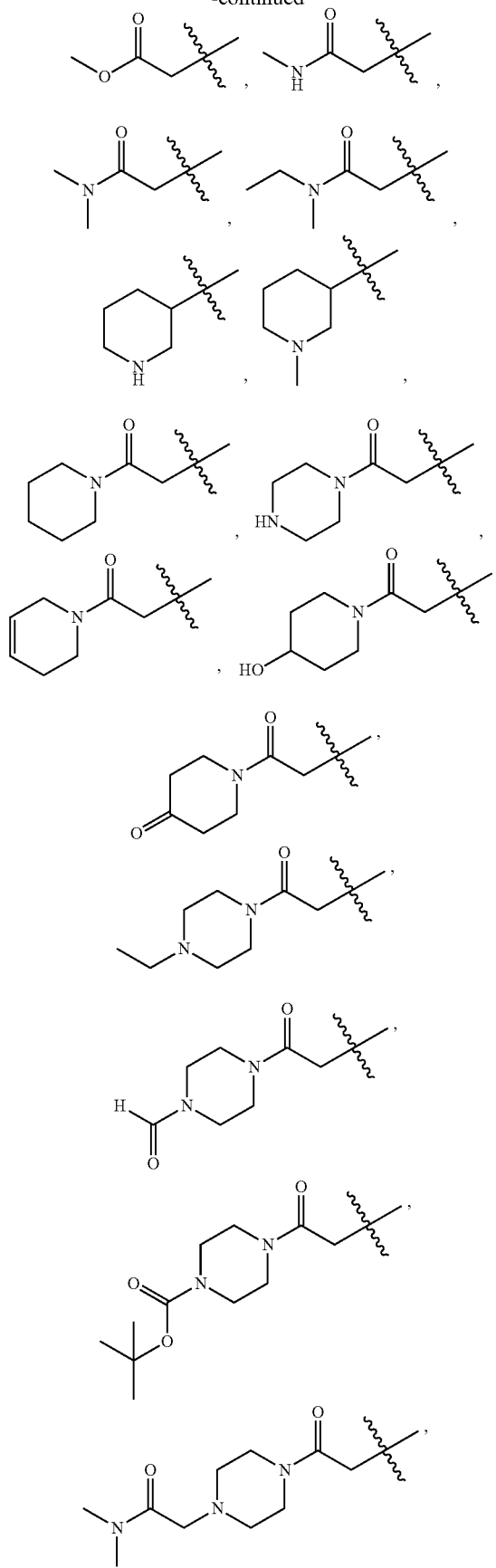
-continued
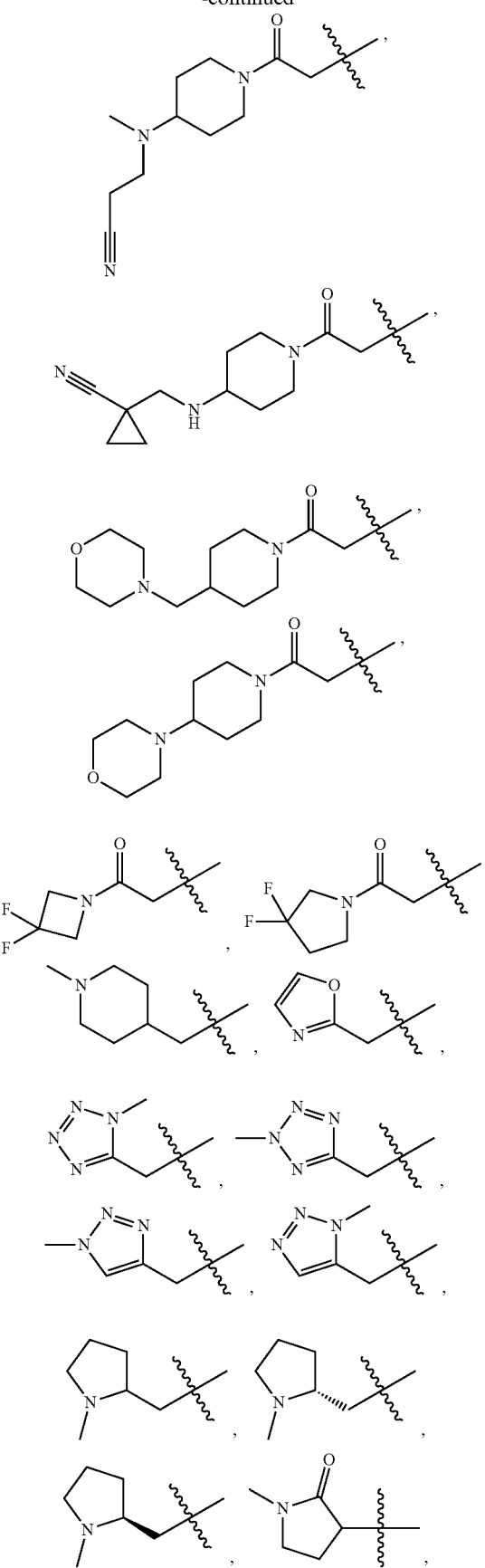

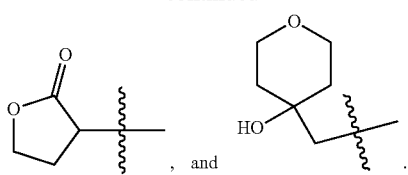, and .

In some embodiments, R² is —C(R³)₃, wherein R³ is independently selected from the group consisting of hydrogen and halogen.

In some embodiments, R² is —C(R³)₃, and each R³ is independently selected from the group consisting of hydrogen and fluoro.

In some embodiments, R² is —CH₃ or —CHF₂.

In some embodiments, the compound of Formula (IA) has the following structure:

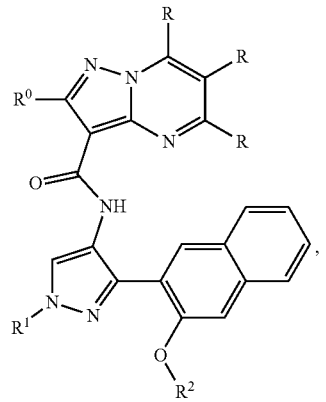

(IB)

or a pharmaceutically acceptable salt thereof;
wherein:
each of R⁰ and R are hydrogen;
R¹ is selected from hydrogen, methyl, ethyl,

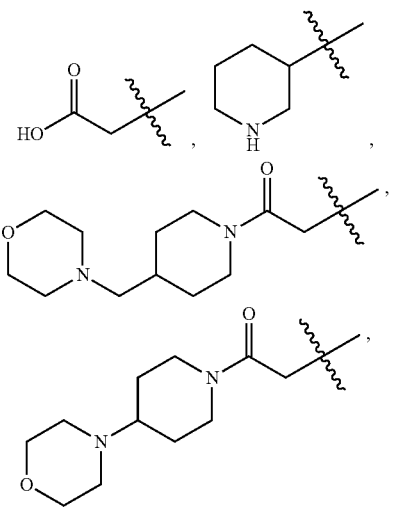

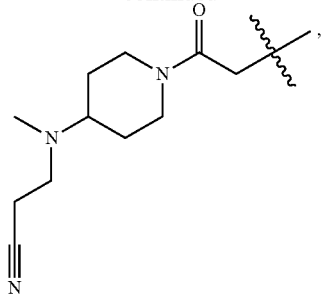,

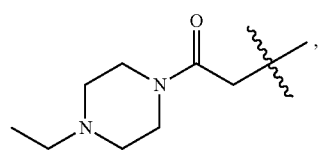,

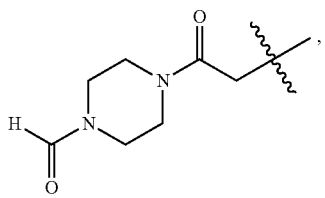,

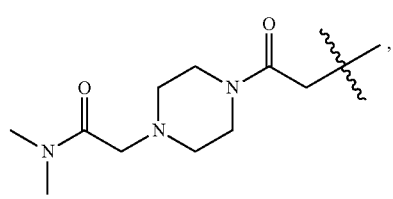,

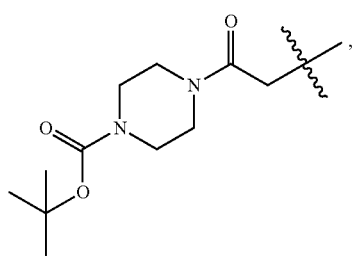,

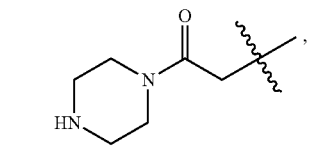, and ;

R² is —CH₃ or —CHF₂.

In some embodiments, the compound of Formula (IA) has the following structure:

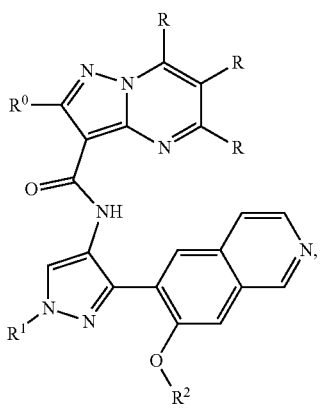

(IC)

or a pharmaceutically acceptable salt thereof;
wherein:
each of $R^0$ and R are hydrogen;
$R^1$ is hydrogen; and
$R^2$ is —$CH_3$.
In some embodiments, the compound of Formula (IA) has the following structure:

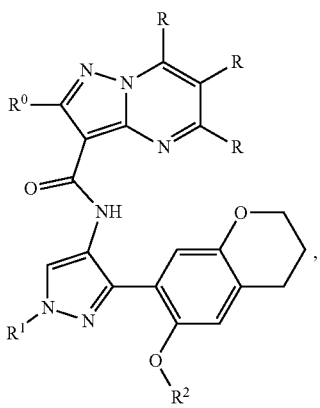

(ID)

or a pharmaceutically acceptable salt thereof;
wherein:
each of $R^0$ and R are hydrogen;
$R^1$ is hydrogen; and
$R^2$ is —$CHF_2$.
In some embodiments, the compound of Formula (IA) has the following structure:

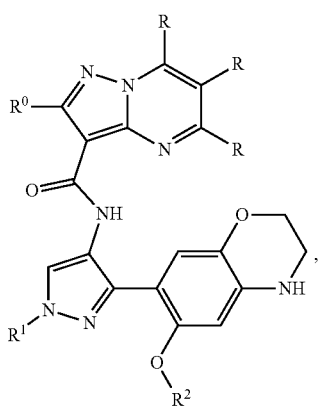

(IE)

or a pharmaceutically acceptable salt thereof;

wherein:
each of $R^0$ and R are hydrogen;
$R^1$ is selected from hydrogen, methyl, —$CH_2CN$,

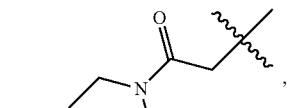

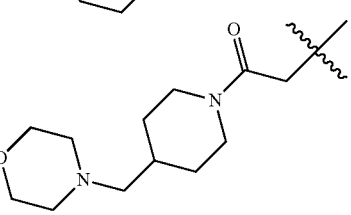

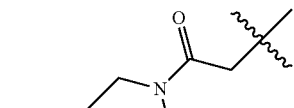

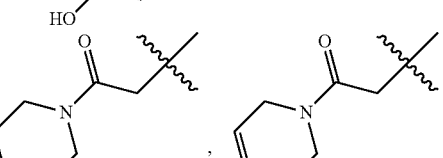

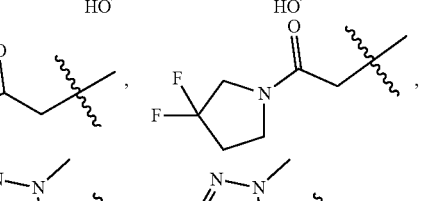

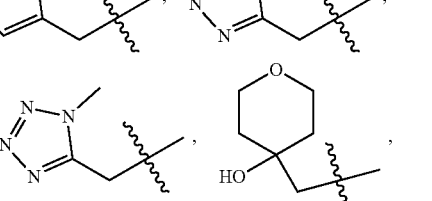

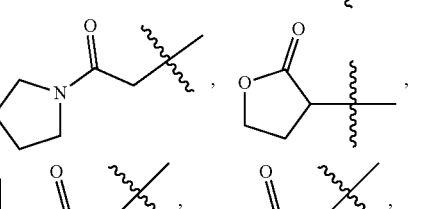

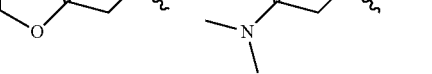

-continued

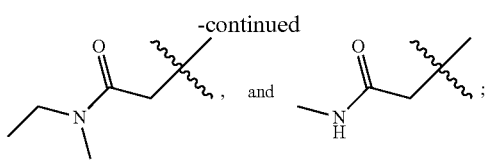

R² is —CHF₂.

In some embodiments, the compound of Formula (IA) has the following structure:

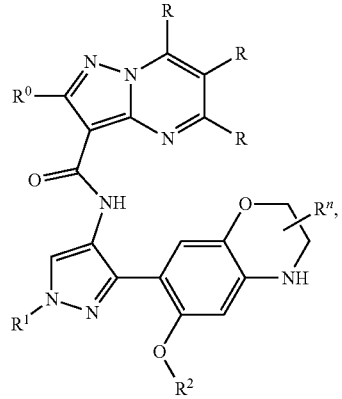

(IF)

or a pharmaceutically acceptable salt thereof;
wherein:
each of R⁰ and R are hydrogen;
R¹ is hydrogen or methyl;
R² is —CHF₂; and
R" is one or more selected from =O, methyl, and

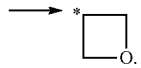

In some embodiments, the compound of Formula (IA) has the following structure:

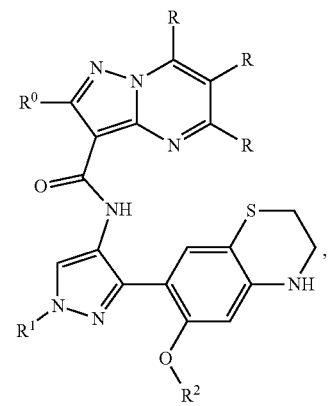

(IG)

or a pharmaceutically acceptable salt thereof;
wherein:
each of R⁰ and R are hydrogen;
R¹ is selected from hydrogen, methyl, —CH₂CN,

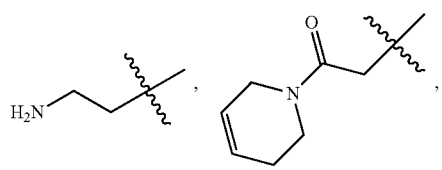

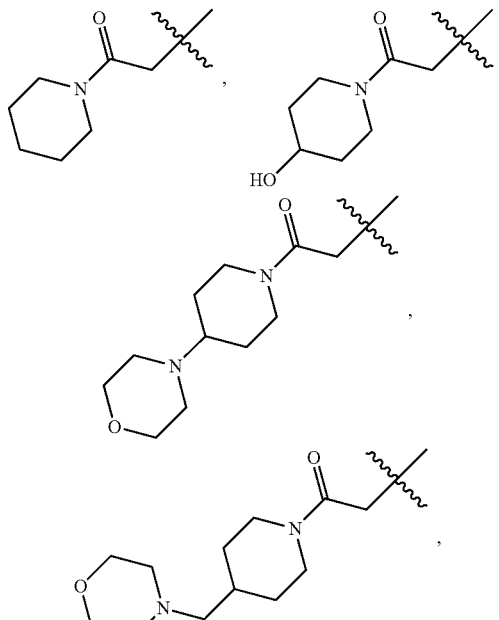

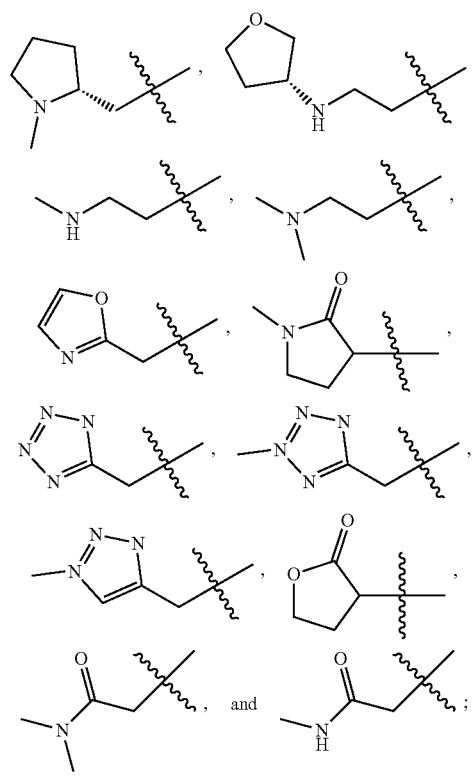

and

R² is —CHF₂.

In some embodiments, the compound of Formula (IA) has the following structure:

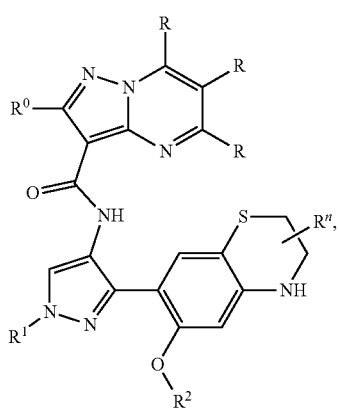
(IH)

or a pharmaceutically acceptable salt thereof;
wherein:
each of $R^0$ and R are hydrogen;
$R^1$ is selected from hydrogen, methyl,

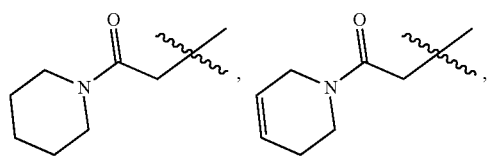

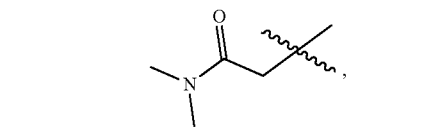

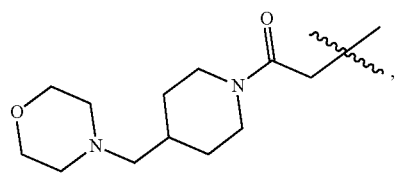

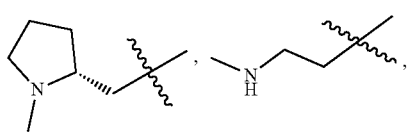

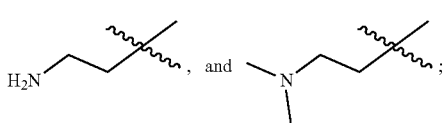

$R^2$ is —$CHF_2$; and
$R''$ is one or more groups selected from =O, methyl, and —$CH_2NH_2$.

In some embodiments, the compound of Formula (IA) has the following structure:

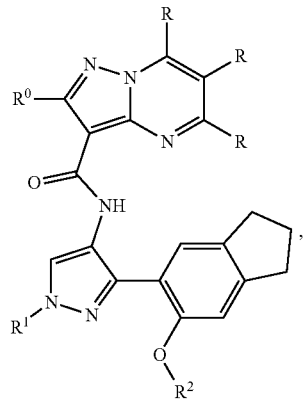
(II)

or a pharmaceutically acceptable salt thereof;
wherein:
each of $R^0$ and R are hydrogen;
$R^1$ is hydrogen; and
$R^2$ is —$CH_3$ or —$CHF_2$.

In some embodiments, the compound of Formula (IA) has the following structure:

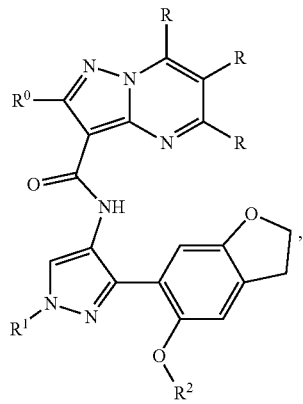
(IJ)

or a pharmaceutically acceptable salt thereof;
wherein:
each of $R^0$ and R are hydrogen;

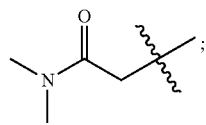 [SMILES: *CC(=O)N(C)C]

$R^1$ is hydrogen or; and
$R^2$ is —$CHF_2$.

In some embodiments, the compound of Formula (IA) has the following structure:

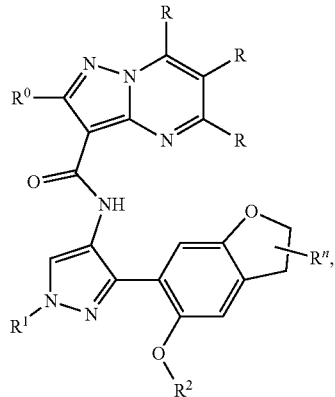
(IK)

or a pharmaceutically acceptable salt thereof;
wherein:
each of $R^0$ and R are hydrogen;
$R^1$ is hydrogen;
$R^2$ is $CHF_2$; and
$R^n$ is —$CH_2OH$.

In some embodiments, the compound of Formula (IA) has the following structure:

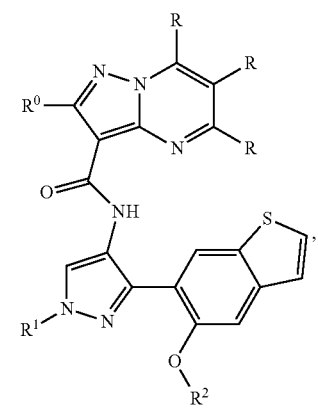
(IL)

or a pharmaceutically acceptable salt thereof;
wherein:
each of $R^0$ and R are hydrogen;
$R^1$ is selected from hydrogen,

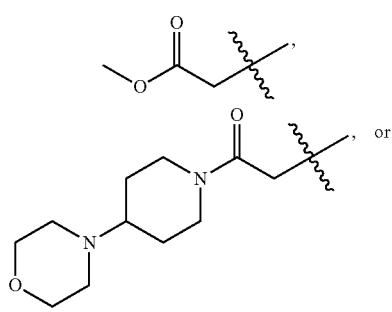

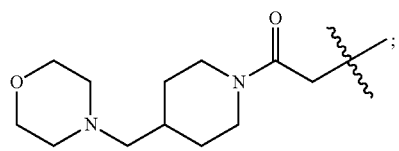

$R^2$ is —$CH_3$ or —$CHF_2$.

In some embodiments, the compound of Formula (IA) has the following structure:

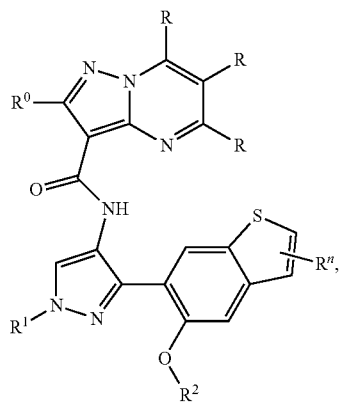
(IM)

or a pharmaceutically acceptable salt thereof;
wherein:
each of $R^0$ and R are hydrogen;
$R^1$ is selected from hydrogen, methyl,

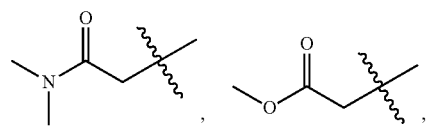

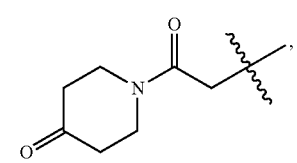

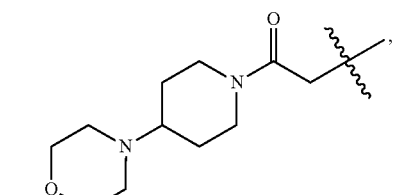

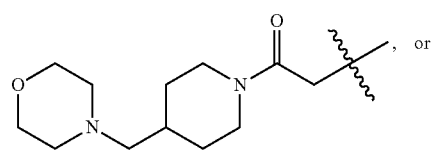

-continued

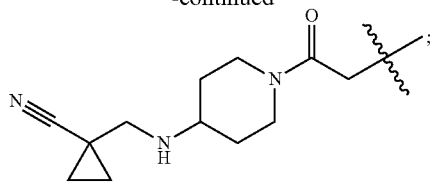

R² is —CH₃ or —CHF₂; and
R″ is selected from methyl, —CN,

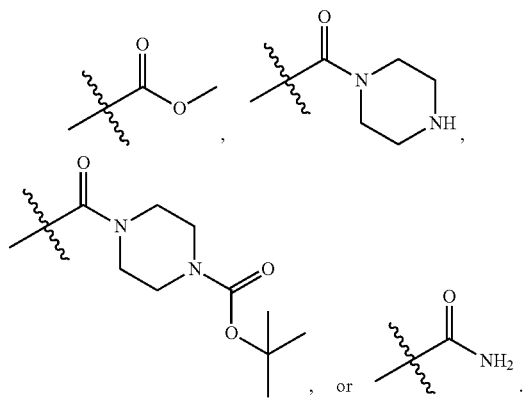

In some embodiments, the compound of Formula (IA) has the following structure:

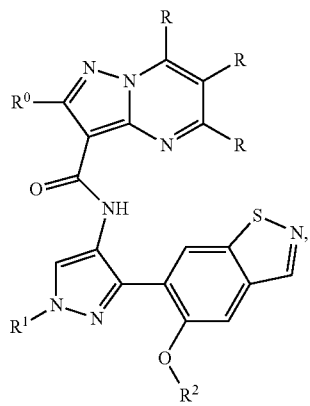

(IN)

or a pharmaceutically acceptable salt thereof;
wherein:
each of R⁰ and R are hydrogen;
R¹ is hydrogen or

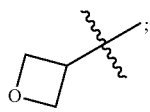

and
R² is —CH₃ or —CHF₂.

In some embodiments, the compound of Formula (IA) has the following structure:

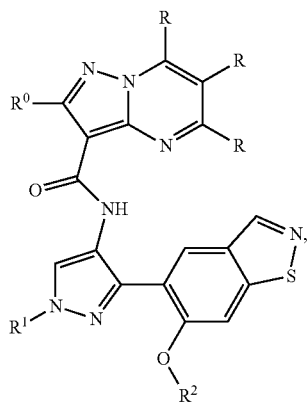

(IO)

or a pharmaceutically acceptable salt thereof;
wherein:
each of R⁰ and R are hydrogen;
R¹ is hydrogen or

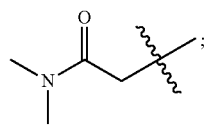

and
R² is —CH₃ or —CHF₂.

In some embodiments, the compound of Formula (IA) has the following structure:

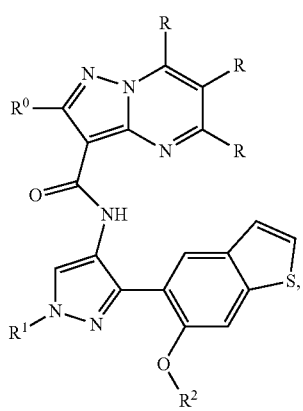

(IP)

or a pharmaceutically acceptable salt thereof;
wherein:
each of R⁰ and R are hydrogen;
R¹ is hydrogen; and
R² is —CH₃.

In some embodiments, the compound of Formula (IA) has the following structure:

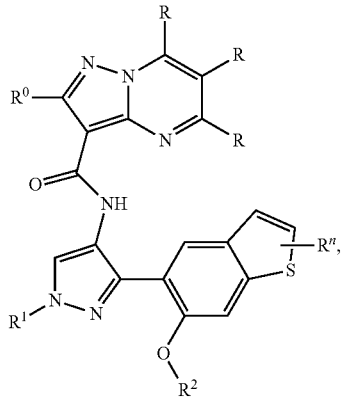
(IQ)

or a pharmaceutically acceptable salt thereof;
wherein:
each of R⁰ and R are hydrogen;
$R^1$ is hydrogen;
$R^2$ is —CH₃; and
R" is selected from —CN,

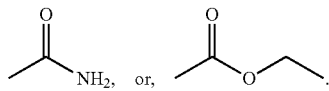

In some embodiments, the compound of Formula (IA) has the following structure:

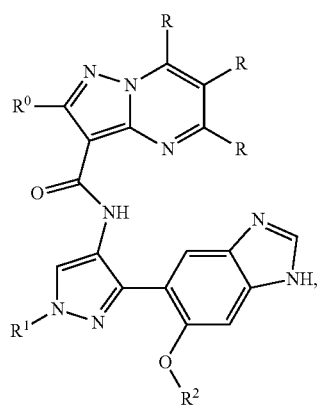
(IR)

or a pharmaceutically acceptable salt thereof;
wherein:
each of R⁰ and R are hydrogen;
$R^1$ is hydrogen; and
$R^2$ is —CH₃.

In some embodiments, the compound of Formula (IA) has the following structure:

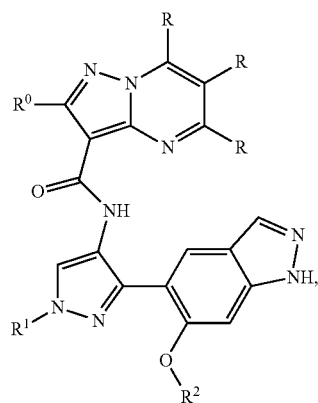
(IS)

or a pharmaceutically acceptable salt thereof;
wherein:
each of R⁰ and R are hydrogen;
$R^1$ is selected from hydrogen,

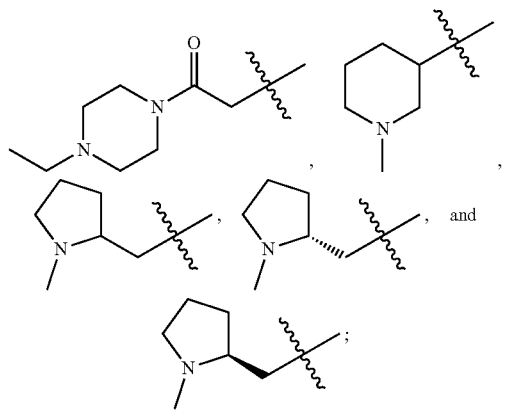

and
$R^2$ is —CH₃ or —CHF₂.

In some embodiments, the compound of Formula (IA) has the following structure:

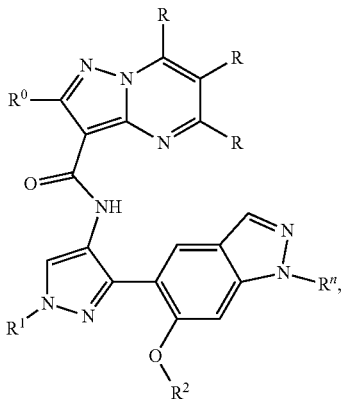
(IT)

or a pharmaceutically acceptable salt thereof;

wherein:
each of R⁰ and R are hydrogen;
R¹ is hydrogen;
R² is —CHF₂; and
R_n is

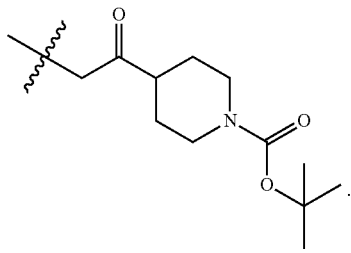 [SMILES: *CC(=O)C1CCN(C(=O)OC(C)(C)C)CC1]

In some embodiments, the compound of Formula (IA) has the following structure:

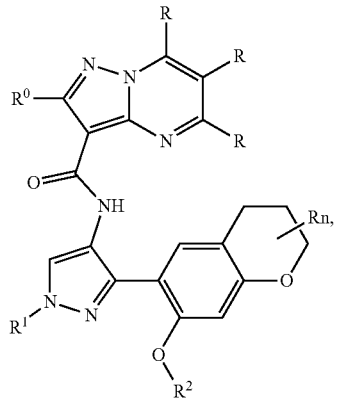
(IU)

or a pharmaceutically acceptable salt thereof;
wherein:
each of R⁰ and R are hydrogen;
R¹ is hydrogen;
R² is —CHF₂; and
R'' is one or more groups selected from =O and methyl.

In some embodiments, the compound of Formula (IA) has the following structure:

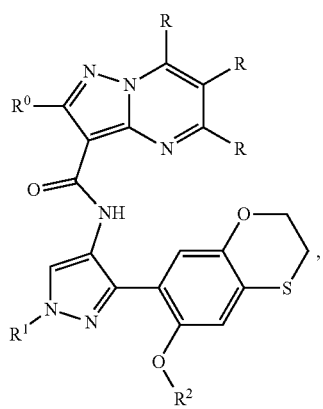
(IV)

or a pharmaceutically acceptable salt thereof;
wherein:
each of R° and R are hydrogen;
R¹ is selected from among hydrogen,

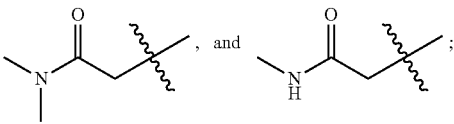

and
R² is —CHF₂.

In some embodiments, the compound of Formula (IA) has the following structure:

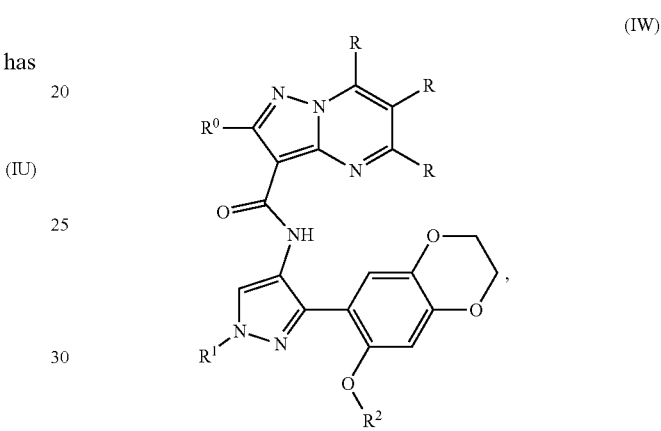
(IW)

or a pharmaceutically acceptable salt thereof;
wherein:
each of R⁰ and R are hydrogen;
R¹ is hydrogen; and
R² is —CHF₂.

In some embodiments, the compound of Formula (IA), or a pharmaceutically acceptable salt thereof, is selected from the group consisting of:
N-[3-[3-(difluoromethoxy)-2-naphthyl]-1H-pyrazol-4-yl] pyrazolo[1,5-a]pyrimidine-3-carboxamide;
2-[3-[3-(difluoromethoxy)-2-naphthyl]-4-(pyrazolo[1,5-a] pyrimidine-3-carbonylamino)pyrazol-1-yl]acetic acid;
N-[3-[3-(difluoromethoxy)-2-naphthyl]-1-[2-[4-(morpholinomethyl)-1-piperidyl]-2-oxo-ethyl]pyrazol-4-yl]pyrazolo[1,5-a]pyrimidine-3-carboxamide;
N-[3-[3-(difluoromethoxy)-2-naphthyl]-1-methyl-pyrazol-4-yl]pyrazolo[1,5-a]pyrimidine-3-carboxamide;
N-[3-[3-(difluoromethoxy)-2-naphthyl]-1-(3-piperidyl) pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[2-oxo-2-(1-piperidyl)ethyl]pyrazol-4-yl] pyrazolo[1,5-a]pyrimidine-3-carboxamide;
methyl 5-(difluoromethoxy)-6-[4-(pyrazolo[1,5-a]pyrimidine-3-carbonylamino)-1H-pyrazol-3-yl]benzothiophene-2-carboxylate;
methyl 2-[3-[5-(difluoromethoxy)benzothiophen-6-yl]-4-(pyrazolo[1,5-a]pyrimidine-3-carbonylamino)pyrazol-1-yl]acetate;
tert-butyl 4-[5-(difluoromethoxy)-6-[4-(pyrazolo[1,5-a]pyrimidine-3-carbonylamino)-1H-pyrazol-3-yl]benzothiophene-2-carbonyl]piperazine-1-carboxylate;
N-[3-[5-(difluoromethoxy)-2-(piperazine-1-carbonyl)benzothiophen-6-yl]-1H-pyrazol-4-yl]pyrazolo[1,5-a]pyrimidine-3-carboxamide;

N-[3-[6-(difluoromethoxy)-3,4-dihydro-2H-1,4-benzoxazin-7-yl]-1H-pyrazol-4-yl]pyrazolo[1,5-a]pyrimidine-3-carboxamide;

N-[3-[6-(difluoromethoxy)-3,4-dihydro-2H-1,4-benzothiazin-7-yl]-1H-pyrazol-4-yl]pyrazolo[1,5-a]pyrimidine-3-carboxamide;

N-[1-(2-aminoethyl)-3-[6-(difluoromethoxy)-3,4-dihydro-2H-1,4-benzothiazin-7-yl]pyrazol-4-yl]pyrazolo[1,5-a]pyrimidine-3-carboxamide;

N-[3-[6-(difluoromethoxy)-3-oxo-4H-1,4-benzothiazin-7-yl]-1H-pyrazol-4-yl]pyrazolo[1,5-a]pyrimidine-3-carboxamide;

N-[3-[5-(difluoromethoxy)-2-(hydroxymethyl)-2,3-dihydrobenzofuran-6-yl]-1H-pyrazol-4-yl]pyrazolo[1,5-a]pyrimidine-3-carboxamide;

N-[3-[5-(difluoromethoxy)-2,3-dihydrobenzofuran-6-yl]-H-pyrazol-4-yl]pyrazolo[1,5-a]pyrimidine-3-carboxamide;

N-[3-[6-(difluoromethoxy)chroman-7-yl]-1H-pyrazol-4-yl]pyrazolo[1,5-a]pyrimidine-3-carboxamide;

tert-butyl 4-[2-[6-(difluoromethoxy)-5-[4-(pyrazolo[1,5-a]pyrimidine-3-carbonylamino)-1H-pyrazol-3-yl]indazol-1-yl]acetyl]piperidine-1-carboxylate;

methyl 2-[3-[2-cyano-5-(difluoromethoxy)benzothiophen-6-yl]-4-(pyrazolo[1,5-a]pyrimidine-3-carbonylamino)pyrazol-1-yl]acetate;

tert-butyl 4-[5-(difluoromethoxy)-6-[1-methyl-4-(pyrazolo[1,5-a]pyrimidine-3-carbonylamino)pyrazol-3-yl]benzothiophene-2-carbonyl]piperazine-1-carboxylate;

N-[5-[6-(difluoromethoxy)-1H-indazol-5-yl]-1H-pyrazol-4-yl]pyrarazolo[1,5-a]pyrimidine-3-carboxamide;

N-[3-(5-methoxy-2-methyl-benzothiophen-6-yl)-1H-pyrazol-4-yl]pyrazolo[1,5-a]pyrimidine-3-carboxamide;

N-[3-(2-carbamoyl-6-methoxy-benzothiophen-5-yl)-1H-pyrazol-4-yl]pyrazolo[1,5-a]pyrimidine-3-carboxamide;

N-[3-(2-cyano-6-methoxy-benzothiophen-5-yl)-H-pyrazol-4-yl]pyrazolo[1,5-a]pyrimidine-3-carboxamide;

N-[3-[5-(difluoromethoxy)-2-methyl-benzothiophen-6-yl]-1H-pyrazol-4-yl]pyrazolo[1,5-a]pyrimidine-3-carboxamide;

N-[3-[6-(difluoromethoxy)indan-5-yl]-1H-pyrazol-4-yl]pyrazolo-[1,5-a]pyrimidine-3-carboxamide;

N-[3-(6-methoxyindan-5-yl)-1H-pyrazol-4-yl]pyrazolo[1,5-a]pyrimidine-3-carboxamide;

N-[3-(3-methoxy-2-naphthyl)-1H-pyrazol-4-yl]pyrazolo[1,5-a]pyrimidine-3-carboxamide;

N-[3-(7-methoxy-6-isoquinolyl)-1H-pyrazol-4-yl]pyrazol[1,5-a]pyrimidine-3-carboxamide;

N-[3-(6-methoxy-1H-indazol-5-yl)-1H-pyrazol-4-yl]pyrazolo[1,5-a]pyrimidine-3-carboxamide;

N-[3-(6-methoxy-1H-benzimidazol-5-yl)-1H-pyrazol-4-yl]pyrazolo[1,5-a]pyrimidine-3-carboxamide;

N-[3-(5-methoxy-1,2-benzothiazol-6-yl)-1H-pyrazol-4-yl]pyrazolo[1,5-a]pyrimidine-3-carboxamide;

N-[3-(6-methoxy-1,2-benzothiazol-5-yl)-1H-pyrazol-4-yl]pyrazolo[1,5-a]pyrimidine-3-carboxamide;

N-[5-(6-methoxybenzothiophen-5-yl)-1H-pyrazol-4-yl]pyrazolo[1,5-a]pyrimidine-3-carboxamide;

N-[3-(5-methoxybenzothiophen-6-yl)-1H-pyrazol-4-yl]pyrazolo[1,5-a]pyrimidine-3-carboxamide;

ethyl 6-methoxy-5-[4-(pyrazolo[1,5-a]pyrimidine-3-carbonylamino)-1H-pyrazol-3-yl]benzothiophene-2-carboxylate;

N-[3-[6-(difluoromethoxy)-2-methyl-3,4-dihydro-2H-1,4-benzothiazin-7-yl]-1H-pyrazol-4-yl]pyrazolo[1,5-a]pyrimidine-3-carboxamide;

N-[3-[2-(aminomethyl)-6-(difluoromethoxy)-3,4-dihydro-2H-1,4-benzothiazin-7-yl]-1H-pyrazol-4-yl]pyrazolo[1,5-a]pyrimidine-3-carboxamide;

N-[3-[6-(difluoromethoxy)-2-methyl-3-oxo-4H-1,4-benzothiazin-7-yl]-1H-pyrazol-4-yl]pyrazolo[1,5-a]pyrimidine-3-carboxamide;

N-[3-[6-(difluoromethoxy)-3-oxo-4H-1,4-benzoxazin-7-yl]-1H-pyrazol-4-yl]pyrazolo[1,5-a]pyrimidine-3-carboxamide;

N-[3-[6-(difluoromethoxy)-3-methyl-3,4-dihydro-2H-1,4-benzothiazin-7-yl]-1H-pyrazol-4-yl]pyrazolo[1,5-a]pyrimidine-3-carboxamide;

N-[3-[(3 S)-6-(difluoromethoxy)-3-methyl-3,4-dihydro-2H-1,4-benzoxazin-7-yl]-1H-pyrazol-4-yl]pyrazolo[1,5-a]pyrimidine-3-carboxamide;

N-[3-[(3R)-6-(difluoromethoxy)-3-methyl-3,4-dihydro-2H-1,4-benzoxazin-7-yl]-1H-pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-[2-[4-(morpholinomethyl)-1-piperidyl]-2-oxo-ethyl]pyrazol-4-yl]pyrazolo[1,5-a]pyrimidine-3-carboxamide;

N-[1-[2-[4-(morpholinomethyl)-1-piperidyl]-2-oxo-ethyl]-3-[(2S)-6-(difluoromethoxy)-2-methyl-3,4-dihydro-2H-1,4-benzothiazin-7-yl]pyrazol-4-yl]pyrazolo[1,5-a]pyrimidine-3-carboxamide;

N-[1-[2-[4-(morpholinomethyl)-1-piperidyl]-2-oxo-ethyl]-3-[(2R)-6-(difluoromethoxy)-2-methyl-3,4-dihydro-2H-1,4-benzothiazin-7-yl]pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-[2-(4-morpholino-1-piperidyl)-2-oxo-ethyl]pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-[2-(4-hydroxy-1-piperidyl)-2-oxo-ethyl]pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-[2-(3,6-dihydro-2H-pyridin-1-yl)-2-oxo-ethyl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-(3,6-dihydro-2H-pyridin-1-yl)-2-oxo-ethyl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-oxo-2-(1-piperidyl)ethyl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-(4-hydroxy-1-piperidyl)-2-oxo-ethyl]pyrazol-4-yl]pyrazolo[1,5-a]pyrimidine-3-carboxamide;

N-[3-[6-(difluoromethoxy)-1H-indazol-5-yl]-1-[2-(4-ethylpiperazin-1-yl)-2-oxo-ethyl]pyrazol-4-yl]pyrazolo[1,5-a]pyrimidine-3-carboxamide;

N-[3-(5-methoxybenzothiophen-6-yl)-1-[2-(4-morpholino-1-piperidyl)-2-oxo-ethyl]pyrazol-4-yl]pyrazolo[1,5-a]pyrimidine-3-carboxamide;

N-[3-[2-cyano-5-(difluoromethoxy)benzothiophen-6-yl]-1-[2-(4-morpholino-1-piperidyl)-2-oxo-ethyl]pyrazol-4-yl]pyrazolo[1,5-a]pyrimidine-3-carboxamide;

N-[3-[2-carbamoyl-5-(difluoromethoxy)benzothiophen-6-yl]-1-[2-(4-morpholino-1-piperidyl)-2-oxo-ethyl]pyrazol-4-yl]pyrazolo[1,5-a]pyrimidine-3-carboxamide;

N-[3-[3-(difluoromethoxy)-2-naphthyl]-1-[2-(4-morpholino-1-piperidyl)-2-oxo-ethyl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-(4-morpholino-1-piperidyl)-2-oxo-ethyl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-[4-(morpholinomethyl)-1-piperidyl]-2-oxo-ethyl]pyrazol-4-yl]pyrazolo[1,5-a]pyrimidine-3-carboxamide;

N-[3-[2-cyano-5-(difluoromethoxy)benzothiophen-6-yl]-1-[2-[4-(morpholinomethyl)-1-piperidyl]-2-oxo-ethyl]pyrazol-4-yl]pyrazolo[1,5-a]pyrimidine-3-carboxamide;

N-[3-[2-carbamoyl-5-(difluoromethoxy)benzothiophen-6-yl]-1-[2-[4-(morpholinomethyl)-1-piperidyl]-2-oxo-ethyl]pyrazol-4-yl]pyrazolo[1,5-a]pyrimidine-3-carboxamide;

N-[3-[2-carbamoyl-5-(difluoromethoxy)benzothiophen-6-yl]-1-[2-oxo-2-(4-oxo-1-piperidyl)ethyl]pyrazol-4-yl]pyrazolo[1,5-a]pyrimidine-3-carboxamide;

N-[1-[2-[4-[2-cyanoethyl(methyl)amino]-1-piperidyl]-2-oxo-ethyl]-3-[3-(difluoromethoxy)-2-naphthyl]pyrazol-4-yl]pyrazolo[1,5-a]pyrimidine-3-carboxamide;

N-[3-[2-carbamoyl-5-(difluoromethoxy)benzothiophen-6-yl]-1-[2-[4-[(1-cyanocyclopropyl)methylamino]-1-piperidyl]-2-oxo-ethyl]pyrazol-4-yl]pyrazolo[1,5-a]pyrimidine-3-carboxamide;

N-[3-[5-(difluoromethoxy)benzothiophen-6-yl]-1-[2-[4-(morpholinomethyl)-1-piperidyl]-2-oxo-ethyl]pyrazol-4-yl]pyrazolo[1,5-a]pyrimidine-3-carboxamide;

N-[3-[5-(difluoromethoxy)benzothiophen-6-yl]-1-[2-(4-morpholino-1-piperidyl)-2-oxo-ethyl]pyrazol-4-yl]pyrazolo[1,5-a]pyrimidine-3-carboxamide;

N-[3-[3-(difluoromethoxy)-2-naphthyl]-1-[2-(4-ethylpiperazin-1-yl)-2-oxo-ethyl]pyrazol-4-yl]pyrazolo[1,5-a]pyrimidine-3-carboxamide;

N-[3-[3-(difluoromethoxy)-2-naphthyl]-1-[2-(4-formylpiperazin-1-yl)-2-oxo-ethyl]pyrazol-4-yl]pyrazolo[1,5-a]pyrimidine-3-carboxamide;

N-[3-[3-(difluoromethoxy)-2-naphthyl]-1-[2-[4-[2-(dimethylamino)-2-oxo-ethyl]piperazin-1-yl]-2-oxo-ethyl]pyrazol-4-yl]pyrazolo[1,5-a]pyrimidine-3-carboxamide;

tert-butyl 4-[2-[3-[3-(difluoromethoxy)-2-naphthyl]-4-(pyrazolo[1,5-a]pyrimidine-3-carbonylamino)pyrazol-1-yl]acetyl]piperazine-1-carboxylate;

N-[3-[3-(difluoromethoxy)-2-naphthyl]-1-(2-oxo-2-piperazin-1-yl-ethyl)pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[[(2R)-1-methylpyrrolidin-2-yl]methyl]pyrazol-4-yl]pyrazolo[1,5-a]pyrimidine-3-carboxamide;

N-[3-[6-(difluoromethoxy)-3-oxo-4H-1,4-benzothiazin-7-yl]-1-[[(2R)-1-methylpyrrolidin-2-yl]methyl]pyrazol-4-yl]pyrazolo[1,5-a]pyrimidine-3-carboxamide;

N-[3-[6-(difluoromethoxy)-1H-indazol-5-yl]-1-(1-methyl-3-piperidyl)pyrazol-4-yl]pyrazolo[1,5-a]pyrimidine-3-carboxamide;

N-[3-[6-(difluoromethoxy)-1H-indazol-5-yl]-1-[(1-methylpyrrolidin-2-yl)methyl]pyrazol-4-yl]pyrazolo[1,5-a]pyrimidine-3-carboxamide;

N-[3-[6-(difluoromethoxy)-1H-indazol-5-yl]-1-[[(2S)-1-methylpyrrolidin-2-yl]methyl]pyrazol-4-yl]pyrazolo[1,5-a]pyrimidine-3-carboxamide;

N-[3-[6-(difluoromethoxy)-1H-indazol-5-yl]-1-[[(2R)-1-methylpyrrolidin-2-yl]methyl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-[[(3R)-tetrahydrofuran-3-yl]amino]ethyl]pyrazol-4-yl]pyrazolo[1,5-a]pyrimidine-3-carboxamide;

N-[3-[6-(difluoromethoxy)-3-oxo-4H-1,4-benzothiazin-7-yl]-1-[2-(methylamino)ethyl]pyrazol-4-yl]pyrazolo[1,5-a]pyrimidine-3-carboxamide;

N-[1-(2-aminoethyl)-3-[6-(difluoromethoxy)-2-methyl-3,4-dihydro-2H-1,4-benzothiazin-7-yl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-(methylamino)ethyl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-(dimethylamino)ethyl]pyrazol-4-yl]pyrazolo[1,5-a]pyrimidine-3-carboxamide;

N-[3-[6-(difluoromethoxy)-3-oxo-4H-1,4-benzothiazin-7-yl]-1-[2-(dimethylamino)ethyl]pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-(oxetan-3-yl)pyrazol-4-yl]pyrazolo[1,5-a]pyrimidine-3-carboxamide;

N-[3-[3-(difluoromethoxy)-2-naphthyl]-1-(2-morpholinoethyl)pyrazol-4-yl]pyrazolo[1,5-a]pyrimidine-3-carboxamide;

N-[3-[3-(difluoromethoxy)-2-naphthyl]-1-[(1-methyl-4-piperidyl)methyl]pyrazol-4-yl]pyrazolo[1,5-a]pyrimidine-3-carboxamide;

N-[3-[3-(difluoromethoxy)-2-naphthyl]-1-ethyl-pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-methyl-pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-methyl-pyrazol-4-yl]pyrazolo[1,5-a]pyrimidine-3-carboxamide;

N-[3-[6-(difluoromethoxy)-3-oxo-4H-1,4-benzothiazin-7-yl]-1-methyl-pyrazol-4-yl]pyrazolo[1,5-a]pyrimidine-3-carboxamide;

N-[3-[5-(difluoromethoxy)-2-(piperazine-1-carbonyl)benzothiophen-6-yl]-1-methyl-pyrazol-4-yl]pyrazolo[1,5-a]pyrimidine-3-carboxamide;

methyl 2-[3-[2-carbamoyl-5-(difluoromethoxy)benzothiophen-6-yl]-4-(pyrazolo[1,5-a]pyrimidine-3-carbonylamino)pyrazol-1-yl]acetate;

N-[3-[6-(difluoromethoxy)-2-methyl-3-oxo-4H-1,4-benzothiazin-7-yl]-1-methyl-pyrazol-4-yl]pyrazolo[1,5-a]pyrimidine-3-carboxamide; N-[3-[6-(difluoromethoxy)-3,4-dihydro-2H-1,4-benzothiazin-7-yl]-1-[2-(dimethylamino)-2-oxo-ethyl]pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-[2-(dimethylamino)-2-oxo-ethyl]pyrazol-4-yl]pyrazolo[1,5-a]pyrimidine-3-carboxamide;

N-[3-[6-(difluoromethoxy)-2-methyl-3,4-dihydro-2H-1,4-benzothiazin-7-yl]-1-[2-oxo-2-(1-piperidyl)ethyl]pyrazol-4-yl]pyrazolo[1,5-a]pyrimidine-3-carboxamide;

N-[3-[6-(difluoromethoxy)-2-methyl-3,4-dihydro-2H-1,4-benzothiazin-7-yl]-1-[2-(3,6-dihydro-2H-pyridin-1-yl)-2-oxo-ethyl]pyrazol-4-yl]pyrazolo[1,5-a]pyrimidine-3-carboxamide;

N-[3-[6-(difluoromethoxy)-2-methyl-3,4-dihydro-2H-1,4-benzothiazin-7-yl]-1-[2-(dimethylamino)-2-oxo-ethyl]pyrazol-4-yl]pyrazolo[1,5-a]pyrimidine-3-carboxamide;

N-[3-[6-(difluoromethoxy)-3-methyl-3,4-dihydro-2H-1,4-benzothiazin-7-yl]-1-[2-oxo-2-(1-piperidyl)ethyl]pyrazol-4-yl]pyrazolo[1,5-a]pyrimidine-3-carboxamide;

N-[3-[5-(difluoromethoxy)-2,3-dihydrobenzofuran-6-yl]-1-[2-(dimethylamino)-2-oxo-ethyl]pyrazol-4-yl]pyrazolo[1,5-a]pyrimidine-3-carboxamide;

N-[3-[6-(difluoromethoxy)-2,2-dimethyl-3,4-dihydro-1,4-benzothiazin-7-yl]-1H-pyrazol-4-yl]pyrazolo[1,5-a]pyrimidine-3-carboxamide;
N-[3-[6-(difluoromethoxy)-3-methyl-3,4-dihydro-2H-1,4-benzothiazin-7-yl]-1-[2-(3,6-dihydro-2H-pyridin-1-yl)-2-oxo-ethyl]pyrazol-4-yl]pyrazolo[1,5-a]pyrimidine-3-carboxamide;
N-[3-[6-(difluoromethoxy)-3-methyl-3,4-dihydro-2H-1,4-benzothiazin-7-yl]-1-[2-(dimethylamino)-2-oxo-ethyl]pyrazol-4-yl]pyrazolo[1,5-a]pyrimidine-3-carboxamide;
N-[3-[7-(difluoromethoxy)-3,3-dimethyl-4-oxo-chroman-6-yl]-1H-pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[2-(methylamino)-2-oxo-ethyl]pyrazol-4-yl]pyrazolo[1,5-a]pyrimidine-3-carboxamide;
N-[3-[6-(difluoromethoxy)-3,4-dihydro-2H-1,4-benzothiazin-7-yl]-1-[2-(methylamino)-2-oxo-ethyl]pyrazol-4-yl]pyrazolo[1,5-a]pyrimidine-3-carboxamide;
N-[3-[(2R)-6-(difluoromethoxy)-2-methyl-3,4-dihydro-2H-1,4-benzoxazin-7-yl]-1H-pyrazol-4-yl]pyrazolo[1,5-a]pyrimidine-3-carboxamide;
N-[3-[6-(difluoromethoxy)-2,3-dihydro-1,4-benzoxathiin-7-yl]-1-[2-(methylamino)-2-oxo-ethyl]pyrazol-4-yl]pyrazolo[1,5-a]pyrimidine-3-carboxamide;
N-[3-[6-(difluoromethoxy)-2,3-dihydro-1,4-benzoxathiin-7-yl]-1-[2-(dimethylamino)-2-oxo-ethyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[(2R)-2-hydroxybutyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[(2S)-2-hydroxybutyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-(oxazol-2-ylmethyl)pyrazol-4-yl]pyrazolo[1,5-a]pyrimidine-3-carboxamide;
N-[3-[6-(difluoromethoxy)-3,4-dihydro-2H-1,4-benzothiazin-7-yl]-1-(oxazol-2-ylmethyl)pyrazol-4-yl]pyrazolo[1,5-a]pyrimidine-3-carboxamide;
N-[3-[6-(difluoromethoxy)-3,4-dihydro-2H-1,4-benzothiazin-7-yl]-1-(1-methyl-2-oxo-pyrrolidin-3-yl)pyrazol-4-yl]pyrazolo[1,5-a]pyrimidine-3-carboxamide;
N-[3-[6-(difluoromethoxy)-3,4-dihydro-2H-1,4-benzothiazin-7-yl]-1-[(1-methyltetrazol-5-yl)methyl]pyrazol-4-yl]pyrazolo[1,5-a]pyrimidine-3-carboxamide;
N-[3-[6-(difluoromethoxy)-3,4-dihydro-2H-1,4-benzothiazin-7-yl]-1-[(2-methyltetrazol-5-yl)methyl]pyrazol-4-yl]pyrazolo[1,5-a]pyrimidine-3-carboxamide;
N-[3-[5-(difluoromethoxy)-1,2-benzothiazol-6-yl]-1-[2-(dimethylamino)-2-oxo-ethyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[2-[ethyl(methyl)amino]-2-oxo-ethyl]pyrazol-4-yl]pyrazolo[1,5-a]pyrimidine-3-carboxamide;
N-[3-[6-(difluoromethoxy)-3,4-dihydro-2H-1,4-benzothiazin-7-yl]-1-[(1-methyltriazol-4-yl)methyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[2-(3,3-difluoropyrrolidin-1-yl)-2-oxo-ethyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[(3-methyltriazol-4-yl)methyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[(4-hydroxytetrahydropyran-4-yl)methyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[(1-methyltetrazol-5-yl)methyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-[(2-methyltetrazol-5-yl)methyl]pyrazol-4-yl]pyrazolo[1,5-a]pyrimidine-3-carboxamide;
N-[3-[6-(difluoromethoxy)-3-oxo-4H-1,4-benzoxazin-7-yl]-1-methyl-pyrazol-4-yl]pyrazolo[1,5-a]pyrimidine-3-carboxamide;
N-[1-[2-(3,3-difluoroazetidin-1-yl)-2-oxo-ethyl]-3-[6-(difluoromethoxy)-3,4-dihydro-2H-1,4-benzoxazin-7-yl]pyrazol-4-yl]pyrazolo[1,5-a]pyrimidine-3-carboxamide;
N-[3-[5-(difluoromethoxy)-1,2-benzothiazol-6-yl]-1-(oxetan-3-yl)pyrazol-4-yl]pyrazolo[1,5-a]pyrimidine-3-carboxamide;
N-[1-(cyanomethyl)-3-[6-(difluoromethoxy)-3,4-dihydro-2H-1,4-benzothiazin-7-yl]pyrazol-4-yl]pyrazolo[1,5-a]pyrimidine-3-carboxamide;
N-[3-[6-(difluoromethoxy)-3,4-dihydro-2H-1,4-benzothiazin-7-yl]-1-(2-oxotetrahydrofuran-3-yl)pyrazol-4-yl]pyrazolo[1,5-a]pyrimidine-3-carboxamide;
N-[3-[6-(difluoromethoxy)-1,2-benzothiazol-5-yl]-1-[2-(dimethylamino)-2-oxo-ethyl]pyrazol-4-yl]pyrazolo[1,5-a]pyrimidine-3-carboxamide;
N-[1-(cyanomethyl)-3-[6-(difluoromethoxy)-3,4-dihydro-2H-1,4-benzoxazin-7-yl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1-(2-oxotetrahydrofuran-3-yl)pyrazol-4-yl]pyrazolo[1,5-a]pyrimidine-3-carboxamide;
N-[3-[6-(difluoromethoxy)spiro[2,4-dihydro-1,4-benzoxazine-3,3'-oxetane]-7-yl]-1-methyl-pyrazol-4-yl]pyrazolo[1,5-a]pyrimidine-3-carboxamide;
N-[3-[(2S)-6-(difluoromethoxy)-2-methyl-3,4-dihydro-2H-1,4-benzoxazin-7-yl]-1H-pyrazol-4-yl]pyrazolo[1,5-a]pyrimidine-3-carboxamide;
N-[3-[6-(difluoromethoxy)-2,2-dimethyl-3,4-dihydro-1,4-benzoxazin-7-yl]-1-methyl-pyrazol-4-yl]pyrazolo[1,5-a]pyrimidine-3-carboxamide
N-[3-[6-(difluoromethoxy)-2,3-dihydro-1,4-benzodioxin-7-yl]-1H-pyrazol-4-yl]pyrazolo[1,5-a]pyrimidine-3-carboxamide;
N-[3-[6-(difluoromethoxy)-2,3-dihydro-1,4-benzoxathiin-7-yl]-1H-pyrazol-4-yl]pyrazolo[1,5-a]pyrimidine-3-carboxamide;
N-[3-[5-(difluoromethoxy)-1,2-benzothiazol-6-yl]-1H-pyrazol-4-yl]pyrazolo[1,5-a]pyrimidine-3-carboxamide;
N-[3-[6-(difluoromethoxy)-1,2-benzothiazol-5-yl]-1H-pyrazol-4-yl]pyrazolo[1,5-a]pyrimidine-3-carboxamide; and
isopropyl 3-[6-(difluoromethoxy)-3,4-dihydro-2H-1,4-benzoxazin-7-yl]-4-(pyrazolo[1,5-a]pyrimidine-3-carbonylamino)pyrazole-1-carboxylate.

In some embodiments, the compound of Formula (IA), or a pharmaceutically acceptable salt thereof, is selected from the group consisting of:
N-[3-[6-(difluoromethoxy)-3,4-dihydro-2H-1,4-benzoxazin-7-yl]-1-[2-oxo-2-(1-piperidyl)ethyl]pyrazol-4-yl]pyrazolo[1,5-a]pyrimidine-3-carboxamide;
N-[3-[6-(difluoromethoxy)-3,4-dihydro-2H-1,4-benzoxazin-7-yl]-1H-pyrazol-4-yl]pyrazolo[1,5-a]pyrimidine-3-carboxamide;

N-[3-[6-(difluoromethoxy)-3,4-dihydro-2H-1,4-benzothiazin-7-yl]-1H-pyrazol-4-yl]pyrazolo[1,5-a]pyrimidine-3-carboxamide;

N-[3-[6-(difluoromethoxy)-3-oxo-4H-1,4-benzothiazin-7-yl]-1H-pyrazol-4-yl]pyrazolo[1,5-a]pyrimidine-3-carboxamide;

N-[3-(5-methoxy-1,2-benzothiazol-6-yl)-1H-pyrazol-4-yl]pyrazolo[1,5-a]pyrimidine-3-carboxamide;

N-[3-[6-(difluoromethoxy)-2-methyl-3,4-dihydro-2H-1,4-benzothiazin-7-yl]-1H-pyrazol-4-yl]pyrazolo[1,5-a]pyrimidine-3-carboxamide;

N-[3-[6-(difluoromethoxy)-2-methyl-3-oxo-4H-1,4-benzothiazin-7-yl]-1H-pyrazol-4-yl]pyrazolo[1,5-a]pyrimidine-3-carboxamide;

N-[3-[6-(difluoromethoxy)-3-oxo-4H-1,4-benzoxazin-7-yl]-1H-pyrazol-4-yl]pyrazolo[1,5-a]pyrimidine-3-carboxamide;

N-[3-[6-(difluoromethoxy)-3-methyl-3,4-dihydro-2H-1,4-benzothiazin-7-yl]-1H-pyrazol-4-yl]pyrazolo[1,5-a]pyrimidine-3-carboxamide;

N-[3-[(3 S)-6-(difluoromethoxy)-3-methyl-3,4-dihydro-2H-1,4-benzoxazin-7-yl]-1H-pyrazol-4-yl]pyrazolo[1,5-a]pyrimidine-3-carboxamide;

N-[3-[(3R)-6-(difluoromethoxy)-3-methyl-3,4-dihydro-2H-1,4-benzoxazin-7-yl]-1H-pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-[2-(3,6-dihydro-2H-pyridin-1-yl)-2-oxoethyl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-(3,6-dihydro-2H-pyridin-1-yl)-2-oxoethyl]pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-[2-oxo-2-(1-piperidyl)ethyl]pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-(oxetan-3-yl)pyrazol-4-yl]pyrazolo[1,5-a]pyrimidine-3-carboxamide;

N-[3-[6-(difluoromethoxy)-3,4-dihydro-2H-1,4-benzothiazin-7-yl]-1-methyl-pyrazol-4-yl]pyrazolo[1,5-a]pyrimidine-3-carboxamide;

N-[3-[6-(difluoromethoxy)-3,4-dihydro-2H-1,4-benzoxazin-7-yl]-1-methyl-pyrazol-4-yl]pyrazolo[1,5-a]pyrimidine-3-carboxamide; and N-[3-[6-(difluoromethoxy)-3-oxo-4H-1,4-benzothiazin-7-yl]-1-methyl-pyrazol-4-yl]pyrazolo[1,5-a]pyrimidine-3-carboxamide.

Also provided is a compound selected from Examples 1-154 or Table 1, or any combination thereof.

TABLE 1

Representative Compounds According to the Present Invention

| Ex. | Stereochemistry | Structure | Name |
| --- | --- | --- | --- |
| 1 |  | 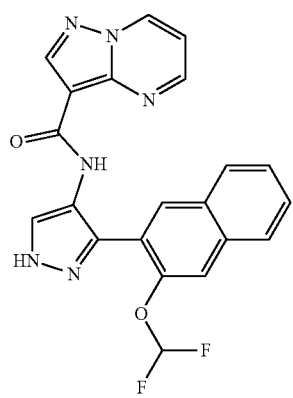 [SMILES: O=C(Nc1c[nH]nc1-c1cc2ccccc2cc1OC(F)F)c1cnn2cccnc12] | N-[3-[3-(difluoromethoxy)-2-naphthyl]-1H-pyrazol-4-yl]pyrazolo[1,5-a]pyrimidine-3-carboxamide |
| 2 |  | 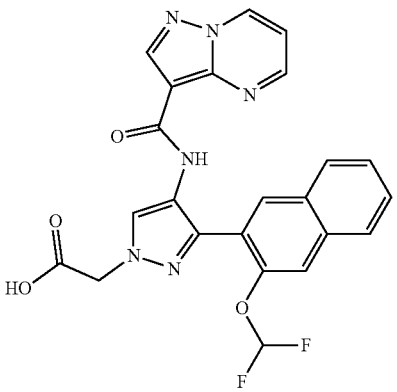 [SMILES: O=C(O)Cn1cc(NC(=O)c2cnn3cccnc23)c(-c2cc3ccccc3cc2OC(F)F)n1] | 2-[3-[3-(difluoromethoxy)-2-naphthyl]-4-(pyrazolo[1,5-a]pyrimidine-3-carbonylamino)pyrazol-1-yl]acetic acid |

TABLE 1-continued

Representative Compounds According to the Present Invention

| Ex. | Stereo-chemistry | Structure | Name |
|---|---|---|---|
| 3 | | 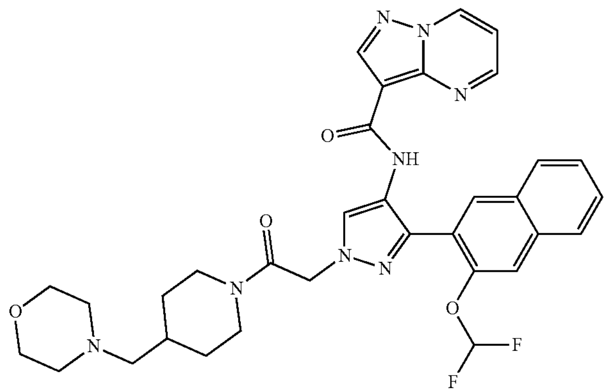 [SMILES: O=C(Nc1cn(CC(=O)N2CCC(CN3CCOCC3)CC2)nc1-c1cc2ccccc2cc1OC(F)F)c1cnn2cccnc12] | N-[3-[3-(difluoromethoxy)-2-naphthyl]-1-[2-[4-(morpholinomethyl)-1-piperidyl]-2-oxo-ethyl]pyrazol-4-yl]pyrazolo[1,5-a]pyrimidine-3-carboxamide |
| 4 | | 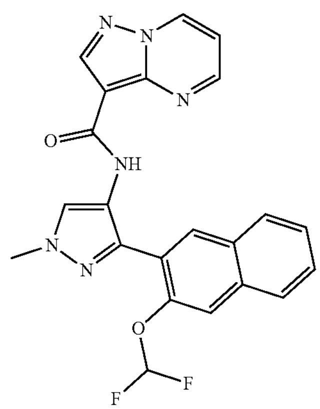 [SMILES: Cn1cc(NC(=O)c2cnn3cccnc23)c(-c2cc3ccccc3cc2OC(F)F)n1] | N-[3-[3-(difluoromethoxy)-2-naphthyl]-1-methyl-pyrazol-4-yl]pyrazolo[1,5-a]pyrimidine-3-carboxamide |
| 5 | racemic | 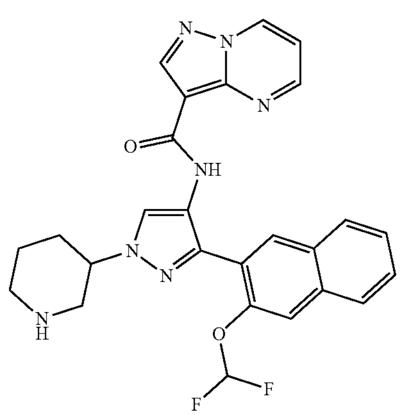 [SMILES: O=C(Nc1cn(C2CCCNC2)nc1-c1cc2ccccc2cc1OC(F)F)c1cnn2cccnc12] | N-[3-[3-(difluoromethoxy)-2-naphthyl]-1-(3-piperidyl)pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 6 | | 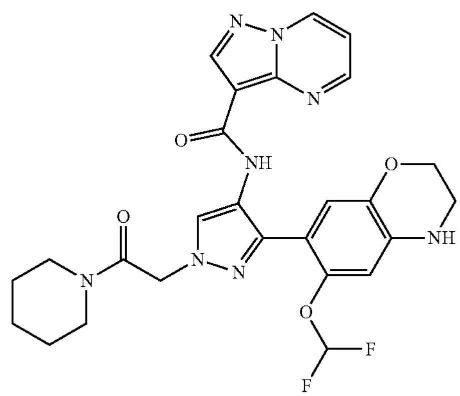 [SMILES: O=C(Nc1cn(CC(=O)N2CCCCC2)nc1-c1cc2c(cc1OC(F)F)NCCO2)c1cnn2cccnc12] | N-[3-[6-(difluoromethoxy)-3,4-dihydro-2H-1,4-benzoxazin-7-yl]-1-[2-oxo-2-(1-piperidyl)ethyl]pyrazol-4-yl]pyrazolo[1,5-a]pyrimidine-3-carboxamide |
| 7 | | 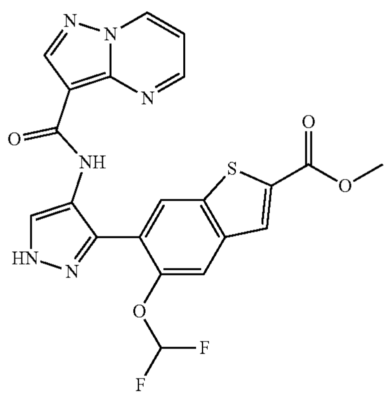 [SMILES: COC(=O)c1cc2cc(OC(F)F)c(-c3n[nH]cc3NC(=O)c3cnn4cccnc34)cc2s1] | methyl 5-(difluoromethoxy)-6-[4-(pyrazolo[1,5-a]pyrimidine-3-carbonylamino)-1H-pyrazol-3-yl]benzothiophene-2-carboxylate |
| 8 | | 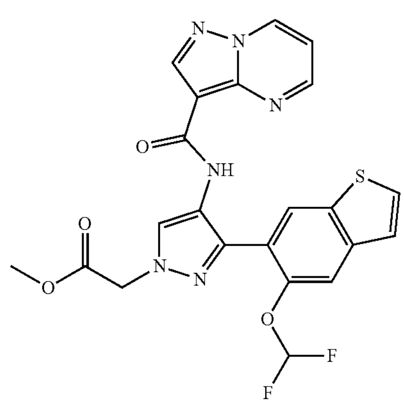 [SMILES: COC(=O)Cn1cc(NC(=O)c2cnn3cccnc23)c(-c2cc3sccc3cc2OC(F)F)n1] | methyl 2-[3-[5-(difluoromethoxy)benzothiophen-6-yl]-4-(pyrazolo[1,5-a]pyrimidine-3-carbonylamino)pyrazol-1-yl]acetate |

TABLE 1-continued

Representative Compounds According to the Present Invention

| Ex. | Stereo-chemistry | Structure | Name |
|---|---|---|---|
| 9 | | 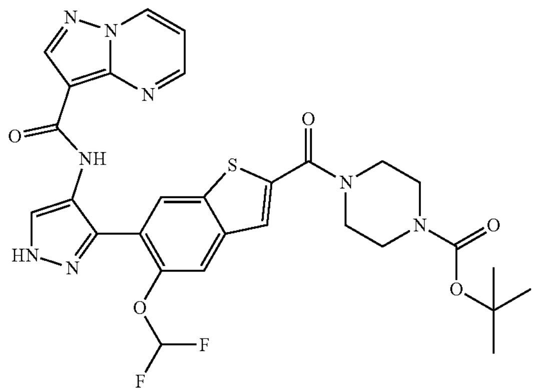 [SMILES: CC(C)(C)OC(=O)N1CCN(C(=O)c2cc3cc(OC(F)F)c(-c4n[nH]cc4NC(=O)c4cnn5cccnc45)cc3s2)CC1] | tert-butyl 4-[5-(difluoromethoxy)-6-[4-(pyrazolo[1,5-a]pyrimidine-3-carbonylamino)-1H-pyrazol-3-yl]benzothiophene-2-carbonyl]piperazine-1-carboxylate |
| 10 | | 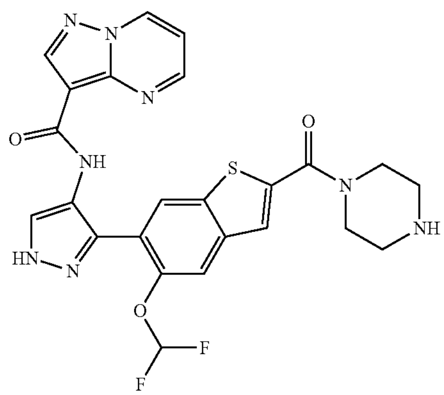 [SMILES: O=C(Nc1c[nH]nc1-c1cc2sc(C(=O)N3CCNCC3)cc2cc1OC(F)F)c1cnn2cccnc12] | N-[3-[5-(difluoromethoxy)-2-(piperazine-1-carbonyl)benzothiophen-6-yl]-1H-pyrazol-4-yl]pyrazolo[1,5-a]pyrimidine-3-carboxamide |
| 11 | | 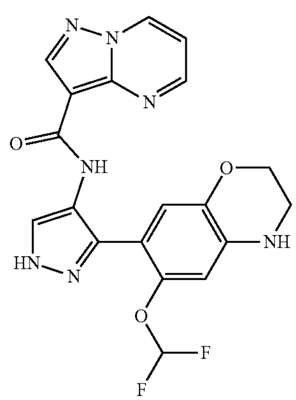 [SMILES: O=C(Nc1c[nH]nc1-c1cc2c(cc1OC(F)F)NCCO2)c1cnn2cccnc12] | N-[3-[6-(difluoromethoxy)-3,4-dihydro-2H-1,4-benzoxazin-7-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 12 | | 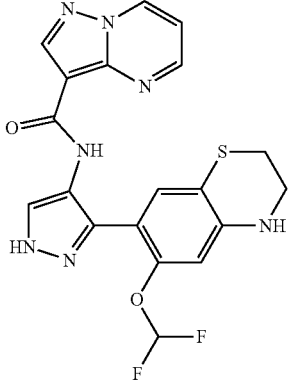 [SMILES: O=C(Nc1c[nH]nc1-c1cc2c(cc1OC(F)F)NCCS2)c1cnn2cccnc12] | N-[3-[6-(difluoromethoxy)-3,4-dihydro-2H-1,4-benzothiazin-7-yl]-1H-pyrazol-4-yl]pyrazolo[1,5-a]pyrimidine-3-carboxamide |
| 13 | | 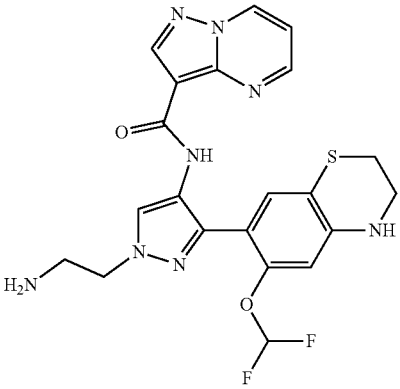 [SMILES: NCCn1cc(NC(=O)c2cnn3cccnc23)c(-c2cc3c(cc2OC(F)F)NCCS3)n1] | N-[1-(2-aminoethyl)-3-[6-(difluoromethoxy)-3,4-dihydro-2H-1,4-benzothiazin-7-yl]pyrazol-4-yl]pyrazolo[1,5-a]pyrimidine-3-carboxamide |
| 14 | | 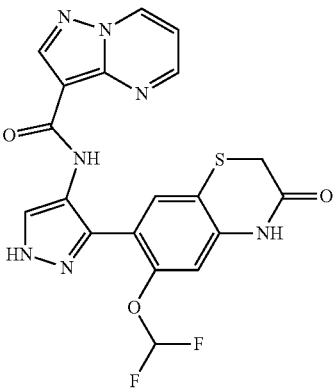 [SMILES: O=C1CSc2cc(-c3n[nH]cc3NC(=O)c3cnn4cccnc34)c(OC(F)F)cc2N1] | N-[3-[6-(difluoromethoxy)-3-oxo-4H-1,4-benzothiazin-7-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 15 | racemic | 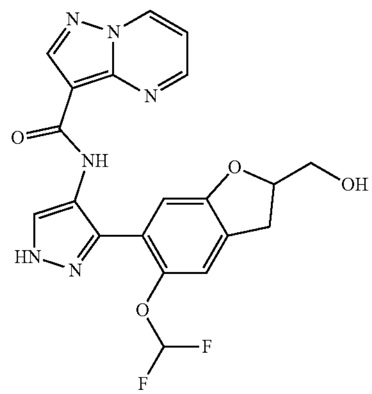 [SMILES: O=C(Nc1c[nH]nc1-c1cc2c(cc1OC(F)F)CC(CO)O2)c1cnn2cccnc12] | N-[3-[5-(difluoromethoxy)-2-(hydroxymethyl)-2,3-dihydrobenzofuran-6-yl]-1H-pyrazol-4-yl]pyrazolo[1,5-a]pyrimidine-3-carboxamide |
| 16 | | 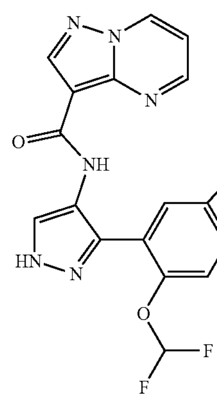 | N-[3-[5-(difluoromethoxy)-2,3-dihydrobenzofuran-6-yl]-1H-pyrazol-4-yl]pyrazolo[1,5-a]pyrimidine-3-carboxamide |
| 17 | | 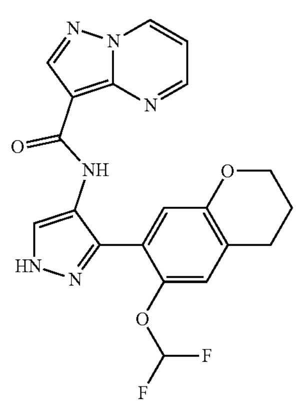 [SMILES: O=C(Nc1c[nH]nc1-c1cc2c(cc1OC(F)F)CCCO2)c1cnn2cccnc12] | N-[3-[6-(difluoromethoxy)chroman-7-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 18 | | 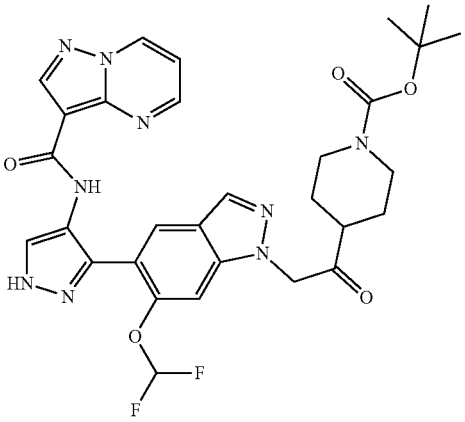 [SMILES: CC(C)(C)OC(=O)N1CCC(C(=O)Cn2ncc3cc(-c4n[nH]cc4NC(=O)c4cnn5cccnc45)c(OC(F)F)cc32)CC1] | tert-butyl 4-[2-[6-(difluoromethoxy)-5-[4-(pyrazolo[1,5-a]pyrimidine-3-carbonylamino)-1H-pyrazol-3-yl]indazol-1-yl]acetyl]piperidine-1-carboxylate |
| 19 | | 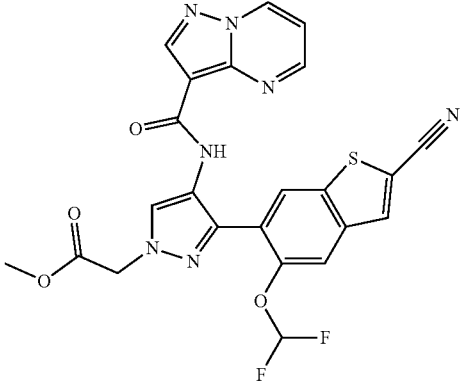 [SMILES: COC(=O)Cn1cc(NC(=O)c2cnn3cccnc23)c(-c2cc3sc(C#N)cc3cc2OC(F)F)n1] | methyl 2-[3-[2-cyano-5-(difluoromethoxy)benzothiophen-6-yl]-4-(pyrazolo[1,5-a]pyrimidine-3-carbonylamino)pyrazol-1-yl]acetate |
| 20 | | 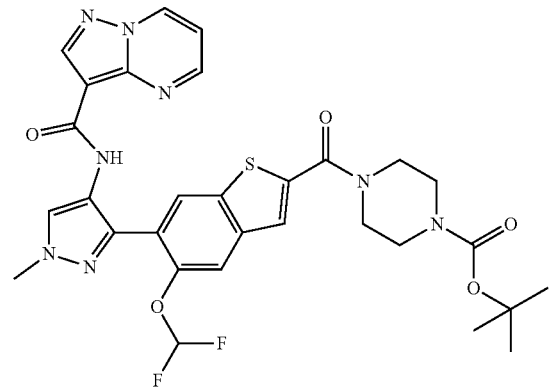 [SMILES: Cn1cc(NC(=O)c2cnn3cccnc23)c(-c2cc3sc(C(=O)N4CCN(C(=O)OC(C)(C)C)CC4)cc3cc2OC(F)F)n1] | tert-butyl 4-[5-(difluoromethoxy)-6-[1-methyl-4-(pyrazolo[1,5-a]pyrimidine-3-carbonylamino)pyrazol-3-yl]benzothiophene-2-carbonyl]piperazine-1-carboxylate |

TABLE 1-continued

Representative Compounds According to the Present Invention

| Ex. | Stereo-chemistry | Structure | Name |
|---|---|---|---|
| 21 | | 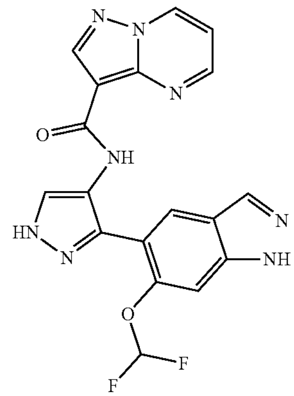 [SMILES: N=Cc1cc(-c2n[nH]cc2NC(=O)c2cnn3cccnc23)c(OC(F)F)cc1N] | N-[5-[6-(difluoromethoxy)-1H-indazol-5-yl]-1H-pyrazol-4-yl]pyrazolo[1,5-a]pyrimidine-3-carboxamide |
| 22 | | 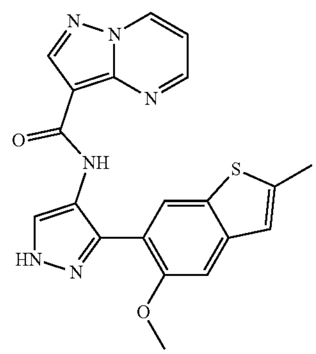 [SMILES: COc1cc2cc(C)sc2cc1-c1n[nH]cc1NC(=O)c1cnn2cccnc12] | N-[3-(5-methoxy-2-methyl-benzothiophen-6-yl)-1H-pyrazol-4-yl]pyrazolo[1,5-a]pyrimidine-3-carboxamide |
| 23 | | 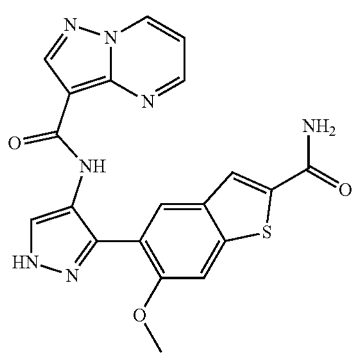 [SMILES: COc1cc2sc(C(N)=O)cc2cc1-c1n[nH]cc1NC(=O)c1cnn2cccnc12] | N-[3-(2-carbamoyl-6-methoxy-benzothiophen-5-yl)-1H-pyrazol-4-yl]pyrazolo[1,5-a]pyrimidine-3-carboxamide |
| 24 | | 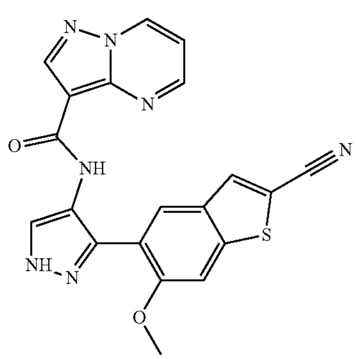 [SMILES: COc1cc2sc(C#N)cc2cc1-c1n[nH]cc1NC(=O)c1cnn2cccnc12] | N-[3-(2-cyano-6-methoxy-benzothiophen-5-yl)-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 25 | | 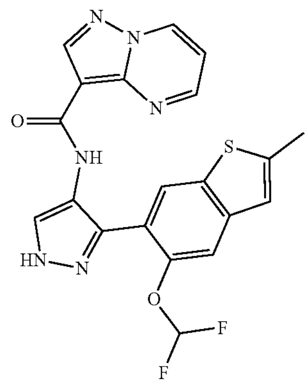 [SMILES: Cc1cc2cc(OC(F)F)c(-c3n[nH]cc3NC(=O)c3cnn4cccnc34)cc2s1] | N-[3-[5-(difluoromethoxy)-2-methyl-benzothiophen-6-yl]-1H-pyrazol-4-yl]pyrazolo[1,5-a]pyrimidine-3-carboxamide |
| 26 | | 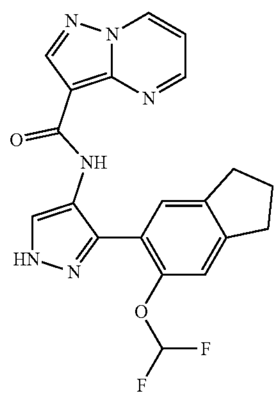 [SMILES: O=C(Nc1c[nH]nc1-c1cc2c(cc1OC(F)F)CCC2)c1cnn2cccnc12] | N-[3-[6-(difluoromethoxy)indan-5-yl]-1H-pyrazol-4-yl]pyrazolo[1,5-a]pyrimidine-3-carboxamide |
| 27 | | 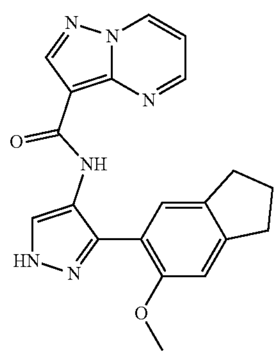 [SMILES: COc1cc2c(cc1-c1n[nH]cc1NC(=O)c1cnn3cccnc13)CCC2] | N-[3-(6-methoxyindan-5-yl)-1H-pyrazol-4-yl]pyrazolo[1,5-a]pyrimidine-3-carboxamide |
| 28 | | 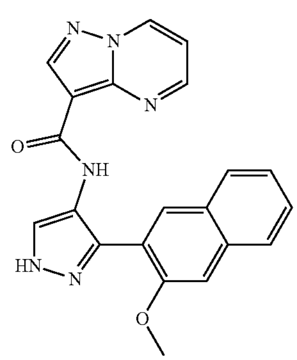 [SMILES: COc1cc2ccccc2cc1-c1n[nH]cc1NC(=O)c1cnn2cccnc12] | N-[3-(3-methoxy-2-naphthyl)-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 29 | | 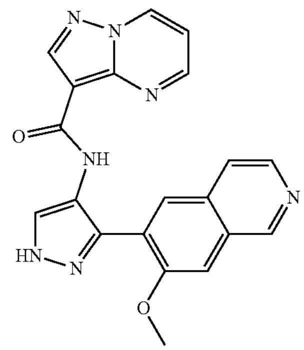 [SMILES: COc1cc2cnccc2cc1-c1n[nH]cc1NC(=O)c1cnn2cccnc12] | N-[3-(7-methoxy-6-isoquinolyl)-1H-pyrazol-4-yl]pyrazolo[1,5-a]pyrimidine-3-carboxamide |
| 30 | | 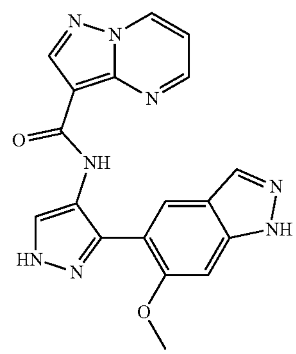 | N-[3-(6-methoxy-1H-indazol-5-yl)-1H-pyrazol-4-yl]pyrazolo[1,5-a]pyrimidine-3-carboxamide |
| 31 | | 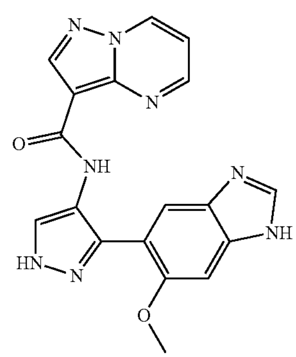 [SMILES: COc1cc2[nH]cnc2cc1-c1n[nH]cc1NC(=O)c1cnn2cccnc12] | N-[3-(6-methoxy-1H-benzimidazol-5-yl)-1H-pyrazol-4-yl]pyrazolo[1,5-a]pyrimidine-3-carboxamide |
| 32 | | 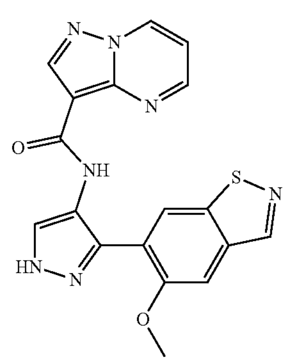 [SMILES: COc1cc2cnsc2cc1-c1n[nH]cc1NC(=O)c1cnn2cccnc12] | N-[3-(5-methoxy-1,2-benzothiazol-6-yl)-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 33 | | 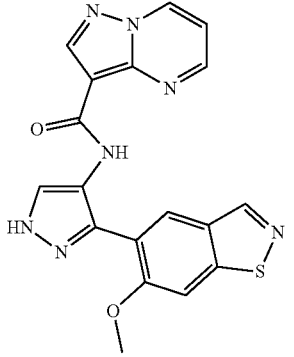 [SMILES: COc1cc2sncc2cc1-c1n[nH]cc1NC(=O)c1cnn2cccnc12] | N-[3-(6-methoxy-1,2-benzothiazol-5-yl)-1H-pyrazol-4-yl]pyrazolo[1,5-a]pyrimidine-3-carboxamide |
| 34 | | 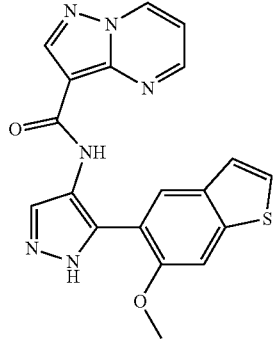 [SMILES: COc1cc2sccc2cc1-c1[nH]ncc1NC(=O)c1cnn2cccnc12] | N-[5-(6-methoxybenzothiophen-5-yl)-1H-pyrazol-4-yl]pyrazolo[1,5-a]pyrimidine-3-carboxamide |
| 35 | | 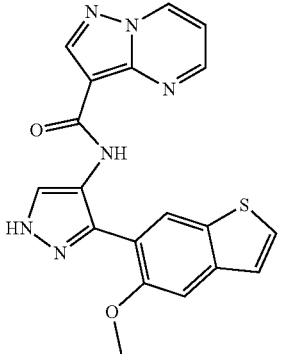 [SMILES: COc1cc2ccsc2cc1-c1n[nH]cc1NC(=O)c1cnn2cccnc12] | N-[3-(5-methoxybenzothiophen-6-yl)-1H-pyrazol-4-yl]pyrazolo[1,5-a]pyrimidine-3-carboxamide |
| 36 | | 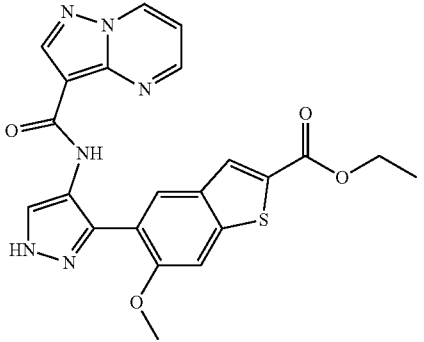 [SMILES: CCOC(=O)c1cc2cc(-c3n[nH]cc3NC(=O)c3cnn4cccnc34)c(OC)cc2s1] | ethyl 6-methoxy-5-[4-(pyrazolo[1,5-a]pyrimidine-3-carbonylamino)-1H-pyrazol-3-yl]benzothiophene-2-carboxylate |

TABLE 1-continued

Representative Compounds According to the Present Invention

| Ex. | Stereochemistry | Structure | Name |
|---|---|---|---|
| 37 | racemic | 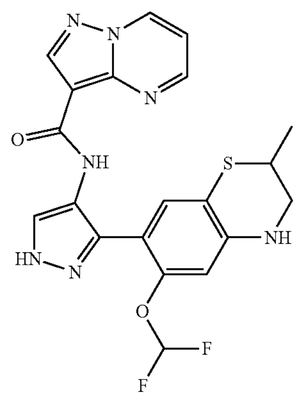 [SMILES: CC1CNc2cc(OC(F)F)c(-c3n[nH]cc3NC(=O)c3cnn4cccnc34)cc2S1] | N-[3-[6-(difluoromethoxy)-2-methyl-3,4-dihydro-2H-1,4-benzothiazin-7-yl]-1H-pyrazol-4-yl]pyrazolo[1,5-a]pyrimidine-3-carboxamide |
| 38 | racemic | 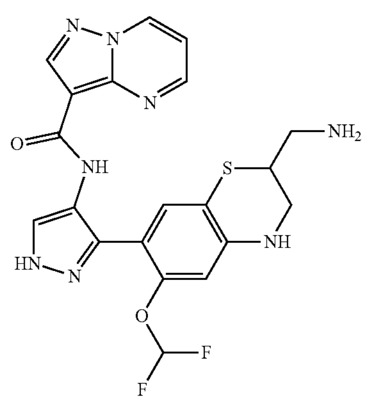 [SMILES: NCC1CNc2cc(OC(F)F)c(-c3n[nH]cc3NC(=O)c3cnn4cccnc34)cc2S1] | N-[3-[2-(aminomethyl)-6-(difluoromethoxy)-3,4-dihydro-2H-1,4-benzothiazin-7-yl]-1H-pyrazol-4-yl]pyrazolo[1,5-a]pyrimidine-3-carboxamide |
| 39 | racemic | 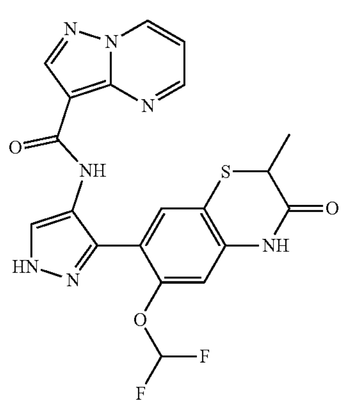 [SMILES: CC1Sc2cc(-c3n[nH]cc3NC(=O)c3cnn4cccnc34)c(OC(F)F)cc2NC1=O] | N-[3-[6-(difluoromethoxy)-2-methyl-3-oxo-4H-1,4-benzothiazin-7-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 40 | | 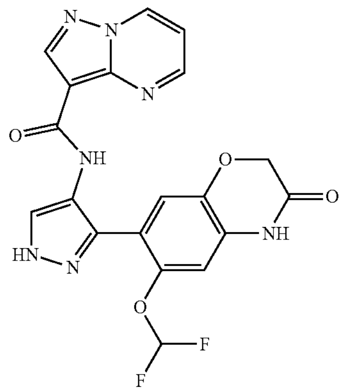 [SMILES: O=C1COc2cc(-c3n[nH]cc3NC(=O)c3cnn4cccnc34)c(OC(F)F)cc2N1] | N-[3-[6-(difluoromethoxy)-3-oxo-4H-1,4-benzoxazin-7-yl]-1H-pyrazol-4-yl]pyrazolo[1,5-a]pyrimidine-3-carboxamide |
| 41 | racemic | 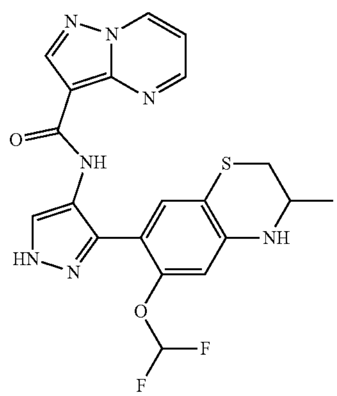 [SMILES: CC1CSc2cc(-c3n[nH]cc3NC(=O)c3cnn4cccnc34)c(OC(F)F)cc2N1] | N-[3-[6-(difluoromethoxy)-3-methyl-3,4-dihydro-2H-1,4-benzothiazin-7-yl]-1H-pyrazol-4-yl]pyrazolo[1,5-a]pyrimidine-3-carboxamide |
| 42 | single known stereoisomer | 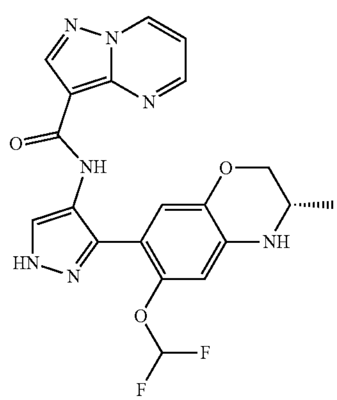 [SMILES: C[C@H]1COc2cc(-c3n[nH]cc3NC(=O)c3cnn4cccnc34)c(OC(F)F)cc2N1] | N-[3-[(3S)-6-(difluoromethoxy)-3-methyl-3,4-dihydro-2H-1,4-benzoxazin-7-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 43 | single known stereoisomer | 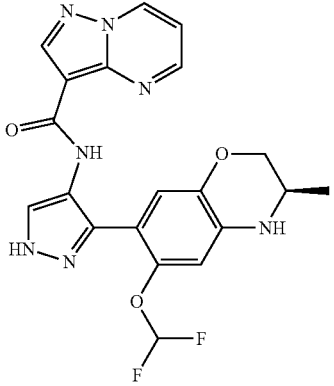 [SMILES: C[C@@H]1COc2cc(-c3n[nH]cc3NC(=O)c3cnn4cccnc34)c(OC(F)F)cc2N1] | N-[3-[(3R)-6-(difluoromethoxy)-3-methyl-3,4-dihydro-2H-1,4-benzoxazin-7-yl]-1H-pyrazol-4-yl]pyrazolo[1,5-a]pyrimidine-3-carboxamide |
| 44 | | 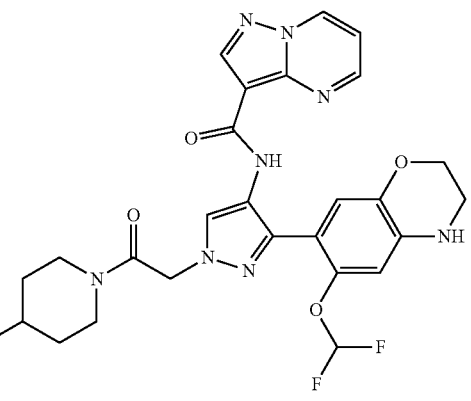 | N-[3-[6-(difluoromethoxy)-3,4-dihydro-2H-1,4-benzoxazin-7-yl]-1-[2-[4-(morpholinomethyl)-1-piperidyl]-2-oxo-ethyl]pyrazol-4-yl]pyrazolo[1,5-a]pyrimidine-3-carboxamide |
| 45 | single known stereoisomer | 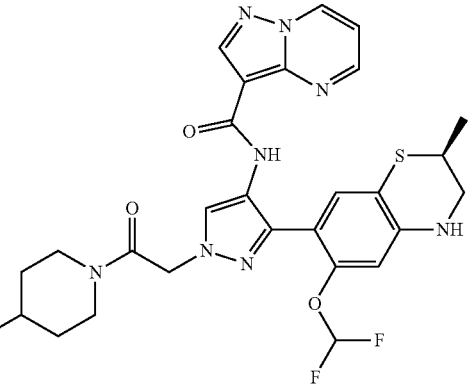 | N-[1-[2-[4-(morpholinomethyl)-1-piperidyl]-2-oxo-ethyl]-3-[(2S)-6-(difluoromethoxy)-2-methyl-3,4-dihydro-2H-1,4-benzothiazin-7-yl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 46 | single known stereoisomer | 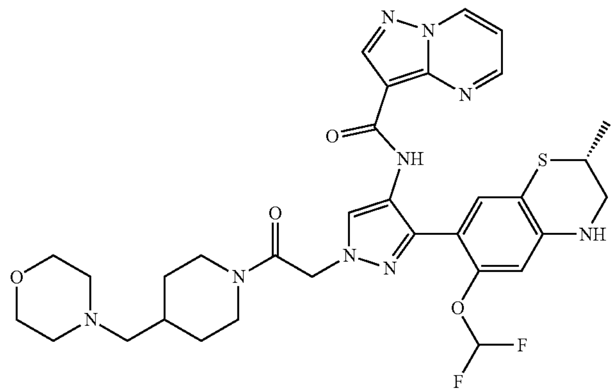 [SMILES: C[C@@H]1CNc2cc(OC(F)F)c(-c3nn(CC(=O)N4CCC(CN5CCOCC5)CC4)cc3NC(=O)c3cnn4cccnc34)cc2S1] | N-[1-[2-[4-(morpholinomethyl)-1-piperidyl]-2-oxo-ethyl]-3-[(2R)-6-(difluoromethoxy)-2-methyl-3,4-dihydro-2H-1,4-benzothiazin-7-yl]pyrazol-4-yl]pyrazolo[1,5-a]pyrimidine-3-carboxamide |
| 47 | | 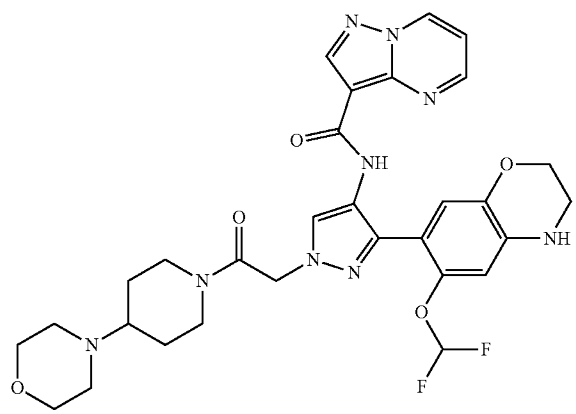 [SMILES: O=C(Nc1cn(CC(=O)N2CCC(N3CCOCC3)CC2)nc1-c1cc2c(cc1OC(F)F)NCCO2)c1cnn2cccnc12] | N-[3-[6-(difluoromethoxy)-3,4-dihydro-2H-1,4-benzoxazin-7-yl]-1-[2-(4-morpholino-1-piperidyl)-2-oxo-ethyl]pyrazol-4-yl]pyrazolo[1,5-a]pyrimidine-3-carboxamide |
| 48 | | 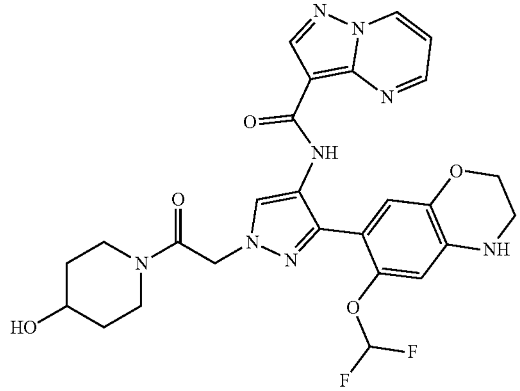 [SMILES: O=C(Nc1cn(CC(=O)N2CCC(O)CC2)nc1-c1cc2c(cc1OC(F)F)NCCO2)c1cnn2cccnc12] | N-[3-[6-(difluoromethoxy)-3,4-dihydro-2H-1,4-benzoxazin-7-yl]-1-[2-(4-hydroxy-1-piperidyl)-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 49 | | 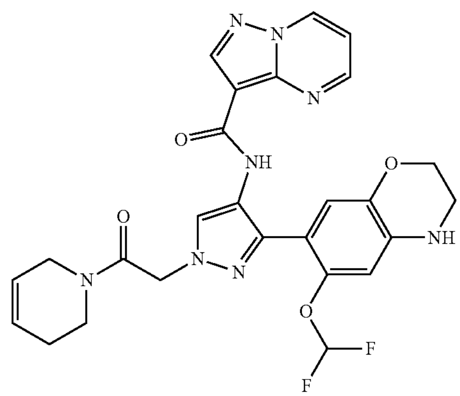 | N-[3-[6-(difluoromethoxy)-3,4-dihydro-2H-1,4-benzoxazin-7-yl]-1-[2-(3,6-dihydro-2H-pyridin-1-yl)-2-oxo-ethyl]pyrazol-4-yl]pyrazolo[1,5-a]pyrimidine-3-carboxamide |
| 50 | | 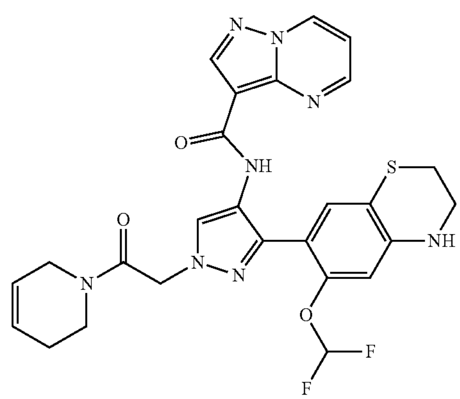 | N-[3-[6-(difluoromethoxy)-3,4-dihydro-2H-1,4-benzothiazin-7-yl]-1-[2-(3,6-dihydro-2H-pyridin-1-yl)-2-oxo-ethyl]pyrazol-4-yl]pyrazolo[1,5-a]pyrimidine-3-carboxamide |
| 51 | | 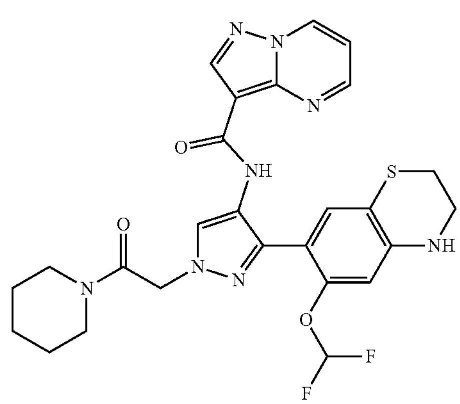 | N-[3-[6-(difluoromethoxy)-3,4-dihydro-2H-1,4-benzothiazin-7-yl]-1-[2-oxo-2-(1-piperidyl)ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 52 | | 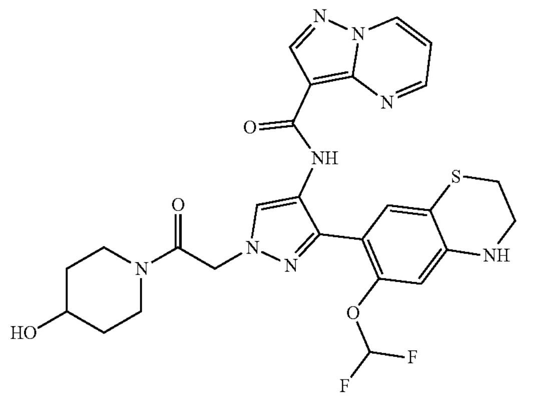 [SMILES: O=C(Nc1cn(CC(=O)N2CCC(O)CC2)nc1-c1cc2c(cc1OC(F)F)NCCS2)c1cnn2cccnc12] | N-[3-[6-(difluoromethoxy)-3,4-dihydro-2H-1,4-benzothiazin-7-yl]-1-[2-(4-hydroxy-1-piperidyl)-2-oxo-ethyl]pyrazol-4-yl]pyrazolo[1,5-a]pyrimidine-3-carboxamide |
| 53 | | 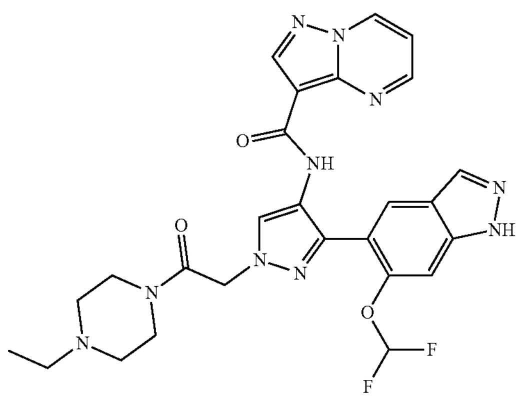 [SMILES: CCN1CCN(C(=O)Cn2cc(NC(=O)c3cnn4cccnc34)c(-c3cc4cn[nH]c4cc3OC(F)F)n2)CC1] | N-[3-[6-(difluoromethoxy)-1H-indazol-5-yl]-1-[2-(4-ethylpiperazin-1-yl)-2-oxo-ethyl]pyrazol-4-yl]pyrazolo[1,5-a]pyrimidine-3-carboxamide |
| 54 | | 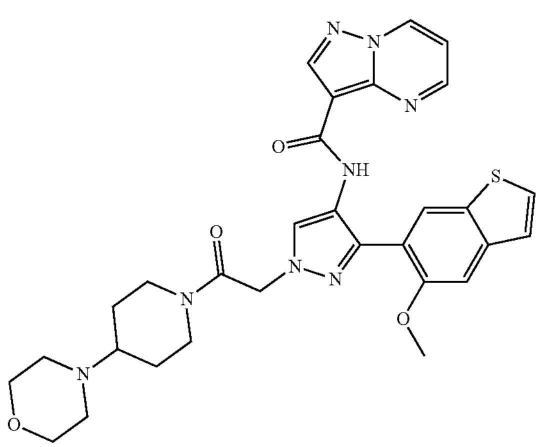 [SMILES: COc1cc2ccsc2cc1-c1nn(CC(=O)N2CCC(N3CCOCC3)CC2)cc1NC(=O)c1cnn2cccnc12] | N-[3-(5-methoxybenzothiophen-6-yl)-1-[2-(4-morpholino-1-piperidyl)-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 55 | | 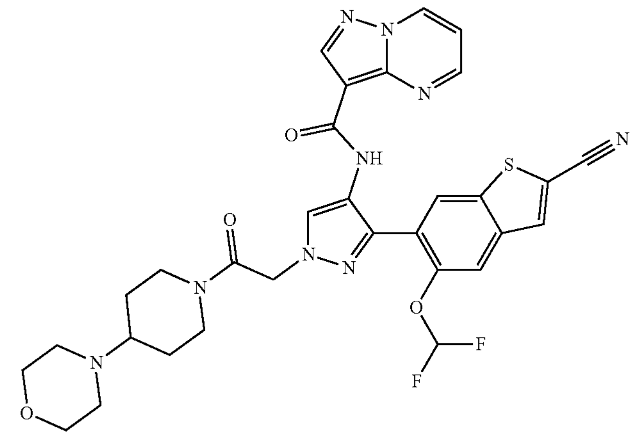 [SMILES: N#Cc1cc2cc(OC(F)F)c(-c3nn(CC(=O)N4CCC(N5CCOCC5)CC4)cc3NC(=O)c3cnn4cccnc34)cc2s1] | N-[3-[2-cyano-5-(difluoromethoxy)benzothiophen-6-yl]-1-[2-(4-morpholino-1-piperidyl)-2-oxo-ethyl]pyrazol-4-yl]pyrazolo[1,5-a]pyrimidine-3-carboxamide |
| 56 | | 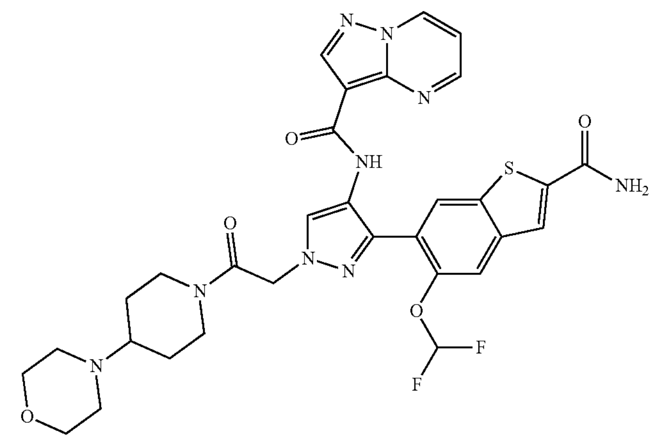 [SMILES: NC(=O)c1cc2cc(OC(F)F)c(-c3nn(CC(=O)N4CCC(N5CCOCC5)CC4)cc3NC(=O)c3cnn4cccnc34)cc2s1] | N-[3-[2-carbamoyl-5-(difluoromethoxy)benzothiophen-6-yl]-1-[2-(4-morpholino-1-piperidyl)-2-oxo-ethyl]pyrazol-4-yl]pyrazolo[1,5-a]pyrimidine-3-carboxamide |
| 57 | | 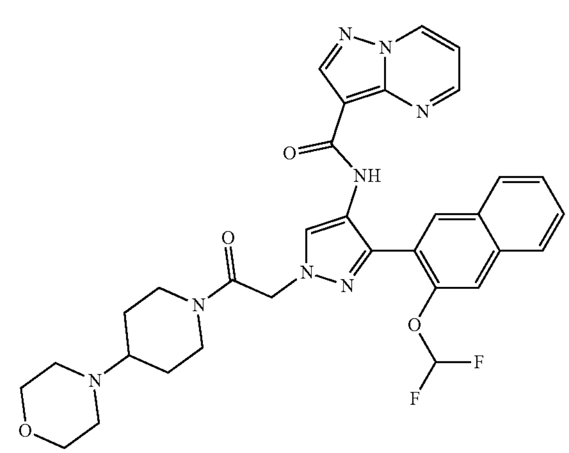 [SMILES: O=C(Nc1cn(CC(=O)N2CCC(N3CCOCC3)CC2)nc1-c1cc2ccccc2cc1OC(F)F)c1cnn2cccnc12] | N-[3-[3-(difluoromethoxy)-2-naphthyl]-1-[2-(4-morpholino-1-piperidyl)-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 58 | | 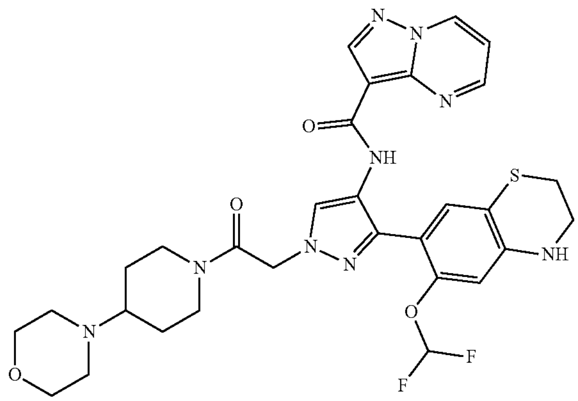 [SMILES: O=C(Nc1cn(CC(=O)N2CCC(N3CCOCC3)CC2)nc1-c1cc2c(cc1OC(F)F)NCCS2)c1cnn2cccnc12] | N-[3-[6-(difluoromethoxy)-3,4-dihydro-2H-1,4-benzothiazin-7-yl]-1-[2-(4-morpholino-1-piperidyl)-2-oxo-ethyl]pyrazol-4-yl]pyrazolo[1,5-a]pyrimidine-3-carboxamide |
| 59 | | 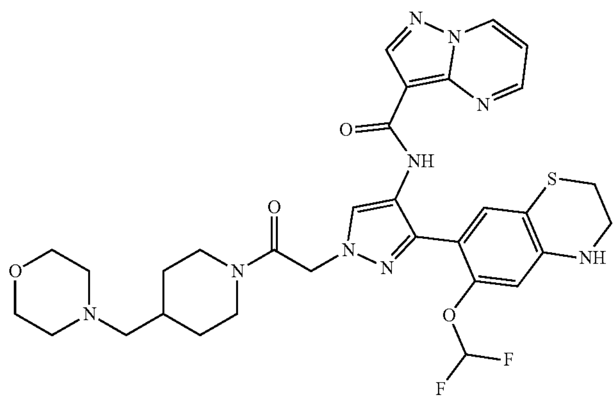 [SMILES: O=C(Nc1cn(CC(=O)N2CCC(CN3CCOCC3)CC2)nc1-c1cc2c(cc1OC(F)F)NCCS2)c1cnn2cccnc12] | N-[3-[6-(difluoromethoxy)-3,4-dihydro-2H-1,4-benzothiazin-7-yl]-1-[2-[4-(morpholinomethyl)-1-piperidyl]-2-oxo-ethyl]pyrazol-4-yl]pyrazolo[1,5-a]pyrimidine-3-carboxamide |
| 60 | | 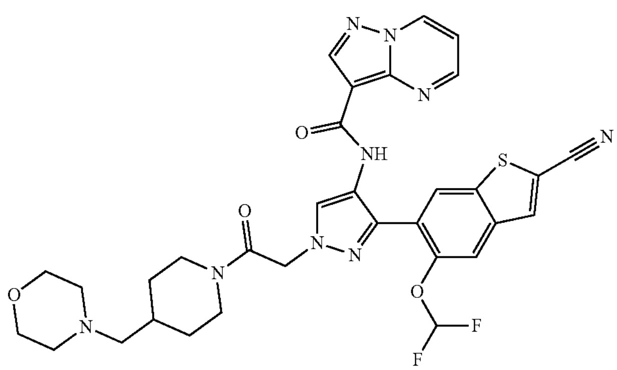 [SMILES: N#Cc1cc2cc(OC(F)F)c(-c3nn(CC(=O)N4CCC(CN5CCOCC5)CC4)cc3NC(=O)c3cnn4cccnc34)cc2s1] | N-[3-[2-cyano-5-(difluoromethoxy)benzothiophen-6-yl]-1-[2-[4-(morpholinomethyl)-1-piperidyl]-2-oxo-ethyl]pyrazol-4-yl]pyrazolo[1,5-a]pyrimidine-3-carboxamide |
| 61 | | 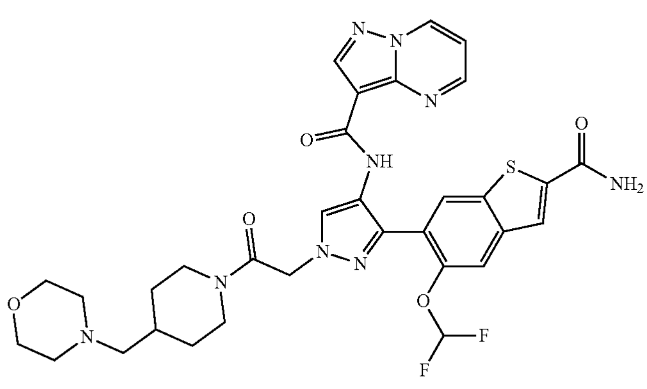 [SMILES: NC(=O)c1cc2cc(OC(F)F)c(-c3nn(CC(=O)N4CCC(CN5CCOCC5)CC4)cc3NC(=O)c3cnn4cccnc34)cc2s1] | N-[3-[2-carbamoyl-5-(difluoromethoxy)benzothiophen-6-yl]-1-[2-[4-(morpholinomethyl)-1-piperidyl]-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 62 | | 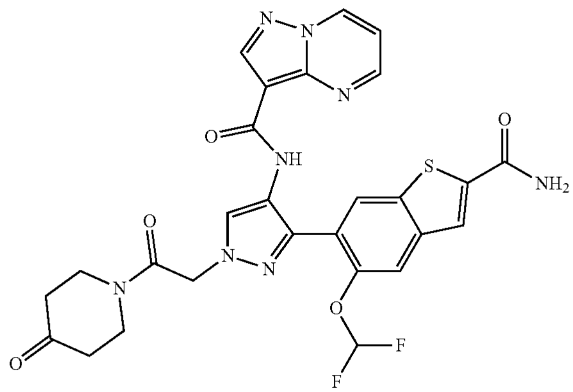 [SMILES: NC(=O)c1cc2cc(OC(F)F)c(-c3nn(CC(=O)N4CCC(=O)CC4)cc3NC(=O)c3cnn4cccnc34)cc2s1] | N-[3-[2-carbamoyl-5-(difluoromethoxy)benzothiophen-6-yl]-1-[2-oxo-2-(4-oxo-1-piperidyl)ethyl]pyrazol-4-yl]pyrazolo[1,5-a]pyrimidine-3-carboxamide |
| 63 | | 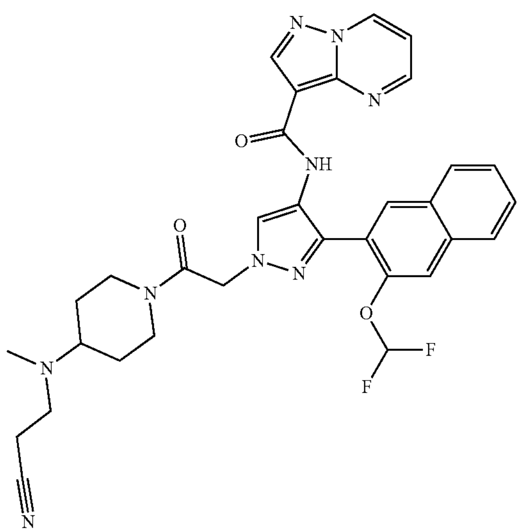 [SMILES: CN(CCC#N)C1CCN(C(=O)Cn2cc(NC(=O)c3cnn4cccnc34)c(-c3cc4ccccc4cc3OC(F)F)n2)CC1] | N-[1-[2-[4-[2-cyanoethyl(methyl)amino]-1-piperidyl]-2-oxo-ethyl]-3-[3-(difluoromethoxy)-2-naphthyl]pyrazol-4-yl]pyrazolo[1,5-a]pyrimidine-3-carboxamide |
| 64 | | 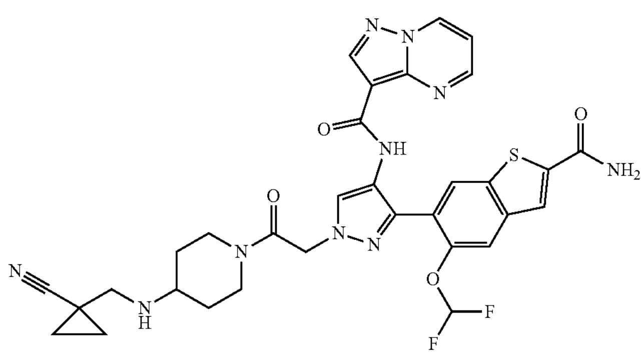 [SMILES: N#CC1(CNC2CCN(C(=O)Cn3cc(NC(=O)c4cnn5cccnc45)c(-c4cc5sc(C(N)=O)cc5cc4OC(F)F)n3)CC2)CC1] | N-[3-[2-carbamoyl-5-(difluoromethoxy)benzothiophen-6-yl]-1-[2-[4-[(1-cyanocyclopropyl)methylamino]-1-piperidyl]-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 65 | | 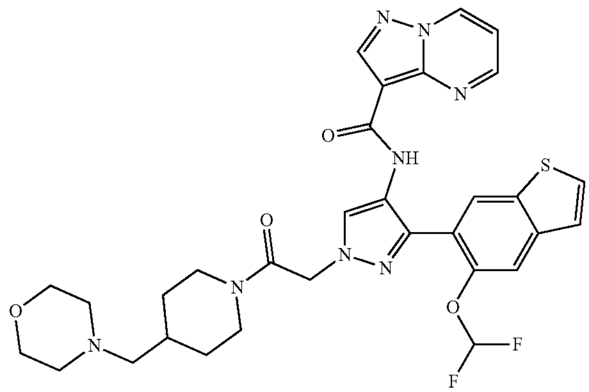 [SMILES: O=C(Nc1cn(CC(=O)N2CCC(CN3CCOCC3)CC2)nc1-c1cc2sccc2cc1OC(F)F)c1cnn2cccnc12] | N-[3-[5-(difluoromethoxy)benzothiophen-6-yl]-1-[2-[4-(morpholinomethyl)-1-piperidyl]-2-oxo-ethyl]pyrazol-4-yl]pyrazolo[1,5-a]pyrimidine-3-carboxamide |
| 66 | | 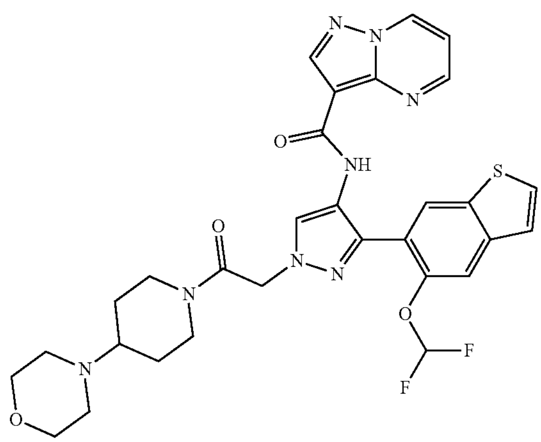 [SMILES: O=C(Nc1cn(CC(=O)N2CCC(N3CCOCC3)CC2)nc1-c1cc2sccc2cc1OC(F)F)c1cnn2cccnc12] | N-[3-[5-(difluoromethoxy)benzothiophen-6-yl]-1-[2-(4-morpholino-1-piperidyl)-2-oxo-ethyl]pyrazol-4-yl]pyrazolo[1,5-a]pyrimidine-3-carboxamide |
| 67 | | 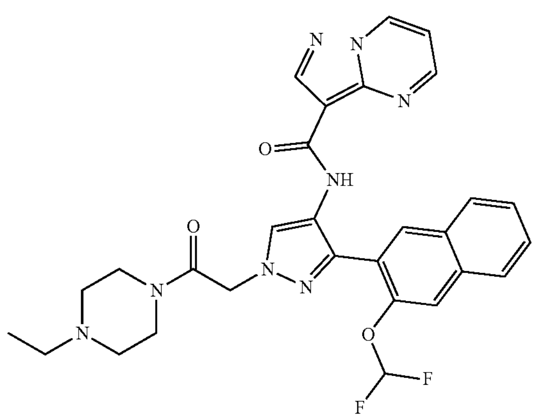 [SMILES: CCN1CCN(C(=O)Cn2cc(NC(=O)/C(C=N)=C3\N=CC=CN3)c(-c3cc4ccccc4cc3OC(F)F)n2)CC1] | N-[3-[3-(difluoromethoxy)-2-naphthyl]-1-[2-(4-ethylpiperazin-1-yl)-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 68 | | 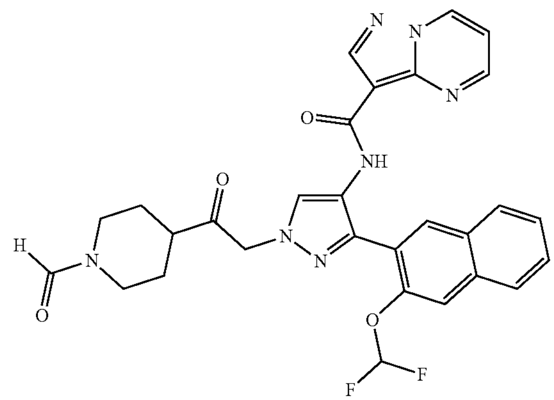 [SMILES: N=C/C(C(=O)Nc1cn(CC(=O)C2CCN(C=O)CC2)nc1-c1cc2ccccc2cc1OC(F)F)=C1/N=CC=CN1] | N-[3-[3-(difluoromethoxy)-2-naphthyl]-1-[2-(4-formylpiperazin-1-yl)-2-oxo-ethyl]pyrazol-4-yl]pyrazolo[1,5-a]pyrimidine-3-carboxamide |
| 69 | | 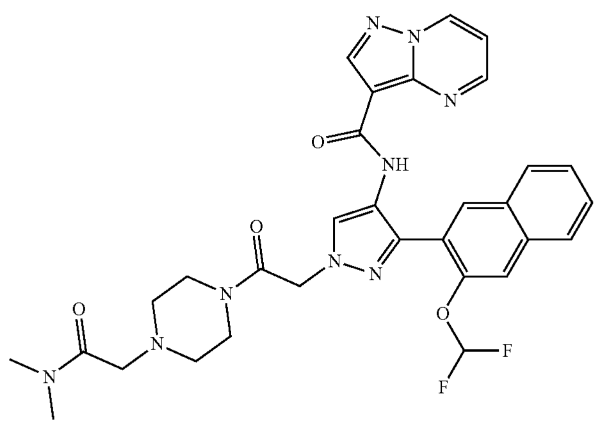 [SMILES: CN(C)C(=O)CN1CCN(C(=O)Cn2cc(NC(=O)c3cnn4cccnc34)c(-c3cc4ccccc4cc3OC(F)F)n2)CC1] | N-[3-[3-(difluoromethoxy)-2-naphthyl]-1-[2-[4-[2-(dimethylamino)-2-oxo-ethyl]piperazin-1-yl]-2-oxo-ethyl]pyrazol-4-yl]pyrazolo[1,5-a]pyrimidine-3-carboxamide |
| 70 | | 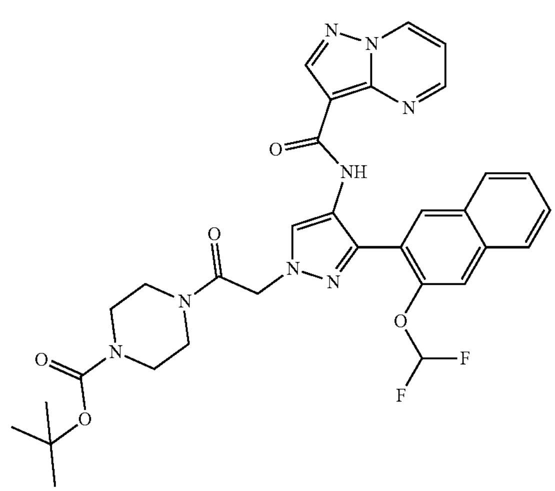 [SMILES: CC(C)(C)OC(=O)N1CCN(C(=O)Cn2cc(NC(=O)c3cnn4cccnc34)c(-c3cc4ccccc4cc3OC(F)F)n2)CC1] | tert-butyl 4-[2-[3-[3-(difluoromethoxy)-2-naphthyl]-4-(pyrazolo[1,5-a]pyrimidine-3-carbonylamino)pyrazol-1-yl]acetyl]piperazine-1-carboxylate |

TABLE 1-continued

Representative Compounds According to the Present Invention

| Ex. | Stereo-chemistry | Structure | Name |
|---|---|---|---|
| 71 | | 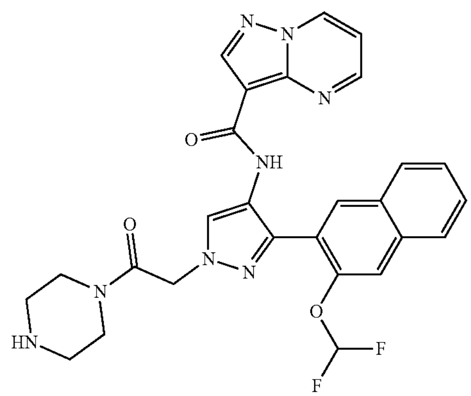 [SMILES: O=C(Nc1cn(CC(=O)N2CCNCC2)nc1-c1cc2ccccc2cc1OC(F)F)c1cnn2cccnc12] | N-[3-[3-(difluoromethoxy)-2-naphthyl]-1-(2-oxo-2-piperazin-1-yl-ethyl)pyrazol-4-yl]pyrazolo[1,5-a]pyrimidine-3-carboxamide |
| 72 | | 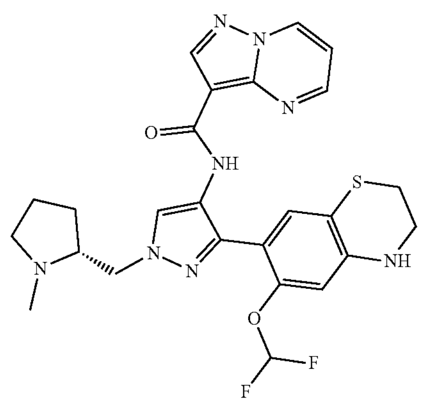 [SMILES: CN1CCC[C@@H]1Cn1cc(NC(=O)c2cnn3cccnc23)c(-c2cc3c(cc2OC(F)F)NCCS3)n1] | N-[3-[6-(difluoromethoxy)-3,4-dihydro-2H-1,4-benzothiazin-7-yl]-1-[[(2R)-1-methylpyrrolidin-2-yl]methyl]pyrazol-4-yl]pyrazolo[1,5-a]pyrimidine-3-carboxamide |
| 73 | | 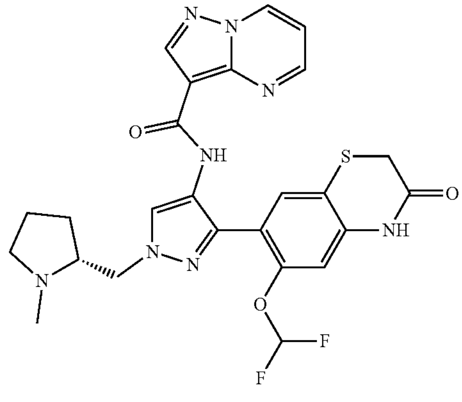 [SMILES: CN1CCC[C@@H]1Cn1cc(NC(=O)c2cnn3cccnc23)c(-c2cc3c(cc2OC(F)F)NC(=O)CS3)n1] | N-[3-[6-(difluoromethoxy)-3-oxo-4H-1,4-benzothiazin-7-yl]-1-[[(2R)-1-methylpyrrolidin-2-yl]methyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 74 | racemic | 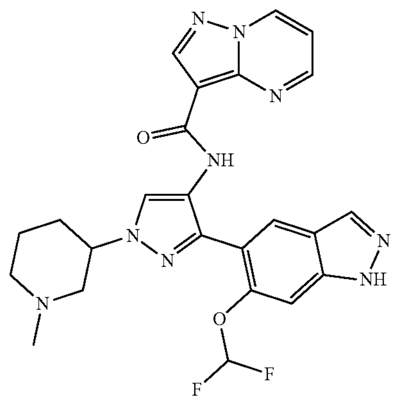 [SMILES: CN1CCCC(n2cc(NC(=O)c3cnn4cccnc34)c(-c3cc4cn[nH]c4cc3OC(F)F)n2)C1] | N-[3-[6-(difluoromethoxy)-1H-indazol-5-yl]-1-(1-methyl-3-piperidyl)pyrazol-4-yl]pyrazolo[1,5-a]pyrimidine-3-carboxamide |
| 75 | racemic | 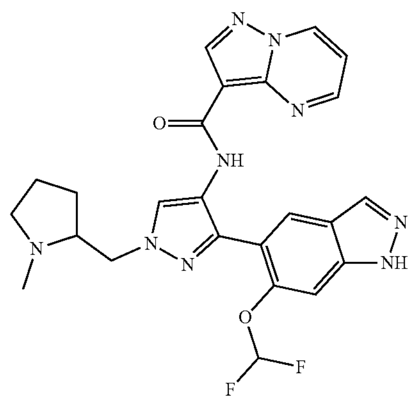 [SMILES: CN1CCCC1Cn1cc(NC(=O)c2cnn3cccnc23)c(-c2cc3cn[nH]c3cc2OC(F)F)n1] | N-[3-[6-(difluoromethoxy)-1H-indazol-5-yl]-1-[(1-methylpyrrolidin-2-yl)methyl]pyrazol-4-yl]pyrazolo[1,5-a]pyrimidine-3-carboxamide |
| 76 | single known stereoisomer | 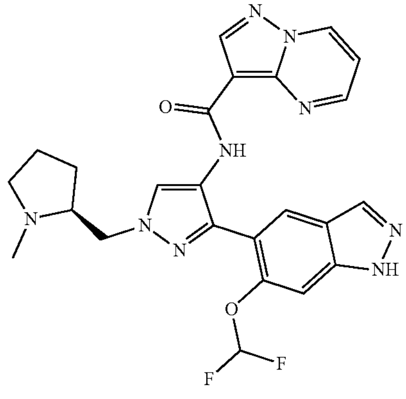 [SMILES: CN1CCC[C@H]1Cn1cc(NC(=O)c2cnn3cccnc23)c(-c2cc3cn[nH]c3cc2OC(F)F)n1] | N-[3-[6-(difluoromethoxy)-1H-indazol-5-yl]-1-[[(2S)-1-methylpyrrolidin-2-yl]methyl]pyrazol-4-yl]pyrazolo[1,5-a]pyrimidine-3-carboxamide |

TABLE 1-continued

Representative Compounds According to the Present Invention

| Ex. | Stereochemistry | Structure | Name |
|---|---|---|---|
| 77 | single known stereoisomer | 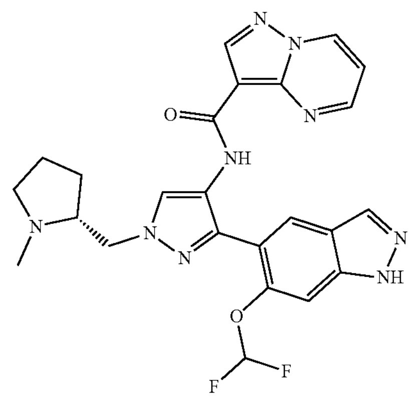 [SMILES: CN1CCC[C@@H]1Cn1cc(NC(=O)c2cnn3cccnc23)c(-c2cc3cn[nH]c3cc2OC(F)F)n1] | N-[3-[6-(difluoromethoxy)-1H-indazol-5-yl]-1-[[(2R)-1-methylpyrrolidin-2-yl]methyl]pyrazol-4-yl]pyrazolo[1,5-a]pyrimidine-3-carboxamide |
| 78 | single known stereoisomer | 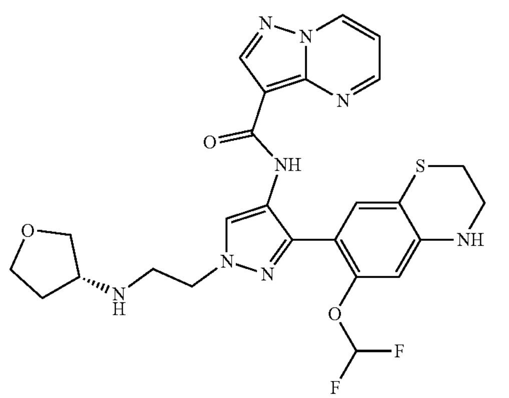 [SMILES: O=C(Nc1cn(CCN[C@@H]2CCOC2)nc1-c1cc2c(cc1OC(F)F)NCCS2)c1cnn2cccnc12] | N-[3-[6-(difluoromethoxy)-3,4-dihydro-2H-1,4-benzothiazin-7-yl]-1-[2-[[(3R)-tetrahydrofuran-3-yl]amino]ethyl]pyrazol-4-yl]pyrazolo[1,5-a]pyrimidine-3-carboxamide |
| 79 | | 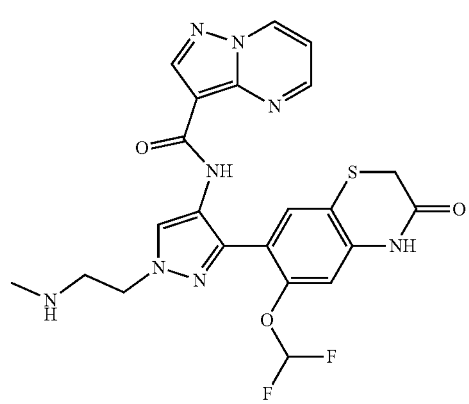 [SMILES: CNCCn1cc(NC(=O)c2cnn3cccnc23)c(-c2cc3c(cc2OC(F)F)NC(=O)CS3)n1] | N-[3-[6-(difluoromethoxy)-3-oxo-4H-1,4-benzothiazin-7-yl]-1-[2-(methylamino)ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 80 | racemic | 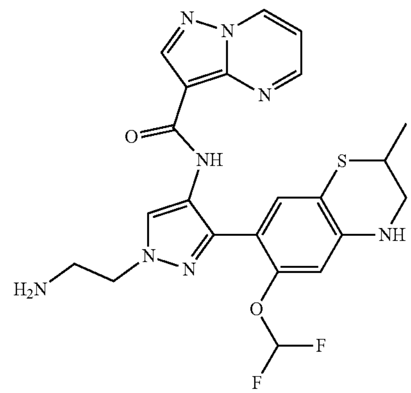 [SMILES: CC1CNc2cc(OC(F)F)c(-c3nn(CCN)cc3NC(=O)c3cnn4cccnc34)cc2S1] | N-[1-(2-aminoethyl)-3-[6-(difluoromethoxy)-2-methyl-3,4-dihydro-2H-1,4-benzothiazin-7-yl]pyrazol-4-yl]pyrazolo[1,5-a]pyrimidine-3-carboxamide |
| 81 | | 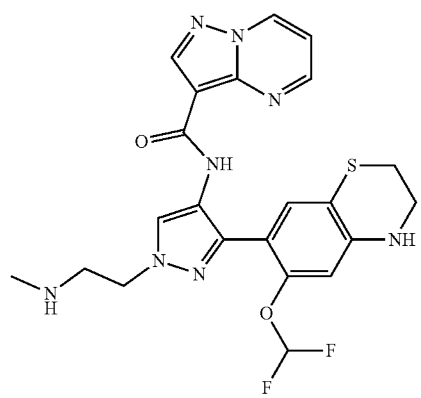 [SMILES: CNCCn1cc(NC(=O)c2cnn3cccnc23)c(-c2cc3c(cc2OC(F)F)NCCS3)n1] | N-[3-[6-(difluoromethoxy)-3,4-dihydro-2H-1,4-benzothiazin-7-yl]-1-[2-(methylamino)ethyl]pyrazol-4-yl]pyrazolo[1,5-a]pyrimidine-3-carboxamide |
| 82 | | 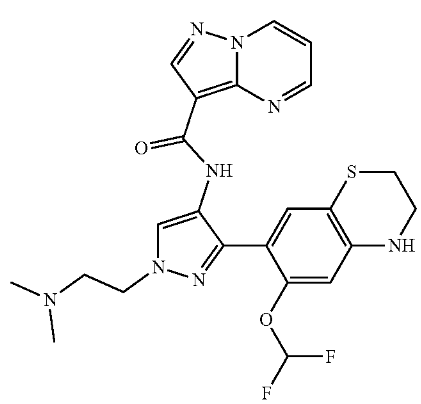 [SMILES: CN(C)CCn1cc(NC(=O)c2cnn3cccnc23)c(-c2cc3c(cc2OC(F)F)NCCS3)n1] | N-[3-[6-(difluoromethoxy)-3,4-dihydro-2H-1,4-benzothiazin-7-yl]-1-[2-(dimethylamino)ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 83 | | 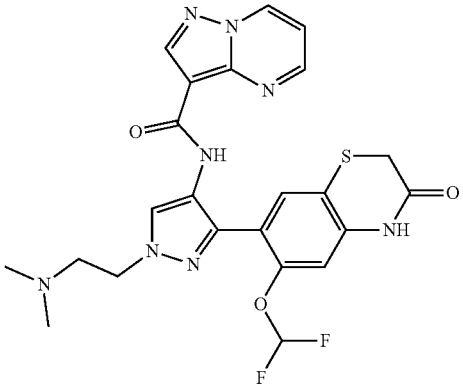 [SMILES: CN(C)CCn1cc(NC(=O)c2cnn3cccnc23)c(-c2cc3c(cc2OC(F)F)NC(=O)CS3)n1] | N-[3-[6-(difluoromethoxy)-3-oxo-4H-1,4-benzothiazin-7-yl]-1-[2-(dimethylamino)ethyl]pyrazol-4-yl]pyrazolo[1,5-a]pyrimidine-3-carboxamide |
| 84 | | 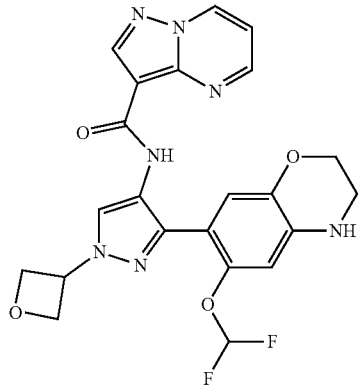 [SMILES: O=C(Nc1cn(C2COC2)nc1-c1cc2c(cc1OC(F)F)NCCO2)c1cnn2cccnc12] | N-[3-[6-(difluoromethoxy)-3,4-dihydro-2H-1,4-benzoxazin-7-yl]-1-(oxetan-3-yl)pyrazol-4-yl]pyrazolo[1,5-a]pyrimidine-3-carboxamide |
| 85 | | 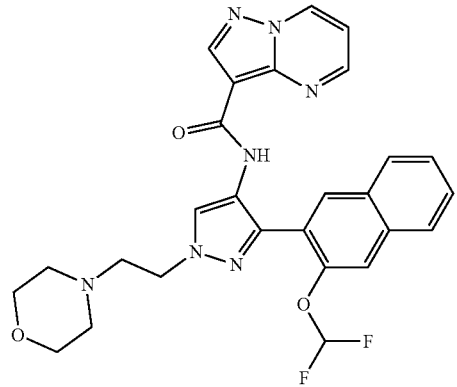 [SMILES: O=C(Nc1cn(CCN2CCOCC2)nc1-c1cc2ccccc2cc1OC(F)F)c1cnn2cccnc12] | N-[3-[3-(difluoromethoxy)-2-naphthyl]-1-(2-morpholinoethyl)pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 86 | | 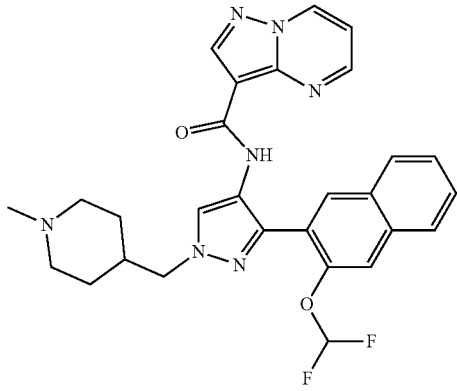 [SMILES: CN1CCC(Cn2cc(NC(=O)c3cnn4cccnc34)c(-c3cc4ccccc4cc3OC(F)F)n2)CC1] | N-[3-[3-(difluoromethoxy)-2-naphthyl]-1-[(1-methyl-4-piperidyl)methyl]pyrazol-4-yl]pyrazolo[1,5-a]pyrimidine-3-carboxamide |
| 87 | | 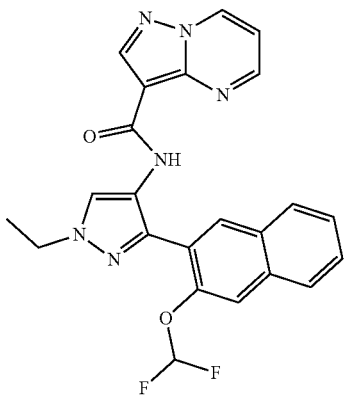 [SMILES: CCn1cc(NC(=O)c2cnn3cccnc23)c(-c2cc3ccccc3cc2OC(F)F)n1] | N-[3-[3-(difluoromethoxy)-2-naphthyl]-1-ethyl-pyrazol-4-yl]pyrazolo[1,5-a]pyrimidine-3-carboxamide |
| 88 | | 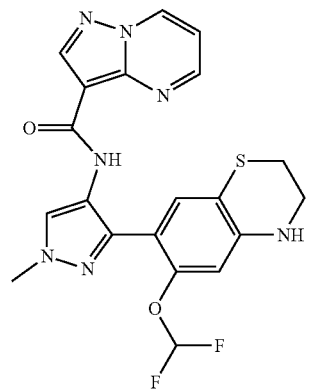 [SMILES: Cn1cc(NC(=O)c2cnn3cccnc23)c(-c2cc3c(cc2OC(F)F)NCCS3)n1] | N-[3-[6-(difluoromethoxy)-3,4-dihydro-2H-1,4-benzothiazin-7-yl]-1-methyl-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 89 | | 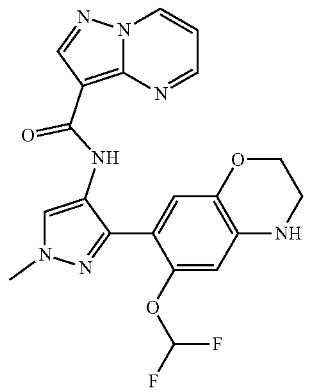 [SMILES: Cn1cc(NC(=O)c2cnn3cccnc23)c(-c2cc3c(cc2OC(F)F)NCCO3)n1] | N-[3-[6-(difluoromethoxy)-3,4-dihydro-2H-1,4-benzoxazin-7-yl]-1-methyl-pyrazol-4-yl]pyrazolo[1,5-a]pyrimidine-3-carboxamide |
| 90 | | 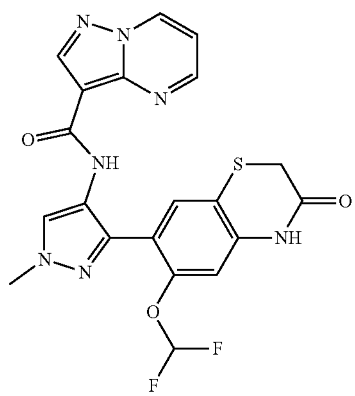 [SMILES: Cn1cc(NC(=O)c2cnn3cccnc23)c(-c2cc3c(cc2OC(F)F)NC(=O)CS3)n1] | N-[3-[6-(difluoromethoxy)-3-oxo-4H-1,4-benzothiazin-7-yl]-1-methyl-pyrazol-4-yl]pyrazolo[1,5-a]pyrimidine-3-carboxamide |
| 91 | | 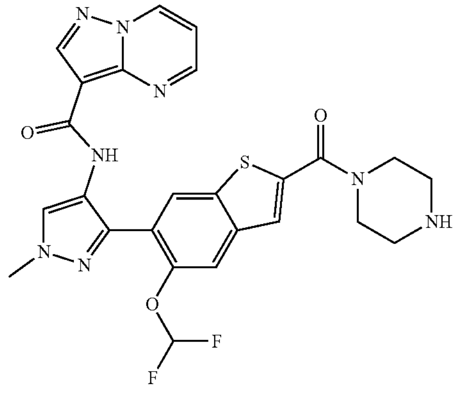 [SMILES: Cn1cc(NC(=O)c2cnn3cccnc23)c(-c2cc3sc(C(=O)N4CCNCC4)cc3cc2OC(F)F)n1] | N-[3-[5-(difluoromethoxy)-2-(piperazine-1-carbonyl)benzothiophen-6-yl]-1-methyl-pyrazol-4-yl]pyrazolo[1,5-a]pyrimidine-3-carboxamide |

… 117 118

TABLE 1-continued

Representative Compounds According to the Present Invention

| Ex. | Stereo-chemistry | Structure | Name |
|---|---|---|---|
| 92 | | 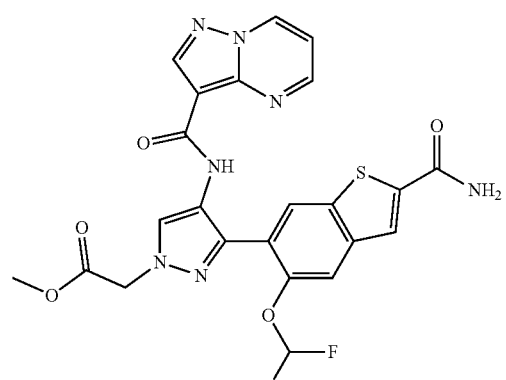 | methyl 2-[3-[2-carbamoyl-5-(difluoromethoxy)benzothiophen-6-yl]-4-(pyrazolo[1,5-a]pyrimidine-3-carbonylamino)pyrazol-1-yl]acetate |
| 93 | single unknown stereoisomer | 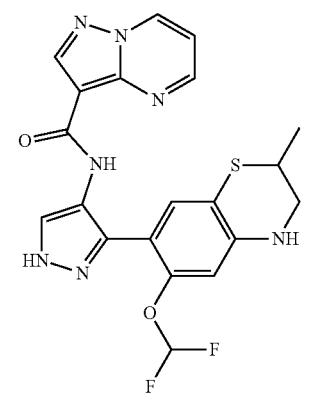 [SMILES: CC1CNc2cc(OC(F)F)c(-c3n[nH]cc3NC(=O)c3cnn4cccnc34)cc2S1]<br>Isomer 1 | N-[3-[6-(difluoromethoxy)-2-methyl-3,4-dihydro-2H-1,4-benzothiazin-7-yl]-1H-pyrazol-4-yl]pyrazolo[1,5-a]pyrimidine-3-carboxamide |
| 94 | single unknown stereoisomer | 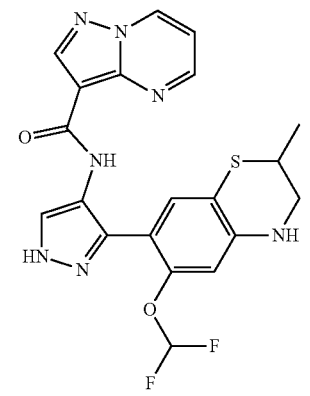 [SMILES: CC1CNc2cc(OC(F)F)c(-c3n[nH]cc3NC(=O)c3cnn4cccnc34)cc2S1]<br>Isomer 2 | N-[3-[6-(difluoromethoxy)-2-methyl-3,4-dihydro-2H-1,4-benzothiazin-7-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 95 | single unknown stereoisomer | Isomer 1 | N-[3-[6-(difluoromethoxy)-2-methyl-3-oxo-4H-1,4-benzothiazin-7-yl]-1H-pyrazol-4-yl]pyrazolo[1,5-a]pyrimidine-3-carboxamide |
| 96 | single unknown stereoisomer | Isomer 2 | N-[3-[6-(difluoromethoxy)-2-methyl-3-oxo-4H-1,4-benzothiazin-7-yl]-1H-pyrazol-4-yl]pyrazolo[1,5-a]pyrimidine-3-carboxamide |
| 97 | single unknown stereoisomer | Isomer 1 | N-[3-[6-(difluoromethoxy)-2-methyl-3-oxo-4H-1,4-benzothiazin-7-yl]-1-methyl-pyrazol-4-yl]pyrazolo[1,5-a]pyrimidine-3-carboxamide |

TABLE 1-continued

Representative Compounds According to the Present Invention

| Ex. | Stereochemistry | Structure | Name |
|---|---|---|---|
| 98 | single unknown stereoisomer | Isomer 2 | N-[3-[6-(difluoromethoxy)-2-methyl-3-oxo-4H-1,4-benzothiazin-7-yl]-1-methyl-pyrazol-4-yl]pyrazolo[1,5-a]pyrimidine-3-carboxamide |
| 99 | | 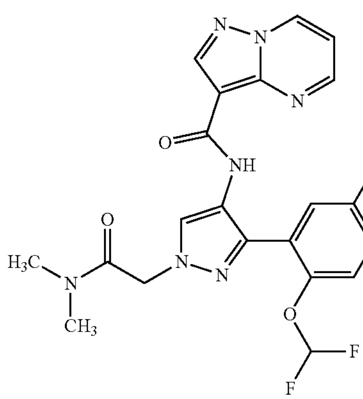 | N-[3-[6-(difluoromethoxy)-3,4-dihydro-2H-1,4-benzothiazin-7-yl]-1-[2-(dimethylamino)-2-oxo-ethyl]pyrazol-4-yl]pyrazolo[1,5-a]pyrimidine-3-carboxamide |
| 100 | | 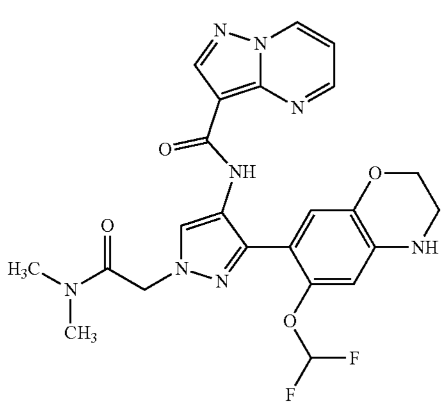 [SMILES: CN(C)C(=O)Cn1cc(NC(=O)c2cnn3cccnc23)c(-c2cc3c(cc2OC(F)F)NCCO3)n1] | N-[3-[6-(difluoromethoxy)-3,4-dihydro-2H-1,4-benzoxazin-7-yl]-1-[2-(dimethylamino)-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 101 | single unknown stereoisomer | Isomer 1 | N-[3-[6-(difluoromethoxy)-2-methyl-3,4-dihydro-2H-1,4-benzothiazin-7-yl]-1-[2-oxo-2-(1-piperidyl)ethyl]pyrazol-4-yl]pyrazolo[1,5-a]pyrimidine-3-carboxamide |
| 102 | single unknown stereoisomer | Isomer 2 | N-[3-[6-(difluoromethoxy)-2-methyl-3,4-dihydro-2H-1,4-benzothiazin-7-yl]-1-[2-oxo-2-(1-piperidyl)ethyl]pyrazol-4-yl]pyrazolo[1,5-a]pyrimidine-3-carboxamide |
| 103 | single unknown stereoisomer | Isomer 1 | N-[3-[6-(difluoromethoxy)-2-methyl-3,4-dihydro-2H-1,4-benzothiazin-7-yl]-1-[2-(3,6-dihydro-2H-pyridin-1-yl)-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 104 | single unknown stereoisomer | 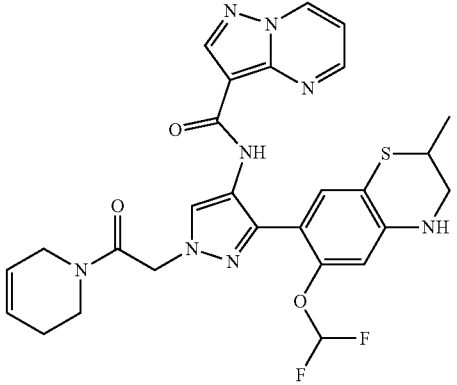 [SMILES: CC1CNc2cc(OC(F)F)c(-c3nn(CC(=O)N4CC=CCC4)cc3NC(=O)c3cnn4cccnc34)cc2S1]<br>Isomer 2 | N-[3-[6-(difluoromethoxy)-2-methyl-3,4-dihydro-2H-1,4-benzothiazin-7-yl]-1-[2-(3,6-dihydro-2H-pyridin-1-yl)-2-oxo-ethyl]pyrazol-4-yl]pyrazolo[1,5-a]pyrimidine-3-carboxamide |
| 105 | single unknown stereoisomer | 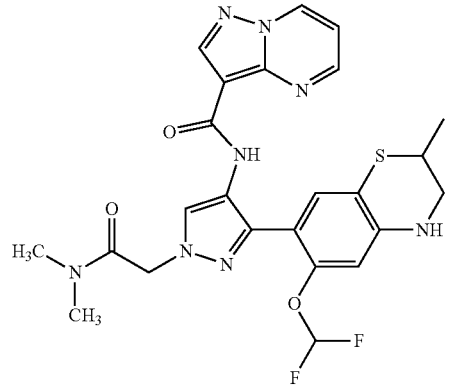<br>Isomer 1 | N-[3-[6-(difluoromethoxy)-2-methyl-3,4-dihydro-2H-1,4-benzothiazin-7-yl]-1-[2-(dimethylamino)-2-oxo-ethyl]pyrazol-4-yl]pyrazolo[1,5-a]pyrimidine-3-carboxamide |
| 106 | single unknown stereoisomer | 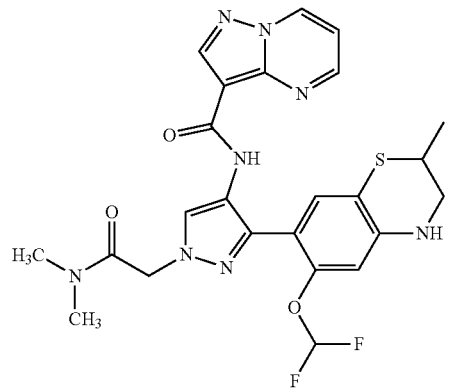<br>Isomer 2 | N-[3-[6-(difluoromethoxy)-2-methyl-3,4-dihydro-2H-1,4-benzothiazin-7-yl]-1-[2-(dimethylamino)-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 107 | single unknown stereoisomer | Isomer 1 | N-[3-[6-(difluoromethoxy)-3-methyl-3,4-dihydro-2H-1,4-benzothiazin-7-yl]-1-[2-oxo-2-(1-piperidyl)ethyl]pyrazol-4-yl]pyrazolo[1,5-a]pyrimidine-3-carboxamide |
| 108 | single unknown stereoisomer | Isomer 2 | N-[3-[6-(difluoromethoxy)-3-methyl-3,4-dihydro-2H-1,4-benzothiazin-7-yl]-1-[2-oxo-2-(1-piperidyl)ethyl]pyrazol-4-yl]pyrazolo[1,5-a]pyrimidine-3-carboxamide |
| 109 | | 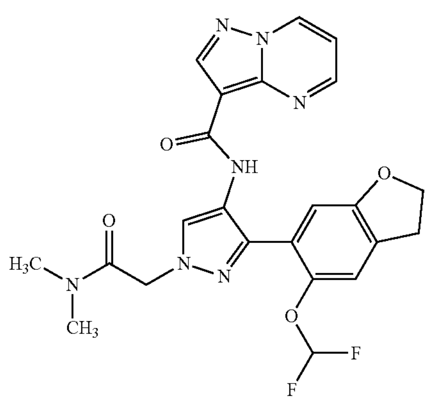 [SMILES: CN(C)C(=O)Cn1cc(NC(=O)c2cnn3cccnc23)c(-c2cc3c(cc2OC(F)F)CCO3)n1] | N-[3-[5-(difluoromethoxy)-2,3-dihydrobenzofuran-6-yl]-1-[2-(dimethylamino)-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 110 | | 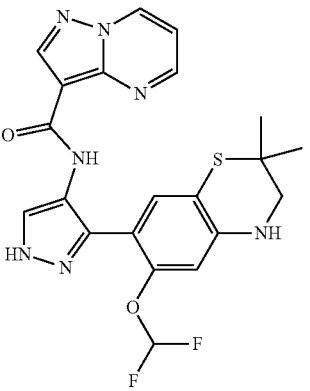 [SMILES: CC1(C)CNc2cc(OC(F)F)c(-c3n[nH]cc3NC(=O)c3cnn4cccnc34)cc2S1] | N-[3-[6-(difluoromethoxy)-2,2-dimethyl-3,4-dihydro-1,4-benzothiazin-7-yl]-1H-pyrazol-4-yl]pyrazolo[1,5-a]pyrimidine-3-carboxamide |
| 111 | single unknown stereoisomer | 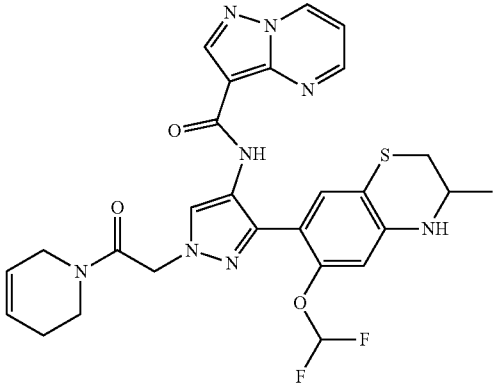 [SMILES: CC1CSc2cc(-c3nn(CC(=O)N4CC=CCC4)cc3NC(=O)c3cnn4cccnc34)c(OC(F)F)cc2N1]  Isomer 1 | N-[3-[6-(difluoromethoxy)-3-methyl-3,4-dihydro-2H-1,4-benzothiazin-7-yl]-1-[2-(3,6-dihydro-2H-pyridin-1-yl)-2-oxo-ethyl]pyrazol-4-yl]pyrazolo[1,5-a]pyrimidine-3-carboxamide |
| 112 | single unknown stereoisomer | 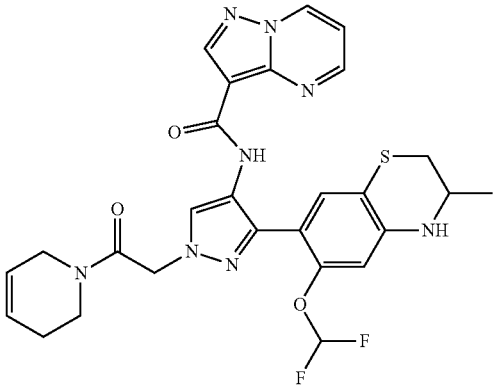 [SMILES: CC1CSc2cc(-c3nn(CC(=O)N4CC=CCC4)cc3NC(=O)c3cnn4cccnc34)c(OC(F)F)cc2N1]  Isomer 2 | N-[3-[6-(difluoromethoxy)-3-methyl-3,4-dihydro-2H-1,4-benzothiazin-7-yl]-1-[2-(3,6-dihydro-2H-pyridin-1-yl)-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 113 | single unknown stereoisomer | 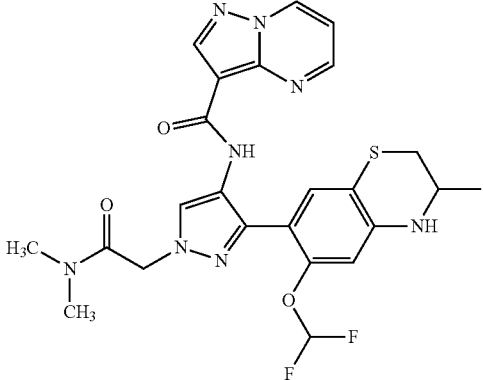 Isomer 1 | N-[3-[6-(difluoromethoxy)-3-methyl-3,4-dihydro-2H-1,4-benzothiazin-7-yl]-1-[2-(dimethylamino)-2-oxo-ethyl]pyrazol-4-yl]pyrazolo[1,5-a]pyrimidine-3-carboxamide |
| 114 | single unknown stereoisomer | 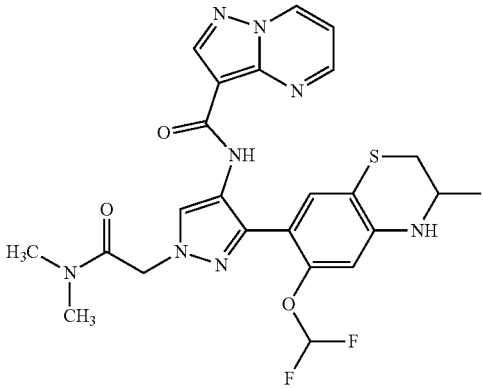 Isomer 2 | N-[3-[6-(difluoromethoxy)-3-methyl-3,4-dihydro-2H-1,4-benzothiazin-7-yl]-1-[2-(dimethylamino)-2-oxo-ethyl]pyrazol-4-yl]pyrazolo[1,5-a]pyrimidine-3-carboxamide |
| 115 | | 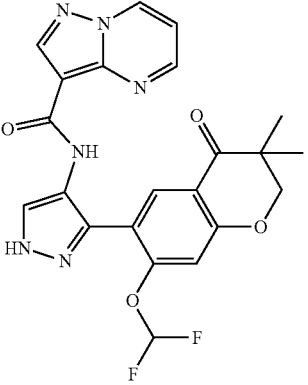 [SMILES: CC1(C)COc2cc(OC(F)F)c(-c3n[nH]cc3NC(=O)c3cnn4cccnc34)cc2C1=O] | N-[3-[7-(difluoromethoxy)-3,3-dimethyl-4-oxo-chroman-6-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 116 | | 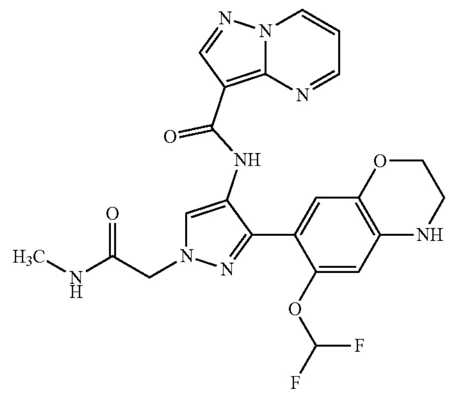 [SMILES: CNC(=O)Cn1cc(NC(=O)c2cnn3cccnc23)c(-c2cc3c(cc2OC(F)F)NCCO3)n1] | N-[3-[6-(difluoromethoxy)-3,4-dihydro-2H-1,4-benzoxazin-7-yl]-1-[2-(methylamino)-2-oxo-ethyl]pyrazol-4-yl]pyrazolo[1,5-a]pyrimidine-3-carboxamide |
| 117 | | 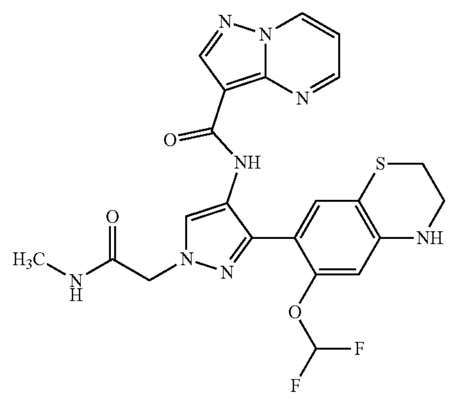 | N-[3-[6-(difluoromethoxy)-3,4-dihydro-2H-1,4-benzothiazin-7-yl]-1-[2-(methylamino)-2-oxo-ethyl]pyrazol-4-yl]pyrazolo[1,5-a]pyrimidine-3-carboxamide |
| 118 | single known stereoisomer | 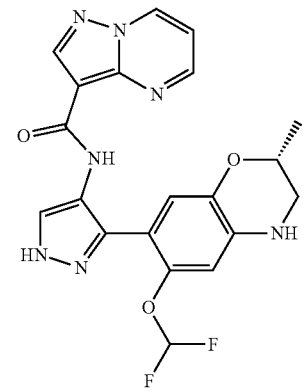 [SMILES: C[C@@H]1CNc2cc(OC(F)F)c(-c3n[nH]cc3NC(=O)c3cnn4cccnc34)cc2O1] | N-[3-[(2R)-6-(difluoromethoxy)-2-methyl-3,4-dihydro-2H-1,4-benzoxazin-7-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 119 | | 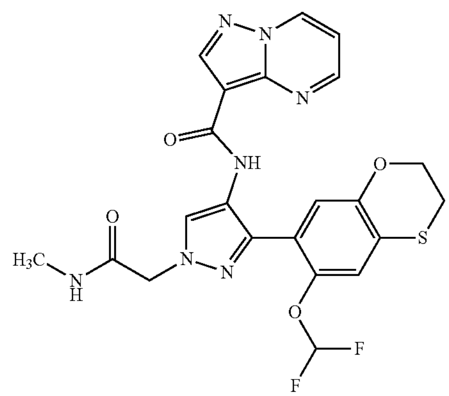 [SMILES: CNC(=O)Cn1cc(NC(=O)c2cnn3cccnc23)c(-c2cc3c(cc2OC(F)F)SCCO3)n1] | N-[3-[6-(difluoromethoxy)-2,3-dihydro-1,4-benzoxathiin-7-yl]-1-[2-(methylamino)-2-oxo-ethyl]pyrazol-4-yl]pyrazolo[1,5-a]pyrimidine-3-carboxamide |
| 120 | | 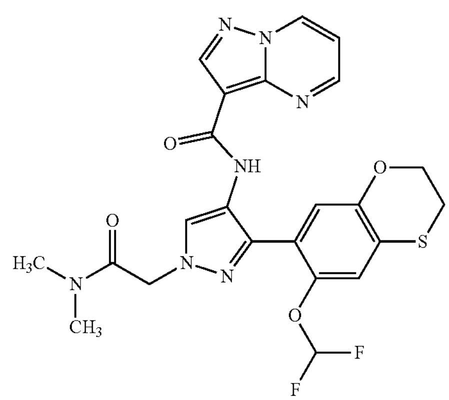 [SMILES: CN(C)C(=O)Cn1cc(NC(=O)c2cnn3cccnc23)c(-c2cc3c(cc2OC(F)F)SCCO3)n1] | N-[3-[6-(difluoromethoxy)-2,3-dihydro-1,4-benzoxathiin-7-yl]-1-[2-(dimethylamino)-2-oxo-ethyl]pyrazol-4-yl]pyrazolo[1,5-a]pyrimidine-3-carboxamide |
| 121 | single known stereoisomer | 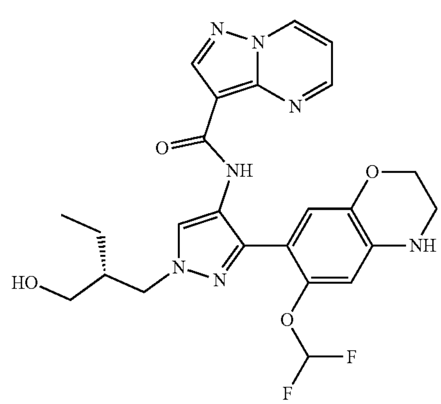 [SMILES: CC[C@@H](CO)Cn1cc(NC(=O)c2cnn3cccnc23)c(-c2cc3c(cc2OC(F)F)NCCO3)n1] | N-[3-[6-(difluoromethoxy)-3,4-dihydro-2H-1,4-benzoxazin-7-yl]-1-[(2R)-2-hydroxybutyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 122 | single known stereoisomer | 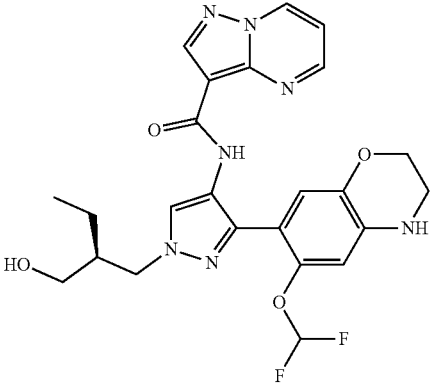 [SMILES: CC[C@H](CO)Cn1cc(NC(=O)c2cnn3cccnc23)c(-c2cc3c(cc2OC(F)F)NCCO3)n1] | N-[3-[6-(difluoromethoxy)-3,4-dihydro-2H-1,4-benzoxazin-7-yl]-1-[(2S)-2-hydroxybutyl]pyrazol-4-yl]pyrazolo[1,5-a]pyrimidine-3-carboxamide |
| 123 | | 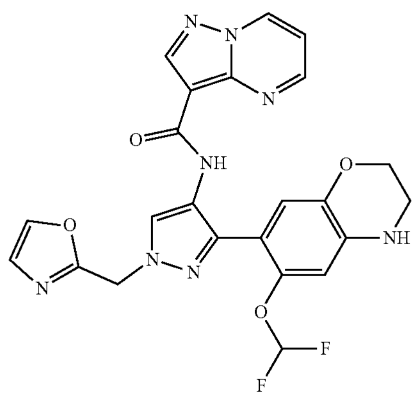 [SMILES: O=C(Nc1cn(Cc2ncco2)nc1-c1cc2c(cc1OC(F)F)NCCO2)c1cnn2cccnc12] | N-[3-[6-(difluoromethoxy)-3,4-dihydro-2H-1,4-benzoxazin-7-yl]-1-(oxazol-2-ylmethyl)pyrazol-4-yl]pyrazolo[1,5-a]pyrimidine-3-carboxamide |
| 124 | | 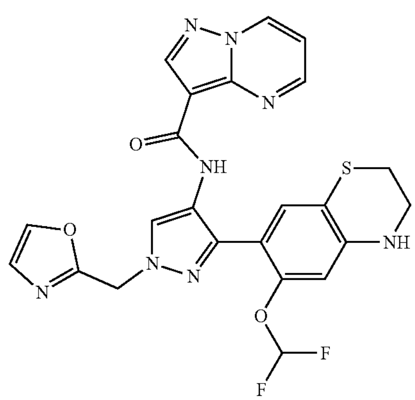 [SMILES: O=C(Nc1cn(Cc2ncco2)nc1-c1cc2c(cc1OC(F)F)NCCS2)c1cnn2cccnc12] | N-[3-[6-(difluoromethoxy)-3,4-dihydro-2H-1,4-benzothiazin-7-yl]-1-(oxazol-2-ylmethyl)pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 125 | single unknown stereoisomer | <br>Isomer 1 | N-[3-[6-(difluoromethoxy)-3,4-dihydro-2H-1,4-benzothiazin-7-yl]-1-(1-methyl-2-oxo-pyrrolidin-3-yl)pyrazol-4-yl]pyrazolo[1,5-a]pyrimidine-3-carboxamide |
| 126 | single unknown stereoisomer | <br>Isomer 2 | N-[3-[6-(difluoromethoxy)-3,4-dihydro-2H-1,4-benzothiazin-7-yl]-1-(1-methyl-2-oxo-pyrrolidin-3-yl)pyrazol-4-yl]pyrazolo[1,5-a]pyrimidine-3-carboxamide |
| 127 | | 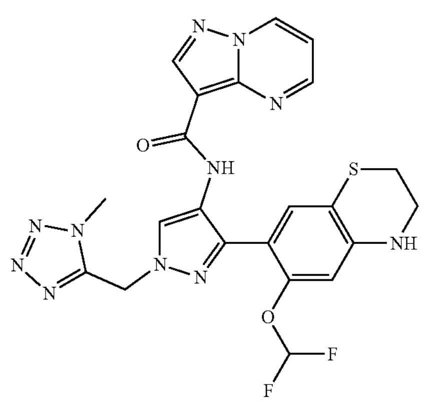 [SMILES: Cn1nnnc1Cn1cc(NC(=O)c2cnn3cccnc23)c(-c2cc3c(cc2OC(F)F)NCCS3)n1] | N-[3-[6-(difluoromethoxy)-3,4-dihydro-2H-1,4-benzothiazin-7-yl]-1-[(1-methyltetrazol-5-yl)methyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 128 | | 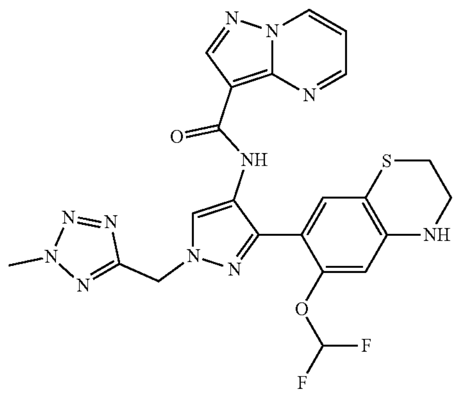 | N-[3-[6-(difluoromethoxy)-3,4-dihydro-2H-1,4-benzothiazin-7-yl]-1-[(2-methyltetrazol-5-yl)methyl]pyrazol-4-yl]pyrazolo[1,5-a]pyrimidine-3-carboxamide |
| 129 | | 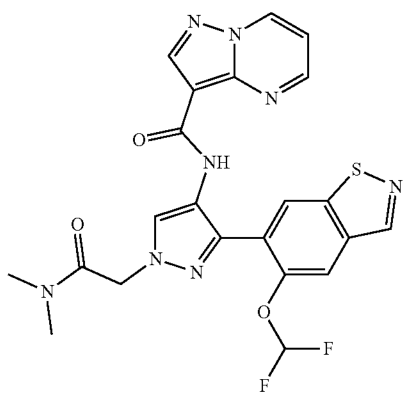 [SMILES: CN(C)C(=O)Cn1cc(NC(=O)c2cnn3cccnc23)c(-c2cc3sncc3cc2OC(F)F)n1] | N-[3-[5-(difluoromethoxy)-1,2-benzothiazol-6-yl]-1-[2-(dimethylamino)-2-oxo-ethyl]pyrazol-4-yl]pyrazolo[1,5-a]pyrimidine-3-carboxamide |
| 130 | | 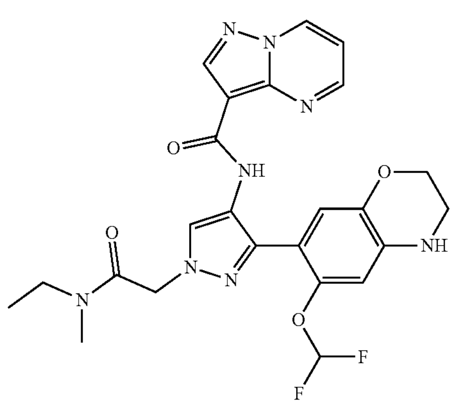 [SMILES: CCN(C)C(=O)Cn1cc(NC(=O)c2cnn3cccnc23)c(-c2cc3c(cc2OC(F)F)NCCO3)n1] | N-[3-[6-(difluoromethoxy)-3,4-dihydro-2H-1,4-benzoxazin-7-yl]-1-[2-[ethyl(methyl)amino]-2-oxo-ethyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 131 | | 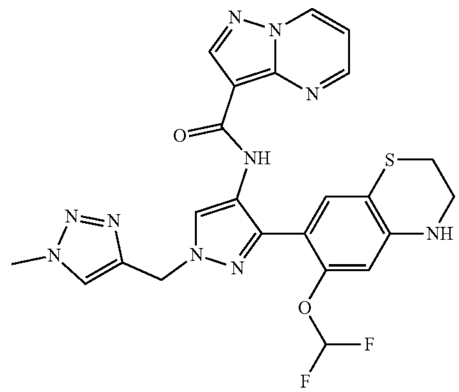 [SMILES: Cn1cc(Cn2cc(NC(=O)c3cnn4cccnc34)c(-c3cc4c(cc3OC(F)F)NCCS4)n2)nn1] | N-[3-[6-(difluoromethoxy)-3,4-dihydro-2H-1,4-benzothiazin-7-yl]-1-[(1-methyltriazol-4-yl)methyl]pyrazol-4-yl]pyrazolo[1,5-a]pyrimidine-3-carboxamide |
| 132 | | 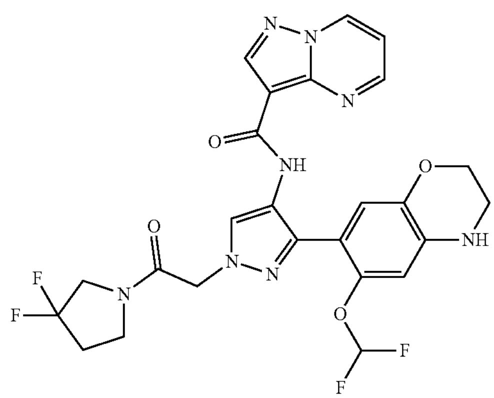 [SMILES: O=C(Nc1cn(CC(=O)N2CCC(F)(F)C2)nc1-c1cc2c(cc1OC(F)F)NCCO2)c1cnn2cccnc12] | N-[3-[6-(difluoromethoxy)-3,4-dihydro-2H-1,4-benzoxazin-7-yl]-1-[2-(3,3-difluoropyrrolidin-1-yl)-2-oxo-ethyl]pyrazol-4-yl]pyrazolo[1,5-a]pyrimidine-3-carboxamide |
| 133 | | 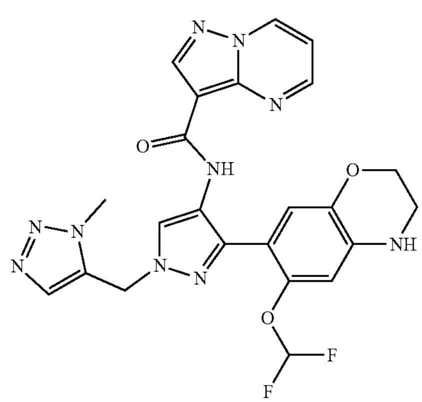 [SMILES: Cn1nncc1Cn1cc(NC(=O)c2cnn3cccnc23)c(-c2cc3c(cc2OC(F)F)NCCO3)n1] | N-[3-[6-(difluoromethoxy)-3,4-dihydro-2H-1,4-benzoxazin-7-yl]-1-[(3-methyltriazol-4-yl)methyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 134 | | 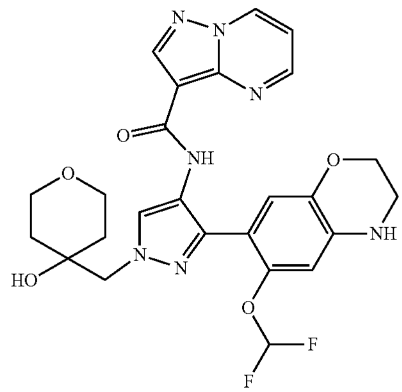 [SMILES: O=C(Nc1cn(CC2(O)CCOCC2)nc1-c1cc2c(cc1OC(F)F)NCCO2)c1cnn2cccnc12] | N-[3-[6-(difluoromethoxy)-3,4-dihydro-2H-1,4-benzoxazin-7-yl]-1-[(4-hydroxytetrahydropyran-4-yl)methyl]pyrazol-4-yl]pyrazolo[1,5-a]pyrimidine-3-carboxamide |
| 135 | | 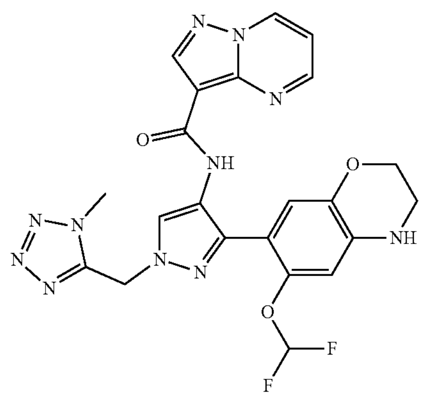 [SMILES: Cn1nnnc1Cn1cc(NC(=O)c2cnn3cccnc23)c(-c2cc3c(cc2OC(F)F)NCCO3)n1] | N-[3-[6-(difluoromethoxy)-3,4-dihydro-2H-1,4-benzoxazin-7-yl]-1-[(1-methyltetrazol-5-yl)methyl]pyrazol-4-yl]pyrazolo[1,5-a]pyrimidine-3-carboxamide |
| 136 | | 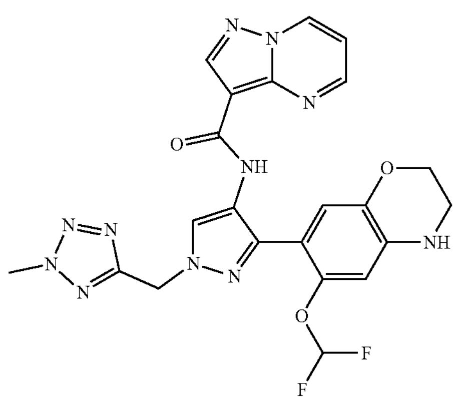 [SMILES: Cn1nnc(Cn2cc(NC(=O)c3cnn4cccnc34)c(-c3cc4c(cc3OC(F)F)NCCO4)n2)n1] | N-[3-[6-(difluoromethoxy)-3,4-dihydro-2H-1,4-benzoxazin-7-yl]-1-[(2-methyltetrazol-5-yl)methyl]pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 137 | | 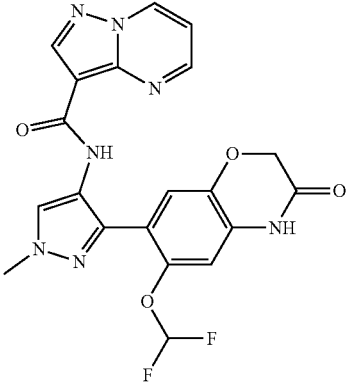 [SMILES: Cn1cc(NC(=O)c2cnn3cccnc23)c(-c2cc3c(cc2OC(F)F)NC(=O)CO3)n1] | N-[3-[6-(difluoromethoxy)-3-oxo-4H-1,4-benzoxazin-7-yl]-1-methyl-pyrazol-4-yl]pyrazolo[1,5-a]pyrimidine-3-carboxamide |
| 138 | | 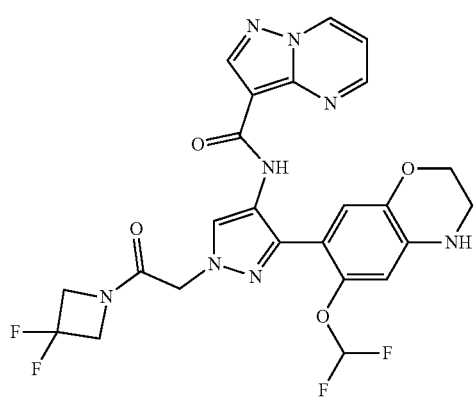 [SMILES: O=C(Nc1cn(CC(=O)N2CC(F)(F)C2)nc1-c1cc2c(cc1OC(F)F)NCCO2)c1cnn2cccnc12] | N-[1-[2-(3,3-difluoroazetidin-1-yl)-2-oxo-ethyl]-3-[6-(difluoromethoxy)-3,4-dihydro-2H-1,4-benzoxazin-7-yl]pyrazol-4-yl]pyrazolo[1,5-a]pyrimidine-3-carboxamide |
| 139 | | 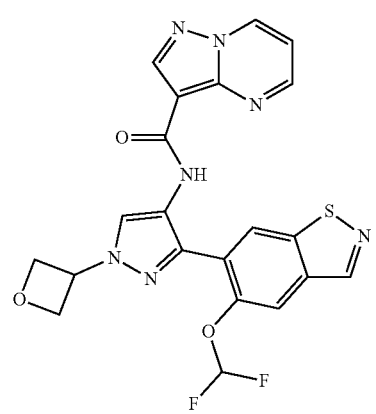 [SMILES: O=C(Nc1cn(C2COC2)nc1-c1cc2sncc2cc1OC(F)F)c1cnn2cccnc12] | N-[3-[5-(difluoromethoxy)-1,2-benzothiazol-6-yl]-1-(oxetan-3-yl)pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 140 | | 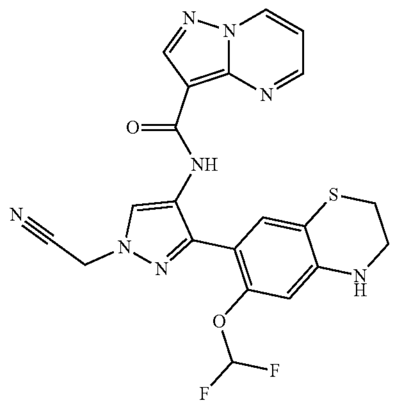 [SMILES: N#CCn1cc(NC(=O)c2cnn3cccnc23)c(-c2cc3c(cc2OC(F)F)NCCS3)n1] | N-[1-(cyanomethyl)-3-[6-(difluoromethoxy)-3,4-dihydro-2H-1,4-benzothiazin-7-yl]pyrazol-4-yl]pyrazolo[1,5-a]pyrimidine-3-carboxamide |
| 141 | single unknown stereoisomer | Isomer 1 | N-[3-[6-(difluoromethoxy)-3,4-dihydro-2H-1,4-benzothiazin-7-yl]-1-(2-oxotetrahydrofuran-3-yl)pyrazol-4-yl]pyrazolo[1,5-a]pyrimidine-3-carboxamide |
| 142 | single unknown stereoisomer | Isomer 2 | N-[3-[6-(difluoromethoxy)-3,4-dihydro-2H-1,4-benzothiazin-7-yl]-1-(2-oxotetrahydrofuran-3-yl)pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 143 | | 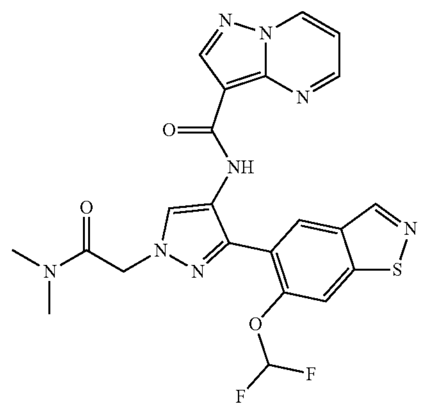 [SMILES: CN(C)C(=O)Cn1cc(NC(=O)c2cnn3cccnc23)c(-c2cc3cnsc3cc2OC(F)F)n1] | N-[3-[6-(difluoromethoxy)-1,2-benzothiazol-5-yl]-1-[2-(dimethylamino)-2-oxo-ethyl]pyrazol-4-yl]pyrazolo[1,5-a]pyrimidine-3-carboxamide |
| 144 | | 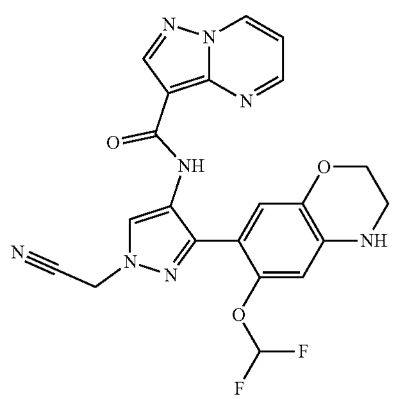 [SMILES: N#CCn1cc(NC(=O)c2cnn3cccnc23)c(-c2cc3c(cc2OC(F)F)NCCO3)n1] | N-[1-(cyanomethyl)-3-[6-(difluoromethoxy)-3,4-dihydro-2H-1,4-benzoxazin-7-yl]pyrazol-4-yl]pyrazolo[1,5-a]pyrimidine-3-carboxamide |
| 145 | single unknown stereoisomer | 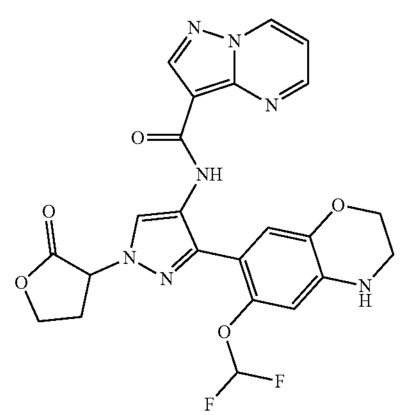 [SMILES: O=C(Nc1cn(C2CCOC2=O)nc1-c1cc2c(cc1OC(F)F)NCCO2)c1cnn2cccnc12] | N-[3-[6-(difluoromethoxy)-3,4-dihydro-2H-1,4-benzoxazin-7-yl]-1-(2-oxotetrahydrofuran-3-yl)pyrazol-4-yl]pyrazolo[1,5-a]pyrimidine-3-carboxamide |

Isomer 1

TABLE 1-continued

Representative Compounds According to the Present Invention

| Ex. | Stereo-chemistry | Structure | Name |
|---|---|---|---|
| 146 | single unknown stereoisomer | Isomer 2 | N-[3-[6-(difluoromethoxy)-3,4-dihydro-2H-1,4-benzoxazin-7-yl]-1-(2-oxotetrahydrofuran-3-yl)pyrazol-4-yl]pyrazolo[1,5-a]pyrimidine-3-carboxamide; formic acid |
| 147 | | 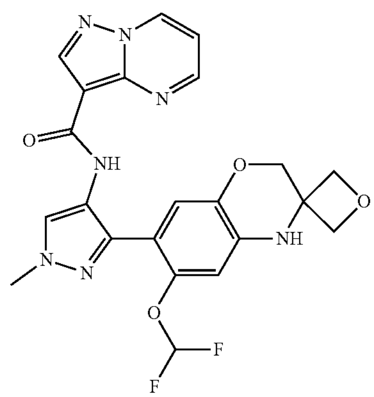 [SMILES: Cn1cc(NC(=O)c2cnn3cccnc23)c(-c2cc3c(cc2OC(F)F)NC2(COC2)CO3)n1] | N-[3-[6-(difluoromethoxy)spiro[2,4-dihydro-1,4-benzoxazine-3,3'-oxetane]-7-yl]-1-methyl-pyrazol-4-yl]pyrazolo[1,5-a]pyrimidine-3-carboxamide |
| 148 | single known stereoisomer | 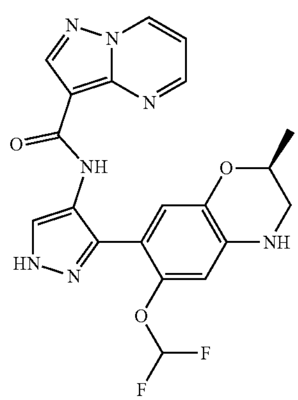 [SMILES: C[C@H]1CNc2cc(OC(F)F)c(-c3n[nH]cc3NC(=O)c3cnn4cccnc34)cc2O1] | N-[3-[(2S)-6-(difluoromethoxy)-2-methyl-3,4-dihydro-2H-1,4-benzoxazin-7-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 149 | | 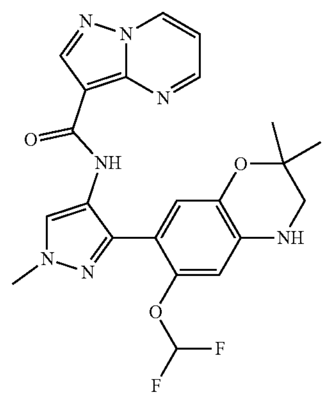 | N-[3-[6-(difluoromethoxy)-2,2-dimethyl-3,4-dihydro-1,4-benzoxazin-7-yl]-1-methyl-pyrazol-4-yl]pyrazolo[1,5-a]pyrimidine-3-carboxamide |
| 150 | | 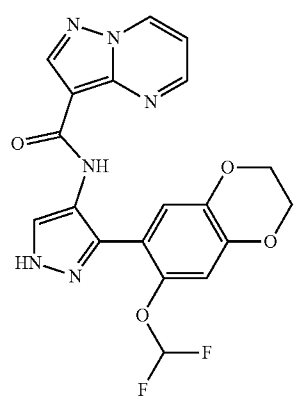 [SMILES: O=C(Nc1c[nH]nc1-c1cc2c(cc1OC(F)F)OCCO2)c1cnn2cccnc12] | N-[3-[6-(difluoromethoxy)-2,3-dihydro-1,4-benzodioxin-7-yl]-1H-pyrazol-4-yl]pyrazolo[1,5-a]pyrimidine-3-carboxamide |
| 151 | | 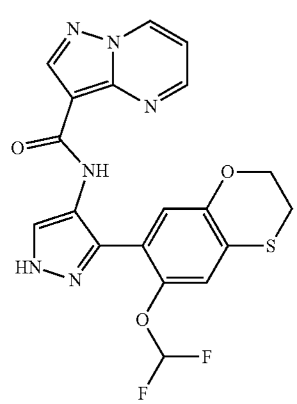 [SMILES: O=C(Nc1c[nH]nc1-c1cc2c(cc1OC(F)F)SCCO2)c1cnn2cccnc12] | N-[3-[6-(difluoromethoxy)-2,3-dihydro-1,4-benzoxathiin-7-yl]-1H-pyrazol-4-yl]pyrazolo[1,5-a]pyrimidine-3-carboxamide |

TABLE 1-continued

Representative Compounds According to the Present Invention

| Ex. | Stereo-chemistry | Structure | Name |
|---|---|---|---|
| 152 | | 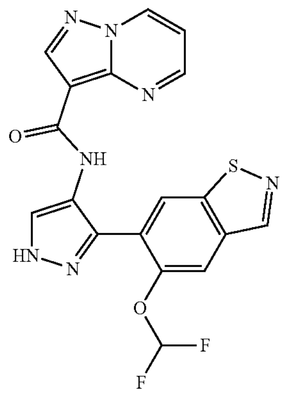 [SMILES: O=C(Nc1c[nH]nc1-c1cc2sncc2cc1OC(F)F)c1cnn2cccnc12] | N-[3-[5-(difluoromethoxy)-1,2-benzothiazol-6-yl]-1H-pyrazol-4-yl]pyrazolo[1,5-a]pyrimidine-3-carboxamide |
| 153 | | 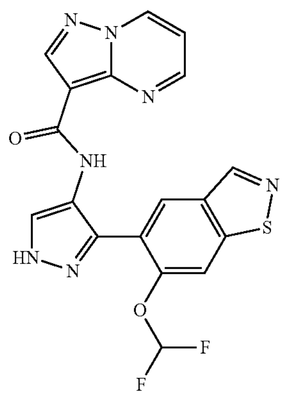 [SMILES: O=C(Nc1c[nH]nc1-c1cc2cnsc2cc1OC(F)F)c1cnn2cccnc12] | N-[3-[6-(difluoromethoxy)-1,2-benzothiazol-5-yl]-1H-pyrazol-4-yl]pyrazolo[1,5-a]pyrimidine-3-carboxamide; formic acid |
| 154 | | 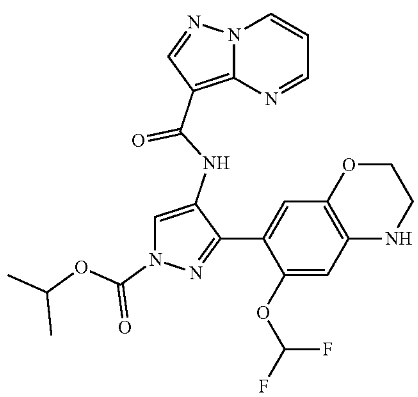 [SMILES: CC(C)OC(=O)n1cc(NC(=O)c2cnn3cccnc23)c(-c2cc3c(cc2OC(F)F)NCCO3)n1] | isopropyl 3-[6-(difluoromethoxy)-3,4-dihydro-2H-1,4-benzoxazin-7-yl]-4-(pyrazolo[1,5-a]pyrimidine-3-carbonylamino)pyrazole-1-carboxylate |

Compounds of the invention may contain one or more asymmetric carbon atoms. Accordingly, the compounds may exist as diastereomers, enantiomers, or mixtures thereof. The syntheses of the compounds may employ racemates, diastereomers, or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the present invention, such as a compound of Formula IA, or a compound of Table 1 or of Examples 1-154, or a pharmaceutically acceptable salt thereof, including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine, and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of Formula IA or a subformula thereof. Prodrugs may be prepared by reacting a compound of the present invention, such as a compound of Formula IA, or a compound of Table 1 or of Examples 1-154, or a pharmaceutically acceptable salt thereof, with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention, such as a compound of Formula IA, or a compound of Table 1 or of Examples 1-154, or a pharmaceutically acceptable salt thereof, can be derivatized as an amide or alkyl ester. As another example, compounds of the present invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

Synthesis of Janus Kinase Inhibitor Compounds

Compounds of the present invention may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or Comprehensive Heterocyclic Chemistry, Editors Katrizky and Rees, Pergamon Press, 1984.

Compounds may be prepared singly or as compound libraries comprising at least 2, for example 5 to 1,000 compounds, or 10 to 100 compounds. Libraries of compounds may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of the present invention, such as a compound of Formula IA, or a compound of Table 1 or of Examples 1-154, or a pharmaceutically acceptable salt thereof.

For illustrative purposes, Reaction Schemes 1-9 depicted below provide routes for synthesizing the compounds of the present invention as well as key intermediates. For a more detailed description of the individual reaction steps, see the Examples section below. Those skilled in the art will appreciate that other synthetic routes may be used. Although some specific starting materials and reagents are depicted in the Reaction Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, benzyl, phenylsulfonyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Other conversions commonly used in the synthesis of compounds of the present invention, and which can be carried out using a variety of reagents and conditions, include the following:

(1) Reaction of a carboxylic acid with an amine to form an amide. Such a transformation can be achieved using various reagents known to those skilled in the art but a comprehensive review can be found in *Tetrahedron*, 2005, 61, 10827-10852.

(2) Reaction of a primary or secondary amine with an aryl halide or pseudo halide, e.g., a triflate, commonly known as a "Buchwald-Hartwig cross-coupling," can be achieved using a variety of catalysts, ligands and bases. A review of these methods is provided in *Comprehensive Organic Name Reactions and Reagents*, 2010, 575-581.

(3) A palladium cross-coupling reaction between an aryl halide and a vinyl boronic acid or boronate ester. This transformation is a type of "Suzuki-Miyaura cross-coupling," a class of reaction that has been thoroughly reviewed in Chemical Reviews, 1995, 95(7), 2457-2483.

(4) The hydrolysis of an ester to give the corresponding carboxylic acid is well known to those skilled in the art and conditions include: for methyl and ethyl esters, the use of a strong aqueous base such as lithium, sodium or potassium hydroxide or a strong aqueous mineral acid such as HCl; for a tert-butyl ester, hydrolysis would be carried out using acid, for example, HCl in dioxane or trifluoroacetic acid (TFA) in dichloromethane (DCM).

In the Reaction Schemes below, the following abbreviations are used:

SEM is a [β-(trimethylsilyl)ethoxy]methyl group;
PyAOP is (7-Azabenzotriazol-1-yloxy)tripyrrolidinophosphonium hexafluorophosphate;
DIPEA is diisopropylethylamine;
DMAP is 4-dimethylaminopyridine;
DMF is N,N-Dimethylformamide;
EtOH is ethanol;
LiHMDS is lithium hexamethyldisilazide;
Boc is tert-butyloxycarbonyl protecting group;
$Pd_2dba_3$ is Tris(dibenzylidineacetone)palladium(0);
SPhos is 2-Dicyclohexylphosphino-2',6'-dimethoxybiphenyl;
TFA is Trifluoroacetic acid;
DCM is dichloromethane;
HATU is N,N,N',N'-tetramethyl-O-(7-azabenzotriazol-1-yl)uronium hexafluorophosphate;
TBAF is tetra-n-butylammonium fluoride;
NMO is n-methylmorpholine-N-oxide; and
BrettPhos Palladacycle Gen. 3 is [(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate.

Other exemplary transformations are discussed following the Reaction Schemes below.

Reaction Scheme 1

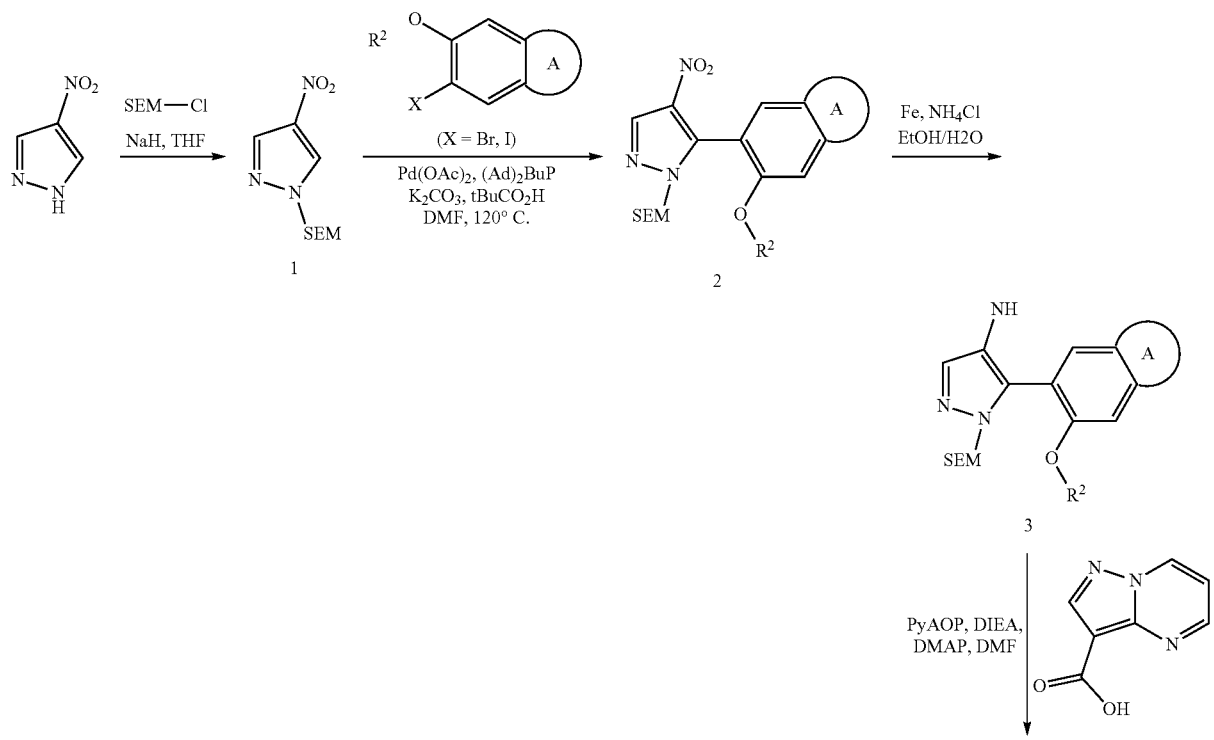

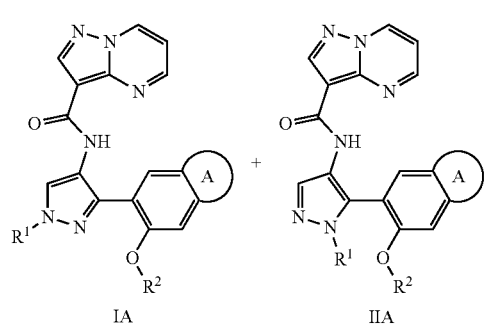
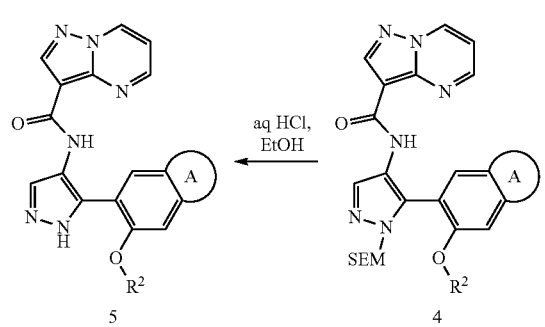

Reaction Scheme 1 illustrates a synthesis for compounds of Formulas IA and IIA. Commercially available 4-nitro-1H-pyrazole may be protected with a [β-(trimethylsilyl)ethoxy]methyl (SEM) group by treatment with sodium hydride and (2-(chloromethoxy)ethyl)trimethylsilane. The resulting compound 1 can be arylated with aryl bromides or iodides under palladium catalyzed conditions to generated 4-nitro-5-aryl-pyrazoles of formula 2. The nitro group of compounds 2 can be reduced in the presence of iron and ammonium chloride to generate amino pyrazoles 3. Amide bond coupling with commercially available pyrazolo[1,5-a]pyrimidine-3-carboxylic acid in the presence of PyAOP, DIPEA, and DMAP provides compounds 4. Removal of the SEM protecting group by aqueous HCl in ethanol generates compounds 5, which may be alkylated with alkyl halides in the presence of a suitable base such as cesium carbonate or with Michael acceptors to provide compounds of Formulas IA and IIA.

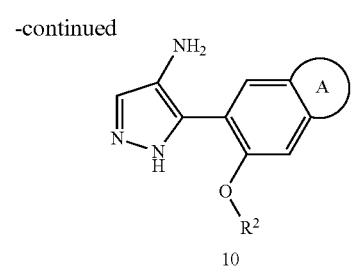

An alternative method for the synthesis of compounds of formula 5 is shown in Reaction Scheme 2. 1-SEM-4-nitro-1H-pyrazole compound 1 may be deprotonated with lithium hexamethyldisilazide at low temperature and quenched with iodine to yield compound 7. The nitro group of compound 7 can be reduced in the presence of iron and ammonium chloride, followed by Boc protection to generate compound 8. Compound 8 may be coupled under Suzuki conditions with aryl boronic acids or aryl boronates to yield compounds of formula 9. After cleavage of the protecting groups with tin tetrachloride, compounds of formula 10 are obtained.

Reaction Scheme 2

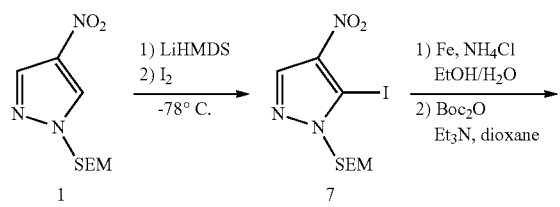

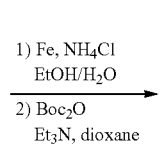

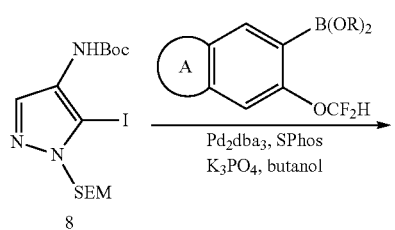

Reaction Scheme 3

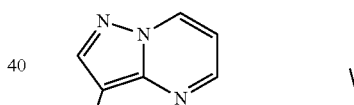

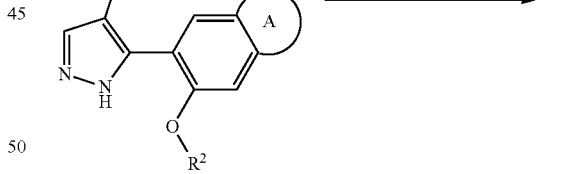

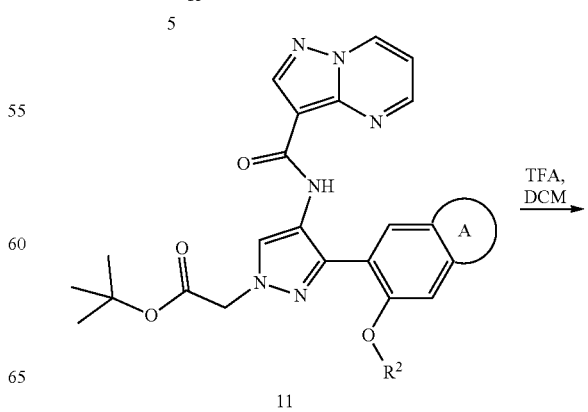

165

-continued

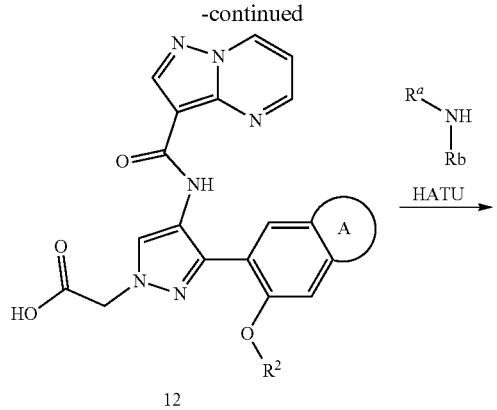

12

166

-continued

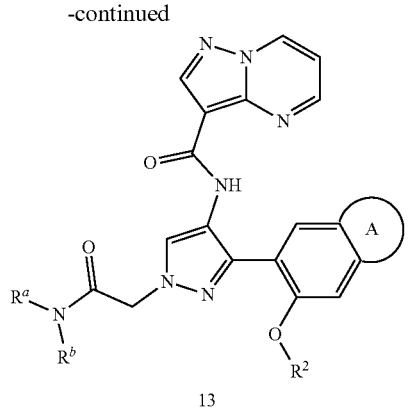

13

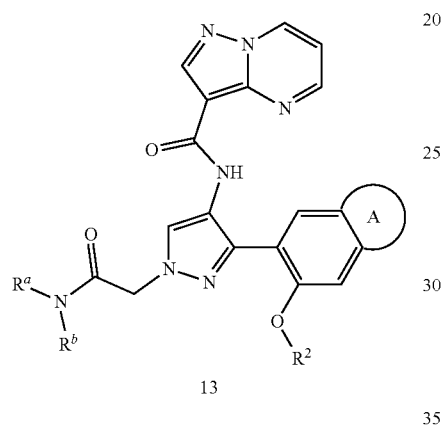

13

Compounds of formula 13 can be synthesized as shown in Reaction Scheme 3. Pyrazole compound 5 (prepared as described herein) may be alkylated with t-butyl-bromoacetate in the presence of cesium carbonate to give intermediate 11. Intermediate 11 may be treated with trifluoroacetic acid to give acids of formula 12, which may then be reacted with primary or secondary amines in the presence of a coupling reagent such as N,N,N',N'-tetramethyl-O-(7-azabenzotriazol-1-yl)uronium hexafluorophosphate (HATU) to give compounds of formula 13.

An alternative synthesis of compounds of formula 13 is shown in Reaction Scheme 4. Compound 5 can be reacted with an α-haloamide in the presence of a base such as cesium carbonate to give compounds of formula 13.

Reaction Scheme 5

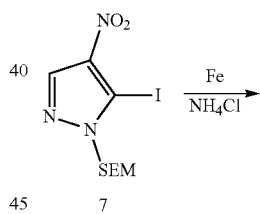

7

Reaction Scheme 4

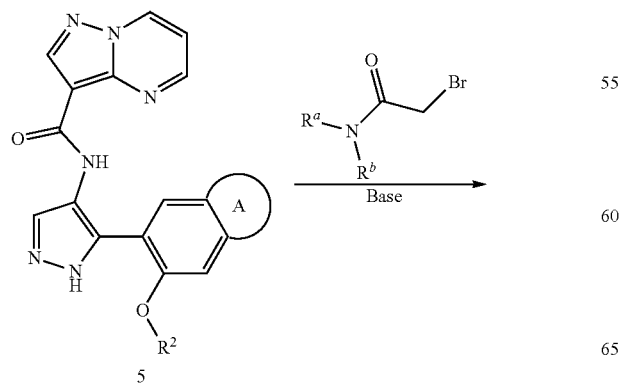

5

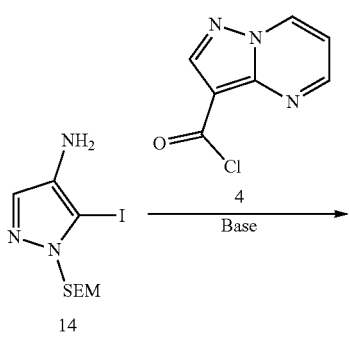

14

167

-continued

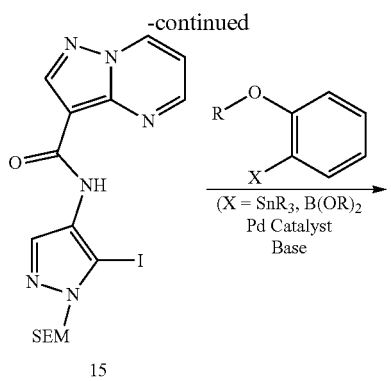

15

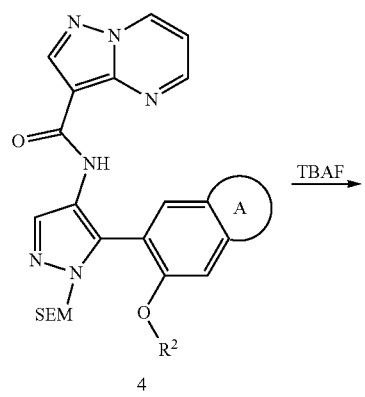

4

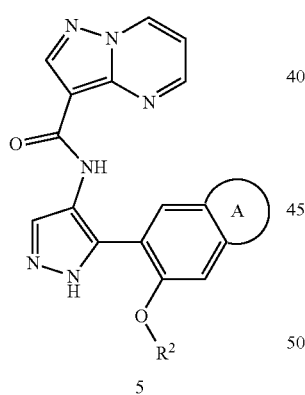

5

Compounds of formula 5 may also be prepared according to Reaction Scheme 5. Pyrazole compound 7 may be reduced in the presence of iron and ammonium chloride to generate amino pyrazoles 14. Amide bond coupling with pyrazolo[1,5-a]pyrimidine-3-carbonyl chloride in the presence of a base such as DIPEA provides compounds 15. Compound 15 can be arylated with aryl boronates and stannanes under palladium catalyzed conditions to generate compounds of formula 4. Compound of formula 4 may be treated with a reagent such as TFA or TBAF to give compound 5.

168

Reaction Scheme 6

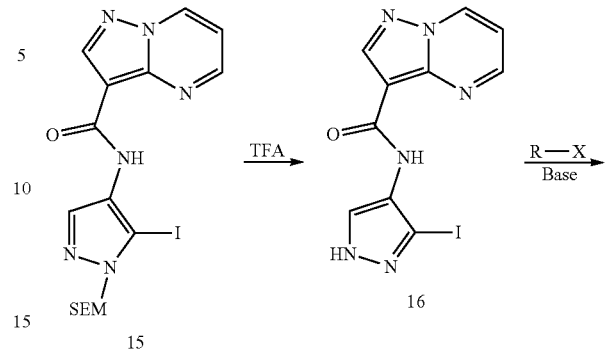

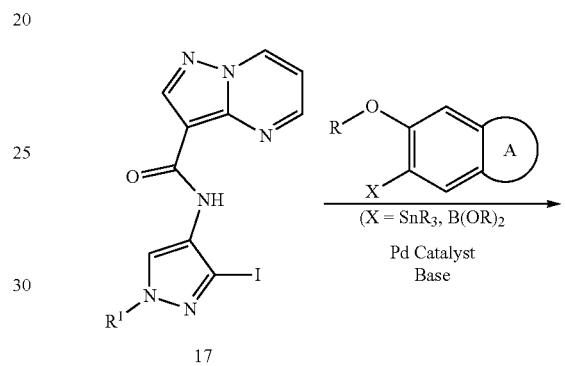

17

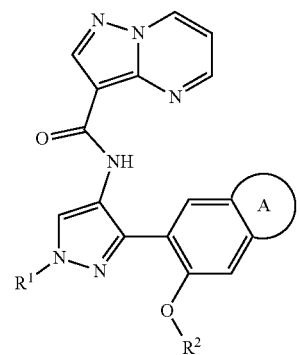

1A

Compounds of formula IA (where $R_1$ is not H) may be synthesized using the synthesis described in Reaction Scheme 6. Compound 15 may be treated with a reagent such as TFA or TBAF to give compound 16. Compound 16 may be alkylated with a suitable alkylating agent in the presence of a base such as cesium carbonate to give compound 17. Compound 17 can be arylated with aryl boronates and stannanes under palladium catalyzed conditions to generate compounds of formula IA.

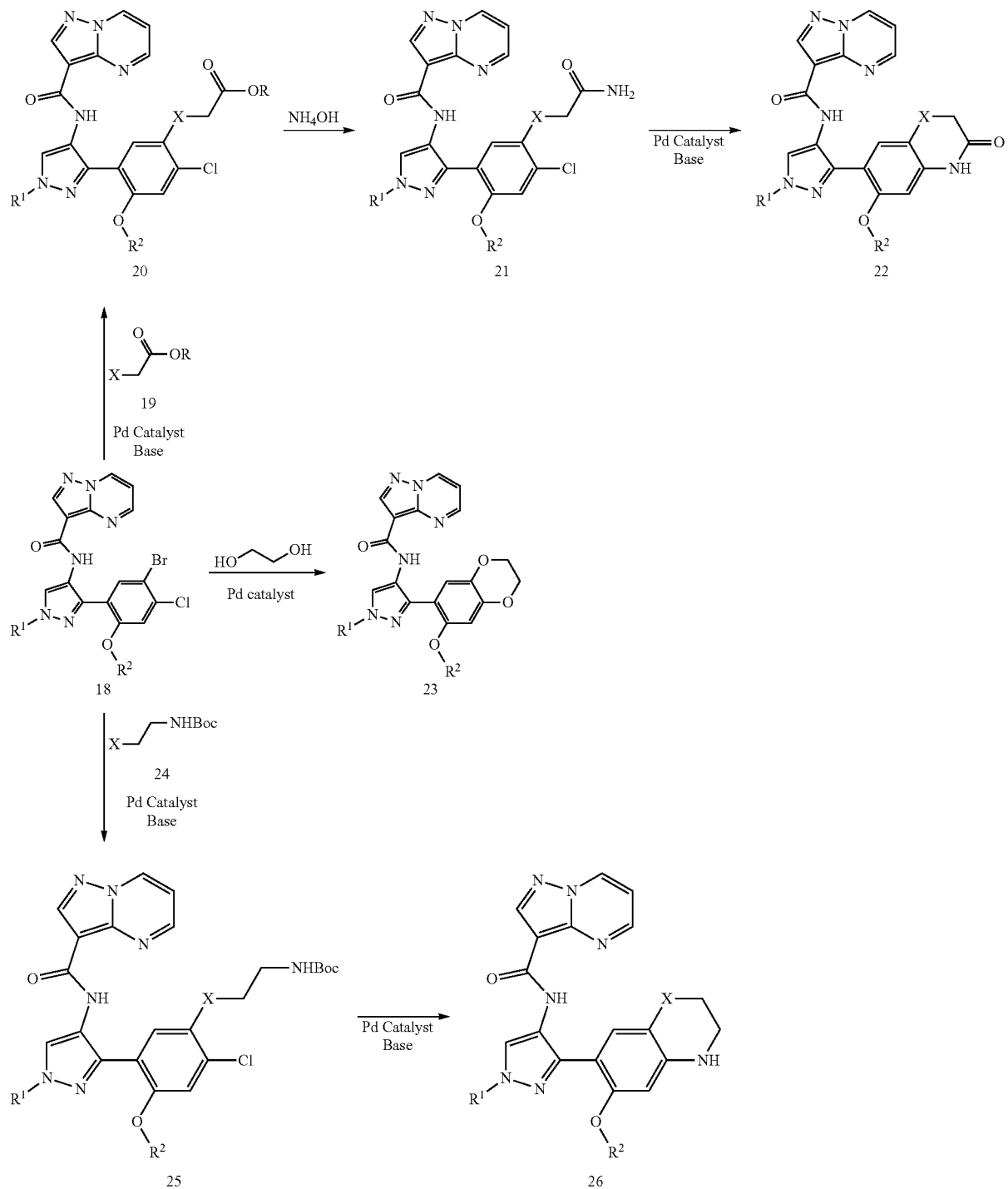

Reaction Scheme 7

Compounds of formulas 22, 23 and 26 may be prepared according to Reaction Scheme 7. Compounds of formula 18 may be treated with a reagent of formula 19 under palladium catalysed conditions to give compound of formula 20. A reaction of compound 20 with ammonia may be used to give compounds of formula 21 which may then be cyclised using palladium catalysed conditions to give compounds of formula 22. Alternatively, compounds of formula 18 may be coupled and cyclised under palladium catalysed conditions with ethane-1,2-diol to give compounds of formula 21. Alternatively, compounds of formula 18 may be coupled a reagent of formula 24 to give compound of formula 25. Compound 5 may be cyclised using palladium catalysed conditions using a catalyst such as BrettPhos Palladacycle Gen. 3 to give compounds of formula 26.

Reaction Scheme 8
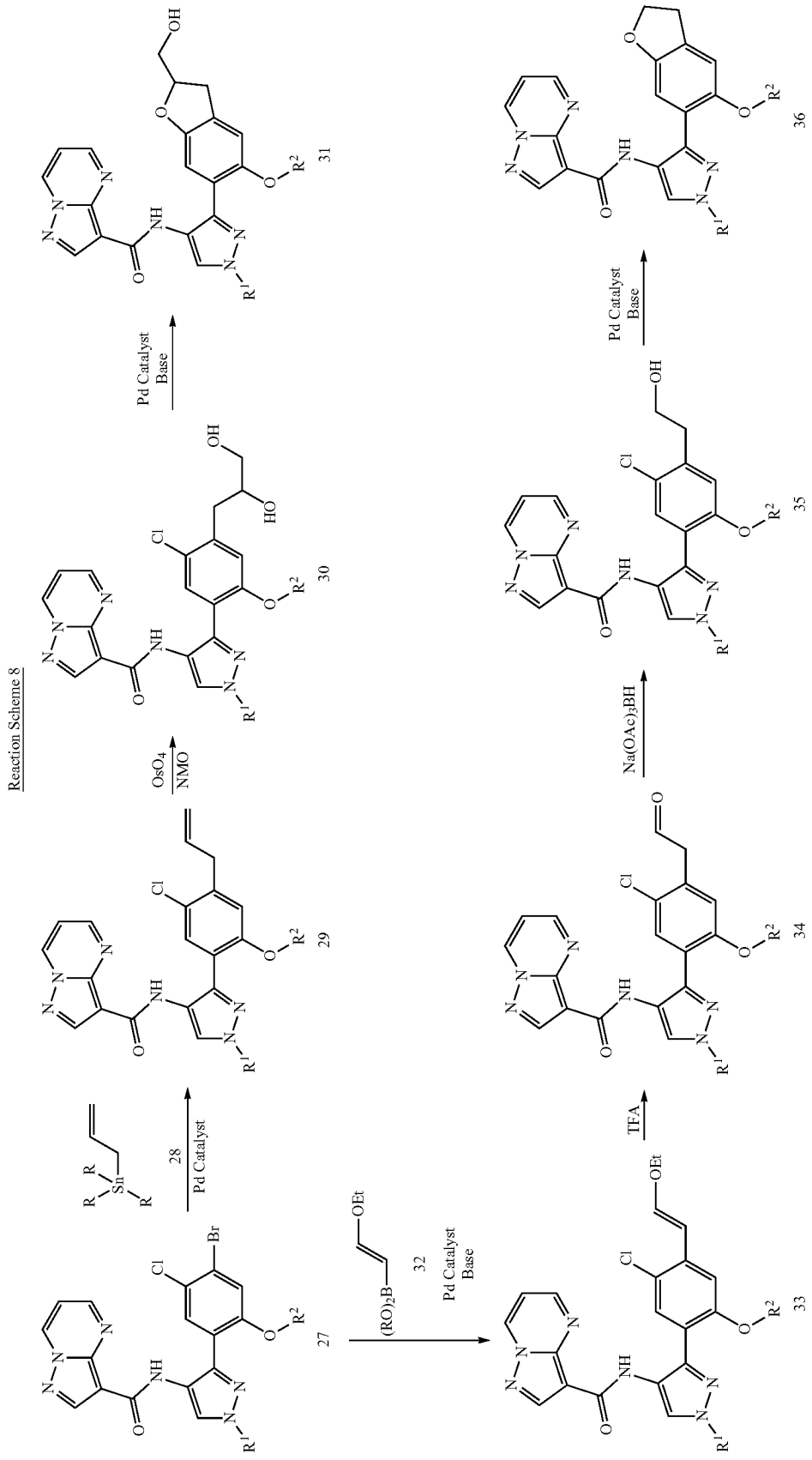

Compounds of formulas 31 and 36 may be prepared according to Reaction Scheme 8. Compound of formula 27 may be coupled with a boronate of formula 32 or stannane of formula 28, such as tributyl(prop-2-en-1-yl)stannane, under palladium catalysed conditions to give compounds of formula 29. Dihydroxylation of compounds 29 may be achieved using a reagent such as Osmium tetroxide in the presence of NMO. Compounds of formula 30 may be cyclised using palladium catalysed conditions to give compounds of formula 31. Alternatively, compounds of formula 27 may be coupled with a reagent such as 2-[(E)-2-ethoxyethenyl]-4,4,5,5-tetramethyl-1,3,2-dioxaborolane.

Treatment of compounds of formula 33 with a reagent such as TFA may give compound 34. Reduction of the aldehyde in compound 34 to the alcohol in compound 35 may be achieved using a reducing reagent such as sodium triacetoxyborohydride. Cyclisation of compounds 35 may be achieved using palladium catalysed conditions to give compounds of formula 36.

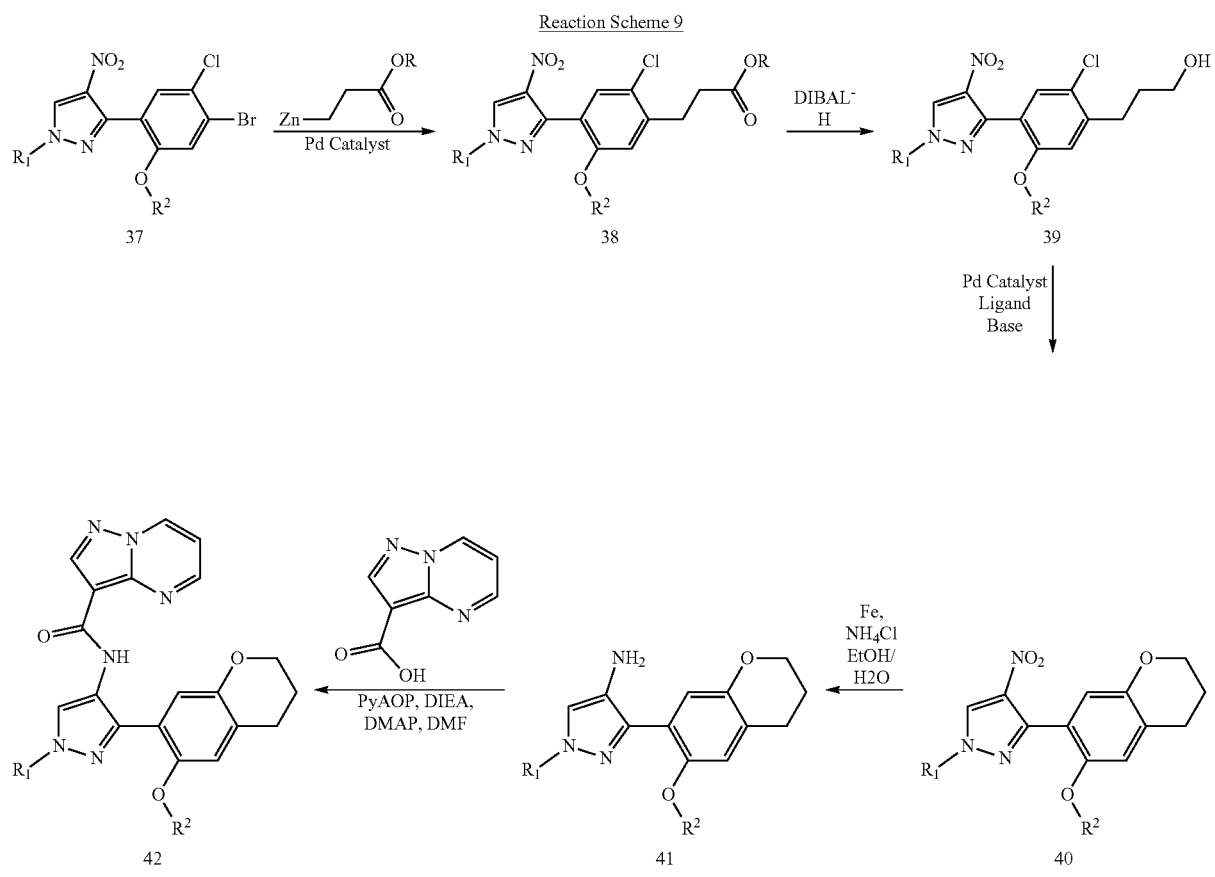

The synthesis of compounds of formula 42 may be achieved following Reaction Scheme 9. Compound of formula 37 may be treated with an alkyl zinc reagent such as ethyl 3-(bromozincio)propanoate under palladium catalyzed conditions to generate compounds of formula 38. Compound of formula 38 may be reduced to compounds of formula 39 using a reagent such as DIBAL-H. Cylisation to give compounds of formula 39 may be achieved under palladium catalyzed conditions. The nitro group of compounds 40 can be reduced in the presence of iron and ammonium chloride to generate amino pyrazoles 41. Amide bond coupling with commercially available pyrazolo[1,5-a]pyrimidine-3-carboxylic acid in the presence of PyAOP, DIPEA, and DMAP provides compounds 42.

Reaction Scheme 10

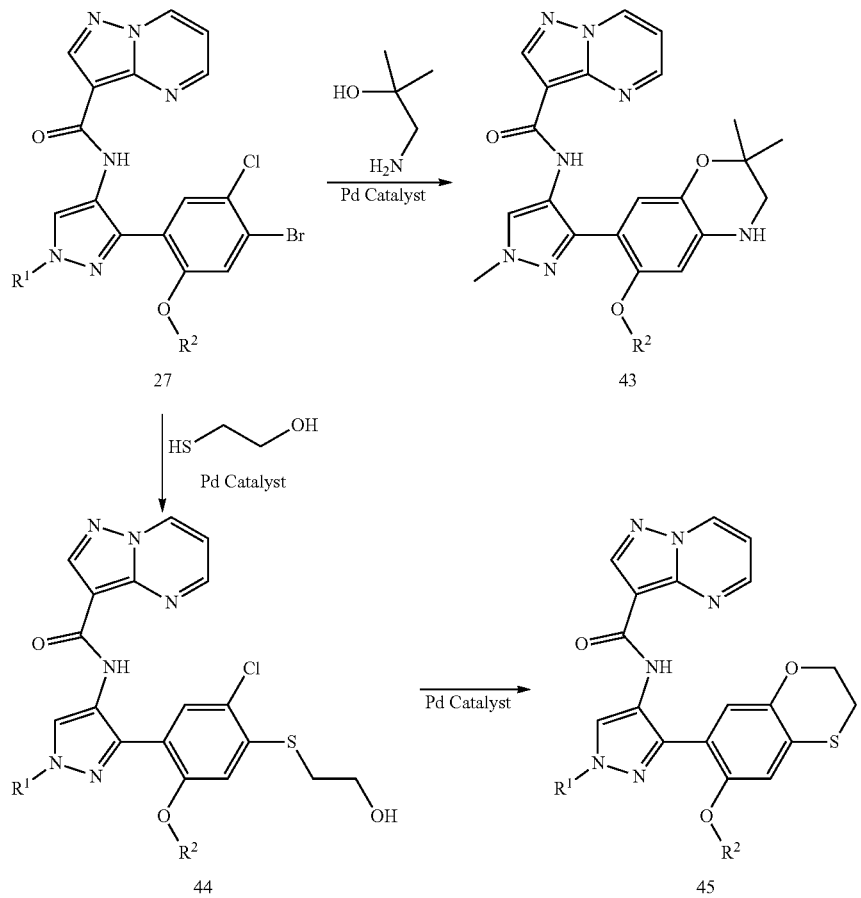

Compounds of formulas 43 and 45 may be prepared according to Reaction Scheme 10. Compounds of formula 27 may be treated with a reagent such as 1-amino-2-methylpropan-2-ol under palladium catalysed conditions with a catalyst such as [Pd(allyl)Cl]$_2$ and a ligand such as t-BuBrettPhos to give compound of formula 43. Alternatively, compounds of formula 27 may be coupled under palladium catalysed conditions with 2-hydroxyethanethiol to give compounds of formula 44. Compounds of formula 44 may be cyclised using palladium catalysed conditions using a catalyst such as [Pd(allyl)Cl]$_2$ and a ligand such as t-BuBrettPhos to give compounds of formula 45.

Reaction Scheme 11

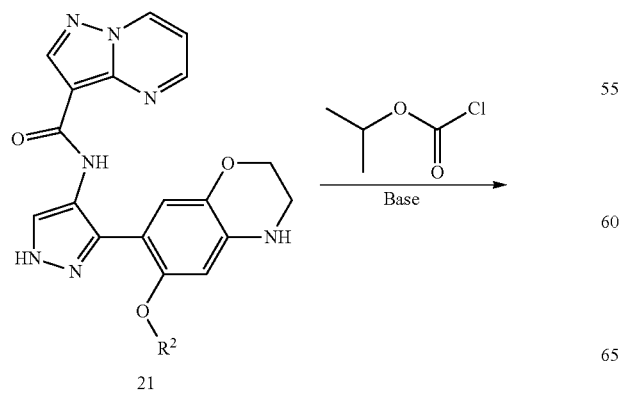

-continued

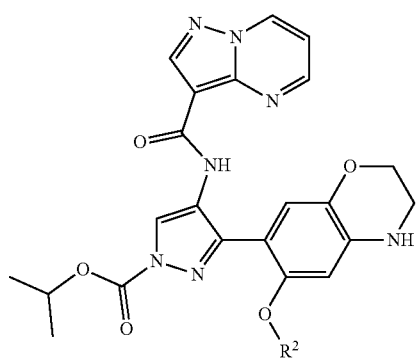

Compounds of formula 46 may be synthesized as shown in Reaction Scheme 11. Compounds of formula 21 may be treated with an alkylating reagent such as isopropyl chloroformate in the presence of a base such as diisopropylethylamine to afford compound of formula 46.

Reaction Scheme 12

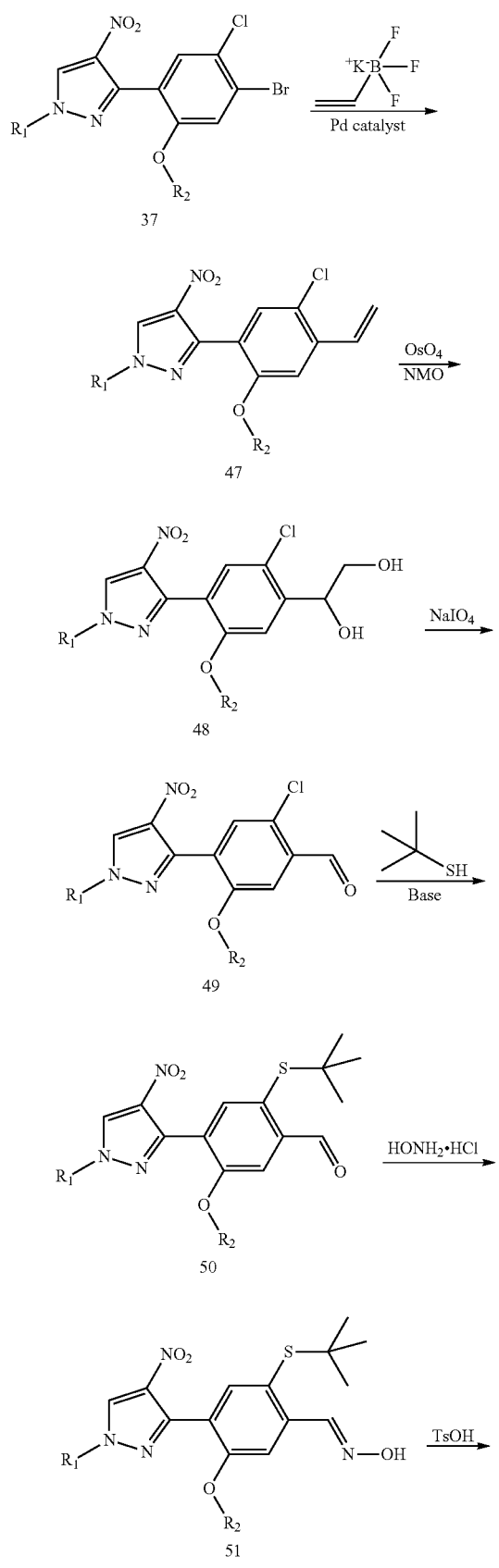

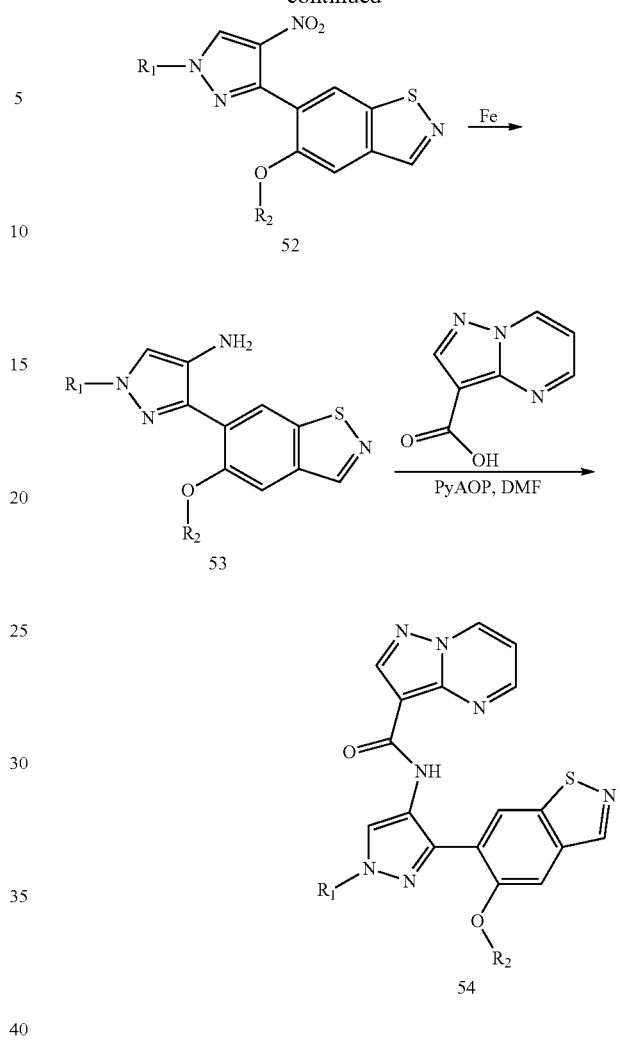

Compounds of formula 37 may be converted to compounds of formula 47 by reaction with a vinyl trifluoroboronate salt such as potassium trifluoro(vinyl)borate using a palladium catalyst such as Pd(dppf)Cl$_2$.CH$_2$Cl$_2$ under microwave irradiation. Compounds of formula 47 may then be oxidized to give compounds of formula 48 using a combination of reagents such as osmium tetroxide and NMO.

Compounds of formula 48 may be converted to compounds of formula 49 using a reagent such as sodium periodate. Treatment of compounds of formula 49 with a reagent such as 2-methylpropane-2-thiol may give compounds of formula 50. Compounds of formula 50 may be converted to compounds of formula 51 by reaction with a reagent such as hydroxylamine hydrochloride salt. Compounds of formula 51 may be cyclized to afford compounds of formula 52 by heating with a reagent such as tosic acid. The nitro group in compounds of formula 52 may be reduced to afford compounds of formula 53 by treatment with a reagent such as Iron. Amide bond coupling with commercially available pyrazolo[1,5-a]pyrimidine-3-carboxylic acid in the presence of PyAOP, DIPEA and DMAP provides compounds 54.

Reaction Scheme 13

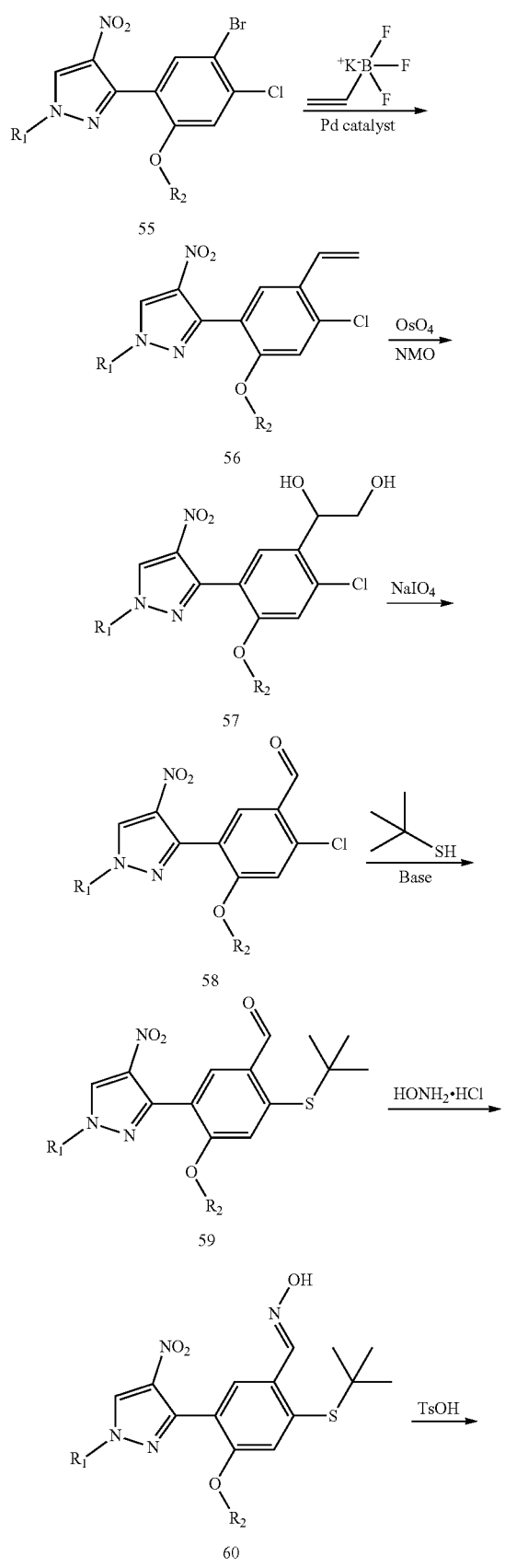

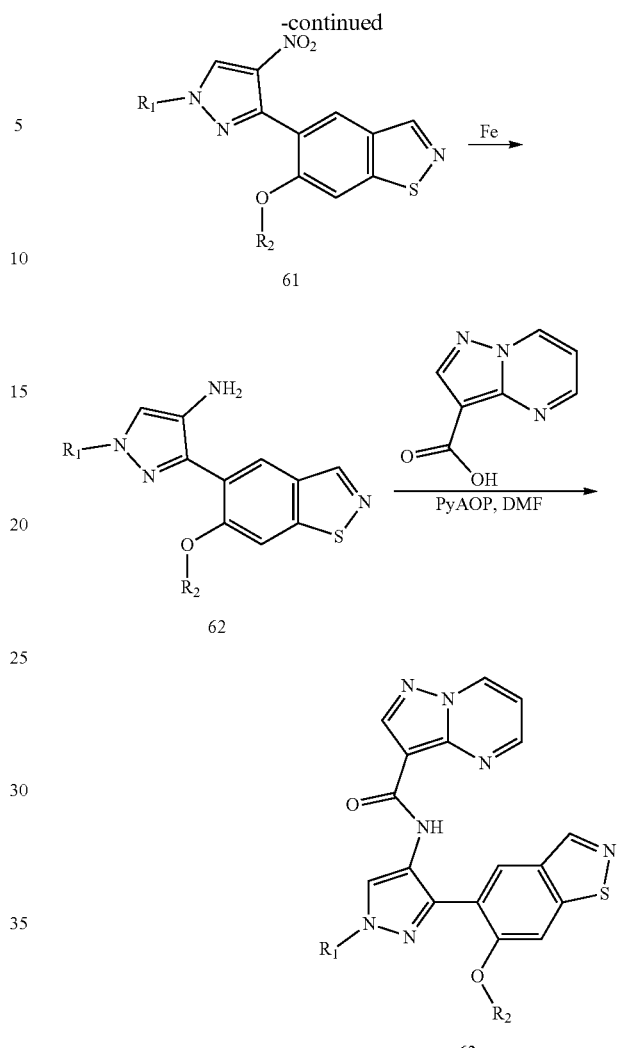

Compounds of formula 55 may be converted to compounds of formula 56 by reaction with a vinyl trifluoroboronate salt such as potassium trifluoro(vinyl)borate using a palladium catalyst such as Pd(dppf)Cl$_2$.CH$_2$Cl$_2$ under microwave irradiation. Compounds of formula 56 may then be oxidized to give compounds of formula 57 using a combination of reagents such as osmium tetroxide and NMO. Compounds of formula 57 may be converted to compounds of formula 58 using a reagent such as sodium periodate. Treatment of compounds of formula 58 with a reagent such as 2-methylpropane-2-thiol may give compounds of formula 59. Compounds of formula 59 may be converted to compounds of formula 60 by reaction with a reagent such as hydroxylamine hydrochloride salt. Compounds of formula 60 may be cyclized to afford compounds of formula 61 by heating with a reagent such as tosic acid. The nitro group in compounds of formula 61 may be reduced to afford compounds of formula 62 by treatment with a reagent such as Iron. Amide bond coupling with commercially available pyrazolo[1,5-a]pyrimidine-3-carboxylic acid in the presence of PyAOP, DIPEA and DMAP provides compounds 63.

Reaction Scheme 14

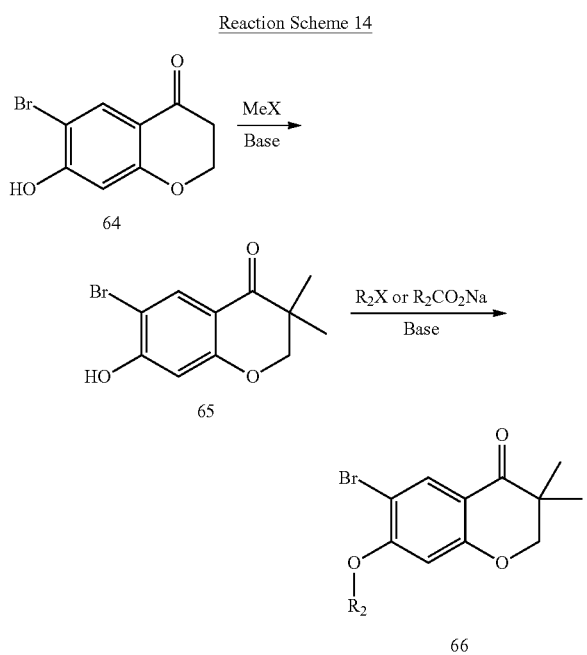

Compounds of formula 66 may be prepared as shown in reaction scheme 14. Benzopyranones 63 may be deprotonated with a base such as potassium tert butoxide and treated an alkylating agent such as methyl iodide to give compounds of formula 65. Compounds of formula 65 may be alkylated using a base such as cesium carbonate with an alkylating agent such as sodium 2-chloro-2,2-difluoroacetate.

It will be appreciated that where appropriate functional groups exist, compounds of various formulas or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulphonamide groups (—NHSO$_2$R' or —NR"SO$_2$R') groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—NH$_2$) may be obtained by reduction of a nitro (—NO$_2$) group, for example by catalytic hydrogenation, using for example hydrogen in the presence of a metal catalyst, for example palladium on a support such as carbon in a solvent such as ethyl acetate or an alcohol e.g., methanol. Alternatively, the transformation may be carried out by chemical reduction using for example a metal, e.g., tin or iron, in the presence of an acid such as hydrochloric acid.

In a further example, amine (—CH$_2$NH$_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g., a cyclic ether such as tetrahydrofuran, at an appropriate temperature, for example from about −78° C. to the reflux temperature of the solvent.

In a further example, amine (—NH$_2$) groups may be obtained from carboxylic acid groups (—CO$_2$H) by conversion to the corresponding acyl azide (—CON$_3$), Curtius rearrangement and hydrolysis of the resultant isocyanate (—N=C=O).

Aldehyde groups (—CHO) may be converted to amine groups (—CH$_2$NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —CO$_2$Et) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—CO$_2$R') may be converted into the corresponding acid group (—CO$_2$H) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—CO$_2$H) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —CO$_2$H to —CH$_2$CO$_2$H) by conversion to the corresponding acid chloride (—COCl) followed by Arndt-Eistert synthesis.

In a further example, —OH groups may be generated from the corresponding ester (e.g., —CO$_2$R'), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—CO$_2$H), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g., trifluoromethylsulfonyloxy or arylsulfonyloxy, e.g., p-toluenesulfonyloxy group using conditions known to those skilled in the art. For example, an alcohol may be reacted with thioyl chloride in a halogenated hydrocarbon (e.g., dichloromethane) to yield the corresponding chloride. A base (e.g., triethylamine) may also be used in the reaction.

In another example, alcohol, phenol or amide groups may be alkylated by coupling a phenol or amide with an alcohol in a solvent such as tetrahydrofuran in the presence of a phosphine, e.g., triphenylphosphine and an activator such as diethyl-, diisopropyl, or dimethylazodicarboxylate. Alternatively alkylation may be achieved by deprotonation using a suitable base e.g., sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g., around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g., palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

Methods of Separation

In each of the exemplary Reaction Schemes it may be advantageous to separate reaction products from one another or from starting materials. The desired products of each step or series of steps is separated or purified (hereinafter separated) to the desired degree of homogeneity by the techniques common in the art. Typically such separations involve multiphase extraction, crystallization or trituration from a solvent or solvent mixture, distillation, sublimation, or chromatography. Chromatography can involve any number of methods including, for example: reverse-phase and normal phase; size exclusion; ion exchange; supercritical fluid; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. Example separation methods include boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column or supercritical fluid chromatography.

A single stereoisomer, e.g., an enantiomer, substantially free of its stereoisomer may be obtained by resolution of the racemic mixture using a method such as formation of diastereomers using optically active resolving agents (Eliel, E. and Wilen, S., Stereochemistry of Organic Compounds, John Wiley & Sons, Inc., New York, 1994; Lochmuller, C. H., J. Chromatogr., 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., Stereochemistry of Organic Compounds, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob, J. Org. Chem. 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111, incorporated herein by reference). By method (3), a racemic mixture of two enantiomers can be separated by chromatography using a chiral stationary phase (Chiral Liquid Chromatography W. J. Lough, Ed., Chapman and Hall, New York, (1989); Okamoto, J. of Chromatogr. 513: 375-378 (1990)). Enriched or purified enantiomers can be distinguished by methods used to distinguish other chiral molecules with asymmetric carbon atoms, such as optical rotation and circular dichroism. The absolute stereochemistry of chiral centers and enatiomers can be determined by x-ray crystallography.

Positional isomers, for example E and Z forms, of compounds of Formula IA, or a compound of Table 1 or of Examples 1-154 and intermediates for their synthesis, may be observed by characterization methods such as NMR and analytical HPLC. For certain compounds where the energy barrier for interconversion is sufficiently high, the E and Z isomers may be separated, for example by preparatory HPLC.

Pharmaceutical Compositions and Administration

The compounds with which the invention is concerned are JAK kinase inhibitors, such as JAK1 inhibitors, and are useful in the treatment of several diseases, for example, inflammatory diseases, such as asthma.

Accordingly, another embodiment provides pharmaceutical compositions or medicaments containing a compound of the invention, such as a compound of Formula IA, or a compound of Table 1 or of Examples 1-154, or a pharmaceutically acceptable salt thereof, and a pharmaceutically acceptable carrier, diluent or excipient, as well as methods of using the compounds of the invention to prepare such compositions and medicaments.

In one example, a compound of Formula IA, or a compound of Table 1 or of Examples 1-154, or a pharmaceutically acceptable salt thereof, may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but typically ranges anywhere from about 3 to about 8. In one example, a compound of Formula IA, or a compound of Table 1 or of Examples 1-154, or a pharmaceutically acceptable salt thereof, is formulated in an acetate buffer, at pH 5. In another embodiment, the compounds of the present invention, such as a compound of Formula IA, or a compound of Table 1 or of Examples 1-154, or a pharmaceutically acceptable salt thereof, are sterile. The compound, or a pharmaceutically acceptable salt thereof, may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases.

The compounds of the invention, such as a compound of Formula IA, or a compound of Table 1 or of Examples 1-154, or a pharmaceutically acceptable salt thereof, may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration. In some embodiments, inhaled administration is employed.

The compounds of the present invention, such as a compound of Formula IA, or a compound of Table 1 or of Examples 1-154, or a pharmaceutically acceptable salt thereof, may be administered in any convenient administrative form, e.g., tablets, powders, capsules, lozenges, granules, solutions, dispersions, suspensions, syrups, sprays, vapors, suppositories, gels, emulsions, patches, etc. Such compositions may contain components conventional in pharmaceutical preparations, e.g., diluents (e.g., glucose, lactose or mannitol), carriers, pH modifiers, buffers, sweeteners, bulking agents, stabilizing agents, surfactants, wetting agents, lubricating agents, emulsifiers, suspending agents, preservatives, antioxidants, opaquing agents, glidants, processing aids, colorants, perfuming agents, flavoring agents, other known additives as well as further active agents.

Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. For example, carriers include solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated. Exemplary excipients include dicalcium phosphate, mannitol, lactose, starch, magnesium stearate, sodium saccharine, cellulose, magnesium carbonate or combinations thereof. A pharmaceutical composition may comprise different types of carriers or excipients depending on whether it is to be administered in solid, liquid or aerosol form, and whether it need to be sterile for such routes of administration.

For example, tablets and capsules for oral administration may be in unit dose presentation form, and may contain conventional excipients such as binding agents, for example syrup, acacia, gelatin, sorbitol, tragacanth, or polyvinylpyrrolidone; fillers, for example, lactose, sugar, maizestarch, calcium phosphate, sorbitol or glycine; tabletting lubricant, for example, magnesium stearate, talc, polyethylene glycol or silica; disintegrants, for example, potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example, sorbitol, syrup, methyl cellulose, glucose syrup, gelatin hydrogenated edible fats; emulsifying agents, for example, lecithin, sorbitan monooleate, or acacia; non-aqueous vehicles (which may include edible oils), for example, almond oil, fractionated coconut oil, oily esters such as glycerine, propylene glycol, or ethyl alcohol; preservatives, for example, methyl or propyl p-hydroxybenzoate or sorbic acid, and if desired conventional flavoring or coloring agents.

For topical application to the skin, a compound may be made up into a cream, lotion or ointment. Cream or ointment formulations which may be used for the drug are conventional formulations well known in the art, for example as described in standard textbooks of pharmaceutics such as the British Pharmacopoeia.

Compounds of the invention, such as a compound of Formula IA, or a compound of Table 1 or of Examples 1-154, or a pharmaceutically acceptable salt thereof, may also be formulated for inhalation, for example, as a nasal spray, or dry powder or aerosol inhalers. For delivery by inhalation, the compound is typically in the form of microparticles, which can be prepared by a variety of techniques, including spray-drying, freeze-drying and micronisation. Aerosol generation can be carried out using, for example, pressure-driven jet atomizers or ultrasonic atomizers, such as by using propellant-driven metered aerosols or propellant-free administration of micronized compounds from, for example, inhalation capsules or other "dry powder" delivery systems.

By way of example, a composition of the invention may be prepared as a suspension for delivery from a nebulizer or as an aerosol in a liquid propellant, for example, for use in a pressurized metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In some embodiments, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of, for example, greater than 90 µm.

In the case of an aerosol-based formulation, an example is:

| | |
|---|---|
| Compound of the invention* | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

*Such as a compound of Formula IA, or a compound of Table 1 or of Examples 1-154.

A compound, such as a compound of Formula IA, or a compound of Table 1 or of Examples 1-154, or a pharmaceutically acceptable salt thereof, may be dosed as described depending on the inhaler system used. In addition to the compound, the administration forms may additionally contain excipients as described above, or, for example, propellants (e.g., Frigen in the case of metered aerosols), surface-active substances, emulsifiers, stabilizers, preservatives, flavorings, fillers (e.g., lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g., Nebulator®, Volumatic®), and automatic devices emitting a puffer spray (Autohaler®), for metered aerosols, in the case of powder inhalers in particular, a number of technical solutions are available (e.g., Diskhaler®, Rotadisk®, Turbohaler® or the inhalers, for example, as described in U.S. Pat. No. 5,263,475, incorporated herein by reference). Additionally, compounds of the invention, such as a compound of Formula IA, or a compound of Table 1 or of Examples 1-154, or a pharmaceutically acceptable salt thereof, may be delivered in multi-chamber devices thus allowing for delivery of combination agents.

The compound, such as a compound of Formula IA, or a compound of Table 1 or of Examples 1-154, or a pharmaceutically acceptable salt thereof, may also be administered parenterally in a sterile medium. Depending on the vehicle and concentration used, the compound can either be suspended or dissolved in the vehicle. Advantageously, adjuvants such as a local anaesthetic, preservative or buffering agents can be dissolved in the vehicle.

Targeted Inhaled Drug Delivery

Optimisation of drugs for delivery to the lung by topical (inhaled) administration has been recently reviewed (Cooper, A. E. et al. Curr. Drug Metab. 2012, 13, 457-473). Due to limitations in the delivery device, the dose of an inhaled drug is likely to be low (approximately <1 mg/day) in humans which necessitates highly potent molecules. For compounds destined to be delivered via dry powder inhalation there is also a requirement to be able to generate crystalline forms of the compound that can be micronized to 1-5 µm in size. Additionally, the compound needs to maintain a sufficient concentration in the lung over a given time period so as to be able to exert a pharmacological effect of the desired duration, and for pharmacological targets where systemic inhibition of said target is undesired, to have a low systemic exposure. The lung has an inherently high permeability to both large molecules (proteins, peptides) as well as small molecules with concomitant short lung half-lives, thus it is necessary to attenuate the lung absorption rate through modification of one or more features of the compounds: minimizing membrane permeability, reducing dissolution rate, or introducing a degree of basicity into the compound to enhance binding to the phospholipid-rich lung tissue or through trapping in acidic sub-cellular compartments such as lysosomes (pH 5). Accordingly, in some embodiments, compounds of the present invention exhibit one or more of these features.

Methods of Treatment with and Uses of Janus Kinase Inhibitors

The compounds of the present invention, such as a compound of Formula IA, or a compound of Table 1 or of Examples 1-154, or a pharmaceutically acceptable salt thereof, inhibit the activity of a Janus kinase, such as JAK1 kinase. For example, a compound of the present invention, such as a compound of Formula IA, or a compound of Table 1 or of Examples 1-154, or a pharmaceutically acceptable salt thereof, inhibits the phosphorylation of signal transducers and activators of transcription (STATs) by JAK1 kinase as well as STAT mediated cytokine production. Compounds of the present invention, such as a compound of Formula IA, or a compound of Table 1 or of Examples 1-154, or a pharmaceutically acceptable salt thereof, are useful for inhibiting JAK1 kinase activity in cells through cytokine pathways, such as IL-6, IL-15, IL-7, IL-2, IL-4, IL-9, IL-10, IL-13, IL-21, G-CSF, IFNalpha, IFNbeta, or IFNgamma pathways. Accordingly, in one embodiment is provided a method of contacting a cell with a compound of the present invention, such as a compound of Formula IA, or a compound of Table 1 or of Examples 1-154, or a pharmaceutically acceptable salt thereof, to inhibit a Janus kinase activity in the cell (e.g., JAK1 activity).

The compounds of the present invention, such as compounds of Formula IA, or a compound of Table 1 or of Examples 1-154, or a pharmaceutically acceptable salt thereof, can be used for the treatment of immunological disorders driven by aberrant IL-6, IL-15, IL-7, IL-2, IL-4, IL9, IL-10, IL-13, IL-21, G-CSF, IFNalpha, IFNbeta, or IFNgamma cytokine signaling.

Accordingly, one embodiment includes compounds of the present invention, such as a compound of Formula IA, or a compound of Table 1 or of Examples 1-154, or a pharmaceutically acceptable salt thereof, for use in therapy.

In some embodiments, there is provided use a compound of the present invention, such as a compound of Formula IA, or a compound of Table 1 or of Examples 1-154, or a pharmaceutically acceptable salt thereof, in the treatment of an inflammatory disease. Further provided is use of a compound of the present invention, such as a compound of Formula IA, or a compound of Table 1 or of Examples 1-154, or a pharmaceutically acceptable salt thereof, for the preparation of a medicament for the treatment of an inflammatory disease, such as asthma. Also provided is a compound of the present invention, such as a compound of Formula IA, or a compound of Table 1 or of Examples 1-154, or a pharmaceutically acceptable salt thereof, for use in the treatment of an inflammatory disease, such as asthma.

Another embodiment includes a method of preventing, treating or lessening the severity of a disease or condition, such as asthma, responsive to the inhibition of a Janus kinase activity, such as JAK1 kinase activity, in a patient. The method can include the step of administering to a patient a therapeutically effective amount of a compound of the present invention, such as a compound of Formula IA, or a compound of Table 1 or of Examples 1-154, or a pharmaceutically acceptable salt thereof. In one embodiment, the disease or condition responsive to the inhibition of a Janus kinase, such as JAK1 kinase, is asthma.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation (e.g., transplant rejection), immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the inflammatory disease is rheumatoid arthritis, psoriasis, asthma, inflammatory bowel disease, contact dermatitis or delayed hypersensitivity reactions. In one embodiment, the autoimmune disease is rheumatoid arthritis, lupus or multiple sclerosis.

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the disease is a myeloproliferative disorder. In one embodiment, the myeloproliferative disorder is polycythemia vera, essential thrombocytosis, myelofibrosis or chronic myelogenous leukemia (CML).

Another embodiment includes the use of a compound of the present invention, such as a compound of Formula IA, or a compound of Table 1 or of Examples 1-154, or a pharmaceutically acceptable salt thereof, for the manufacture of a medicament for the treatment of a disease described herein (e.g., an inflammatory disorder, an immunological disorder or cancer). In one embodiment, the invention provides a method of treating a disease or condition as described herein e.g., an inflammatory disorder, an immunological disorder or cancer) by targeting inhibition of a JAK kinase, such as JAK1.

Combination Therapy

The compounds of the present invention, such as a compound of Formula IA, or a compound of Table 1 or of Examples 1-154, or a pharmaceutically acceptable salt thereof, may be employed alone or in combination with other agents for treatment. The second compound of a pharmaceutical composition or dosing regimen typically has complementary activities to the compound of this invention such that they do not adversely affect each other. Such agents are suitably present in combination in amounts that are effective for the purpose intended. The compounds may be administered together in a unitary pharmaceutical composition or separately and, when administered separately this may occur simultaneously or sequentially. Such sequential administration may be close or remote in time.

For example, other compounds may be combined with compounds with which the invention is concerned for the prevention or treatment of inflammatory diseases, such as asthma. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: an adenosine A2A receptor antagonist; an anti-infective; a non-steroidal Glucocorticoid Receptor (GR Receptor) agonist; an antioxidant; a β2 adrenoceptor agonist; a CCR1 antagonist; a chemokine antagonist (not CCR1); a corticosteroid; a CRTh2 antagonist; a DP1 antagonist; a formyl peptide receptor antagonist; a histone deacetylase activator; a chloride channel hCLCA1 blocker; an epithelial sodium channel blocker (ENAC blocker; an inter-cellular adhesion molecule 1 blocker (ICAM blocker); an IKK2 inhibitor; a JNK inhibitor; a cyclooxygenase inhibitor (COX inhibitor); a lipoxygenase inhibitor; a leukotriene receptor antagonist; a dual β2 adrenoceptor agonist/M3 receptor antagonist (MABA compound); a MEK-1 inhibitor; a myeloperoxidase inhibitor (MPO inhibitor); a muscarinic antagonist; a p38 MAPK inhibitor; a phosphodiesterase PDE4 inhibitor; a phosphatidylinositol 3-kinase δ inhibitor (PI3-kinase δ inhibitor); a phosphatidylinositol 3-kinase γ inhibitor (PI3-kinase γ inhibitor); a peroxisome proliferator activated receptor agonist (PPARγ agonist); a protease inhibitor; a retinoic acid receptor modulator (RAR γ modulator); a statin; a thromboxane antagonist; a TLR7 receptor agonist; or a vasodilator.

In addition, compounds of the invention, such as a compound of Formula IA, or a compound of Table 1 or of Examples 1-154, or a pharmaceutically acceptable salt thereof, may be combined with: (1) corticosteroids, such as alclometasone dipropionate, amelometasone, beclomethasone dipropionate, budesonide, butixocort propionate, biclesonide, blobetasol propionate, desisobutyrylciclesonide, dexamethasone, dtiprednol dicloacetate, fluocinolone acetonide, fluticasone furoate, fluticasone propionate, loteprednol etabonate (topical) or mometasone furoate; (2) β2-adrenoreceptor agonists such as salbutamol, albuterol, terbutaline, fenoterol, bitolterol, carbuterol, clenbuterol, pirbuterol, rimoterol, terbutaline, tretoquinol, tulobuterol and long acting β2-adrenoreceptor agonists such as metaproterenol, isoproterenol, isoprenaline, salmeterol, indacaterol, formoterol (including formoterol fumarate), arformoterol, carmoterol, abediterol, vilanterol trifenate, olodaterol; (3) corticosteroid/long acting β2 agonist combination products such as salmeterol/fluticasone propionate (Advair®, also sold as Seretide®), formoterol/budesonide (Symbicort®), formoterol/fluticasone propionate (Flutiform®), formoterol/ciclesonide, formoterol/mometasone furoate, indacaterol/mometasone furoate, vilanterol trifenate/fluticasone furoate, or arformoterol/ciclesonide; (4) anticholinergic agents, for example, muscarinic-3 (M3) receptor antagonists such as ipratropium bromide, tiotropium bromide, aclidinium (LAS-34273), glycopyrronium bromide, umeclidinium bromide; (5) M3-anticholinergic/β2-adrenoreceptor agonist combination products such as vilanterol/umeclidinium (Anoro® Ellipta®), olodaterol/tiotropium bromide, glycopyrronium bromide/indacaterol (Ultibro®, also sold as Xoterna®), fenoterol hydrobromide/ipratropium bromide (Berodual®), albuterol sulfate/ipratropium bromide (Combivent®), formoterol fumarate/glycopyrrolate, or aclidinium bromide/formoterol (6) dual pharmacology M3-anticholinergic/β2-adrenoreceptor agonists such as batefenterol succinate, AZD-2115 or LAS-190792; (7) leukotriene modulators, for example, leukotriene antagonists such as montelukast, zafirulast or pranlukast or leukotriene biosynthesis inhibitors such as zileuton, or LTB4 antagonists such as amelubant, or FLAP inhibitors such as fiboflapon, GSK-2190915; (8) phosphodiesterase-IV (PDE-IV) inhibitors (oral or inhaled), such as roflumilast, cilomilast, oglemilast, rolipram, tetomilast, AVE-8112, revamilast, CHF 6001; (9) antihistamines, for example, selective histamine-1 (H1) receptor antagonists such as fexofenadine, citirizine, loratidine or astemizole or dual H1/H3 receptor antagonists such as GSK 835726, or GSK 1004723; (10) antitussive agents, such as codeine or dextramorphan; (11) a mucolytic, for example, N-acetyl cysteine or fudostein; (12) a expectorant/mucokinetic modulator, for example, ambroxol, hypertonic solutions (e.g., saline or mannitol) or surfactant; (13) a peptide mucolytic, for example, recombinant human deoxyribonuclease I (dornase-alpha and rhDNase) or helicidin; (14) antibiotics, for example azithromycin, tobramycin or aztreonam; (15) non-selective COX-1/COX-2 inhibitors, such as ibuprofen or ketoprofen; (16) COX-2 inhibitors, such as celecoxib and rofecoxib; (17) VLA-4 antagonists, such as those described in WO97/03094 and WO97/02289, each incorporated herein by reference; (18) TACE inhibitors and TNF-α inhibitors, for example anti-TNF monoclonal antibodies, such as Remicade® and CDP-870 and TNF receptor immunoglobulin molecules, such as Enbrel®; (19) inhibitors of matrix metalloprotease, for example MMP-12; (20) human neutrophil elastase inhibitors, such as BAY-85-8501 or those described in WO2005/026124, WO2003/053930 and WO06/082412, each incorporated herein by reference; (21) A2b antagonists such as those described in WO2002/42298, incorporated herein by reference; (22) modulators of chemokine receptor function, for example antagonists of CCR3 and CCR8; (23) compounds which modulate the action of other prostanoid receptors, for example, a thromboxane $A_2$ antagonist; DP1 antagonists such as laropiprant or asapiprant CRTH2 antagonists such as OC000459, fevipiprant, ADC 3680 or ARRY 502; (24) PPAR agonists including PPAR alpha agonists (such as fenofibrate), PPAR delta agonists, PPAR gamma agonists such as pioglitazone, rosiglitazone and balaglitazone; (25) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (26) A2a agonists such as those described in EP1052264 and EP1241176; (27) CXCR2 or IL-8 antagonists such as AZD-5069, AZD-4721, danirixin; (28) IL-R signalling modulators such as kineret and ACZ 885; (29) MCP-1 antagonists such as ABN-912; (30) a p38 MAPK inhibitor such as BCT197, JNJ49095397, losmapimod or PH-797804; (31) TLR7 receptor agonists such as AZD 8848; (32) PI3-kinase inhibitors such as RV1729 or GSK2269557.

In some embodiments, the compounds of the present invention, such as a compound of Formula IA, or a compound of Table 1 or of Examples 1-154, or a pharmaceutically acceptable salt thereof, can be used in combination with one or more additional drugs, for example anti-hyperproliferative, anti-cancer, cytostatic, cytotoxic, anti-inflammatory or chemotherapeutic agents, such as those agents disclosed in U.S. Publ. Appl. No. 2010/0048557, incorporated herein by reference. A compound of the present invention, such as a compound of Formula IA, or a compound of Table 1 or of Examples 1-154, or a pharmaceutically acceptable salt thereof, can be also used in combination with radiation therapy or surgery, as is known in the art.

Articles of Manufacture

Another embodiment includes an article of manufacture (e.g., a kit) for treating a disease or disorder responsive to the inhibition of a Janus kinase, such as a JAK1 kinase. The kit can comprise:

(a) a first pharmaceutical composition comprising a compound of the present invention, such as a compound of Formula IA, or a compound of Table 1 or of Examples 1-154, or a pharmaceutically acceptable salt thereof; and (b) instructions for use.

In another embodiment, the kit further comprises:

(c) a second pharmaceutical composition, such as a pharmaceutical composition comprising an agent for treatment as described above, such as an agent for treatment of an inflammatory disorder, or a chemotherapeutic agent.

In one embodiment, the instructions describe the simultaneous, sequential or separate administration of said first and second pharmaceutical compositions to a patient in need thereof.

In one embodiment, the first and second compositions are contained in separate containers. In another embodiment, the first and second compositions are contained in the same container.

Containers for use include, for example, bottles, vials, syringes, blister pack, etc. The containers may be formed from a variety of materials such as glass or plastic. The container includes a compound of the present invention, such as a compound of Formula IA, or a compound of Table 1 or of Examples 1-154, or a pharmaceutically acceptable salt thereof, or composition thereof, which is effective for treating the condition and may have a sterile access port (for example the container may be an intravenous solution bag or a vial having a stopper pierceable by a hypodermic injection needle). The label or package insert indicates that the compound or composition is used for treating the condition of choice, such as asthma or cancer. In one embodiment, the label or package inserts indicates that the compound or composition can be used to treat a disorder. In addition, the label or package insert may indicate that the patient to be treated is one having a disorder characterized by overactive or irregular Janus kinase activity, such as overactive or irregular JAK1 activity. The label or package insert may also indicate that the compound or composition can be used to treat other disorders.

Alternatively, or additionally, the kit may further comprise a second (or third) container comprising a pharmaceutically acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of the present invention, and alternative methods for preparing the compounds are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

ABBREVIATIONS t-BuBrettPhos 2-(Di-tert-butylphosphino)-2',4',6'-triisopropyl-3,6-dimethoxy-1,1'-biphenyl Brettphos 2-(Dicyclohexylphosphino)3,6-dimethoxy-2',4',6'-triisopropyl-1,1'-biphenyl
t-BuOH tert butanol
$CH_3CN$ Acetonitrile
$CuBr_2$ Copper (II) bromide
$Cs_2CO_3$ Cesium carbonate
CsF Cesium fluoride
CuI Copper (I) iodide
DCM Dichloromethane
DIBA1-H Disiobutylaluminium hydride
DIPEA Diisopropylethylamine
DMA N,N-Dimethylacetamide
DMF N,N-Dimethylformamide
DMSO Dimethylsulfoxide
DMSO-d6 Deuterated dimethylsulfoxide
EtOAc Ethyl acetate
EtOH Ethanol
g Gram
HATU (O-(7-azabenzotriazol-1-yl)-N,N,N',N',N-tetramethyluronium hexafluorophosphate)
HCl Hydrochloric acid
HM-N Isolute HM-N is a modified form of diatomaceous earth
$K_2CO_3$ Potassium carbonate
KI Potassium iodide
L Litre
LiHMDS Lithium bis(trimethylsilyl)amide
$Na_2S_2O_3$ Sodium thiosulfate
$Na_2SO_3$ Sodium sulfite
MeCN Acetonitrile
MeOH Methanol
NBS N-Bromosuccinimide
$NH_4Cl$ Ammonium chloride
NMO N-Methyl morpholine N-oxide
mg Milligram
mL Millilitre
$NaBH(OAc)_3$ Sodium triacetoxyborohydride
NaOH Sodium hydroxide
$Na_2SO_4$ Sodium sulfate
$OsO_4$ Osmium tetroxide
$Pd_2(dba)_3$ Tris(dibenzylidineacetone)palladium(0)
$Pd_2(dba)_3.CHCl_3$ Tris(dibenzylidineacetone)palladium(0) complex with chloroform
$Pd(dppf)Cl_2.CH_2Cl_2$ [1,1'-Bis(diphenylphosphino)ferrocene]-dichloropalladium-(II), complex with dichloromethane
$PdCl_2(allyl)_2$ Allyl palladium (II) chloride dimer
$Pd(PPh_3)_4$ Tetrakis(triphenylphosphine)palladium(0)
PyAOP 7-Azabenzotriazol-1-yloxy)tripyrrolidinophosphonium hexafluorophosphate
RT Ambient temperature
$R_T$ Retention time
TBAF Tetra-n-butylammonium fluoride
THF Tetrahydrofuran
TFA Trifluoroacetic acid
TLC Thin layer chromatography
XantPhos 4,5-Bis(diphenylphosphino)-9,9-dimethylxanthene
X-phos 2-Dicyclohexylphosphino-2',4',6'-triisopropylbiphenyl
$ZnCl_2$ Zinc (II) chloride NMR Analytical Methods 1H NMR spectra were recorded at ambient temperature using a Bruker Avance III 300 (300 MHz) spectrometer with a 5 mm Broadband liquid probe BBFO with ATM+Z and a Bruker Avance III HD (400 MHz) spectrometer with a 5 mm Broadband liquid probe BBFO with ATM+Z. Chemical shifts are expressed in ppm relative to tetramethylsilane. The following abbreviations have been used: br=broad signal, s=singlet, d=doublet, dd=double doublet, t=triplet, q=quartet, m=multiplet.

LCMS Analytical Methods

High Pressure Liquid Chromatography—Mass Spectrometry (LCMS) experiments to determine retention times ($R_T$) and associated mass ions were performed using one of the following methods with either UV detector monitoring at 220 nm and 254 nm or evaporative light scattering detection, and mass spectrometry scanning 110-800 amu in ESI+ ionization mode.

Method A

Experiments were performed on a SHIMADZU 20A HPLC with a C18-reverse-phase column (50×3 mm Shim-Pack XR-ODS, 2.2 µm particle size), elution with solvent A: water+0.05% trifluoroacetic acid; solvent B: acetonitrile+0.05% trifluoroacetic acid. Gradient:

| Detection-UV (220 and 254 nm) and ELSD | | | |
|---|---|---|---|
| Gradient-Time | flow ml/min | % A | % B |
| 0.00 | 1.0 | 80 | 20 |
| 3.70 | 1.0 | 35 | 65 |
| 4.60 | 1.0 | 35 | 65 |
| 4.70 | 1.0 | 95 | 5 |

Method B

Experiments were performed on a SHIMADZU 20A HPLC with a C18-reverse-phase column (50×2.1 mm Xtimate TM-C18, 2.7 µm particle size), elution with solvent A: water+0.05% trifluoroacetic acid; solvent B: acetonitrile+0.05% trifluoroacetic acid. Gradient:

| Detection-UV (220 and 254 nm) and ELSD | | | |
|---|---|---|---|
| Gradient-Time | flow ml/min | % A | % B |
| 0.00 | 1.0 | 95 | 5 |
| 2.00 | 1.0 | 5 | 95 |
| 2.60 | 1.0 | 5 | 95 |
| 2.70 | 1.0 | 95 | 5 |

Method C

Experiments were performed on a SHIMADZU 20A HPLC with a C18-reverse-phase column (50×3 mm, Gemini-NX 3µ-C18 110A, 3.0 µm particle size), elution with solvent A: water/5 mM NH$_4$HCO$_3$; solvent B: acetonitrile. Gradient:

| Detection-UV (220 and 254 nm) and ELSD | | | |
|---|---|---|---|
| Gradient-Time | flow ml/min | % A | % B |
| 0.00 | 1.2 | 90 | 10 |
| 4.00 | 1.2 | 40 | 60 |
| 5.20 | 1.2 | 40 | 60 |
| 5.30 | 1.2 | 90 | 10 |

Method D

Experiments were performed on a SHIMADZU 20A HPLC with a C18-reverse-phase column (50×3 mm Shim-Pack XR-ODS, 2.2 µm particle size), elution with solvent A: water+0.05% trifluoroacetic acid; solvent B: acetonitrile+0.05% trifluoroacetic acid. Gradient:

| Detection-UV (220 and 254 nm) and ELSD | | | |
|---|---|---|---|
| Gradient-Time | flow ml/min | % A | % B |
| 0.00 | 1.0 | 95 | 5 |
| 2.20 | 1.0 | 0 | 100 |
| 3.20 | 1.0 | 0 | 100 |
| 3.30 | 1.0 | 95 | 5 |

Method E

Experiments were performed on a SHIMADZU 20A HPLC with a C18-reverse-phase column (50×2.1 mm Xtimate TM-C18, 2.6 µm particle size), elution with solvent A: Water/0.05% TFA; solvent B: Acetonitrile/0.05% TFA:

| Detection-UV (220 and 254 nm) and ELSD | | | |
|---|---|---|---|
| Gradient-Time | flow ml/min | % A | % B |
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Method F

Experiments were performed on a SHIMADZU 20A HPLC with a C18-reverse-phase column (50×2.1 mm Xtimate TM-C18, 2.7 µm particle size), elution with solvent A: water+0.05% trifluoroacetic acid; solvent B: acetonitrile+0.05% trifluoroacetic acid. Gradient:

| Detection-UV (220 and 254 nm) and ELSD | | | |
|---|---|---|---|
| Gradient-Time | flow ml/min | % A | % B |
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Method G

Experiments were performed on a SHIMADZU 20A HPLC with a C18-reverse-phase column (50×3 mm, Gemini-NX 3µ-C18 110A, 3.0 µm particle size), elution with solvent A: water/5 mM NH$_4$HCO$_3$; solvent B: acetonitrile. Gradient:

| Gradient-Time | flow ml/min | % A | % B |
|---|---|---|---|
| 0.00 | 1.2 | 90 | 10 |
| 2.20 | 1.2 | 5 | 95 |
| 3.20 | 1.2 | 5 | 95 |
| 3.30 | 1.2 | 90 | 10 |
| Detection-UV (220 and 254 nm) and ELSD | | | |

Method H

Experiments were performed on a SHIMADZU 20A HPLC with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
|---|---|---|---|
| 0.00 | 1.2 | 95 | 5 |
| 3.00 | 1.2 | 5 | 95 |
| 3.70 | 1.2 | 5 | 95 |
| 4.00 | 1.2 | 95 | 5 |
| Detection-UV (220 and 254 nm) and ELSD | | | |

Method I

Experiments were performed on a SHIMADZU LCMS-2020 with a C18-reverse-phase column (Waters BEH 30×2.1 mm, 1.7 μm particle size), elution with solvent A: water+0.1% formic acid; solvent B: acetonitrile+0.1% formic acid. Gradient:

| Gradient-Time (min) | flow ml/min | % A | % B |
|---|---|---|---|
| 0 | 0.7 | 98 | 2 |
| 2 | 0.7 | 2 | 98 |
| 2.19 | 0.7 | 2 | 98 |
| 2.2 | 0.7 | 98 | 2 |
| 2.5 | 0.7 | 98 | 2 |
| Detection-UV (254 nm) | | | |

Method J

Experiments were performed on a Thermo QE LCMS system with a Kinetex XB-C18 column (50×2.1 mm, 1.7 μm particle size). Mobile phase A: water+0.1% FA and mobile phase B: Acetonitrile+0.1% FA.

| UV detector: UV220 & UV254. Mass spectrometer: positive ESI. HPLC Gradient: | | | |
|---|---|---|---|
| Time (min) | flow (ml/min) | % A | % B |
| 0.0 | 0.7 | 97 | 3 |
| 0.2 | 0.7 | 97 | 3 |
| 6.5 | 0.7 | 3 | 97 |
| 7.2 | 0.7 | 3 | 97 |
| 7.3 | 0.7 | 97 | 3 |

Method K

Experiments were performed on a SHIMADZU LCMS-2020 with a C18-reverse-phase column (Waters BEH 50×2.1 mm, 1.7 μm particle size), elution with solvent A: water+0.1% formic acid; solvent B: acetonitrile+0.1% formic acid. Gradient:

| Gradient-Time (min) | flow ml/min | % A | % B |
|---|---|---|---|
| 0 | 0.7 | 98 | 2 |
| 4.5 | 0.7 | 2 | 98 |
| 5.0 | 0.7 | 2 | 98 |
| 5.01 | 0.7 | 98 | 2 |
| 5.5 | 0.7 | 98 | 2 |
| Detection-UV (254 nm) | | | |

Method L

Experiments were performed on a SHIMADZU 20A HPLC with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
|---|---|---|---|
| 0.00 | 1.0 | 95 | 5 |
| 3.50 | 1.0 | 30 | 70 |
| 3.80 | 1.0 | 0 | 100 |
| 4.60 | 1.0 | 0 | 100 |
| 4.75 | 1.0 | 95 | 5 |
| Detection-UV (220 and 254 nm) and ELSD | | | |

Method M

Experiments were performed on a SHIMADZU 20A HPLC with a C18-reverse-phase column (50×3 mm Poroshell HPH-C18, 2.7 μm particle size), elution with solvent A: water/5 mM NH4HCO3; solvent B: acetonitrile. Gradient:

| Gradient-Time | flow ml/min | % A | % B |
|---|---|---|---|
| 0.00 | 1.2 | 90 | 10 |
| 3.00 | 1.2 | 5 | 95 |
| 3.70 | 1.2 | 5 | 95 |
| 3.80 | 1.2 | 90 | 10 |
| Detection-UV (220 and 254 nm) and ELSD | | | |

Method N

Experiments were performed on a SHIMADZU 20A HPLC with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
|---|---|---|---|
| 0.00 | 1.2 | 95 | 5 |
| 2.00 | 1.2 | 5 | 95 |
| 2.70 | 1.2 | 5 | 95 |
| 2.75 | 1.2 | 95 | 5 |
| Detection-UV (220 and 254 nm) and ELSD | | | |

Method O

Experiments were performed on a SHIMADZU 20A HPLC with a C18-reverse-phase column (50×2.1 mm Ascentis Express C18, 2.7 μm particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.0 | 95 | 5 |
| 2.00 | 1.0 | 5 | 95 |
| 2.70 | 1.0 | 5 | 95 |
| 2.80 | 1.0 | 95 | 5 |
| Detection-UV (220 and 254 nm) and ELSD | | | |

Method P

Experiments were performed on a SHIMADZU 20A HPLC with a C18-reverse-phase column (50×3 mm Shim-Pack XR-ODS, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.2 | 95 | 5 |
| 3.50 | 1.2 | 30 | 70 |
| 3.70 | 1.2 | 0 | 100 |
| 4.50 | 1.2 | 0 | 100 |
| 4.75 | 1.2 | 95 | 5 |
| Detection-UV (220 and 254 nm) and ELSD | | | |

Method Q

Experiments were performed on a SHIMADZU 20A HPLC with a C18-reverse-phase column (50×3 mm Poroshell HPH-C18, 2.7 m particle size), elution with solvent A: water/5 mM NH4HCO3; solvent B: acetonitrile. Gradient:

| Gradient-Time | flow ml/min | % A | % B |
| --- | --- | --- | --- |
| 0.00 | 1.2 | 80 | 20 |
| 3.50 | 1.2 | 40 | 60 |
| 4.00 | 1.2 | 5 | 95 |
| 4.70 | 1.2 | 5 | 95 |
| 4.80 | 1.2 | 90 | 10 |
| Detection-UV (220 and 254 nm) and ELSD | | | |

Method R

Experiments were performed on a SHIMADZU 20A HPLC with a C18-reverse-phase column (50×2.1 mm Ascentis Express C18, 2.7 m particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.0 | 95 | 5 |
| 2.70 | 1.0 | 5 | 95 |
| 3.70 | 1.0 | 5 | 95 |
| 3.80 | 1.0 | 95 | 5 |
| Detection-UV (220 and 254 nm) and ELSD | | | |

Method S

Experiments were performed on a SHIMADZU 20A HPLC with a C18-reverse-phase column (50×3 mm Shim-Pack XR-ODS, 2.2 m particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.2 | 95 | 5 |
| 1.10 | 1.2 | 0 | 100 |
| 1.70 | 1.2 | 0 | 100 |
| 1.75 | 1.2 | 95 | 5 |
| Detection-UV (220 and 254 nm) and ELSD | | | |

Intermediate 1

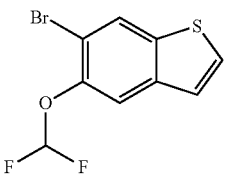 [SMILES: FC(F)Oc1cc2ccsc2cc1Br]

6-bromo-5-(difluoromethoxy)benzo[b]thiophene

To a solution of 6-bromo-5-methoxybenzo[b]thiophene (1.00 g, 4.11 mmol) in DCM (12 mL) in an ice bath under an atmosphere of $N_2$ was added boron tribromide (1M in DCM, 21 mL, 20.6 mmol) dropwise. The mixture was stirred at 0° C. for 30 minutes, poured onto ice and an aqueous solution of sodium hydrogen carbonate was added. The mixture was stirred for 15 min and extracted with DCM (2×100 mL). The combined organic extract was washed with brine, dried over magnesium sulfate and concentrated under reduced pressure to afford 6-bromobenzo[b]thiophen-5-ol as a black solid, which was used in the next step without any further purification. LC/MS (Method C, ESI): [M+H]$^+$=No ionization, $R_T$=2.16 min.

A solution of 6-bromobenzo[b]thiophen-5-ol (942 mg, 4.11 mmol), sodium chlorodifluoroacetate (1.57 g, 10.28 mmol) and cesium carbonate (4.02 g, 12.34 mmol) in N,N-dimethylacetamide (25 mL) was stirred at 100° C. for 18 h. The reaction mixture was allowed to cool to ambient temperature, poured into water (50 mL) and extracted with ethyl acetate (2×100 mL). The combined organic extracts was washed with brine, dried over magnesium sulfate and concentrated under reduced pressure. The crude residue was purified by column chromatography (silica gel, 100-200 mesh, 0 to 40% ethyl acetate in heptane). Appropriate fractions were combined and concentrated to afford 6-bromo-5-(difluoromethoxy)benzo[b]thiophene (537 mg, 48%) as a white solid. LC/MS (Method C, ESI): [M+H]$^+$=No ionization, $R_T$=2.84 min. $^1$H NMR (400 MHz, DMSO-$d_6$) δ 8.48 (d, J=0.7 Hz, 1H), 7.90 (d, J=5.5 Hz, 1H), 7.85 (s, 1H), 7.49 (dd, J=5.4, 0.8 Hz, 1H), 7.28 (t, J=73.4 Hz, 1H).

Intermediate 2

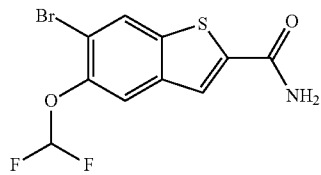 [SMILES: NC(=O)c1cc2cc(OC(F)F)c(Br)cc2s1]

6-bromo-5-(difluoromethoxy)benzo[b]thiophene-2-carboxamide

A solution of 6-bromo-5-hydroxybenzo[b]thiophene-2-carbonitrile (2.00 g, 7.87 mmol), sodium chlorodifluoroacetate (3.00 mg, 19.68 mmol) and cesium carbonate (7.69 mg, 23.61 mmol) in N,N-dimethylacetamide (40 mL) was heated at 100° C. for 18 h. The reaction mixture was allowed to cool to RT, poured into water (50 mL) and extracted with ethyl acetate (2×100 mL). The combined organic extracts was washed with brine, dried over magnesium sulfate and concentrated under reduced pressure. The crude residue was purified by column chromatography (silica gel, 100-200 mesh, 0 to 100% ethyl acetate in heptane). Appropriate fractions were combined and evaporated to afford 6-bromo-5-(difluoromethoxy)benzo[b]thiophene-2-carboxamide (1797 mg, 71%) as a white solid. LC/MS (Method K, ESI): [M+H]$^+$=322, R$_T$=2.12 min.

Intermediate 3

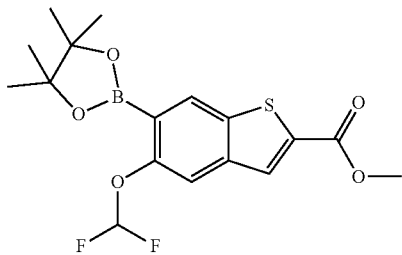

methyl 5-(difluoromethoxy)-6-(4,4,5,5-tetramethyl-1,3,2-dioxaborolan-2-yl)benzo[b]thiophene-2-carboxylate To a solution of 6-bromo-5-(difluoromethoxy)benzo[b]thiophene-2-carboxylic acid (2.50 g, 7.74 mmol) in methanol (110 mL) was added a catalytic amount of sulfuric acid (2 mL). The reaction mixture was heated at 65° C. for 18 h. The reaction mixture was allowed to cool to RT and concentrated under reduced pressure. To the crude residue was added water (50 mL) with saturated aqueous sodium bicarbonate (100 mL), the precipitated solid was collected by filtration, and dried in-vacuo to afford methyl 6-bromo-5-(difluoromethoxy)benzo[b]thiophene-2-carboxylate (1.25 g, 48%) as a white solid, which was used in the next step without further purification. LC/MS (Method K, ESI): [M+H]$^+$=No ionization, R$_T$=2.87 min.

A degassed mixture of 1,1'-bis(diphenylphosphino)ferrocenepalladium (II) chloride (304 mg, 0.372 mmol), bis-pinacolato diboron (1.70 g, 6.69 mmol), potassium acetate (1.82 g, 18.58 mmol) and methyl 6-bromo-5-(difluoromethoxy)benzo[b]thiophene-2-carboxylate (1.25 g, 3.72 mmol) were dissolved in 1,4-dioxane (15 mL) and heated at 95° C. in a heating block for 3 h. The reaction mixture was allowed to cool to RT, poured into water (50 mL) and extracted with ethyl acetate (2×100 mL). The combined organic layer was washed with saturated aqueous sodium chloride, dried over magnesium sulfate, filtered, and concentrated under reduced pressure. The crude residue was purified by silica gel chromatography (silica gel, 0% to 40% ethyl acetate in heptane). Appropriate fractions were combined and concentrated under reduced pressure to afford the title compound (1.44 mg, 99%). LC/MS (Method K, ESI): [M+H]$^+$=No ionization, R$_T$=3.25 min. $^1$H NMR (400 MHz, DMSO-d$_6$) δ 8.33 (s, 1H), 8.20 (s, 1H), 7.81 (s, 1H), 7.06 (t, J=74.7 Hz, 1H), 3.90 (s, 3H), 1.17 (s, 12H).

Intermediate 4

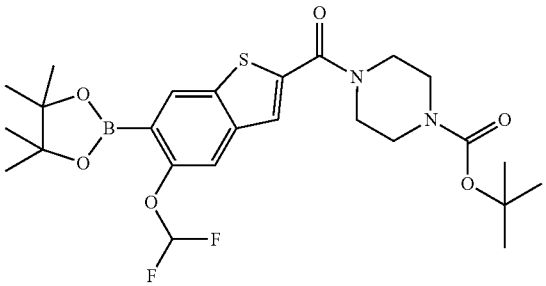 [SMILES: CC(C)(C)OC(=O)N1CCN(C(=O)c2cc3cc(OC(F)F)c(B4OC(C)(C)C(C)(C)O4)cc3s2)CC1]

4-[5-Difluoromethoxy-6-(4,4,5,5-tetramethyl-[1,3,2] dioxaborolan-2-yl)-benzo[b]thiophene-2-carbonyl]-piperazine-1-carboxylic acid tert-butyl ester A mixture of 6-bromo-5-(difluoromethoxy)benzo[b]thiophene-2-carboxylic acid (500 mg, 1.55 mmol), piperazine-1-carboxylic acid tert-butyl ester (432 mg, 2.32 mmol), HATU (910 mg, 2.32 mmol) and N,N-diisopropylethylamine (1.62 mL, 9.29 mmol) in N,N-dimethylformamide (8 mL) was stirred at RT overnight. The reaction mixture was poured into water (20 mL) and extracted with ethyl acetate (2×50 mL). The combined organic layer was washed with brine, dried over magnesium sulfate, filtered and concentrated under reduced pressure. The crude residue was purified by flash column chromatography (silica gel, 0% to 100% ethyl acetate in heptane). Appropriate fractions were combined and concentrated under reduced pressure to afford tert-butyl 4-(6-bromo-5-(difluoromethoxy)benzo[b]thiophene-2-carbonyl)piperazine-1-carboxylate (353 mg, 47%). LC/MS (Method K, ESI): [M+H]$^+$=No ionization, R$_T$=2.95 min. $^1$H NMR (400 MHz, DMSO-d$_6$) δ 8.49 (s, 1H), 7.86 (s, 1H), 7.75 (s, 1H), 7.26 (m, 1H), 3.69-3.61 (m, 4H), 3.47-3.40 (m, 4H), 1.42 (s, 9H).

A degassed mixture of tert-butyl 4-(6-bromo-5-(difluoromethoxy)benzo[b]thiophene-2-carbonyl)piperazine-1-carboxylate (353 mg, 0.72 mmol), bis-pinacolato diborane (328 mg, 1.29 mmol), 1,1'-bis(diphenylphosphino)ferrocenepalladium (II) chloride (59 mg, 0.072 mmol) and potassium acetate (353 mg, 3.60 mmol) in 1,4-dioxane (4 mL) was heated at 95° C. in a heating block for 2 h. The reaction mixture was allowed to cool to RT, poured into water (50 mL) and extracted with ethyl acetate (2×100 mL). The combined organic layer was washed with saturated aqueous sodium chloride solution, dried over magnesium sulfate, filtered, and concentrated under reduced pressure. The crude residue was purified by flash column chromatography (silica gel, 0% to 100% ethyl acetate in heptane). Appropriate fractions were combined and concentrated under reduced pressure to afford tert-butyl 4-(5-(difluoromethoxy)-6-(4,4,5,5-tetramethyl-1,3,2-dioxaborolan-2-yl)benzo[b]thiophene-2-carbonyl)piperazine-1-carboxylate (264 mg, 68%). LC/MS (Method K, ESI): [2M+H]$^+$=1077, R$_T$=3.26 min.

Intermediate 5

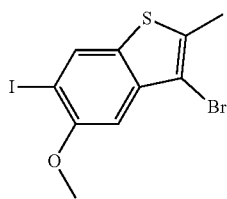

3-Bromo-6-iodo-5-methoxy-2-methyl-benzo[b]thiophene

To a cooled (−78° C.) solution of 5-methoxybenzothiophene (1.00 g, 6.09 mmol) in tetrahydrofuran (24.4 mL) was added n-butyllithium (1 M in hexanes, 7.31 mL, 7.31 mmol). The reaction mixture was stirred at −78° C. for 2 h then iodomethane (2.59 g, 0.864 mL, 18.3 mmol) was added. The mixture was quenched with water and extracted with ethyl acetate (2×). The combined organic layer was concentrated under reduced pressure and the residue was purified by flash chromatography on silica gel eluting with ethyl acetate/heptane (0-100%). The appropriate fractions were combined and concentrated under reduced pressure to give 5-methoxy-2-methylbenzo[b]thiophene (0.87 g, 80%) as a solid.

To a solution of 5-methoxy-2-methylbenzo[b]thiophene (0.865 g, 4.85 mmol) in chloroform (4.85 mL) and acetic acid (4.85 mL) at 0° C. was added 1-bromopyrrolidine-2,5-dione (0.950 g, 5.34 mmol). The reaction mixture was allowed to warm to RT and stirred for 16 h. The mixture was diluted with chloroform (5 mL), quenched with saturated sodium thiosulfate solution (10 mL) and concentrated under reduced pressure. The residue was purified by flash chromatography on silica gel eluting with 1% ethyl acetate in heptane. The appropriate fractions were combined and concentrated under reduced pressure to give 3-bromo-5-methoxy-2-methylbenzo[b]thiophene (0.645 g, 52%) as a solid.

To a solution of 3-bromo-5-methoxy-2-methylbenzo[b]thiophene (0.638 g, 2.48 mmol) in acetic acid (99.2 mL), water (4.96 mL) and sulfuric acid (3.31 mL) was added periodic acid (0.204 g, 0.146 mL, 0.893 mmol) and molecular iodine (0.472 g, 1.86 mmol). The reaction mixture was stirred at 60° C. for 16 h. The mixture was allowed to cool to RT, diluted with water (100 mL) and extracted with ethyl acetate (3×). The combined organic layer was concentrated under reduced pressure and the residue was purified by flash chromatography on silica gel eluting with ethyl acetate/heptane (0-50%). The appropriate fractions were combined and concentrated under reduced pressure to give 3-bromo-6-iodo-5-methoxy-2-methylbenzo[b]thiophene (0.331 g, 35%) as a solid.

Intermediate 6

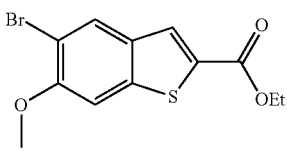 [SMILES: CCOC(=O)c1cc2cc(Br)c(OC)cc2s1]

Ethyl 5-bromo-6-methoxybenzo[b]thiophene-2-carboxylate

To a solution of 5-bromo-2-fluoro-4-methoxybenzaldehyde (1.0 g, 4.29 mmol) in tetrahydrofuran (20 mL) was added cesium carbonate (2.796 g, 8.58 mmol) and ethyl thioglycolate (542 mg, 4.51 mmol). The mixture was stirred at 70° C. for 16 h, allowed to cool to RT, diluted with ethyl acetate and washed with water and saturated aqueous sodium chloride. The organic layer was dried over magnesium sulfate, filtered, and concentrated under reduced pressure to afford ethyl 5-bromo-6-methoxybenzo[b]thiophene-2-carboxylate (1068 mg, 79%) as a white solid, which was used in the next step without further purification. LC/MS (Method K, ESI): [M+H]$^+$=317, R$_T$=2.84 min.

Intermediate 7

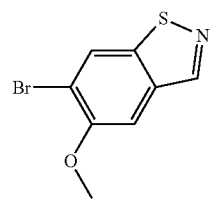

6-Bromo-5-methoxy-benzo[d]isothiazole

A solution of 4-bromo-2-fluoro-5-methoxy-benzaldehyde (3.20 g, 13.7 mmol), 2-methylpropane-2-thiol (1.49 g, 16.5 mmol) and potassium carbonate (1.90 g, 13.7 mmol) in dimethyl sulfoxide (13.7 mL) was stirred at 80° C. for 16 h. The mixture was allowed to cool to RT, diluted with water and extracted with ethyl acetate (4×). The combined organic layer was concentrated under reduced pressure and the residue was purified by flash chromatography on silica gel eluting with ethyl acetate/heptane (0-5%). The appropriate fractions were combined and concentrated under reduced pressure to give 4-bromo-2-(tert-butylthio)-5-methoxybenzaldehyde (4.16 g, 67%) as an oil. LC/MS (Method X, ESI): [M+H]$^+$=303.

A solution of 4-bromo-2-(tert-butylthio)-5-methoxybenzaldehyde (2.80 g, 9.23 mmol) and hydroxylamine hydrochloride (706 mg, 10.2 mmol) in 2-propanol (57.7 mL) and water (11.5 mL) was heated at 90° C. for 2 h. The mixture was allowed to cool to RT, concentrated under reduced pressure, diluted with saturated sodium bicarbonate solution and extracted with isopropyl acetate (2×). The combined organic layer was concentrated under reduced pressure and the resultant residue recrystallized from heptanes/DCM (3/1) to afford 4-bromo-2-(tert-butylthio)-5-methoxybenzaldehyde oxime (1.97 g, 67%) as a solid. LC/MS (Method X, ESI): [M+H]$^+$=320.

A solution of 4-bromo-2-(tert-butylthio)-5-methoxybenzaldehyde oxime (1.95 g, 6.13 mmol) and benzenesulfonic acid (0.0969 g, 0.613 mmol) in 1-propanol (8.17 mL) was heated at 100° C. for 16 h. The mixture was allowed to cool to RT, concentrated under reduced pressure and purified by flash chromatography on silica gel eluting with ethyl acetate/heptane (0-50%). The appropriate fractions were combined and concentrated under reduced pressure to give 6-bromo- 5-methoxybenzo[d]isothiazole (1.07 g, 72%) as a solid. LC/MS (Method X, ESI): [M+H]⁺=246.

Intermediate 8

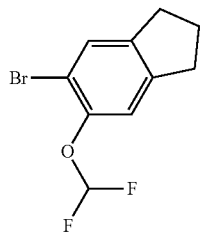 [SMILES: FC(F)Oc1cc2c(cc1Br)CCC2]

5-bromo-6-(difluoromethoxy)-2,3-dihydro-1H-indene

To a solution of 6-bromo-2,3-dihydro-1H-inden-5-ol (500 mg, 2.34 mmol) in N,N-dimethylformamide (30 mL) was added sodium hydride (800 mg, 60% in mineral oil, 20.0 mmol) under nitrogen. Methyl 2-chloro-2,2-difluoroacetate (1.70 g, 11.7 mmol) was added and the resulting mixture was stirred at 90° C. for 20 h. The reaction mixture was allowed to cool to RT and diluted with ethyl acetate (100 mL). Water (30 mL) was added and the phases were separated. The organic phase was washed with water (2×), brine, dried and concentrated under vacuum. The residue was purified by silica gel chromatography eluting with ethyl acetate/hexane (1/10). The appropriate fractions were combined and concentrated under vacuum to afford 5-bromo-6-(difluoromethoxy)-2,3-dihydro-1H-indene (240 mg, 39%) as an off-white solid.

Intermediate 9

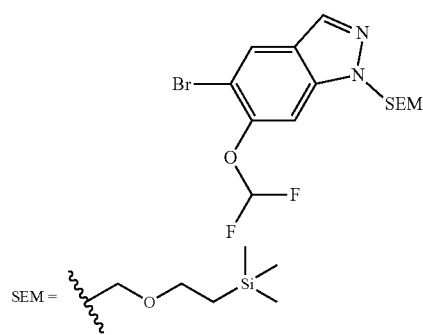

5-bromo-6-(difluoromethoxy)-1-((2-(trimethylsilyl)ethoxy)methyl)-1H-indazole

A solution of 5-bromo-1H-indazol-6-ol (1000 mg, 4.69 mmol), sodium chlorodifluoroacetate (1789 mg, 11.74 mmol) and cesium carbonate (4588 mg, 14.08 mmol) in N,N-dimethylacetamide (25 mL) and water (2.5 mL) was stirred at 100° C. for 18 h. The reaction mixture was allowed to cool to RT, poured into water (50 mL) and extracted with ethyl acetate (2×100 mL). The combined organic layer was washed with brine, dried over magnesium sulfate and concentrated under reduced pressure. The crude residue was purified by column chromatography (silica gel, 100-200 mesh, 0 to 100% ethyl acetate in heptane). Appropriate fractions were combined and evaporated to afford 5-bromo-6-(difluoromethoxy)-1H-indazole (430 mg, 35%) as a white solid. LC/MS (Method I, ESI): [M+H]⁺=263, $R_T$=1.31 min.

To a solution of 5-bromo-6-(difluoromethoxy)-1H-indazole (200 mg, 0.760 mmol) in tetrahydrofuran (5 mL) cooled in an ice bath was added sodium hydride (61 mg, 60% dispersion in mineral oil, 1.521 mmol) portion-wise. The reaction mixture was stirred for 20 min at 0° C. and 2-(trimethylsilyl)ethoxymethyl chloride (0.18 mL, 1.026 mmol) was added dropwise under nitrogen. The reaction mixture was stirred at 0° C. for 1 h and then allowed to warm to RT and stirred for 3 h. The reaction mixture was poured into water (20 mL) and saturated aqueous NH₄Cl (20 mL) and extracted with ethyl acetate (3×100 mL). The combined organic layer was washed successively with water and brine, dried over magnesium sulfate and concentrated under reduced pressure. The crude residue was purified by flash column chromatography (silica gel, 0% to 10% ethyl acetate in heptane). Appropriate fractions were combined and evaporated to afford the desired product as two regioisomers. Fractions from the first eluted product peak were combined and concentrated under reduced pressure to afford 5-bromo-6-(difluoromethoxy)-1-((2-(trimethylsilyl)ethoxy)methyl)-1H-indazole (173 mg, 58%) as an oil. LC/MS (Method I, ESI): [M+H]⁺=393, $R_T$=1.87 min. ¹H NMR (400 MHz, DMSO-d₆) δ 8.22 (d, J=0.4 Hz, 1H), 8.14 (d, J=0.9 Hz, 1H), 7.76 (p, J=0.7 Hz, 1H), 7.53-7.11 (m, 1H), 5.75 (s, 2H), 3.58-3.44 (m, 2H), 0.86-0.70 (m, 2H), −0.12 (s, 9H). The second peak was the undesired regioisomer. The fractions were collected and concentrated under reduced pressure to afford 5-bromo-6-(difluoromethoxy)-2-((2-(trimethylsilyl)ethoxy)methyl)-2H-indazole (69 mg, 23%) as an oil. LC/MS (Method I, ESI): [M+H]⁺=393, $R_T$=1.81 min.

Intermediate 10

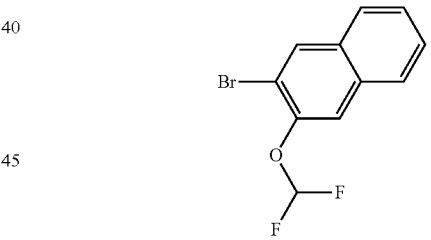

2-Bromo-3-difluoromethoxy-naphthalene

A solution of 3-bromonaphthalen-2-ol (3.00 g, 13.45 mmol), sodium chlorodifluoroacetate (5.13 g, 33.62 mmol) and cesium carbonate (13.15 g, 40.35 mmol) in N,N-dimethylacetamide (40 mL) and water (4 mL) was heated at 100° C. for 48 h. The reaction mixture was allowed to cool to RT, poured into water (100 mL) and extracted with ethyl acetate (2×150 mL). The combined organic layer was washed with brine, dried over magnesium sulfate and concentrated under reduced pressure. The crude residue was purified by column chromatography (silica gel, 100-200 mesh, 0 to 100% ethyl acetate in heptane). Appropriate fractions were combined and evaporated to afford 2-bromo-3-(difluoromethoxy)naphthalene (2.01 mg, 55%) as a yellow oil. ¹H NMR (400 MHz, DMSO-d₆) δ 8.40 (d, J=0.8 Hz, 1H), 8.00-7.88 (m, 2H), 7.84 (d, J=1.0 Hz, 1H), 7.64-7.18 (m, 3H).

Intermediate 11

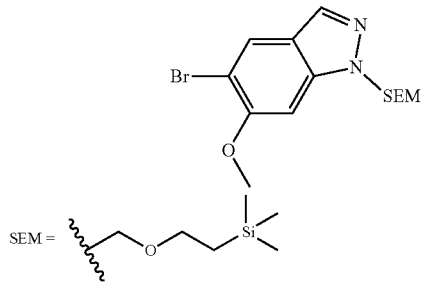

5-bromo-6-methoxy-1-((2-(trimethylsilyl)ethoxy) methyl)-1H-indazole

To a solution of 5-bromo-6-methoxy-1H-indazole (800 mg, 3.52 mmol) in tetrahydrofuran (15 mL) cooled in an ice bath was added sodium hydride (282 mg, 60% dispersion in mineral oil, 7.05 mmol) portion-wise. The reaction mixture was stirred for 20 min at 0° C., and then 2-(trimethylsilyl) ethoxymethyl chloride (0.84 mL, 4.76 mmol) was added dropwise under nitrogen. The resulting solution was stirred at 0° C. for 1 h and then allowed to warm to RT and stirred for 3 h. The reaction mixture was poured into water (20 mL) and saturated aqueous NH$_4$Cl (20 mL) and extracted with ethyl acetate (3×100 mL). The combined organic layer was washed successively with water and brine, dried over magnesium sulfate and concentrated under reduced pressure. The crude residue was purified by flash column chromatography (silica gel, 0% to 15% ethyl acetate in heptane). Appropriate fractions were combined and evaporated to afford the desired product as two regioisomers. The first peak to elute was the desired regioisomer. Fractions were combined and concentrated under reduced pressure to afford 5-bromo-6-methoxy-1-((2-(trimethylsilyl)ethoxy)methyl)-1H-indazole (831 mg, 66%) as an oil. LC/MS (Method I, ESI): [M+H]$^+$=357, R$_T$=1.81 min. $^1$H NMR (400 MHz, DMSO-d$_6$) δ 8.03 (s, 1H), 7.99 (d, J=0.9 Hz, 1H), 7.44-7.34 (m, 1H), 5.73 (s, 2H), 3.93 (s, 3H), 3.61-3.46 (m, 2H), 0.86-0.74 (m, 2H), −0.11 (s, 9H). The second peak to elute was the undesired regioisomer The fractions were collected and concentrated under reduced pressure to afford 5-bromo-6-methoxy-2-((2-(trimethylsilyl)ethoxy)methyl)-2H-indazole (214 mg, 17%) as an oil. LC/MS (Method I, ESI): [M+H]$^+$=357, R$_T$=1.71 min. $^1$H NMR (400 MHz, DMSO-d$_6$) δ 8.40 (d, J=0.9 Hz, 1H), 8.04 (d, J=0.4 Hz, 1H), 7.18-7.07 (m, 1H), 5.66 (s, 2H), 3.88 (s, 3H), 3.67-3.55 (m, 2H), 0.91-0.78 (m, 2H), −0.05 (s, 9H).

Intermediate 12

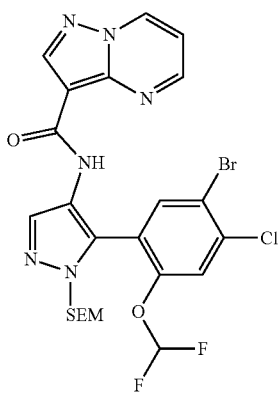

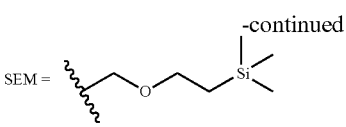

N-[5-[5-bromo-4-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide To a solution of 5-chloro-2-iodophenol (100 g, 393 mmol) in CH$_3$CN (1 L) at 70° C. was added CuBr$_2$ (264 g, 1.18 mol) in several batches. The resulting mixture was stirred at 70° C. for 4 h, allowed to cool to RT and concentrated under vacuum. The residue was quenched by the addition of water/ice (3 L) and extracted with ethyl acetate (3×2 L). The combined organic layer was washed with brine, dried over sodium sulfate, and concentrated under vacuum. The residue was purified by silica gel chromatography eluting with ethyl acetate/petroleum ether (1:30). The reaction was repeated on the same scale and the product from the two reactions were combined. This resulted in 140 g (53%) of 4-bromo-5-chloro-2-iodophenol as a white solid. $^1$H NMR (400 MHz, CDCl$_3$): δ (ppm) 7.89 (s, 1H), 7.14 (s, 1H), 5.32 (s, 1H).

To a solution of 4-bromo-5-chloro-2-iodophenol (140 g, 420 mmol) in N,N-dimethylformamide (1.2 L) was added sodium 2-chloro-2,2-difluoroacetate (95.8 g, 628 mmol) and Cs$_2$CO$_3$ (274 g, 840 mmol). The reaction mixture was heated at 120° C. for 2 h, allowed to cool to RT and quenched by the addition of water/ice (2.5 L). The resulting solution was extracted with ethyl acetate (3×2 L) and the organic layers combined. The organic layer was washed with brine, dried over anhydrous sodium sulfate and concentrated under vacuum. The residue was purified by silica gel chromatography eluting with ethyl acetate/petroleum ether (1:30). The appropriate fractions were combined and concentrated under vacuum to give 130 g (81%) of 1-bromo-2-chloro-4-(difluoromethoxy)-5-iodobenzene as a light yellow solid.

To a solution of 4-nitro-1-[[2-(trimethylsilyl)ethoxy] methyl]-1H-pyrazole (67.0 g, 275 mmol) in tetrahydrofuran (1 L) at −70° C. under nitrogen was added LiHMDS (340 mL, 1M in THF) dropwise. The resulting solution was stirred at −70° C. for 1 h before addition of a solution of ZnCl$_2$ (400 mL, 0.7 M in THF) dropwise. The mixture was stirred at −70° C. for 2 h, allowed to warm to RT, degassed with nitrogen, 1-bromo-2-chloro-4-(difluoromethoxy)-5-iodobenzene (105 g, 274 mmol) and Pd(PPh$_3$)$_4$ (16.0 g, 13.9 mmol) added and the resultant solution was heated overnight at 90° C. The resulting mixture was allowed to cool to RT and concentrated under vacuum. The residue was purified by silica gel chromatography eluting with ethyl acetate/petroleum ether (1:20). Appropriate fractions were combined and evaporated to afford 5-[5-bromo-4-chloro-2-(difluoromethoxy)phenyl]-4-nitro-1-[[2-(trimethylsilyl)ethoxy]-methyl]-1H-pyrazole (115 g, 84%) as a light yellow solid. LC/MS (Method F, ESI): [M+H]$^+$=498 & 500, R$_T$=1.27 min.

To a solution of 5-[5-bromo-4-chloro-2-(difluoromethoxy)phenyl]-4-nitro-1-[[2-(trimethylsilyl)ethoxy] methyl]-1H-pyrazole (102 g, 205 mmol) in ethanol (1 L) and water (100 mL) was added iron powder (102 g, 1.82 mol) and NH$_4$Cl (53 g, 1.00 mol). The reaction mixture was heated at 100° C. for 3 h. The reaction was allowed to cool to RT and the solid removed by filtration. The filtrate was concentrated under vacuum, dissolved in ethyl acetate (2 L), washed with brine, dried over anhydrous sodium sulfate and concentrated under vacuum to afford 5-[5-bromo-4-chloro-2-(difluoromethoxy)phenyl]-1-[[2-(trimethylsilyl)ethoxy]

methyl]-1H-pyrazol-4-amine (102 g crude) as light yellow oil. LC/MS (Method E, ESI): [M+H]⁺=468 & 470, R$_T$=1.29 min.

To a solution of 5-[5-bromo-4-chloro-2-(difluoromethoxy)phenyl]-1-[[2-(trimethylsilyl)-ethoxy]methyl]-1H-pyrazol-4-amine (100 g, 213 mmol) in DMA (800 mL) was added pyrazolo[1,5-a]pyrimidine-3-carboxylic acid (52.0 g, 319 mmol), PyAOP (166 g, 319 mmol), DIPEA (82.3 g, 638 mmol) and 4-dimethylaminopyridine (2.59 g, 21.2 mmol). The resulting solution was stirred overnight at 60° C. The reaction was allowed to cool to RT, quenched by the addition of water/ice (2 L), extracted with ethyl acetate (3×1.5 L). The combined organic layer was washed with brine, dried over anhydrous sodium sulfate and concentrated under vacuum. The residue was purified by silica gel chromatography eluting with ethyl acetate/petroleum ether (2:1). The appropriate fractions were combined and concentrated under vacuum. The residue was suspended in water (800 mL) and stirred for 1 h. The solid was collected by filtration to afford the title compound (112.7 g, 86%) as an off-white solid. LC/MS (Method D, ESI) [M+H]⁺=613.2 & 615.2, R$_T$=2.29 min. ¹H NMR (400 MHz, CDCl₃): δ 9.56 (s, 1H), 8.81 (d, J=6.8, 1.5 Hz, 1H), 8.73 (s, 1H), 8.53 (d, J=4.0 Hz, 1H), 8.33 (s, 1H), 7.92 (s, 1H), 7.54 (s, 1H), 7.03 (dd, J=6.8 Hz, 4.0 Hz, 1H), 6.45 (t, J=72.2 Hz, 1H), 5.43 (d, J=11.2 Hz, 1H), 5.35 (d, J=11.2 Hz, 1H), 3.68-3.56 (m, 2H), 0.94-0.84 (m, 2H), 0.00 (s, 9H).

Intermediate 13

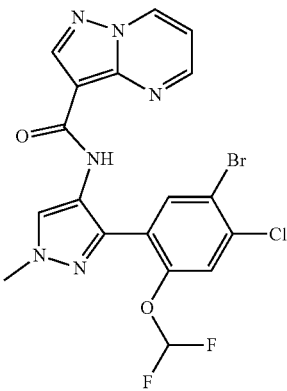 [SMILES: Cn1cc(NC(=O)c2cnn3cccnc23)c(-c2cc(Br)c(Cl)cc2OC(F)F)n1]

N-(3-(5-bromo-4-chloro-2-(difluoromethoxy)phenyl)-1-methyl-1H-pyrazol-4-yl)pyrazolo[1,5-a]pyrimidine-3-carboxamide To a solution of N-[5-[5-bromo-4-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (Intermediate 11) (600 mg, 0.977 mmol) in dichloromethane (20 mL) was added Me₃O⁺.BF₄⁻ (148 mg, 1.03 mmol). The resulting solution was stirred under nitrogen at RT for 20 h, quenched with ethanol (1.0 mL) and concentrated under vacuum. The residue was dissolved in ethanol (5.0 mL) and HCl (conc.) (5.0 mL) was added. The resulting solution was stirred overnight at RT and concentrated under vacuum. The residue was diluted with dichloromethane (10 mL) and DIPEA (2 mL) and concentrated under vacuum. The residue was purified by silica gel chromatography eluting with ethyl acetate/hexane (1/1). The appropriate fractions were combined and concentrated under vacuum to give the title compound (370 mg, 76%) as a light yellow solid. LC/MS (Method D, ESI): [M+H]⁺=499, R$_T$=1.50 min.

Intermediate 14

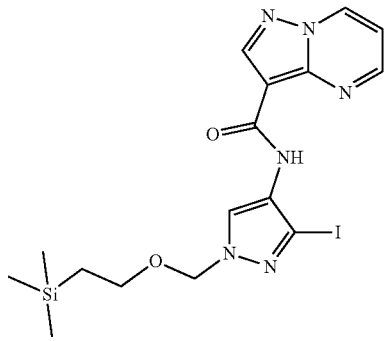 [SMILES: C[Si](C)(C)CCOCn1cc(NC(=O)c2cnn3cccnc23)c(I)n1]

N-(3-iodo-1-((2-(trimethylsilyl)ethoxy)methyl)-1H-pyrazol-4-yl)pyrazolo[1,5-a]pyrimidine-3-carboxamide To a solution of 4-nitro-1-((2-(trimethylsilyl)ethoxy)methyl)-1H-pyrazole (5.10 g, 21.0 mmol) in tetrahydrofuran (50 mL) at −78° C. under nitrogen was added lithium bis(trimethylsilyl)amide (1M) in tetrahydrofuran (27.2 mL, 27.2 mmol) dropwise over 10 minutes. The mixture was stirred at −78° C. under nitrogen for 40 minutes before iodine (5.85 g, 23.10 mmol) was added in one portion. The mixture was stirred at −78° C. under nitrogen for 1 h and quenched by the addition of saturated ammonium chloride (30 mL). Saturated aq. Na₂S₂O₃ (30 mL) was added and the mixture was allowed to warm to RT and extracted with ethyl acetate. The organic layer was washed with water and saturated aqueous sodium chloride, dried over magnesium sulfate, filtered, and concentrated under reduced pressure to afford 5-iodo-4-nitro-1-((2-(trimethylsilyl)ethoxy)methyl)-1H-pyrazole (7331 mg, 95%) as a yellow gel, which was used in the next step without further purification. LC/MS (Method K, ESI): [M+H]⁺ No ionization, R$_T$=2.99 min. ¹H NMR (400 MHz, DMSO-d₆) δ 8.46 (s, 1H), 5.62 (s, 2H), 3.76-3.57 (m, 2H), 1.00-0.82 (m, 2H), 0.00 (s, 9H).

A solution of 5-iodo-4-nitro-1-((2-(trimethylsilyl)ethoxy)methyl)-1H-pyrazole (5.00 g, 13.54 mmol) in dioxane (10 mL) was treated with 4N HCl in dioxane (30 mL, 120.00 mmol) and t resulting solution was stirred at RT for 16 h. The reaction mixture was poured into water (50 mL) and saturated aqueous sodium bicarbonate solution (100 mL) and the mixture was extracted with ethyl acetate (2×250 mL). The combined organic extract was washed with brine, dried over magnesium sulfate and concentrated under reduced pressure. The crude residue was purified by silica gel chromatography (silica gel, 100-200 mesh, 0 to 100% ethyl acetate in heptane). The appropriate fractions were collected and concentrated under reduced pressure to afford 3-iodo-4-nitro-1H-pyrazole (2118 mg, 66%) as a gel. LC/MS (Method K, ESI): [2M+H]⁺=477, R$_T$=1.12 min.

To a solution of 3-iodo-4-nitro-1H-pyrazole (2118 mg, 8.86 mmol) in tetrahydrofuran (50 mL) cooled in an ice bath was added sodium hydride (745 mg, 60% dispersion in mineral oil, 18.61 mmol) portion-wise. The resulting solution was stirred for 20 min at 0° C. before 2-(trimethylsilyl)ethoxymethyl chloride (1.7 mL, 9.75 mmol) was added dropwise under nitrogen. The solution was stirred at 0° C. for about 1 h and then allowed to warm to RT and stirred for an additional 2 h. The reaction mixture was poured into water (50 mL) and saturated aqueous NH$_4$Cl (20 mL) and the mixture was extracted with ethyl acetate (3×100 mL). The combined organic extract was washed successively with water and brine, dried over magnesium sulfate and concentrated under reduced pressure. The crude residue was purified by flash column chromatography (silica gel, 0% to 60% ethyl acetate in heptane) to afford desired product as two regioisomers. The fraction d from the second peak were combined and concentrated under reduced pressure to afford the desired regioisomer 3-iodo-4-nitro-1-((2-(trimethylsilyl)ethoxy)methyl)-1H-pyrazole (1298 mg, 40%) as an oil. LC/MS (Method K, ESI): [M+H]$^+$=No ionization, R$_T$=2.96 min. $^1$H NMR (400 MHz, DMSO-d$_6$) δ 9.05 (s, 1H), 5.46 (s, 2H), 3.65-3.52 (m, 2H), 0.94-0.75 (m, 2H), 0.01--0.16 (s, 9H). The first peak fractions were collected and concentrated under reduced pressure to afford another regioisomer 5-iodo-4-nitro-1-((2-(trimethylsilyl)ethoxy)methyl)-1H-pyrazole (1205 mg, 37%) as an oil, which was the undesired regioisomer. LC/MS (Method K, ESI): [M+H]$^+$=No ionization, R$_T$=2.96 min. $^1$H NMR (400 MHz, DMSO-d$_6$) δ 8.46 (s, 1H), 5.58 (s, 2H), 3.73-3.47 (m, 2H), 0.95-0.69 (m, 2H), –0.04 (s, 9H).

To a solution of 3-iodo-4-nitro-1-((2-(trimethylsilyl)ethoxy)methyl)-1H-pyrazole (1.30 g, 3.52 mmol) in ethanol (14 mL) and water (7 mL) at RT was added ammonium chloride (940 mg, 17.58 mmol). The reaction mixture was heated to 70° C. and iron powder (1023 mg, 17.58 mmol) was added portion-wise. The reaction mixture was heated to 80° C. for 4 h, allowed to cool to RT, the precipitated solid removed by filtration through celite, and the filtrate evaporated. The residue was dissolved into ethyl acetate and washed with water and saturated aqueous sodium chloride. The organic layer was dried over magnesium sulfate, filtered, and concentrated under reduced pressure to afford 3-iodo-1-((2-(trimethylsilyl)ethoxy)methyl)-1H-pyrazol-4-amine (1.12 g, 99%) as a gel, which was used in the next step without further purification. LC/MS (Method K, ESI): [M+H]$^+$=340.0, R$_T$=2.12 min.

To a solution of 3-iodo-1-((2-(trimethylsilyl)ethoxy)methyl)-1H-pyrazol-4-amine (1.12 g, 3.17 mmol) in dichloromethane (15 mL) was added pyrazolo[1,5-a]pyrimidine-3-carbonyl chloride (726 mg, 3.80 mmol) and triethylamine (1.77 mL, 12.66 mmol). The reaction mixture was stirred at RT for 16 h. The mixture was concentrated under reduced pressure and the residue was dissolved in ethyl acetate, washed with water and saturated aqueous sodium chloride solution. The organic layer was dried over magnesium sulfate, filtered, and concentrated under reduced pressure. The crude residue was triturated with ethyl acetate. The precipitated solid was collected by filtration, and dried in-vacuo to afford the title compound (1.34 g, 87%) as a tan solid. LC/MS (Method K, ESI): [M+H]$^+$=485, R$_T$=2.74 min.

Intermediate 15

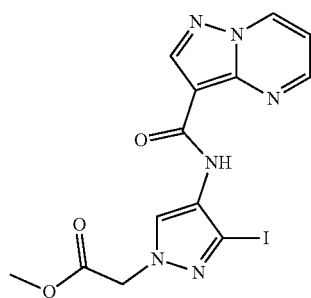 [SMILES: COC(=O)Cn1cc(NC(=O)c2cnn3cccnc23)c(I)n1]

Methyl 2-(3-iodo-4-(pyrazolo[1,5-a]pyrimidine-3-carboxamido)-1H-pyrazol-1-yl)acetate 4N HCl in dioxane (10 mL, 40.00 mmol) was added to a solution of N-(5-iodo-1-((2-(trimethylsilyl)ethoxy)methyl)-1H-pyrazol-4-yl)pyrazolo[1,5-a]pyrimidine-3-carboxamide (900 mg, 1.86 mmol) in dioxane (10 mL) and the mixture was stirred at RT for 18 h. The precipitated solid was collected by filtration, and dried in-vacuo to afford N-(5-iodo-1H-pyrazol-4-yl)pyrazolo[1,5-a]pyrimidine-3-carboxamide hydrochloride (720 mg, 100%) as a white solid, which was used in the next step without further purification. LC/MS (Method K, ESI): [M+H]$^+$=355, R$_T$=1.35 min.

A solution of N-(5-iodo-1H-pyrazol-4-yl)pyrazolo[1,5-a]pyrimidine-3-carboxamide hydrochloride (450 mg, 1.15 mmol) in N,N-dimethylformamide (6 mL) was treated with N,N-diisopropylethylamine (1.41 mL, 8.06 mmol) and methyl 2-bromoacetate (0.16 mL, 1.73 mmol) and the reaction mixture was heated to 80° C. overnight. The reaction mixture was allowed to cool to RT, poured into water (50 mL) and extracted with ethyl acetate (2×100 mL). The organic extracts were combined, washed with brine, dried over magnesium sulfate and concentrated under reduced pressure. The crude residue was triturated with ethyl acetate and the precipitated solid was collected by filtration and dried in-vacuo to afford methyl 2-(3-iodo-4-(pyrazolo[1,5-a]pyrimidine-3-carboxamido)-1H-pyrazol-1-yl)acetate (253 mg, 52%) as a white solid. LC/MS (Method K, ESI): [M+H]$^+$=427, R$_T$=1.60 min.

Intermediate 16

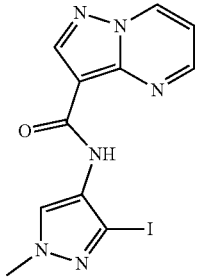 [SMILES: Cn1cc(NC(=O)c2cnn3cccnc23)c(I)n1]

N-(3-iodo-1-methyl-1H-pyrazol-4-yl)pyrazolo[1,5-a]pyrimidine-3-carboxamide

To a suspension of N-(3-iodo-1H-pyrazol-4-yl)pyrazolo[1,5-a]pyrimidine-3-carboxamide hydrochloride (Contained within the procedure for Example 14) (1.75 g, 4.93 mmol) in N,N-dimethylformamide (20 mL) was added iodomethane (2.53 g, 5.42 mmol) in N,N-dimethylacetamide (1 mL) followed by cesium carbonate (2.17 g, 6.65 mmol). The reaction mixture was heated to 40° C. overnight. The reaction mixture was allowed to cool to RT and diluted with ethyl acetate (100 mL). The resulting mixture was poured into water (50 mL). The precipitated solid was collected by filtration, and dried under vacuum to afford the desired regioisomer N-(3-iodo-1-methyl-1H-pyrazol-4-yl)pyrazolo[1,5-a]pyrimidine-3-carboxamide (320 mg, 18% yield) as a white solid. LC/MS (Method K, ESI): [M+H]$^+$=369, R$_T$=1.50 min. $^1$H NMR (400 MHz, DMSO-d$_6$) δ 9.65 (s, 1H), 9.35 (dd, J=7.0, 1.6 Hz, 1H), 8.87 (dd, J=4.2, 1.6 Hz, 1H), 8.67 (s, 1H), 8.07 (s, 1H), 7.33 (dd, J=7.0, 4.2 Hz, 1H), 3.88 (s, 3H). The mother liquor was washed with brine, dried over magnesium sulfate and concentrated under reduced pressure. The crude residue was triturated with ethyl acetate. The precipitated solid was collected by filtration, and dried in-vacuo to afford second crop of desired product (875 mg, 48%).

Intermediate 17

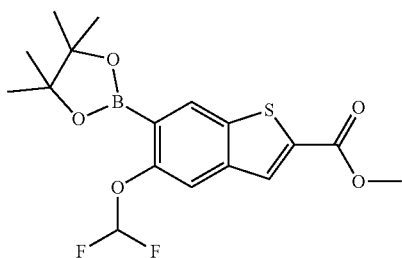

Methyl 5-(difluoromethoxy)-6-(4,4,5,5-tetramethyl-1,3,2-dioxaborolan-2-yl)benzo[b]thiophene-2-carboxylate A solution of 6-bromo-5-(difluoromethoxy)benzo[b]thiophene-2-carboxylic acid (2.5 g, 7.74 mmol) and sulfuric acid (2 mL) in methanol (110 mL) was heated at 65° C. for 18 h. The reaction mixture was allowed to cool to RT and the solvent evaporated. Water (50 mL) and saturated aqueous sodium bicarbonate solution (100 mL) were added, the precipitated solid was collected by filtration and dried under vacuum to afford methyl 6-bromo-5-(difluoromethoxy)benzo[b]thiophene-2-carboxylate (1.25 g, 48%) as a white solid, which was used in the next step without further purification. LC/MS (Method C, ESI): [M+H]$^+$=No ionization, $R_T$=2.87 min.

A degassed mixture of methyl 6-bromo-5-(difluoromethoxy)benzo[b]thiophene-2-carboxylate (1.25 g, 3.72 mmol), bispinacolato diboron (1.70 g, 6.69 mmol), potassium acetate (1.82 g, 18.58 mmol) and 1,1'-bis(diphenylphosphino)ferrocenepalladium (II) chloride (304 mg, 0.372 mmol) in 1,4-dioxane (15 mL) was heated at 95° C. in heating block for 3 h. The reaction mixture was allowed to cool to RT, poured into water (50 mL) and extracted with ethyl acetate (2×100 mL). The combined organic layer was washed with saturated aqueous sodium chloride solution, dried over magnesium sulfate, filtered and concentrated under reduced pressure. The crude residue was purified by flash column chromatography (silica gel, 0% to 40% ethyl acetate in heptane). Appropriate fractions were combined and concentrated under reduced pressure to afford methyl 5-(difluoromethoxy)-6-(4,4,5,5-tetramethyl-1,3,2-dioxaborolan-2-yl)benzo[b]-thiophene-2-carboxylate (1.44 g, 99%). LC/MS (Method C, ESI): [M+H]$^+$=No ionization, $R_T$=3.25 min. $^1$H NMR (400 MHz, DMSO-d$_6$) δ 8.33 (s, 1H), 8.20 (s, 1H), 7.81 (s, 1H), 7.06 (t, J=74.7 Hz, 1H), 3.90 (s, 3H), 1.17 (s, 12H).

Intermediate 18

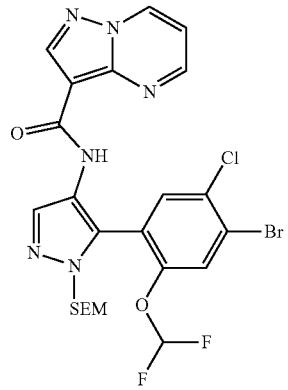 [SMILES: C[Si](C)(C)CCOCn1ncc(NC(=O)c2cnn3cccnc23)c1-c1cc(Cl)c(Br)cc1OC(F)F]

N-(5-(4-bromo-5-chloro-2-(difluoromethoxy)phenyl)-1-((2-(trimethylsilyl)ethoxy)methyl)-1H-pyrazol-4-yl)pyrazolo[1,5-a]pyrimidine-3-carboxamide To a solution of 3-bromo-4-chlorophenol (50.0 g, 241 mmol) and sodium hydroxide (19.0 g, 475 mmol) in water at 0° C. (500 mL) was added I$_2$ (66.0 g, 260 mmol) and a solution of KI (40.0 g, 241 mmol) in water dropwise. The resulting solution was stirred for at RT for 2 h. The pH of the solution was adjusted to 4 by the addition of 2M HCl. A saturated solution of Na$_2$SO$_3$ (1 L) was added, followed by ethyl acetate (1 L). The aqueous phase was extracted with ethyl acetate (2×). The combined organic layers was washed with brine and dried over anhydrous sodium sulfate and concentrated under vacuum. The residue was purified by silica gel chromatography eluting with dichloromethane/petroleum ether (1/20). The appropriate fractions were combined and concentrated under vacuum to afford 5-bromo-4-chloro-2-iodophenol (20.1 g, 25%) as a white solid. $^1$H NMR (400 MHz, CDCl$_3$): δ (ppm) 7.74 (s, 1H), 7.28 (s, 1H), 5.28 (s, 1H).

A solution of 5-bromo-4-chloro-2-iodophenol (1.00 g, 3.00 mmol), 2-chloro-2,2-difluoroacetate (690 mg, 4.53 mmol) and Cs$_2$CO$_3$ (1.95 g, 5.99 mmol) in N,N-dimethylformamide (10 mL) was heated at 120° C. for 4 h. The mixture was allowed to cool to RT and quenched by the addition of ice water (20 mL). The resulting solution was extracted with ethyl acetate (3×50 mL). The combined organic layers was dried over anhydrous sodium sulfate and concentrated under vacuum. The residue was purified by silica gel chromatography eluting with ethyl acetate/petroleum ether (1/20). Appropriate fractions were combined and evaporated to afford 1-bromo-2-chloro-5-(difluoromethoxy)-4-iodobenzene (1.01 g, 87%) as a white solid.

LiHMDS (40 mL, 1.0 mol/L in THF, 40.0 mmol) was added dropwise to a solution of 4-nitro-1-[[2-(trimethylsilyl)ethoxy]methyl]-1H-pyrazole (8.00 g, 32.9 mmol) in tetrahydrofuran (100 mL) at −70° C. under atmosphere of nitrogen. The resulting solution was stirred for 1 h at −70° C. and ZnCl$_2$ (47 mL, 0.70 mol/L in THF, 32.9 mmol) was added dropwise. The mixture was allowed to warm to RT and stirred for 1 h. 1-Bromo-2-chloro-5-(difluoromethoxy)-4-iodobenzene (12.6 g, 32.9 mmol) and Pd(PPh$_3$)$_4$ (1.90 g, 1.64 mmol) were added and the resulting solution was heated at 90° C. overnight under nitrogen. The mixture was allowed to cool to RT and concentrated under vacuum. The residue was purified by silica gel chromatography eluting with ethyl acetate/petroleum ether (1/20). Appropriate fractions were combined and evaporated to afford 5-[4-bromo-5-chloro-2-(difluoromethoxy)phenyl]-4-nitro-1-[[2-(trimethylsilyl)ethoxy]methyl]-1H-pyrazole (8.01 g, 49%) as a light yellow solid. LC/MS (Method F, ESI): [M+H]=498 & 500, $R_T$=1.42 min.

To a solution of 5-[4-bromo-5-chloro-2-(difluoromethoxy)phenyl]-4-nitro-1-[[2-(trimethylsilyl)ethoxy]methyl]-1H-pyrazole (5.00 g, 10.0 mmol) in ethanol (50 mL) and water (5.0 mL) was added iron powder (5.00 g, 89.5 mmol) and $NH_4Cl$ (5.50 g, 103 mmol). The reaction mixture was stirred for 2 h at 100° C. and allowed to cool to RT. The solid was removed by filtration and the filtercake washed with ethanol. The filtrate was concentrated under vacuum and the residue dissolved in ethyl acetate (200 mL). The organic layer was washed with brine, dried over anhydrous sodium sulfate and concentrated under vacuum to afford 5-[4-bromo-5-chloro-2-(difluoromethoxy)phenyl]-1-[[2-(trimethylsilyl)ethoxy]methyl]-1H-pyrazol-4-amine (5.00 g, crude) as a yellow oil. LC/MS (Method F, ESI): [M+H]$^+$=468 & 470, $R_T$=1.12 min.

To a solution of 5-[4-bromo-5-chloro-2-(difluoromethoxy)phenyl]-1-[[2-(trimethylsilyl)ethoxy]methyl]-1H-pyrazol-4-amine (5.00 g, crude) in DMA (50.0 mL) was added pyrazolo[1,5-a]pyrimidine-3-carboxylic acid (2.80 g, 17.2 mmol), PyAOP (9.00 g, 17.3 mmol), DIPEA (5.00 g, 38.7 mmol) and 4-dimethylaminopyridine (140 mg, 1.15 mmol). The reaction mixture was heated overnight at 60° C. The mixture was allowed to cool to RT, water (200 mL) was added and the mixture was extracted with ethyl acetate (3×300 mL). The combined organic layer was washed with brine, dried over anhydrous sodium sulfate and concentrated under vacuum. The residue was purified by silica gel chromatography eluting with ethyl acetate/petroleum ether (4/1) to afford the title compound (5.70 g, 92% over two steps) as a light yellow solid. LC/MS (Method F, ESI): [M+H]$^+$=613.0 & 615.0, $R_T$=1.31 min. $^1$H NMR (400 MHz, $CDCl_3$): δ 9.57 (s, 1H), 8.81 (dd, J=7.0, 1.8 Hz, 1H), 8.73 (s, 1H), 8.52 (dd, J=4.4, 1.6 Hz, 1H), 8.32 (s, 1H), 7.76 (s, 1H), 7.69 (s, 1H), 7.03 (dd, J=7.0, 4.2 Hz, 1H), 6.44 (t, J=72.2 Hz, 1H), 5.43 (d, J=11.2 Hz, 1H), 5.35 (d, J=11.2 Hz, 1H), 3.66-3.58 (m, 2H), 0.92-0.83 (m, 2H), 0.00 (s, 9H).

Intermediate 19

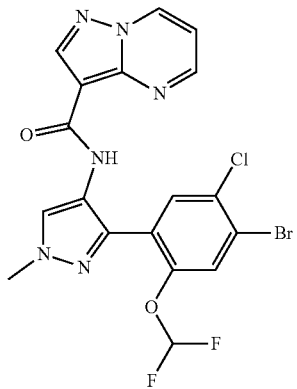 [SMILES: Cn1cc(NC(=O)c2cnn3cccnc23)c(-c2cc(Cl)c(Br)cc2OC(F)F)n1]

N-(3-(4-bromo-5-chloro-2-(difluoromethoxy)phenyl)-1-methyl-1H-pyrazol-4-yl)pyrazolo[1,5-a]pyrimidine-3-carboxamide N-[5-[4-bromo-5-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (1.00 g, 1.63 mmol, intermediate 18) was treated with trimethyloxonium tetrafluoroborate (314 mg, 2.12 mmol) in dichloromethane (20 mL) and the mixture stirred at RT for 1 h. The reaction was quenched by the addition of ethanol and the pH of the solution was adjusted to 7 by the addition of aqueous hydrogen chloride solution. The resulting mixture was concentrated under reduced pressure and the residue was purified by flash chromatography on silica gel eluting with DCM/MeOH (94/6). Appropriate fractions were combined and concentrated under reduced pressure to afford N-[3-[4-bromo-5-chloro-2-(difluoromethoxy)phenyl]-1-methyl-1H-pyrazol-4-yl]pyrazolo[1,5-a]pyrimidine-3-carboxamide (515.4 mg, 64%) as a yellow solid. LC/MS (Method S, ESI): [M+H]$^+$=499.1, $R_T$=1.31 min. $^1$H NMR (300 MHz, DMSO-$d_6$): δ 9.70 (s, 1H), 9.36 (dd, J=6.9, 1.8 Hz, 1H), 8.72 (dd, J=4.4, 1.7 Hz, 1H), 8.67 (s, 1H), 8.32 (s, 1H), 7.87 (s, 1H), 7.79 (s, 1H), 7.35 (t, J=72.9 Hz, 1H), 7.32 (dd, J=6.9, 4.2 Hz, 1H).

Intermediate 20

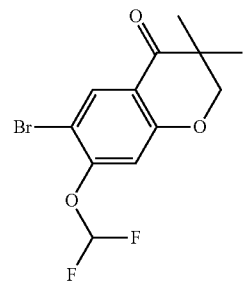 [SMILES: CC1(C)COc2cc(OC(F)F)c(Br)cc2C1=O]

6-bromo-7-(difluoromethoxy)-3,3-dimethylchroman-4-one

A mixture of 3-chloropropanoic acid (577 mg, 5.32 mmol), 4-bromobenzene-1,3-diol (1.00 g, 5.29 mmol) and trifluoromethanesulfonic acid (3.18 g, 21.2 mmol) was heated at 85° C. for 1 h under nitrogen. The reaction mixture was allowed to cool to room temperature, ice water (20 mL) was added and the resulting solution was extracted with dichloromethane (3×20 mL). The combined organic layer was concentrated under reduced pressure and the residue was purified by flash chromatography on silica gel eluting with dichloromethane/methanol (97/3). Appropriate fractions were combined and concentrated under reduced pressure to afford 1-(5-bromo-2,4-dihydroxyphenyl)-3-chloropropan-1-one (250 mg, 17%) as a yellow solid.

1-(5-bromo-2,4-dihydroxyphenyl)-3-chloropropan-1-one (250 mg, 0.894 mmol) was added to a cooled (0° C.) solution of sodium hydroxide (320 mg, 8.00 mmol) in water (4.0 mL) under nitrogen and the resulting solution was stirred for 2 h. The pH of the solution was adjusted to 2 with 6N HCl aqueous solution and the resulting solution was extracted with dichloromethane (3×20 mL). The combined organic layer was concentrated under reduced pressure to obtain 6-bromo-7-hydroxy-3,4-dihydro-2H-1-benzopyran-4-one (160 mg, 74%) as a yellow solid. $^1$H NMR (400 MHz, $CD_3OD$): δ (ppm) 7.92 (s, 1H), 6.47 (s, 1H), 4.51 (t, J=6.4 Hz, 2H), 2.74 (t, J=6.4 Hz, 2H).

t-BuOK (112 mg, 0.998 mmol) was added to cooled (−70° C.) solution of 6-bromo-7-hydroxy-3,4-dihydro-2H-1-benzopyran-4-one (80 mg, 0.329 mmol) in tetrahydrofuran (2.0 mL) under nitrogen. The resulting solution was stirred for 0.5 h at −70° C. before addition of iodomethane (94 mg, 0.662 mmol). The resulting solution was stirred for 1 h at −70° C. then allowed to warm to room temperature. The reaction mixture was partitioned between water and ethyl acetate, the aqueous phase was extracted with ethyl acetate (2×) and the combined organic phase was washed with water, brine and dried over sodium sulfate, and concentrated under reduced pressure to afford 6-bromo-7-hydroxy-3,3-dimethyl-3,4-dihydro-2H-1-benzopyran-4-one (80 mg, 90%) as a yellow solid. $^1$H NMR (400 MHz, DMSO-d$_6$): δ 11.49 (s, 1H), 7.80 (s, 1H), 6.53 (s, 1H), 4.19 (s, 2H), 1.07 (s, 6H).

A mixture of 6-bromo-7-hydroxy-3,3-dimethyl-3,4-dihydro-2H-1-benzopyran-4-one (85 mg, 0.314 mmol, Cs$_2$CO$_3$ (196 mg, 0.602 mmol) and sodium 2-chloro-2,2-difluoroacetate (92.0 mg, 0.603 mmol) in DMF (2.0 mL) was heated at 120° C. for 16 h. The mixture was allowed to cool to room temperature and concentrated under reduced pressure. The residue was purified by flash chromatography on silica gel eluting with ethyl acetate/petroleum ether (1/4). Appropriate fractions were combined and concentrated under reduced pressure to afford 6-bromo-7-(difluoromethoxy)-3,3-dimethyl-3,4-dihydro-2H-1-benzopyran-4-one (80 mg, 79%) as a yellow solid. $^1$H NMR (400 MHz, DMSO-d$_6$): δ 7.96 (s, 1H), 7.48 (t, J=72.6 Hz, 1H), 7.05 (s, 1H), 4.31 (s, 2H), 1.11 (s, 6H).

Example 1 (General Procedure A)

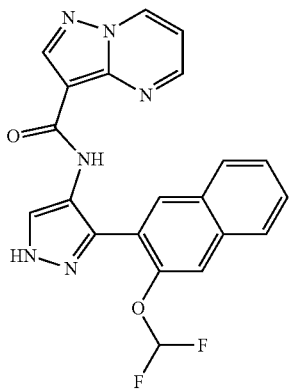 [SMILES: O=C(Nc1c[nH]nc1-c1cc2ccccc2cc1OC(F)F)c1cnn2cccnc12]

N-(3-(3-(difluoromethoxy)naphthalen-2-yl)-1H-pyrazol-4-yl)pyrazolo[1,5-a]pyrimidine-3-carboxamide A solution of 4-nitro-1-((2-(trimethylsilyl)ethoxy)methyl)-1H-pyrazole (1.87 g, 7.69 mmol), 2-bromo-3-difluoromethoxynaphthalene (Intermediate 10) (1.5 g, 5.49 mmol), butyl-di-1-adamantylphosphine (332 mg, 0.879 mmol), palladium (II) acetate (123 mg, 0.549 mmol), potassium carbonate (2.35 g, 17.03 mmol) and pivalic acid (142 mg, 1.37 mmol) in N,N-dimethylacetamide (18 mL) was stirred at 120° C. in a microwave for 18 h. The solution was allowed to cool to RT, ethyl acetate was added and the precipitated solid was removed by filtration through celite. The filtrate was washed with water and saturated aqueous sodium chloride. The organic layer was dried over magnesium sulfate, filtered, and concentrated in-vacuo. The residue was purified by column chromatography (silica gel, 100-200 mesh, 0 to 80% ethyl acetate in heptane) to afford 5-(3-(difluoromethoxy)naphthalen-2-yl)-4-nitro-1-((2-(trimethylsilyl)ethoxy)methyl)-1H-pyrazole (2.41 g, 98%) as an oil. $^1$H NMR (400 MHz, DMSO-d$_6$) δ 8.56 (s, 1H), 8.26 (s, 1H), 8.06 (dq, J=8.2, 0.7 Hz, 1H), 8.03-7.96 (m, 1H), 7.85 (s, 1H), 7.71 (ddd, J=8.2, 6.9, 1.3 Hz, 1H), 7.62 (ddd, J=8.1, 6.9, 1.2 Hz, 1H), 7.28 (dd, J=74.0, 71.9 Hz, 1H), 5.57-5.46 (m, 1H), 5.32 (d, J=11.3 Hz, 1H), 3.55-3.37 (m, 2H), 0.81-0.70 (m, 2H), −0.10 (s, 9H).

To a solution of 5-(3-(difluoromethoxy)naphthalen-2-yl)-4-nitro-1-((2-(trimethylsilyl)ethoxy)methyl)-1H-pyrazole (1.58 g, 5.91 mmol) in ethanol (24 mL) and water at 25° C. (12 mL) was added ammonium chloride (1.58 g, 29.6 mmol). The reaction mixture was heated to 70° C. and iron powder (1.72 g, 29.6 mmol) was added portionwise. The reaction mixture was heated to 80° C. for 1 h. The reaction mixture was allowed to cool to RT, the solid removed by filtration through celite, the filtercake was washed with methanol and the filtrate concentrated in-vacuo. The residue was dissolved in ethyl acetate and washed with water and saturated aqueous sodium chloride. The organic layer was dried over magnesium sulfate, filtered, and concentrated under reduced pressure to afford 5-(3-(difluoromethoxy)naphthalen-2-yl)-1-((2-(trimethylsilyl)ethoxy)methyl)-1H-pyrazol-4-amine (2354 mg, 98%) as a gel, which was used in the next step without further purification. LC/MS (Method I, ESI): [M+H]$^+$=406, R$_T$=1.56 min.

A solution of 5-(3-(difluoromethoxy)naphthalen-2-yl)-1-((2-(trimethylsilyl)ethoxy)methyl)-1H-pyrazol-4-amine (1.80 g, 4.44 mmol), pyrazolo[1,5-a]pyrimidine-3-carbonyl chloride (849 mg, 4.44 mmol) and triethylamine (1.86 mL, 13.3 mmol) in dichloromethane (20 mL) was stirred at RT for 16 h. The mixture was concentrated under reduced pressure, the residue dissolved in ethyl acetate and the organic phase was washed with water and saturated aqueous sodium chloride. The organic layer was dried over magnesium sulfate, filtered, and concentrated under reduced pressure. The crude residue was purified by column chromatography (silica gel, 100-200 mesh, 0 to 100% ethyl acetate in heptane). Appropriate fractions were combined and evaporated to afford N-(5-(3-(difluoromethoxy)naphthalen-2-yl)-1-((2-(trimethylsilyl)ethoxy)methyl)-1H-pyrazol-4-yl)pyrazolo[1,5-a]pyrimidine-3-carboxamide (1.31 g, 54%) as a foam. LC/MS (Method I, ESI): [M+H]$^+$=551, R$_T$=1.73 min.

A solution of N-(5-(3-(difluoromethoxy)naphthalen-2-yl)-1-((2-(trimethylsilyl)ethoxy)methyl)-1H-pyrazol-4-yl) pyrazolo[1,5-a]pyrimidine-3-carboxamide (1.00 g, 1.82 mmol) and 4N HCl in dioxane (20 mL, 18.16 mmol) in dioxane (10 mL) was stirred at RT for 18 h. The mixture was concentrated under reduced pressure, the residue was dissolved in ethyl acetate and washed with water and saturated aqueous sodium bicarbonate. The crude residue was purified by flash column chromatography (silica gel, 0% to 100% ethyl acetate in heptane). Appropriate fractions were combined and evaporated to afford the title compound (667 mg, 82%) as a white solid. LC/MS (Method I, ESI): [M+H]$^+$=421, R$_T$=1.22 min. $^1$H NMR (400 MHz, DMSO-d$_6$) δ 13.02 (s, 1H), 9.82 (s, 1H), 9.31 (dt, J=7.0, 1.7 Hz, 1H), 8.66 (s, 1H), 8.43 (m, 1H), 8.31 (d, J=1.4 Hz, 1H), 8.26-8.12 (m, 1H), 8.10-7.96 (m, 2H), 7.90 (m, 1H), 7.73-7.52 (m, 2H), 7.53-7.08 (m, 2H).

Example 2 (General Procedure B)

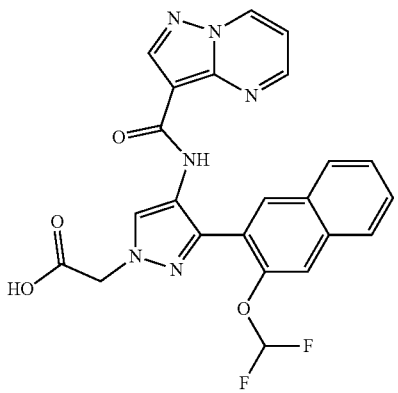 [SMILES: O=C(O)Cn1cc(NC(=O)c2cnn3cccnc23)c(-c2cc3ccccc3cc2OC(F)F)n1]

2-(3-(3-(difluoromethoxy)naphthalen-2-yl)-4-(pyrazolo[1,5-a]pyrimidine-3-carboxamido)-1H-pyrazol-1-yl)acetic acid A solution of N-(3-(3-(difluoromethoxy)naphthalen-2-yl)-1H-pyrazol-4-yl)pyrazolo[1,5-a]pyrimidine-3-carboxamide (Example 1) (558 mg, 1.33 mmol), cesium carbonate (584 mg, 1.79 mmol) and methyl 2-bromoacetate (0.20 mL, 1.99 mmol) in N,N-dimethylformamide (10 mL) was stirred at RT overnight. The reaction mixture was poured into water (50 mL) and extracted with ethyl acetate (2×100 mL). The combined organic layer was washed with brine, dried over magnesium sulfate and concentrated under reduced pressure. The crude residue was triturated with ethyl acetate and the precipitated solid collected by filtration and dried in-vacuo to afford methyl 2-(3-(3-(difluoromethoxy)naphthalen-2-yl)-4-(pyrazolo[1,5-a]pyrimidine-3-carboxamido)-1H-pyrazol-1-yl)acetate (288 mg, 44%) as a white solid. LC/MS (Method I, ESI): [M+H]$^+$=493, $R_T$=1.37 min.

To a solution of methyl 2-(3-(3-(difluoromethoxy)naphthalen-2-yl)-4-(pyrazolo[1,5-a]pyrimidine-3-carboxamido)-1H-pyrazol-1-yl)acetate (326 mg, 0.662 mmol) in tetrahydrofuran (16 mL) and methanol (4 mL) was added 1M aqueous sodium hydroxide (4 mL, 3 mmol). The reaction mixture was stirred at RT for 1 h. The mixture was concentrated in-vacuo. The residue was diluted with water (25 mL) and then adjusted to pH 1 by addition of 1N hydrochloric acid. The solution was extracted with ethyl acetate (3×100 mL). The combined organic layer was dried over sodium sulfate and concentrated in vacuo. The crude residue was triturated with ethyl acetate, the precipitated solid was collected by filtration, and dried in vacuo to afford the title compound (284 mg, 90% yield) as a light yellow solid. LC/MS (Method I, ESI): [M+H]$^+$=479, $R_T$=1.23 min. $^1$H NMR (400 MHz, DMSO-d$_6$) δ 13.13 (s, 1H), 9.84 (s, 1H), 9.31 (dd, J=7.0, 1.6 Hz, 1H), 8.67 (s, 1H), 8.51-8.37 (m, 2H), 8.15 (s, 1H), 8.04 (dd, J=8.0, 6.3 Hz, 2H), 7.90 (s, 1H), 7.70-7.13 (m, 4H), 5.09 (s, 2H).

Example 3 (General Procedure C)

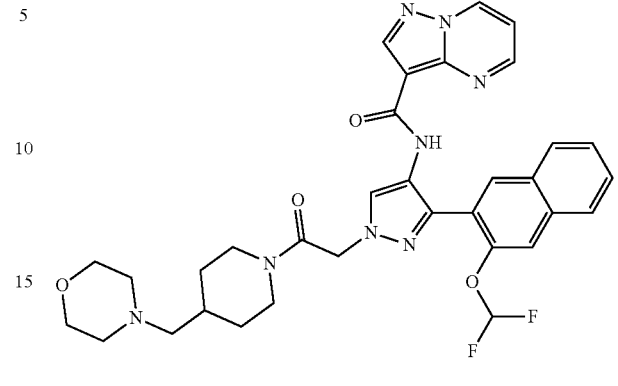

N-(3-(3-(difluoromethoxy)naphthalen-2-yl)-1-(2-(4-(morpholinomethyl)piperidin-1-yl)-2-oxoethyl)-1H-pyrazol-4-yl)pyrazolo[1,5-a]pyrimidine-3-carboxamide To a solution of 2-(3-(3-hydroxynaphthalen-2-yl)-4-(pyrazolo[1,5-a]pyrimidine-3-carboxamido)-1H-pyrazol-1-yl)acetic acid (Example 2) (40 mg, 0.084 mmol) and 4-(4-piperidylmethyl)morpholine dihydrochloride-ethylpiperazine (32 mg, 0.125 mmol) in N,N-dimethylformamide (1.5 mL) was added HATU (49 mg, 0.125 mmol), N,N-diisopropylethylamine (0.09 mL, 0.502 mmol) and pyridine (0.02 mL, 0.251 mmol). The reaction mixture was stirred at RT overnight and evaporated. The residue was purified by Prep-HPLC (Column: Gemini-NX C18 5 um, 110A, 100×30 mm; mobile phase: Water (0.1% NH$_4$OH) and CH$_3$CN (20% CH$_3$CN up to 60% in 15 min); Detector, UV 254 nm) to afford the title compound (20.6 mg, 38%) as a white solid. LC/MS (Method I, ESI): [M+H]$^+$=645, $R_T$=1.06 min. $^1$H NMR (400 MHz, DMSO-d6) δ 9.84 (s, 1H), 9.31 (dd, J=7.0, 1.6 Hz, 1H), 8.67 (s, 1H), 8.44 (dd, J=4.2, 1.6 Hz, 1H), 8.33 (s, 1H), 8.12 (s, 1H), 8.06-7.99 (m, 2H), 7.90 (s, 1H), 7.60 (m, 2H), 7.27-7.17 (m, 2H), 5.31-5.16 (m, 2H), 4.35 (d, J=13.0 Hz, 1H), 3.94 (d, J=13.5 Hz, 1H), 3.57 (t, J=4.5 Hz, 4H), 3.08 (t, J=12.8 Hz, 1H), 2.67-2.51 (m, 1H), 2.33 (m, 4H), 2.14 (d, J=6.9 Hz, 2H), 1.80 (m, 3H), 1.12 (d, J=12.5 Hz, 1H), 0.98 (d, J=12.7 Hz, 1H).

Example 4 (General Procedure D)

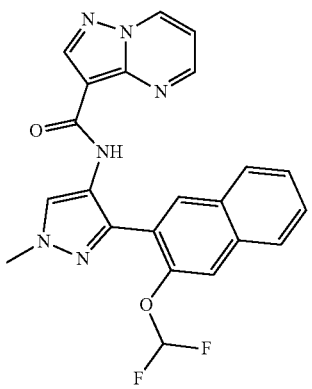 [SMILES: Cn1cc(NC(=O)c2cnn3cccnc23)c(-c2cc3ccccc3cc2OC(F)F)n1]

N-(3-(3-(difluoromethoxy)naphthalen-2-yl)-1-methyl-1H-pyrazol-4-yl)pyrazolo[1,5-a]pyrimidine-3-carboxamide To a solution of N-(5-(3-(difluoromethoxy)naphthalen-2-yl)-1-((2-(trimethylsilyl)ethoxy)methyl)-1H-pyrazol-4-yl)pyrazolo[1,5-a]pyrimidine-3-carboxamide (Contained within the procedure for Example 1) (30 mg, 0.0545 mmol) in dichloromethane (4 mL) was added trimethyloxonium tetrafluoroborate (12 mg, 0.0817 mmol) in one portion. The reaction mixture was stirred at RT for 40 min. The mixture was concentrated under reduced pressure and the residue dissolved in ethyl acetate and washed with water and saturated aqueous sodium chloride. The organic layer was dried over magnesium sulfate, filtered, and concentrated under reduced pressure. The crude residue was purified by column chromatography (silica gel, 100-200 mesh, 0 to 100% ethyl acetate in heptane). Appropriate fractions were combined and evaporated to afford the title compound (15 mg, 64%) as a light yellow solid. LC/MS (Method K, ESI): [M+H]$^+$=435, R$_T$=2.44 min. $^1$H NMR (500 MHz, DMSO-d$_6$) δ 9.82 (s, 1H), 9.32 (dd, J=7.1, 1.6 Hz, 1H), 8.67 (s, 1H), 8.46 (dd, J=4.3, 1.6 Hz, 1H), 8.34 (s, 1H), 8.16 (s, 1H), 8.03 (dd, J=8.0, 2.8 Hz, 2H), 7.90 (s, 1H), 7.63 (t, J=7.5 Hz, 1H), 7.60-7.50 (m, 1H), 7.40 (s, 1H), 7.24 (m, 1H), 3.97 (s, 3H).

Example 5 (General Procedure E)

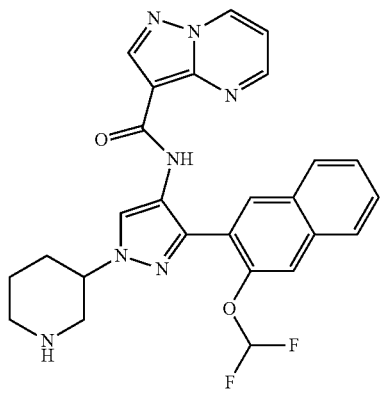 [SMILES: O=C(Nc1cn(C2CCCNC2)nc1-c1cc2ccccc2cc1OC(F)F)c1cnn2cccnc12]

N-(3-(3-(difluoromethoxy)naphthalen-2-yl)-1-(piperidin-3-yl)-1H-pyrazol-4-yl)pyrazolo[1,5-a]pyrimidine-3-carboxamide A solution of N-(3-(3-(difluoromethoxy)naphthalen-2-yl)-1H-pyrazol-4-yl)pyrazolo[1,5-a]pyrimidine-3-carboxamide (Example 1) (50 mg, 0.119 mmol), potassium carbonate (58 mg, 0.416 mmol) and 3-methanesulfonyloxypiperidine-1-carboxylic acid tert-butyl ester (170 mg, 0.594 mmol) in N,N-dimethylacetamide (1.5 mL) was stirred at 80° C. overnight. The reaction mixture was allowed to cool to RT, poured into water (50 mL) and extracted with ethyl acetate (2×100 mL). The combined organic layer was washed with brine, dried over magnesium sulfate and concentrated under reduced pressure. The crude residue was purified by column chromatography (silica gel, 100-200 mesh, 0 to 10% methanol in DCM). The appropriate fractions were combined and concentrated under reduced pressure to afford tert-butyl 3-(3-(3-(difluoromethoxy)naphthalen-2-yl)-4-(pyrazolo[1,5-a]pyrimidine-3-carboxamido)-1H-pyrazol-1-yl)piperidine-1-carboxylate (66 mg, 92%) as a yellow gel. LC/MS (Method K, ESI): [M+H]$^+$=604, R$_T$=3.18 min.

To a solution of tert-butyl 3-(3-(3-(difluoromethoxy)naphthalen-2-yl)-4-(pyrazolo[1,5-a]pyrimidine-3-carboxamido)-1H-pyrazol-1-yl)piperidine-1-carboxylate (66 mg, 0.109 mmol) in dioxane (1 mL) was added 4N HCl in dioxane (1 mL, 4.00 mmol). The resulting solution was stirred at RT for 2 h. The mixture was concentrated under reduced pressure and the residue dissolved in ethyl acetate and washed with water and saturated aqueous sodium bicarbonate. The organic extract was washed with brine, dried over magnesium sulfate and concentrated under reduced pressure. The crude residue was further purified by achiral SFC (Cyano, 150×21.2 mm 5 u, 15% methanol+0.1% ammonium hydroxide isocratic elution with carbon dioxide) to afford the title compound (2.2 mg, 4%) as a white solid. LC/MS (Method K, ESI): [M+H]$^+$=504, R$_T$=2.01 min. $^1$H NMR (500 MHz, DMSO-d$_6$) δ 9.82 (s, 1H), 9.35-9.29 (m, 1H), 8.65 (s, 1H), 8.46-8.37 (m, 2H), 8.17 (s, 1H), 8.03 (t, J=7.5 Hz, 2H), 7.88 (s, 1H), 7.63 (t, J=7.5 Hz, 1H), 7.57 (t, J=7.5 Hz, 1H), 7.46 (t, J=73.8 Hz, 1H), 7.24 (dd, J=6.7, 4.5 Hz, 1H), 4.26 (ddd, J=14.4, 10.5, 3.9 Hz, 1H), 3.27 (d, J=12.9 Hz, 1H), 2.88 (q, J=12.2, 11.1 Hz, 2H), 2.19 (d, J=9.6 Hz, 1H), 1.98 (qd, J=12.1, 3.9 Hz, 1H), 1.79-1.73 (m, 1H), 1.55 (q, J=12.2 Hz, 1H).

Example 6 (General Procedure F)

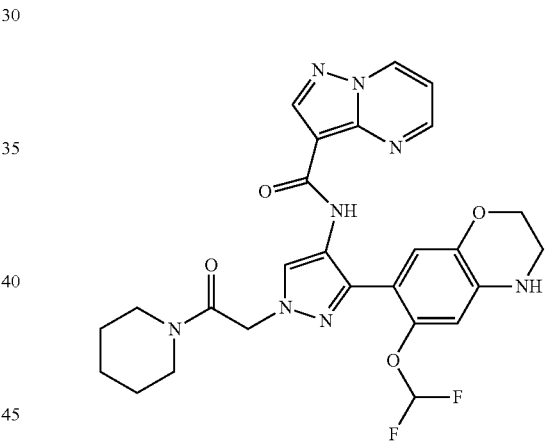

N-[3-[6-(difluoromethoxy)-3,4-dihydro-2H-1,4-benzoxazin-7-yl]-1-[2-oxo-2-(piperidin-1-yl)ethyl]-1H-pyrazol-4-yl]pyrazolo[1,5-a]pyrimidine-3-carboxamide A solution of N-[3-[6-(difluoromethoxy)-3,4-dihydro-2H-1,4-benzoxazin-7-yl]-1H-pyrazol-4-yl]pyrazolo[1,5-a]pyrimidine-3-carboxamide (Example 11) (100 mg, 0.234 mmol), Cs$_2$CO$_3$ (156 mg, 0.479 mmol) and 2-bromo-1-(piperidin-1-yl)ethan-1-one (100 mg, 0.485 mmol) in N,N-dimethylformamide (10 mL) was stirred at RT overnight. The solvent was evaporated and the residue was passed through a short pad of silica gel column with dichloromethane/methanol (20/1). The crude product was purified by Prep-HPLC (Column, Xbridge Phenyl OBD Column, 5 um, 19*150 mm; mobile phase, Waters (0.05% NH$_4$OH) and acetonitrile (5% acetonitrile to 35% over 10 min); Detector, UV 220 nm) to afford the title compound (39.6 mg, 31%) as a white solid. LC/MS (Method A, ESI): [M+H]$^+$=553, $R_T$=2.53 min; $^1$H NMR (400 MHz, DMSO-d$_6$): δ 9.79 (s, 1H), 9.35 (dd, J=7.2, 1.6 Hz, 1H), 8.67-8.64 (m, 2H), 8.22 (s, 1H), 7.30 (dd, J=7.2, 4.0 Hz, 1H), 6.90 (t, J=75.0 Hz, 1H), 6.78 (s, 1H), 6.59 (s, 1H), 6.33 (s, 1H), 5.13 (s, 2H), 4.17 (t, J=4.2 Hz, 2H), 3.46-3.44 (m, 4H), 3.37-3.32 (m, 2H), 1.61-1.59 (m, 2H), 1.52-1.46 (m, 4H).

Example 7 (General Procedure G)

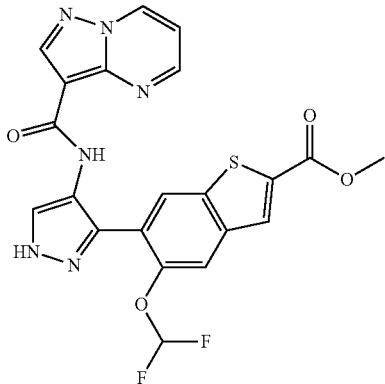 [SMILES: COC(=O)c1cc2cc(OC(F)F)c(-c3n[nH]cc3NC(=O)c3cnn4cccnc34)cc2s1]

Methyl 5-(difluoromethoxy)-6-(4-(pyrazolo[1,5-a]pyrimidine-3-carboxamido)-1H-pyrazol-3-yl)benzo[b]thiophene-2-carboxylate A degassed mixture of N-(3-iodo-1-((2-(trimethylsilyl)ethoxy)methyl)-1H-pyrazol-4-yl)pyrazolo[1,5-a]pyrimidine-3-carboxamide (Intermediate 14) (1.0 g, 2.06 mmol), methyl 5-(difluoromethoxy)-6-(4,4,5,5-tetramethyl-1,3,2-dioxaborolan-2-yl)benzo[b]thiophene-2-carboxylate (Intermediate 17) (1.03 g, 2.68 mmol), potassium carbonate (1141 mg, 8.26 mmol) and bis(di-tert-butyl(4-dimethylaminophenyl)phosphine)dichloropalladium(II) (308 mg, 0.41 mmol) in 1,4-dioxane (8 mL) and N,N-dimethylacetamide (4 mL) was heated at 100° C. in a sealed tube for 16 h. The reaction mixture was allowed to cool to RT, poured into water (50 mL) and extracted with ethyl acetate (2×100 mL). The combined organic layer was washed with saturated aqueous sodium chloride solution, dried over magnesium sulfate, filtered, and concentrated under reduced pressure. The crude residue was triturated with ethyl acetate, the precipitated solid was collected by filtration and dried under vacuum to afford methyl 5-(difluoromethoxy)-6-(4-(pyrazolo[1,5-a]pyrimidine-3-carboxamido)-1-((2-(trimethylsilyl)ethoxy)methyl)-1H-pyrazol-3-yl)benzo[b]thiophene-2-carboxylate (484 mg, 38% yield) as a brown solid. LC/MS (Method K, ESI): [M+H]$^+$=615, $R_T$=3.16 min.

4N HCl in dioxane (1 mL, 4.00 mmol) was added to a solution of methyl 5-(difluoromethoxy)-6-(4-(pyrazolo[1,5-a]pyrimidine-3-carboxamido)-1-((2-(trimethylsilyl)ethoxy)methyl)-1H-pyrazol-3-yl)benzo[b]thiophene-2-carboxylate (50 mg, 0.081 mmol) in 1,4-dioxane (0.5 mL). The resulting solution was stirred for at RT for 18 h and concentrated under reduced pressure. The residue dissolved in ethyl acetate and washed with saturated aqueous sodium bicarbonate solution. The organic layer was washed with brine, dried over magnesium sulfate and concentrated under reduced pressure to afford methyl 5-(difluoromethoxy)-6-(4-(pyrazolo[1,5-a]pyrimidine-3-carboxamido)-1H-pyrazol-3-yl)benzo[b]thiophene-2-carboxylate (23 mg, 50%) as a white solid. LC/MS (Method K, ESI): [M+H]$^+$=485 $R_T$=1.97 min. $^1$H NMR (400 MHz, DMSO-d$_6$) δ 9.78 (s, 1H), 9.32 (dd, J=7.0, 1.6 Hz, 1H), 8.65 (s, 1H), 8.57-8.49 (m, 1H), 8.32 (s, 1H), 8.30 (s, 1H), 8.26 (s, 1H), 8.07 (s, 1H), 7.51-6.98 (m, 2H), 3.92 (s, 3H).

Example 8 (General Procedure H)

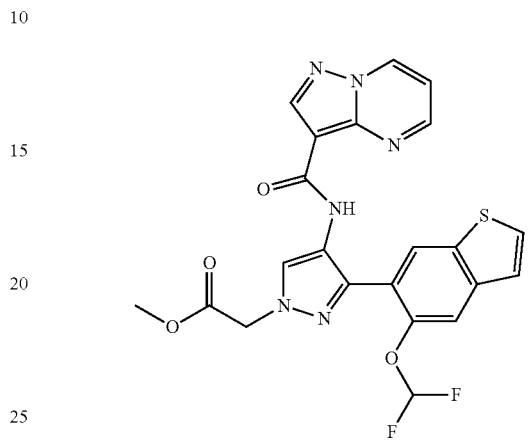

Methyl 2-(3-(5-(difluoromethoxy)benzo[b]thiophen-6-yl)-4-(pyrazolo[1,5-a]pyrimidine-3-carboxamido)-1H-pyrazol-1-yl)acetate A degassed mixture of 6-bromo-5-(difluoromethoxy)benzothiophene (Intermediate 1) (172 mg, 0.62 mmol), bispinacol ester boronate (283 mg, 1.11 mmol), 1,1'-bis(diphenylphosphino)ferrocene palladium (II) chloride (50 mg, 0.062 mmol) and potassium acetate (302 mg, 3.08 mmol) in 1,4-dioxane (4 mL) was heated in a sealed tube on a heating block at 95° C. for 16 h. The reaction mixture was allowed to cool to RT. Bis(di-tert-butyl(4-dimethylaminophenyl)phosphine)dichloropalladium(ii) (92 mg, 0.13 mmol), potassium carbonate (341 mg, 2.46 mmol), methyl 2-(3-iodo-4-(pyrazolo[1,5-a]pyrimidine-3-carboxamido)-1H-pyrazol-1-yl)acetate (Intermediate 15) (263 mg, 0.62 mmol) and 1,4-dioxane (1.5 mL) were added and the mixture heated in a heating block at 95° C. for 5 h. The reaction mixture was allowed to cool to RT, poured into water (50 mL) and extracted with ethyl acetate (2×100 mL). The combined organic layer was washed with saturated aqueous sodium chloride solution, dried over magnesium sulfate, filtered, and concentrated under reduced pressure. The crude residue was purified by column chromatography (silica gel, 100-200 mesh, 0 to 10% methanol in DCM). Appropriate fractions were combined and concentrated under reduced pressure to afford methyl 2-(3-(5-(difluoromethoxy)-benzo[b]thiophen-6-yl)-4-(pyrazolo[1,5-a]pyrimidine-3-carboxamido)-1H-pyrazol-1-yl)acetate (150 mg, 49%) as a tan solid. LC/MS (Method K, ESI): [M+H]$^+$=499, $R_T$=2.18 min. $^1$H NMR (400 MHz, DMSO-d$_6$) δ 9.83 (s, 1H), 9.32 (dd, J=7.0, 1.7 Hz, 1H), 8.67 (s, 1H), 8.53-8.47 (m, 1H), 8.42 (s, 1H), 8.19 (s, 1H), 7.99-7.91 (m, 2H), 7.58 (d, J=5.5 Hz, 1H), 7.45-7.00 (m, 2H), 5.20 (s, 2H), 3.73 (s, 3H).

Example 9 (General Procedure I)

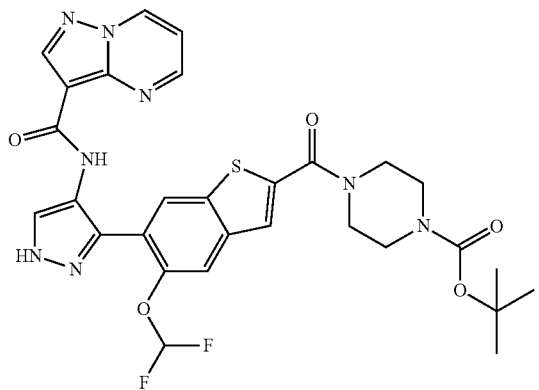 [SMILES: CC(C)(C)OC(=O)N1CCN(C(=O)c2cc3cc(OC(F)F)c(-c4n[nH]cc4NC(=O)c4cnn5cccnc45)cc3s2)CC1]

tert-Butyl 4-(5-(difluoromethoxy)-6-(4-(pyrazolo[1,5-a]pyrimidine-3-carboxamido)-1H-pyrazol-3-yl)benzo[b]thiophene-2-carbonyl)piperazine-1-carboxylate 1M aqueous sodium hydroxide solution (0.25 mL, 0.25 mmol) was added to a solution of methyl 5-(difluoromethoxy)-6-(4-(pyrazolo[1,5-a]pyrimidine-3-carboxamido)-1-((2-(trimethylsilyl)ethoxy)methyl)-1H-pyrazol-3-yl)benzo[b]thiophene-2-carboxylate (Synthesised following General Procedure A and Intermediate 3) (100 mg, 0.16 mmol) in tetrahydrofuran (1 mL) and methanol (0.25 mL). The reaction mixture was stirred at RT for 1 h and concentrated to dryness. The resultant residue was diluted with water (25 mL) and the pH adjusted 1 by the addition of 1 N hydrochloric acid. The precipitated solid was collected by filtration and left to dry under vacuum to afford 5-(difluoromethoxy)-6-(4-(pyrazolo[1,5-a]pyrimidine-3-carboxamido)-1-((2-(trimethylsilyl)ethoxy)methyl)-1H-pyrazol-3-yl)benzo[b]thiophene-2-carboxylic acid (72 mg, 74% yield) as a yellow solid. LC/MS (Method K, ESI): [M+H]$^+$=601, R$_T$=2.74 min.

To a solution of 5-(difluoromethoxy)-6-(4-(pyrazolo[1,5-a]pyrimidine-3-carboxamido)-1-((2-(trimethylsilyl)ethoxy)methyl)-1H-pyrazol-3-yl)benzo[b]thiophene-2-carboxylic acid (235 mg, 0.39 mmol) and piperazine-1-carboxylic acid tert-butyl ester (110 mg, 0.59 mmol) in N,N-dimethylformamide (3 mL) was added HATU (230 mg, 0.59 mmol), and N,N-diisopropylethylamine (0.41 mL, 2.35 mmol). The reaction mixture was stirred at RT for 16 h, poured into water (20 mL) and extracted with ethyl acetate (2×50 mL). The combined organic layer was washed with brine, dried over magnesium sulfate and concentrated under reduced pressure to afford tert-butyl 4-(5-(difluoromethoxy)-6-(4-(pyrazolo[1,5-a]pyrimidine-3-carboxamido)-1H-pyrazol-3-yl)benzo[b]thiophene-2-carbonyl)piperazine-1-carboxylate (332 mg, 100%) as a gel, which was used in the next step without further purification. LC/MS (Method K, ESI): [M+H]$^+$=769, R$_T$=3.22 min.

To a solution of tert-butyl 4-(5-(difluoromethoxy)-6-(4-(pyrazolo[1,5-a]pyrimidine-3-carboxamido)-1H-pyrazol-3-yl)benzo[b]thiophene-2-carbonyl)piperazine-1-carboxylate (90 mg, 0.117 mmol) in tetrahydrofuran (4 mL) was added a 1M solution of tetrabutylammonium fluoride in tetrahydrofuran (1 mL, 1.00 mmol). The resulting solution was stirred at RT for 30 minutes then heated at 65° C. for 2 h. The reaction mixture was allowed to cool to RT and concentrated. The residue was dissolved with ethyl acetate, washed with water and saturated aqueous sodium bicarbonate solution, dried over magnesium sulfate, filtered, and concentrated under reduced pressure. The crude residue was purified by Prep-HPLC using the following conditions: Column: Gemini-NX C18 5 um, 110A, 50×30 mm; mobile phase: Water (0.1% Formic Acid in Water) and CH$_3$CN (20% CH$_3$CN to 60% over 10 min); Detector, UV 240 nm to afford tert-butyl 4-(5-(difluoromethoxy)-6-(4-(pyrazolo[1,5-a]pyrimidine-3-carboxamido)-1H-pyrazol-3-yl)benzo[b]thiophene-2-carbonyl)piperazine-1-carboxylate (66 mg, 84%) as a white solid. LC/MS (Method K, ESI): [M+H]$^+$=639, R$_T$=2.20 min. $^1$H NMR (400 MHz, DMSO-d$_6$) δ 13.04 (s, 1H), 9.77 (s, 1H), 9.33 (dd, J=7.0, 1.7 Hz, 1H), 8.65 (s, 1H), 8.58-8.50 (m, 1H), 8.29 (s, 1H), 8.25 (s, 1H), 7.94 (s, 1H), 7.84 (s, 1H), 7.50-7.00 (m, 2H), 3.78-3.61 (m, 4H), 3.48-3.43 (m, 4H), 1.43 (s, 9H).

Example 10 (General Procedure J)

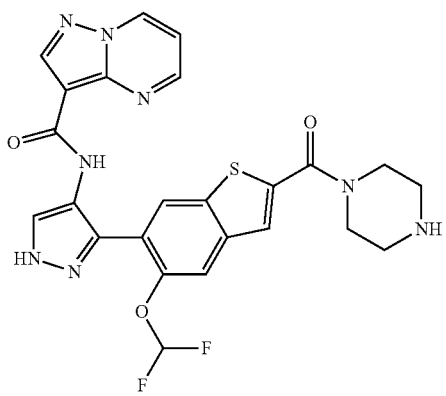 [SMILES: O=C(Nc1c[nH]nc1-c1cc2sc(C(=O)N3CCNCC3)cc2cc1OC(F)F)c1cnn2cccnc12]

N-(3-(5-(difluoromethoxy)-2-(piperazine-1-carbonyl)benzo[b]thiophen-6-yl)-1H-pyrazol-4-yl)pyrazolo[1,5-a]pyrimidine-3-carboxamide Trifluoroacetic acid (0.5 mL, 4 mmol) was added to a solution of tert-butyl 4-(5-(difluoromethoxy)-6-(4-(pyrazolo[1,5-a]pyrimidine-3-carboxamido)-1-((2-(trimethylsilyl)ethoxy)methyl)-1H-pyrazol-3-yl)benzo[b]thiophene-2-carbonyl)piperazine-1-carboxylate (Contained within the procedure for Example 7) (50 mg, 0.065 mmol) in dichloromethane (1 mL). The reaction mixture was stirred at RT for 2 h and evaporated. The residue was dissolved in dichloromethane, washed with water and saturated aqueous sodium bicarbonate solution. The precipitated solid was collected by filtration and dried under vacuum to afford N-(3-(5-(difluoromethoxy)-2-(piperazine-1-carbonyl)benzo[b]thiophen-6-yl)-1H-pyrazol-4-yl)pyrazolo[1,5-a]pyrimidine-3-carboxamide (20 mg, 57%) as a tan solid. LC/MS (Method K, ESI): [M+H]$^+$=539, R$_T$=1.12 min. $^1$H NMR (400 MHz, DMSO-d$_6$) δ 9.72 (s, 1H), 9.28 (d, J=7.0 Hz, 1H), 8.63 (s, 1H), 8.55 (d, J=4.2 Hz, 1H), 8.26-8.18 (m, 2H), 7.94 (s, 1H), 7.82-7.74 (m, 1H), 7.41-6.92 (m, 2H), 3.71 (dt, J=10.3, 4.8 Hz, 2H), 3.65-3.48 (m, 2H), 2.85-2.71 (m, 2H), 2.69-2.55 (m, 2H).

Example 11 (General Procedure K)

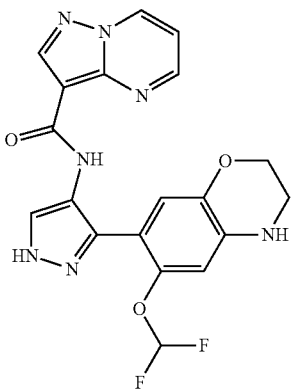 [SMILES: O=C(Nc1c[nH]nc1-c1cc2c(cc1OC(F)F)NCCO2)c1cnn2cccnc12]

N-[5-[6-(difluoromethoxy)-3,4-dihydro-2H-1,4-benzoxazin-7-yl]-1-[[2-(trimethylsilyl) ethoxy]methyl]-1H-pyrazol-4-yl]pyrazolo[1,5-a]pyrimidine-3-carboxamide To a solution of N-[5-[5-bromo-4-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (Intermediate 12) (200 mg, 0.326 mmol) in toluene (10 mL) was added tert-butyl N-(2-hydroxyethyl)carbamate (105 mg, 0.651 mmol), [PdCl(allyl)]$_2$ (6.01 mg, 0.0161 mmol), t-BuBrettPhos (16.0 mg, 0.0329 mmol) and Cs$_2$CO$_3$ (213 mg, 0.654 mmol) under nitrogen. The reaction mixture was stirred at 60° C. for 4 h, allowed to cool to RT and concentrated under vacuum. The residue was purified by silica gel chromatography eluting with dichloromethane/methanol (19/1). The appropriate fractions were combined and concentrated under vacuum to afford tert-butyl N-[2-[2-chloro-4-(difluoromethoxy)-5-(4-[pyrazolo[1,5-a]pyrimidine-3-amido]-1-[[2-(trimethylsilyl)ethoxy]methyl]-1H-pyrazol-5-yl)phenoxy]ethyl]carbamate (182 mg, 80%) as a yellow oil. LC/MS (Method G, ESI): [M+H]$^+$=694, R$_T$=1.54 min.

To a solution of tert-butyl N-[2-[4-(difluoromethoxy)-5-(4-[pyrazolo[1,5-a]pyrimidine-3-amido]-1-[[2-(trimethylsilyl)ethoxy]methyl]-1H-pyrazol-5-yl)phenoxy]-ethyl]carbamate (182 mg, 0.270 mmol) in t-BuOH (15 mL) was added BrettPhos Palladacycle Gen. 3 (CAS 1470372-59-8, vendor J&K Scientific Ltd) (48.0 mg, 0.0530 mmol), BrettPhos (56.0 mg, 0.104 mmol) and potassium carbonate (73.0 mg, 0.528 mmol) under nitrogen. The reaction mixture was stirred at 110° C. for 20 h. The resulting mixture was allowed to cool to RT and concentrated under vacuum. The residue was purified by silica gel chromatography eluting with ethyl acetate/petroleum ether (1/1). The appropriate fractions were combined and concentrated under vacuum to afford tert-butyl 6-(difluoromethoxy)-7-(4-[pyrazolo[1,5-a]pyrimidine-3-amido]-1-[[2-(trimethylsilyl)ethoxy]methyl]-1H-pyrazol-5-yl)-3,4-dihydro-2H-1,4-benzoxazine-4-carboxylate (95 mg, 53%) as a yellow solid. LC/MS (Method F, ESI): [M+H]$^+$=658, R$_T$=1.17 min.

To a solution of tert-butyl 6-(difluoromethoxy)-7-(4-[pyrazolo[1,5-a]pyrimidine-3-amido]-1-[[2-(trimethylsilyl)ethoxy]methyl]-1H-pyrazol-5-yl)-3,4-dihydro-2H-1,4-benzoxazine-4-carboxylate (80 mg, 0.122 mmol) in methanol (8.0 mL) was added HCl (6M) (4.0 mL). The reaction mixture was stirred at RT for 4 h. The resulting mixture was concentrated under vacuum. The crude product was purified by Prep-HPLC (Column, XBridge Shield RP18 OBD Column, 19*150 mm, 5 um; mobile phase, 10 mM NH$_4$HCO$_3$ in water and CH$_3$CN (10.0% CH$_3$CN to 38.0% over 10 min); Detector, UV 254 nm) to afford the title compound (16.1 mg, 24%) as a yellow solid. LC/MS (Method C, ESI): [M+H]$^+$=428, R$_T$=2.05 min; $^1$H NMR (400 MHz, CD$_3$OD): δ 8.98 (d, J=6.8 Hz, 1H), 8.57-8.51 (m, 2H), 8.12 (s, 1H), 7.10 (dd, J=7.0, 4.2 Hz, 1H), 6.79 (s, 1H), 6.51 (s, 1H), 6.40 (t, J=75.2 Hz, 1H), 4.13-4.11 (m, 2H), 3.39-3.32 (m, 2H).

Example 12 (General Procedure L)

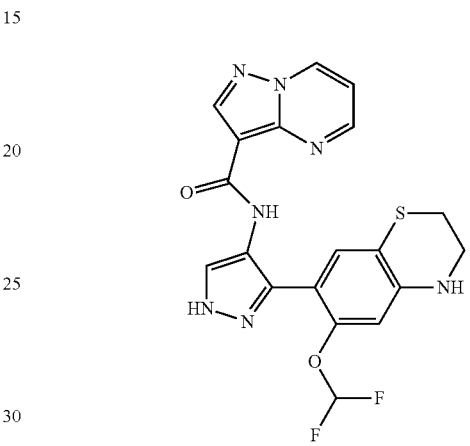

N-(3-(6-(difluoromethoxy)-3,4-dihydro-2H-benzo[b][1,4]thiazin-7-yl)-1H-pyrazol-4-yl)pyrazolo[1,5-a]pyrimidine-3-carboxamide A degassed mixture of N-[5-[5-bromo-4-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (Intermediate 12) (1.00 g, 1.62 mmol), tert-butyl N-(2-sulfanylethyl)carbamate (867 mg, 4.89 mmol), Pd$_2$(dba)$_3$.CHCl$_3$ (338 mg, 0.327 mmol), XantPhos (380 mg, 0.657 mmol) and potassium carbonate (676 mg, 4.89 mmol) in toluene (14 mL) was heated at 80° C. overnight. The reaction mixture was allowed to cool to RT and concentrated under vacuum. The residue was purified by silica gel chromatography eluting with ethyl acetate/petroleum ether (1/1-4/1). The appropriate fractions were combined and concentrated under vacuum to afford tert-butyl N-(2-[[2-chloro-4-(difluoromethoxy)-5-(4-[pyrazolo[1,5-a]pyrimidine-3-amido]-1-[[2-(trimethylsilyl)ethoxy]-methyl]-1H-pyrazol-5-yl)phenyl]sulfanyl]ethyl)carbamate (670 mg, 58%) as a light yellow solid. LC/MS (Method F, ESI): [M+Na]$^+$=732, R$_T$=1.43 min.

A degassed mixture of tert-butyl N-(2-[[2-chloro-4-(difluoromethoxy)-5-(4-[pyrazolo[1,5-a]pyrimidine-3-amido]-1-[[2-(trimethylsilyl)ethoxy]methyl]-1H-pyrazol-5-yl)phenyl]sulfanyl]-ethyl)carbamate (670 mg, 0.943 mmol), BrettPhos Palladacycle Gen. 3 (CAS 1470372-59-8, vendor J&K Scientific Ltd) (86.0 mg, 0.095 mmol), BrettPhos (101 mg, 0.188 mmol) and potassium carbonate (260 mg, 1.88 mmol) in toluene (14 mL) was stirred overnight at 110° C. The reaction mixture was cooled and concentrated under vacuum. The residue was purified by silica gel chromatography eluting with ethyl acetate/petroleum ether (1/1~3/2). The appropriate fractions were combined and concentrated under vacuum to afford tert-butyl 6-(difluoromethoxy)-7-(4-[pyrazolo[1,5-a]pyrimidine-3-amido]-1-[[2-(trimethylsilyl)ethoxy]methyl]-1H-pyrazol-5-yl)-3,4-dihydro-2H-1,4-benzothiazine-4-carboxylate (530 mg, 83%) as a light yellow solid. LC/MS (Method F, ESI): [M+H]$^+$=674, $R_T$=1.23 min.

tert-butyl 6-(difluoromethoxy)-7-(4-[pyrazolo[1,5-a]pyrimidine-3-amido]-1-[[2-(trimethylsilyl)ethoxy]methyl]-1H-pyrazol-5-yl)-3,4-dihydro-2H-1,4-benzothiazine-4-carboxylate (30.0 mg, 0.0445 mmol) was dissolved in HCl/dioxane (10 ml, 4 M). The resulting solution was stirred at RT for 3 h. The mixture was concentrated under vacuum, the residue diluted with dichloromethane (5 mL) and DIPEA (1 mL) were added. The resulting mixture was concentrated under vacuum and the residue was purified by silica gel chromatography eluting with methanol/dichloromethane (1/10). The crude product was purified by Prep-HPLC (Column, Xbridge Phenyl OBD Column, 19*150 mm, 5 um; mobile phase, Water (0.05% NH$_4$OH) and CH$_3$CN (10% CH$_3$CN to 40% over 15 min); Detector, UV 254 nm) to afford the title compound (5.1 mg, 26%) as a yellow solid. LC/MS (Method F, ESI): [M+H]$^+$=444.2, $R_T$=0.75 min; $^1$H NMR (300 MHz, DMSO-d$_6$): δ 12.97 (s, 1H), 9.67 (s, 1H), 9.34 (dd, J=6.9, 1.5 Hz, 1H), 8.71 (dd, J=4.2, 1.5 Hz, 1H), 8.65 (s, 1H), 8.12 (s, 1H), 7.30 (dd, J=7.1, 4.4 Hz, 1H), 7.04 (s, 1H), 6.97 (t, J=73.2 Hz, 1H), 6.64 (s, 1H), 6.53 (s, 1H), 3.56 (t, J=3.0 Hz, 2H), 3.02-2.99 (m, 2H).

Example 13 (General Procedure M)

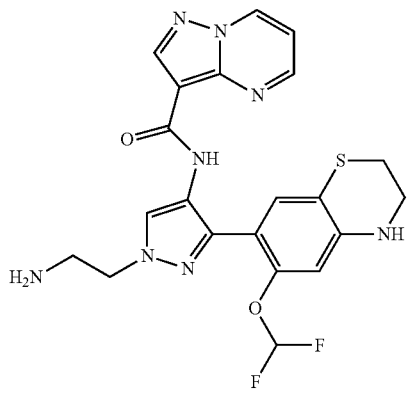 [SMILES: NCCn1cc(NC(=O)c2cnn3cccnc23)c(-c2cc3c(cc2OC(F)F)NCCS3)n1]

N-(1-(2-aminoethyl)-3-(6-(difluoromethoxy)-3,4-dihydro-2H-benzo[b][1,4]thiazin-7-yl)-1H-pyrazol-4-yl)pyrazolo[1,5-a]pyrimidine-3-carboxamide A mixture of N-[5-[5-bromo-4-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (Intermediate 12) (2.00 g, 3.258 mmol) and concentrated hydrochloric acid (15 mL, 12 M) in methanol (30 mL) was stirred at RT for 3 h. The precipitated solid was collected by filtration to afford N-[3-[5-bromo-4-chloro-2-(difluoromethoxy)phenyl]-1H-pyrazol-4-yl]pyrazolo[1,5-a]pyrimidine-3-carboxamide (1.57 g) as a white solid. LC/MS (Method F, ESI): [M+H]$^+$=485, $R_T$=0.87 min.

A mixture of N-[3-[5-bromo-4-chloro-2-(difluoromethoxy)phenyl]-1H-pyrazol-4-yl]pyrazolo[1,5-a]pyrimidine-3-carboxamide (2.30 g, crude), tert-butyl N-(2-bromoethyl)carbamate (4.30 g, 19.2 mmol) and Cs$_2$CO$_3$ (6.30 g, 19.3 mmol) in tetrahydrofuran (100 mL) was heated at 55° C. for 3.5 h. The resulting mixture was allowed to cool to RT, concentrated under vacuum and the residue was purified by silica gel chromatography eluting with ethyl acetate/petroleum ether (1/1) to afford tert-butyl N-(2-[3-[5-bromo-4-chloro-2-(difluoromethoxy)phenyl]-4-[pyrazolo[1,5-a]pyrimidine-3-amido]-1H-pyrazol-1-yl]ethyl)carbamate (2.5 g, 76% yield over two steps) as a white solid. LC/MS (Method F, ESI): [M+H]$^+$=628, $R_T$=1.04 min.

A degassed mixture of tert-butyl N-(2-[3-[5-bromo-4-chloro-2-(difluoromethoxy)phenyl]-4-[pyrazolo[1,5-a]pyrimidine-3-amido]-1H-pyrazol-1-yl]ethyl)carbamate (300 mg, 0.479 mmol), tert-butyl N-(2-sulfanylethyl)carbamate (170 mg, 0.959 mmol), XantPhos (112 mg, 0.194 mmol), Pd$_2$(dba)$_3$ (96.0 mg, 0.262 mmol) and potassium carbonate (133 mg, 0.962 mmol) in tetrahydrofuran (100 mL) was heated at 100° C. overnight. The reaction was allowed to cool to RT and concentrated under vacuum. The residue was purified by silica gel column eluting with ethyl acetate/petroleum ether (4/1). Appropriate fractions were combined and evaporated to give tert-butyl N-[2-(3-[5-[(2-[[(tert-butoxy)carbonyl]amino]ethyl) sulfanyl]-4-chloro-2-(difluoromethoxy)phenyl]-4-[pyrazolo[1,5-a]pyrimidine-3-amido]-1H-pyrazol-1-yl]ethyl]carbamate (310 mg, 90%) as a yellow solid. LC/MS (Method F, ESI): [M+H]$^+$=723, $R_T$=1.05 min.

A degassed mixture of tert-butyl N-[2-(3-[5-[(2-[[(tert-butoxy)carbonyl]-amino]ethyl)sulfanyl]-4-chloro-2-(difluoromethoxy)phenyl]-4-[pyrazolo[1,5-a]pyrimidine-3-amido]-1H-pyrazol-1-yl]ethyl]carbamate (310 mg, 0.429 mmol), BrettPhos (93 mg, 0.173 mmol), K$_2$CO$_3$ (119 mg, 0.861 mmol) and BrettPhos Palladacycle Gen. 3 (CAS 1470372-59-8, vendor J&K Scientific Ltd) (86.0 mg, 0.111 mmol) in t-BuOH (20 mL) was heated overnight at 110° C. The reaction mixture was allowed to cool to RT and concentrated under vacuum. The residue was purified by silica gel chromatography eluting with ethyl acetate to afford tert-butyl 7-[1-(2-[[(tert-butoxy)carbonyl]amino]ethyl)-4-[pyrazolo[1,5-a]pyrimidine-3-amido]-1H-pyrazol-3-yl]-6-(difluoromethoxy)-3,4-dihydro-2H-1,4-benzothiazine-4-carboxylate (210 mg, 71%) as a yellow solid. LC/MS (Method H, ESI): [M+H]$^+$=687, $R_T$=1.18 min.

To a solution of tert-butyl 7-[1-(2-[[(tert-butoxy)carbonyl]amino]ethyl)-4-[pyrazolo[1,5-a]pyrimidine-3-amido]-1H-pyrazol-3-yl]-6-(difluoromethoxy)-3,4-dihydro-2H-1,4-benzothiazine-4-carboxylate (210 mg, 0.306 mmol) in methanol (10 mL) was added concentrated hydrochloric acid (5.0 mL, 12 M). The reaction mixture was stirred for 2 days at RT. The resulting mixture was concentrated under vacuum, DIPEA (0.5 mL) was added and the mixture concentrated. The residue was passed through a short pad of silica gel eluting with CH$_2$Cl$_2$/MeOH=5/1. The crude product was purified by Prep-HPLC (Column, XBridge Shield RP18 OBD Column, 19*150 mm, 5 um; mobile phase: 10 mM NH$_4$HCO$_3$ in water and CH$_3$CN (33% CH$_3$CN to 55% over 14 min); Detector, UV 254 nm) to afford N-[1-(2-aminoethyl)-3-[6-(difluoromethoxy)-3,4-dihydro-2H-1,4-benzothiazin-7-yl]-1H-pyrazol-4-yl]pyrazolo[1,5-a]pyrimidine-3-carboxamide (49.4 mg, 33%) as a yellow solid. LC/MS (Method A, ESI): [M+H]$^+$=487, $R_T$=2.22 min. $^1$H NMR (400 MHz, DMSO-d$_6$): δ 9.10 (dd, J=6.8, 1.2 Hz, 1H), 8.74 (dd, J=4.4, 1.6 Hz, 1H), 8.65 (s, 1H), 8.29 (s, 1H), 7.23 (dd, J=7.0, 4.2 Hz, 1H), 7.14 (s, 1H), 6.61 (t, J=74.6 Hz, 1H), 6.54 (s, 1H), 4.26 (t, J=6.0 Hz, 2H), 3.69-3.67 (m, 2H), 3.15 (t, J=6.0 Hz, 2H), 3.07-3.04 (m, 2H).

Example 14 (General Procedure N)

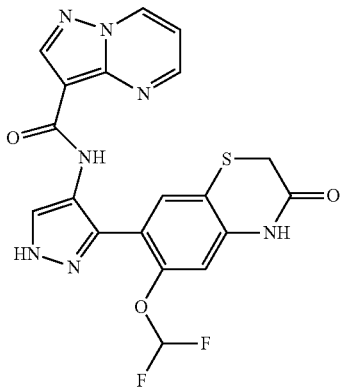 [SMILES: O=C1CSc2cc(-c3n[nH]cc3NC(=O)c3cnn4cccnc34)c(OC(F)F)cc2N1]

N-[3-[6-(difluoromethoxy)-3-oxo-3,4-dihydro-2H-1,4-benzothiazin-7-yl]-1H-pyrazol-4-yl]pyrazolo[1,5-a]pyrimidine-3-carboxamide A degassed mixture of N-[5-[5-bromo-4-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (Intermediate 12) (400 mg, 0.652 mmol), methyl 2-sulfanylacetate (212 mg, 1.99 mmol), $Pd_2(dba)_3 \cdot CHCl_3$ (67.0 mg, 0.065 mmol), XantPhos (75.0 mg, 0.130 mmol) and potassium carbonate (276 mg, 1.99 mmol) in toluene (15 mL) was stirred at 80° C. for 20 h. The reaction mixture was cooled to RT and concentrated under vacuum. The residue was purified by silica gel chromatography eluting with ethyl acetate/hexane (1/2-1/1). The appropriate fractions were combined and concentrated under vacuum to afford methyl 2-[[2-chloro-4-(difluoromethoxy)-5-(4-[pyrazolo[1,5-a]pyrimidine-3-amido]-1-[[2-(trimethylsilyl)ethoxy]methyl]-1H-pyrazol-5-yl)phenyl]sulfanyl]acetate (140 mg, 4%) of as light yellow oil.

Methyl 2-[[2-chloro-4-(difluoromethoxy)-5-(4-[pyrazolo[1,5-a]pyrimidine-3-amido]-1-[[2-(trimethylsilyl)ethoxy]methyl]-1H-pyrazol-5-yl)phenyl]sulfanyl]acetate (140 mg, 0.219 mmol) was dissolved in $NH_3$/ethanol (18%, 10 ml) and the mixture was stirred for 2 days at RT. The resulting mixture was concentrated under vacuum to afford N-(5-[5-[(carbamoylmethyl)sulfanyl]-4-chloro-2-(difluoromethoxy)phenyl]-1-[[2-(trimethylsilyl)ethoxy]methyl]-1H-pyrazol-4-yl)pyrazolo[1,5-a]pyrimidine-3-carboxamide (130 mg, 95%) as a red solid. LC/MS (Method F, ESI): [M+H]$^+$=625, $R_T$=1.21 min.

A degassed mixture of N-(5-[5-[(carbamoylmethyl)sulfanyl]-4-chloro-2-(difluoromethoxy)phenyl]-1-[[2-(trimethylsilyl)ethoxy]methyl]-1H-pyrazol-4-yl)pyrazolo[1,5-a]pyrimidine-3-carboxamide (130 mg, 0.208 mmol), BrettPhos Palladacycle Gen. 3 (CAS 1470372-59-8, vendor J&K Scientific Ltd) (4.00 mg, 0.00501 mmol), BrettPhos (5.00 mg, 0.00899 mmol) and potassium carbonate (55.0 mg, 0.398 mmol) in t-BuOH (12 mL) was stirred at 110° C. for 40 h. The reaction mixture was allowed to cool to RT and concentrated under vacuum. The residue was purified by silica gel chromatography eluting with ethyl acetate/hexane (1/1~4/1). The appropriate fractions were combined and concentrated under vacuum to afford N-[5-[6-(difluoromethoxy)-3-oxo-3,4-dihydro-2H-1,4-benzothiazin-7-yl]-1-[[2-(trimethylsilyl)ethoxy]methyl]-1H-pyrazol-4-yl]pyrazolo[1,5-a]pyrimidine-3-carboxamide (70 mg, 57%) as a light yellow oil. LC/MS (Method F, ESI): [M+H]$^+$=588, $R_T$=1.08 min.

N-[5-[6-(difluoromethoxy)-3-oxo-3,4-dihydro-2H-1,4-benzothiazin-7-yl]-1-[[2-(trimethylsilyl)ethoxy]methyl]-1H-pyrazol-4-yl]pyrazolo[1,5-a]pyrimidine-3-carboxamide (60 mg, 0.102 mmol) was dissolved in HCl/dioxane (4.0 mL, 4M) and the mixture was stirred at RT for 20 h. The mixture was concentrated under vacuum and the pH of the solution was adjusted to 8 by the addition of DIPEA. The residue was purified by Prep-HPLC (Column, Xbridge Phenyl OBD Column, 19*150 mm, 5 um; mobile phase, Water (0.05% $NH_4OH$) and $CH_3CN$ (20% $CH_3CN$ to 50% over 15 min); Detector, UV 254 nm) to afford N-[3-[6-(difluoromethoxy)-3-oxo-3,4-dihydro-2H-1,4-benzothiazin-7-yl]-1H-pyrazol-4-yl]pyrazolo[1,5-a]pyrimidine-3-carboxamide (12.1 mg, 26%) as a white solid. LC/MS (Method B, ESI): [M+H]$^+$=458, $R_T$=1.04 min; $^1$H NMR (300 MHz DMSO-$d_6$): δ 12.97 (s, 1H), 10.79 (s, 1H), 9.71 (s, 1H), 9.35 (dd, J=7.1, 1.7 Hz, 1H), 8.68-8.65 (m, 2H), 8.25 (s, 1H), 7.52 (s, 1H), 7.30 (dd, J=6.9, 4.2 Hz, 1H), 7.07 (t, J=73.8 Hz, 1H), 7.04 (s, 1H), 3.57 (s, 2H).

Example 15 (General Procedure O)

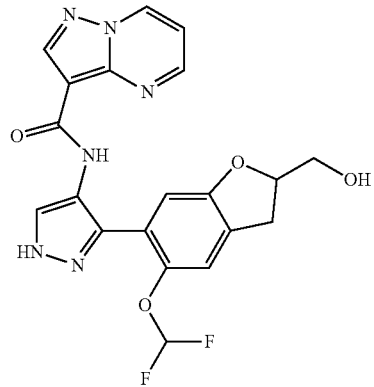 [SMILES: O=C(Nc1c[nH]nc1-c1cc2c(cc1OC(F)F)CC(CO)O2)c1cnn2cccnc12]

N-(3-(5-(difluoromethoxy)-2-(hydroxymethyl)-2,3-dihydrobenzofuran-6-yl)-1H-pyrazol-4-yl)pyrazolo[1,5-a]pyrimidine-3-carboxamide A degassed mixture of N-[5-[4-bromo-5-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (Intermediate 18) (1.00 g, 1.63 mmol), tributyl(prop-2-en-1-yl)stannane (1.08 g, 3.26 mmol), CsF (866 mg, 5.70 mmol) and $Pd(PPh_3)_4$ (188 mg, 0.163 mmol) in dioxane (30 mL) was heated at 80° C. overnight. The mixture was allowed to cool to RT and concentrated under vacuum. The residue was purified by silica gel chromatography eluting with ethyl acetate/petroleum ether (3/2). The appropriate fractions were combined and concentrated under vacuum to afford N-[5-[5-chloro-2-(difluoromethoxy)-4-(prop-2-en-1-yl)phenyl]-1-[[2-(trimethylsilyl)ethoxy]methyl]-1H-pyrazol-4-yl]pyrazolo[1,5-a]pyrimidine-3-carboxamide (1.00 g, 70%) of as a yellow solid. LC/MS (Method H, ESI): [M+H]$^+$=577, RT=3.07 min.

To a mixture of N-[5-[5-chloro-2-(difluoromethoxy)-4-(prop-2-en-1-yl)phenyl]-1-[[2-(trimethylsilyl)ethoxy]methyl]-1H-pyrazol-4-yl]pyrazolo[1,5-a]pyrimidine-3-carboxamide (1.00 g) in tetrahydrofuran (10 mL) and water (10 mL) was added NMO (430 mg, 3.67 mmol) and $OsO_4$ (840 mg, 3.304 mmol) under nitrogen. The reaction mixture was stirred at RT overnight then quenched by the addition of 1M aqueous $Na_2SO_3$ solution (10 mL). The resulting solution was extracted with ethyl acetate (3×100 mL) and the organic layers were combined. The organic phase was washed with brine, dried over anhydrous sodium sulfate and concentrated under vacuum. The residue was purified by silica gel chromatography eluting with ethyl acetate. Appropriate fractions were combined and concentrated under vacuum to afford N-[5-[5-chloro-2-(difluoromethoxy)-4-(2,3-dihydroxypropyl)phenyl]-1-[[2-(trimethylsilyl)-ethoxy]methyl]-1H-pyrazol-4-yl]pyrazolo[1,5-a]pyrimidine-3-carboxamide (1.00 g, 84%) as a light yellow solid. LC/MS (Method H, ESI): $[M+H]^+$=611, $R_T$=2.39 min.

A degassed mixture of N-[5-[5-chloro-2-(difluoromethoxy)-4-(2,3-dihydroxypropyl)phenyl]-1-[[2-(trimethylsilyl)ethoxy]methyl]-1H-pyrazol-4-yl]pyrazolo[1,5-a]pyrimidine-3-carboxamide (300 mg), [PdCl(allyl)]$_2$ (7.21 mg, 0.0187 mmol), t-BuBrettPhos (23.9 mg, 0.0493 mmol) and $Cs_2CO_3$ (401 mg, 1.23 mmol) in toluene (15 mL) was heated overnight at 95° C. The resulting mixture was allowed to cool to RT and concentrated under vacuum. The residue was purified by silica gel chromatography eluting with ethyl acetate. The appropriate fractions were combined and concentrated under vacuum to give N-[5-[6-(difluoromethoxy)-3-hydroxy-3,4-dihydro-2H-1-benzopyran-7-yl]-1-[[2-(trimethylsilyl)-ethoxy]methyl]-1H-pyrazol-4-yl]pyrazolo[1,5-a]pyrimidine-3-carboxamide (180 mg, 64% over three steps) as a yellow solid. LC/MS (Method H, ESI): $[M+H]^+$=573, $R_T$=2.40 min.

N-(5-(5-(difluoromethoxy)-2-(hydroxymethyl)-2,3-dihydrobenzofuran-6-yl)-1-((2-(trimethylsilyl)ethoxy)methyl)-1H-pyrazol-4-yl)pyrazolo[1,5-a]pyrimidine-3-carboxamide (100 mg) was dissolved in HCl/dioxane (10 mL, 4M). The resulting solution was stirred for 3 h at RT and concentrated under vacuum. The residue was purified by reverse-phase flash chromatography on C18 silica gel eluting with $CH_3CN/H_2O$ (0.5% $NH_4HCO_3$, 0-40% $CH_3CN$ over 40 min). Appropriate fractions were combined and concentrated under vacuum to afford the title compound (25 mg, 32%) as an off-white solid. LC/MS (Method H, ESI): $[M+H]^+$=443, $R_T$=1.52 min. $^1$H NMR (400 MHz, DMSO-d$_6$): δ 12.93 (s, 1H), 9.81 (s, 1H), 9.35 (dd, J=7.2, 1.6 Hz, 1H), 8.67 (dd, J=4.2, 1.6 Hz, 1H), 8.66 (s, 1H), 8.25 (s, 1H), 7.45-7.23 (m, 2H), 6.97 (t, J=74.8 Hz, 1H), 6.89 (s, 1H), 5.08 (t, J=5.4 Hz, 1H), 4.96-4.85 (m, 1H), 3.78-3.52 (m, 2H), 3.36-3.30 (m, 1H), 3.16-3.10 (m, 1H).

Example 16 (General Procedure P)

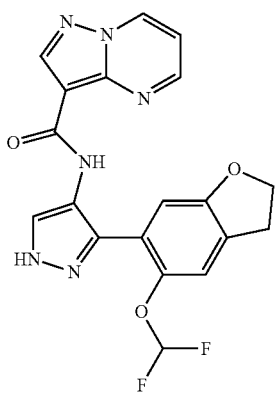 [SMILES: O=C(Nc1c[nH]nc1-c1cc2c(cc1OC(F)F)CCO2)c1cnn2cccnc12]

N-(3-(5-(difluoromethoxy)-2,3-dihydrobenzofuran-6-yl)-1H-pyrazol-4-yl)pyrazolo[1,5-a]pyrimidine-3-carboxamide A degassed mixture of N-[5-[4-bromo-5-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (Intermediate 18) (300 mg, 0.489 mmol), 2-[(E)-2-ethoxyethenyl]-4,4,5,5-tetramethyl-1,3,2-dioxaborolane (194 mg, 0.979 mmol), Pd(dppf)Cl$_2$.CH$_2$Cl$_2$ (40.0 mg, 0.0490 mmol) and Cs$_2$CO$_3$ (320 mg, 0.982 mmol) in dioxane (10 mL) and water (2.0 mL) was stirred at 80° C. overnight. The resulting mixture was allowed to cool to RT and concentrated under vacuum. The residue was purified by silica gel chromatography eluting with ethyl acetate/petroleum ether (55/45) to give N-[5-[5-chloro-2-(difluoromethoxy)-4-[(E)-2-ethoxyethenyl]phenyl]-1-[[2-(trimethylsilyl)ethoxy]methyl]-1H-pyrazol-4-yl]pyrazolo[1,5-a]pyrimidine-3-carboxamide (340 mg, 75%) as a yellow solid. LC/MS (Method D, ESI): $[M+H]^+$=605, $R_T$=1.55 min.

To a solution of N-[5-[5-chloro-2-(difluoromethoxy)-4-[(Z)-2-ethoxyethenyl]phenyl]-1-[[2-(trimethylsilyl)ethoxy]methyl]-1H-pyrazol-4-yl]pyrazolo[1,5-a]pyrimidine-3-carboxamide (340 mg) in dichloromethane (10 mL) was added trifluoroacetic acid (0.5 mL). The reaction mixture was stirred at RT for 3 h. The resulting mixture was concentrated under vacuum to afford N-[5-[5-chloro-2-(difluoromethoxy)-4-(2-oxoethyl)phenyl]-1-[[2-(trimethylsilyl)ethoxy]methyl]-1H-pyrazol-4-yl]pyrazolo[1,5-a]pyrimidine-3-carboxamide (400 mg, 60%) as yellow oil. LC/MS (Method D, ESI): $[M+H]^+$=577, $R_T$=1.40 min.

To a solution of N-[5-[5-chloro-2-(difluoromethoxy)-4-(2-oxoethyl)phenyl]-1-[[2-(trimethylsilyl)ethoxy]methyl]-1H-pyrazol-4-yl]pyrazolo[1,5-a]pyrimidine-3-carboxamide (300 mg, 60% purity by LCMS) in dichloromethane (10.0 mL) was added NaBH(OAc)$_3$ (221 mg, 1.04 mmol) in several batches. The resulting solution was stirred at RT for 30 min and concentrated under vacuum. The residue was purified by silica gel chromatography eluting with dichloromethane/methanol (20/1) to afford N-[5-[5-chloro-2-(difluoromethoxy)-4-(2-hydroxyethyl)phenyl]-1-[[2-(trimethylsilyl)ethoxy]methyl]-H-pyrazol-4-yl]pyrazolo[1,5-a]pyrimidine-3-carboxamide (50 mg, 24% yield over three steps) of as a yellow solid. LC/MS (Method E, ESI): $[M+H]^+$=579, $R_T$=0.99 min.

A degassed mixture of N-[5-[5-chloro-2-(difluoromethoxy)-4-(2-hydroxyethyl)phenyl]-1-[[2-(trimethylsilyl)ethoxy]methyl]-1H-pyrazol-4-yl]pyrazolo[1,5-a]pyrimidine-3-carboxamide (50.0 mg, 0.0864 mmol), Pd$_2$(Allyl)$_2$Cl$_2$ (1.58 mg, 0.00409 mmol), t-BuBrettphos (4.20 mg, 0.00866 mmol) and Cs$_2$CO$_3$ (70.5 mg, 0.216 mmol) in toluene (2.0 mL) was stirred at 95° C. overnight. The resulting mixture was allowed to cool to RT and concentrated under vacuum. The residue was purified by silica gel chromatography eluting with ethyl acetate/petroleum ether (7/3) to afford N-[5-[5-(difluoromethoxy)-2,3-dihydro-1-benzofuran-6-yl]-1-[[2-(trimethylsilyl)ethoxy]methyl]-1H-pyrazol-4-yl]pyrazolo[1,5-a]pyrimidine-3-carboxamide (35 mg, 75%) as yellow oil. LC/MS (Method D, ESI): $[M+H]^+$=543, $R_T$=1.42 min.

To a solution of N-[5-[5-(difluoromethoxy)-2,3-dihydro-1-benzofuran-6-yl]-1-[[2-(trimethylsilyl)ethoxy]methyl]-1H-pyrazol-4-yl]pyrazolo[1,5-a]pyrimidine-3-carboxamide (35 mg, 0.0645 mmol) in dichloromethane (5.0 mL) was added trifluoroacetic acid (4.0 mL). The reaction mixture was stirred at RT for 3 h. The resulting mixture was concentrated under vacuum. The residue was purified by Prep-HPLC (Column, Xbridge Phenyl OBD Column, 19*150 mm, 5 um; mobile phase, Water (0.05% NH₄OH) and CH₃CN (25.0% CH₃CN to 35.0% over 7 min); Detector, UV 220, 254 nm) to afford the title compound (7.7 mg, 29%) as an off-white solid. LC/MS (Method H, ESI): [M+H]⁺=413, $R_T$=1.42 min. ¹H NMR (400 MHz, DMSO-d6): δ 12.99 & 12.94 (s, 1H), 9.80 & 9.72 (s, 1H), 9.35 (dd, J=6.8, 1.6 Hz, 1H), 8.69-8.66 (m, 2H), 8.25 & 8.06 (s, 1H), 7.32-7.29 (m, 2H), 6.97 (t, J=74.2 Hz, 1H), 6.91 (s, 1H), 4.64 (t, J=8.6 Hz, 2H), 3.34 (t, J=8.6 Hz, 2H).

Example 17 (General Procedure Q)

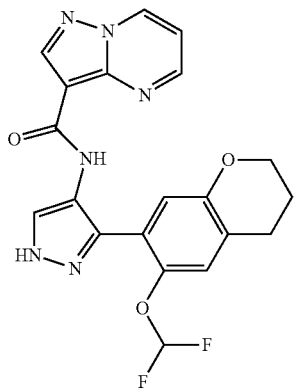 [SMILES: O=C(Nc1c[nH]nc1-c1cc2c(cc1OC(F)F)CCCO2)c1cnn2cccnc12]

N-[3-[6-(difluoromethoxy)-3,4-dihydro-2H-1-benzopyran-7-yl]-H-pyrazol-4-yl]pyrazolo[1,5-a]pyrimidine-3-carboxamide A degassed mixture of 5-[4-bromo-5-chloro-2-(difluoromethoxy)phenyl]-4-nitro-1-[[2-(trimethylsilyl)ethoxy] methyl]-1H-pyrazole (Intermediate 18) (1.50 g, 3.00 mmol), ethyl 3-(bromozincio)propanoate (9.0 mL, 0.5 M in THF) and Pd(PPh₃)₄ (360 mg, 0.312 mmol) in tetrahydrofuran (10 mL) was stirred at 70° C. for 4 h. The reaction was allowed to cool to RT and quenched by the addition of NH₄Cl aqueous solution (10 mL). Ethyl acetate (50 ml) was added and phases were separated. The organic layer was washed with water and brine, dried over sodium sulfate and concentrated under vacuum. The residue was purified by silica gel chromatography eluting with petroleum ether/ethyl acetate (6/1). Appropriate fractions were combined and evaporated to afford ethyl 3-[2-chloro-5-(difluoromethoxy)-4-(4-nitro-1-[[2-(trimethylsilyl)ethoxy]methyl]-1H-pyrazol-5-yl)phenyl]propanoate (1.45 g, 92%) of as a white solid. LC/MS (Method F, ESI): [M+Na]⁺=542, $R_T$=1.42 min.

To a solution of ethyl 3-[2-chloro-5-(difluoromethoxy)-4-(4-nitro-1-[[2-(trimethylsilyl)ethoxy]methyl]-1H-pyrazol-5-yl)phenyl]propanoate (1.45 g, 2.78 mmol) in tetrahydrofuran (15 mL) at 0° C. was added DIBAL-H (10.8 mL, 10.8 mmol, 1M in hexane) drop-wise. The reaction mixture was allowed to warm to RT and stirred for 1 h. The reaction was quenched by the addition of 10 mL of NH₄Cl solution. Ethyl acetate (50 ml) was added and phases were separated. The organic layer was washed with water and brine, dried over anhydrous sodium sulfate and concentrated under vacuum. The residue was purified by silica gel chromatography eluting with ethyl acetate/petroleum ether (1/5) to give 3-[2-chloro-5-(difluoromethoxy)-4-(4-nitro-1-[[2-(trimethylsilyl)ethoxy]methyl]-1H-pyrazol-5-yl)phenyl]propan-1-ol (0.90 g, 68%) as light yellow oil. LC/MS (Method F, ESI): [M+Na]⁺=500, $R_T$=1.31 min.

A degassed mixture of 3-[2-chloro-5-(difluoromethoxy)-4-(4-nitro-1-[[2-(trimethylsilyl)ethoxy]methyl]-1H-pyrazol-5-yl)phenyl]propan-1-ol (100 mg, 0.209 mmol), [PdCl(allyl)]₂ (3.00 mg, 0.00799 mmol), t-BuBrettPhos (10.0 mg, 0.0209 mmol) and Cs₂CO₃ (170 mg, 0.522 mmol) in toluene (3.0 mL) was stirred at 95° C. for 18 h. The reaction was repeated 3 times. The three batches were combined and partitioned between ethyl acetate and water. The organic layer was washed with water and brine, dried over anhydrous sodium sulfate and concentrated under vacuum. The residue was purified by silica gel chromatography eluting with ethyl acetate/petroleum ether (1/9) to obtain 193 mg (70%) of 5-[6-(difluoromethoxy)-3,4-dihydro-2H-1-benzopyran-7-yl]-4-nitro-1-[[2-(trimethylsilyl)ethoxy]methyl]-1H-pyrazole as a colorless oil. LC/MS (Method F, ESI): [M+H]⁺=442, $R_T$=1.22 min.

A mixture of 5-[6-(difluoromethoxy)-3,4-dihydro-2H-1-benzopyran-7-yl]-4-nitro-1-[[2-(trimethylsilyl)ethoxy] methyl]-1H-pyrazole (190 mg, 0.430 mmol), iron powder (192 mg, 3.43 mmol) and NH₄Cl (70.0 mg, 1.30 mmol) in a mixed solvent of ethanol and water (5.0 mL, v/v=10/1) was heated under reflux for 10 min. The mixture was allowed to cool to $R_T$ and the precipitated solid was removed by filtration. The filtrate was partitioned between ethyl acetate and water. The organic phase was washed with water and brine, dried over anhydrous sodium sulfate and concentrated under vacuum. The residue was purified by silica gel chromatography eluting with ethyl acetate/petroleum ether (2/3) to give 5-[6-(difluoromethoxy)-3,4-dihydro-2H-1-benzopyran-7-yl]-1-[[2-(trimethylsilyl)ethoxy]methyl]-1H-pyrazol-4-amine (0.154 g, 87%) as a colorless solid.

To a solution of 5-[6-(difluoromethoxy)-3,4-dihydro-2H-1-benzopyran-7-yl]-1-[[2-(trimethylsilyl)ethoxy]methyl]-1H-pyrazol-4-amine (154 mg, 0.374 mmol) in DMA (3.0 mL) was added pyrazolo[1,5-a]pyrimidine-3-carboxylic acid (92.0 mg, 0.564 mmol), 4-DMAP (5.00 mg, 0.0409 mmol), DIPEA (145 mg, 1.12 mmol) and PyAOP (293 mg, 0.562 mmol). The reaction mixture was stirred at 45° C. for 18 h. The reaction mixture was allowed to cool to $R_T$ and partitioned between ethyl acetate and water. The organic phase was washed with water and brine, dried over anhydrous sodium sulfate and concentrated under vacuum. The residue was purified by silica gel chromatography eluting with ethyl acetate/petroleum ether (1/1) to afford N-[5-[6-(difluoromethoxy)-3,4-dihydro-2H-1-benzopyran-7-yl]-1-[[2-(trimethylsilyl)ethoxy]methyl]-1H-pyrazol-4-yl]pyrazolo[1,5-a]pyrimidine-3-carboxamide (170 mg, 82%) as an off-white solid. LC/MS (Method F, ESI): [M+H]⁺=557, $R_T$=1.26 min.

To a solution of N-[5-[6-(difluoromethoxy)-3,4-dihydro-2H-1-benzopyran-7-yl]-1-[[2-(trimethylsilyl)ethoxy] methyl]-1H-pyrazol-4-yl]pyrazolo[1,5-a]pyrimidine-3-carboxamide (170 mg, 0.305 mmol) in dichloromethane (8.0 mL) was added trifluoroacetic acid (2.0 mL). The reaction mixture was stirred for 4 h at $R_T$ and concentrated under vacuum. The residue was purified by flash chromatography on silica gel eluting with dichloromethane/methanol (10/1). The crude product was further purified by Prep-HPLC (Column, XBridge Shield RP18 OBD Column, 5 um, 19*150 mm; Mobile Phase A: Water with 10 mM NH₄HCO₃, Mobile Phase B: CH₃CN; Flow rate: 25 mL/min; Gradient: 20% B to 55% B over 8 min; 254 nm) to afford the title compound (91.4 mg, 70%) as a white solid. LC/MS (Method C, ESI): [M+H]⁺=427, $R_T$=2.26 min; ¹H NMR (400 MHz, DMSO-d6): δ 12.94 (s, 1H), 9.78 (s, 1H), 9.35 (dd, J=7.2, 1.6 Hz, 1H), 8.70 (dd, J=4.4, 1.6 Hz, 1H), 8.66 (s, 1H), 8.20 (s, 1H), 7.30 (dd, J=7.0, 4.2 Hz, 1H), 7.13 (s, 1H), 7.01 (t, J=74.4 Hz, 1H), 6.93 (s, 1H), 4.20 (t, J=5.0 Hz, 2H), 2.86 (t, J=6.4 Hz, 2H), 2.01-1.95 (m, 2H).

Example 18

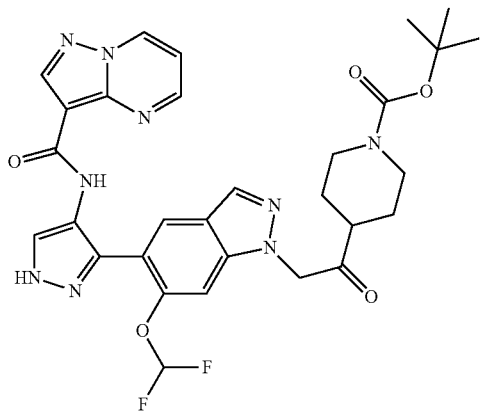 [SMILES: CC(C)(C)OC(=O)N1CCC(C(=O)Cn2ncc3cc(-c4n[nH]cc4NC(=O)c4cnn5cccnc45)c(OC(F)F)cc32)CC1]

tert-butyl 4-(2-(6-(difluoromethoxy)-5-(4-(pyrazolo[1,5-a]pyrimidine-3-carboxamido)-1H-pyrazol-3-yl)-1H-indazol-1-yl)acetyl)piperidine-1-carboxylate To a solution of N-(5-(6-(difluoromethoxy)-1-((2-(trimethylsilyl)ethoxy)methyl)-1H-indazol-5-yl)-1-((2-(trimethylsilyl)ethoxy)methyl)-1H-pyrazol-4-yl)pyrazolo[1,5-a]pyrimidine-3-carboxamide (Preparation contained within Example 21) (36 mg, 0.104 mmol) in dioxane (0.5 mL) was added 4M HCl in dioxane solution (2 mL). The resulting solution was stirred at $R_T$ for 2 h. The mixture was concentrated under reduced pressure, the residue was dissolved in ethyl acetate and washed with water and saturated aqueous sodium bicarbonate. The organic layer was dried over magnesium sulfate, filtered, and concentrated under reduced pressure to afford N-(3-(6-(difluoromethoxy)-1H-indazol-5-yl)-1H-pyrazol-4-yl)pyrazolo[1,5-a]pyrimidine-3-carboxamide (20 mg, 91%) as a tan solid, which was used in the next step without further purification. LC/MS (Method I, ESI): [M+H]⁺=411, $R_T$=0.94 min.

To a solution of N-(3-(6-(difluoromethoxy)-1H-indazol-5-yl)-1H-pyrazol-4-yl)pyrazolo[1,5-a]pyrimidine-3-carboxamide (20 mg, 0.0487 mmol) in N,N-dimethylformamide (0.5 mL) was added cesium carbonate (22 mg, 0.0658 mmol) and tert-butyl 4-(2-bromoacetyl)piperidine-1-carboxylate (24 mg, 0.073 mmol). The reaction mixture was stirred at $R_T$ for 30 minutes. The reaction mixture was poured into water (10 mL) and extracted with ethyl acetate (2×50 mL). The combined organic layer was washed with brine, dried over magnesium sulfate and concentrated under reduced pressure. The crude residue was purified by column chromatography (silica gel, 100-200 mesh, 0 to 10% methanol in DCM). The appropriate fractions were combined and concentrated under reduced pressure to the title compound (4 mg, 9.5%) as a tan solid. LC/MS (Method K, ESI): [M+H]⁺=636, $R_T$=2.40 min. ¹H NMR (500 MHz, DMSO-d₆) δ 12.92 (br s, 1H), 9.76 (s, 1H), 9.36-9.28 (m, 1H), 8.67-8.60 (s, 1H), 8.41 (s, 2H), 8.22 (s, 1H), 8.03-7.90 (s, 1H), 7.56 (s, 1H), 7.39-6.94 (m, 1H), 5.67 (s, 1H), 4.01 (m, 4H), 2.91-2.69 (m, 4H), 1.98 (m, 1H), 1.40 (s, 9H).

Example 19 (General Procedure R)

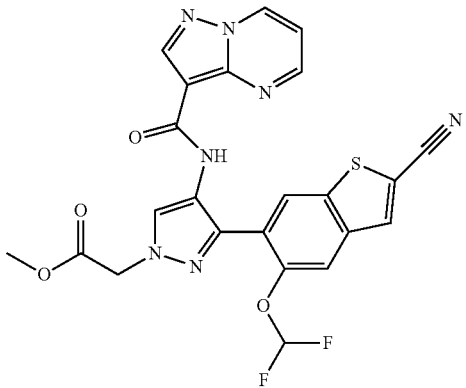 [SMILES: COC(=O)Cn1cc(NC(=O)c2cnn3cccnc23)c(-c2cc3sc(C#N)cc3cc2OC(F)F)n1]

Methyl 2-(3-(2-cyano-5-(difluoromethoxy)benzo[b]thiophen-6-yl)-4-(pyrazolo[1,5-a]pyrimidine-3-carboxamido)-1H-pyrazol-1-yl)acetate A mixture of methyl 2-(3-(2-carbamoyl-5-(difluoromethoxy)benzo[b]thiophen-6-yl)-4-(pyrazolo[1,5-a]pyrimidine-3-carboxamido)-1H-pyrazol-1-yl)acetate (Example 92) (25 mg, 0.046 mmol) and cyanuric chloride (30 mg, 0.16 mmol) in N,N-dimethylformamide (0.7 mL) was stirred at $R_T$ overnight. The reaction mixture was poured into water (10 mL), extracted with ethyl acetate (2×30 mL). The combined organic layer was washed with saturated aqueous sodium chloride solution, dried over magnesium sulfate, filtered, and concentrated under reduced pressure. The crude residue was purified by column chromatography (silica gel, 100-200 mesh, 0 to 100% ethyl acetate in heptane). Collecting appropriate fractions followed by evaporation gave methyl 2-(3-(2-cyano-5-(difluoromethoxy)benzo[b]thiophen-6-yl)-4-(pyrazolo[1,5-a]pyrimidine-3-carboxamido)-1H-pyrazol-1-yl)acetate (13 mg, 54%) as a white solid. LC/MS (Method K, ESI): [M+H]⁺=524, $R_T$=2.21 min. ¹H NMR (400 MHz, DMSO-d₆) δ 9.83 (s, 1H), 9.33 (dd, J=7.0, 1.6 Hz, 1H), 8.67 (s, 1H), 8.57-8.52 (m, 1H), 8.47 (s, 1H), 8.45 (s, 1H), 8.40 (s, 1H), 8.08 (s, 1H), 7.53-7.05 (m, 2H), 5.21 (s, 2H), 3.73 (s, 3H).

Example 20 (General Procedure S)

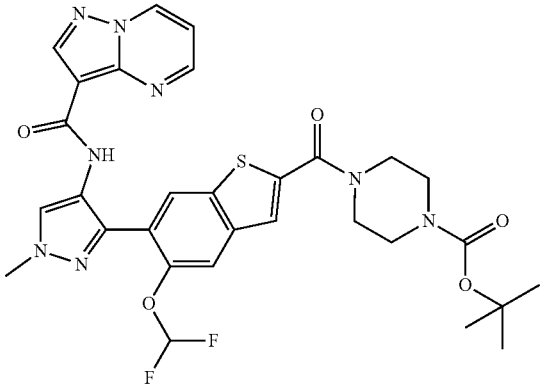 [SMILES: Cn1cc(NC(=O)c2cnn3cccnc23)c(-c2cc3sc(C(=O)N4CCN(C(=O)OC(C)(C)C)CC4)cc3cc2OC(F)F)n1]

tert-Butyl 4-(5-(difluoromethoxy)-6-(1-methyl-4-(pyrazolo[1,5-a]pyrimidine-3-carboxamido)-1H-pyrazol-3-yl)benzo[b]thiophene-2-carbonyl)piperazine-1-carboxylate A degassed mixture of N-(3-iodo-1-methyl-1H-pyrazol-4-yl)pyrazolo[1,5-a]pyrimidine-3-carboxamide (Intermediate 16) (308 mg, 0.84 mmol), tert-butyl 4-(5-(difluoromethoxy)-6-(4,4,5,5-tetramethyl-1,3,2-dioxaborolan-2-yl)benzo[b]thiophene-2-carbonyl)piperazine-1-carboxylate (Intermediate 3) (150 mg, 0.28 mmol), bis(di-tert-butyl(4-dimethylaminophenyl)phosphine)dichloropalladium(ii) (42 mg, 0.056 mmol) and potassium carbonate (154 mg, 1.12 mmol) in 1,4-dioxane (4 mL) and N,N-dimethylacetamide (4 mL) were heated at 100° C. in heating block for 16 h. The reaction mixture was allowed to cool to $R_T$, poured into water (50 mL) and extracted with ethyl acetate (2×100 mL). The combined organic layer was washed with saturated aqueous sodium chloride solution, dried over magnesium sulfate, filtered, and concentrated under reduced pressure. The crude residue was further purified by chiral SFC with the following conditions: Column: Cellulose-1, 150×21.2 mm; mobile phase: Carbon Dioxide and 40% neat methanol); Detector, UV 242 nm to afford tert-butyl 4-(5-(difluoromethoxy)-6-(1-methyl-4-(pyrazolo[1,5-a]pyrimidine-3-carboxamido)-1H-pyrazol-3-yl)benzo[b]thiophene-2-carbonyl)piperazine-1-carboxylate (48.7 mg, 26%) as a white solid. LC/MS (Method C, ESI): [M+H]$^+$=653, $R_T$=2.37 min. $^1$H NMR (500 MHz, DMSO-d6) δ 9.79 (s, 1H), 9.34 (dd, J=6.9, 1.6 Hz, 1H), 8.67 (s, 1H), 8.57 (dd, J=4.3, 1.7 Hz, 1H), 8.33 (s, 1H), 8.23 (s, 1H), 7.95 (s, 1H), 7.27 (dd, J=7.0, 4.2 Hz, 1H), 7.20 (t, J=73.7 Hz, 1H), 3.95 (s, 3H), 3.70 (s, 4H), 3.50-3.40 (m, 4H), 1.43 (s, 9H).

Example 21 (General Procedure T)

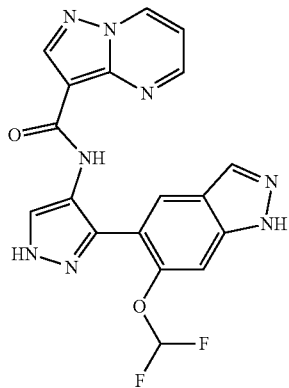 [SMILES: O=C(Nc1c[nH]nc1-c1cc2cn[nH]c2cc1OC(F)F)c1cnn2cccnc12]

N-(3-(6-(difluoromethoxy)-1H-indazol-5-yl)-1H-pyrazol-4-yl)pyrazolo[1,5-a]pyrimidine-3-carboxamide A solution of 4-nitro-1-((2-(trimethylsilyl)ethoxy)methyl)-1H-pyrazole (961 mg, 3.95 mmol), 5-bromo-6-(difluoromethoxy)-1-((2-(trimethylsilyl)ethoxy)methyl)-1H-indazole (Intermediate 9) (1.11 g, 2.82 mmol), butyl-di-1-adamantylphosphine (170 mg, 0.452 mmol), palladium acetate (64 mg, 0.282 mmol), potassium carbonate (1209 mg, 8.75 mmol) and pivalic acid (73 mg, 0.705 mmol) in N,N-dimethylacetamide (18 mL) was stirred at 120° C. in a sealed vial for 18 h. The mixture was allowed to cool to $R_T$, ethyl acetate was added and the precipitated solid was removed by filtration through celite. The filtrate was washed with water and a saturated aqueous sodium chloride solution. The organic layer was dried over magnesium sulfate, filtered, and concentrated in-vacuo. The residue was purified by column chromatography (silica gel, 100-200 mesh, 0 to 80% ethyl acetate in heptane). Appropriate fractions were combined and evaporated to afford 6-(difluoromethoxy)-5-(4-nitro-1-((2-(trimethylsilyl)ethoxy)methyl)-1H-pyrazol-5-yl)-1-((2-(trimethylsilyl)ethoxy)methyl)-1H-indazole (1081 mg, 69%) as an oil. LC/MS (Method I, ESI): [M+H]$^+$=556, $R_T$ 2.07 min.

A mixture of 6-(difluoromethoxy)-5-(4-nitro-1-((2-(trimethylsilyl)ethoxy)methyl)-1H-pyrazol-5-yl)-1-((2-(trimethylsilyl)ethoxy)methyl)-1H-indazole (1.08 g, 1.95 mmol) and ammonium chloride (520 mg, 9.73 mmol) in ethanol (12 mL) and water (6 mL) was heated to 70° C. and iron powder (566 mg, 9.73 mmol) was added portion-wise. The reaction mixture was heated for 1 h at 80° C., allowed to cool to $R_T$ and the precipitated solid removed by filtration through celite. The filter cake was washed with methanol and the combined filtrate concentrated in-vacuo. The residue was dissolved into ethyl acetate and washed with water and saturated aqueous sodium chloride solution. The organic layer was dried over magnesium sulfate, filtered, and concentrated under reduced pressure to afford 5-(6-(difluoromethoxy)-1-((2-(trimethylsilyl)ethoxy)methyl)-1H-indazol-5-yl)-1-((2-(trimethylsilyl)ethoxy)methyl)-1H-pyrazol-4-amine (930 mg, 91%) as a gel, which was used in the next step without further purification. LC/MS (Method A, ESI): [M+H]$^+$=527, $R_T$=1.96 min.

To a solution of 5-(6-(difluoromethoxy)-1-((2-(trimethylsilyl)ethoxy)methyl)-1H-indazol-5-yl)-1-((2-(trimethylsilyl)ethoxy)methyl)-1H-pyrazol-4-amine (1.30 g, 2.51 mmol) in dichloromethane (13 mL) was added pyrazolo[1,5-a]pyrimidine-3-carbonyl chloride (480 mg, 2.51 mmol) and triethylamine (1.05 mL, 7.53 mmol) and the reaction mixture was stirred at $R_T$ for 16 h. The mixture was concentrated under reduced pressure and the residue was dissolved in ethyl acetate. The organic phase was washed with water and a saturated aqueous sodium chloride solution. The organic layer was dried over magnesium sulfate, filtered, and concentrated under reduced pressure. The residue was purified by column chromatography (silica gel, 100-200 mesh, 0 to 100% ethyl acetate in heptane) to afford N-(5-(6-(difluoromethoxy)-1-((2-(trimethylsilyl)ethoxy)methyl)-1H-indazol-5-yl)-1-((2-(trimethylsilyl)ethoxy)methyl)-1H-pyrazol-4-yl)pyrazolo[1,5-a]pyrimidine-3-carboxamide (737 mg, 44%) as a tan solid. LC/MS (Method I, ESI): [M+H]$^+$=671, $R_T$=1.90 min.

To a solution of N-(5-(6-(difluoromethoxy)-1-((2-(trimethylsilyl)ethoxy)methyl)-1H-indazol-5-yl)-1-((2-(trimethylsilyl)ethoxy)methyl)-1H-pyrazol-4-yl)pyrazolo[1,5-a]pyrimidine-3-carboxamide (70 mg, 0.104 mmol) in dioxane (0.5 mL) was added 4M HCl in dioxane (2 mL). The reaction mixture was stirred at $R_T$ for 2 h. The mixture was concentrated under reduced pressure. The residue was dissolved into ethyl acetate and washed with water and saturated aqueous sodium bicarbonate. The organic layer was dried over magnesium sulfate, filtered, and concentrated under reduced pressure. The crude residue was further purified by SFC (Phenomenex Cellulose-1; 150×21.1 mm, 5 um; 30% methanol+0.1% ammonium hydroxide isocratic elution with Carbon Dioxide) to afford the title compound (9.4 mg, 22%) as a white solid. LC/MS (Method J, ESI): [M+H]$^+$=411, $R_T$=3.99 min. $^1$H NMR (400 MHz, DMSO-d$_6$) δ 12.97 (s, 2H), 9.73 (s, 1H), 9.31 (dd, J=7.0, 1.7 Hz, 1H), 8.64 (s, 1H), 8.49 (s, 1H), 8.19 (s, 1H), 7.96 (s, 1H), 7.63-7.04 (m, 3H).

Example 22 (General Procedure U)

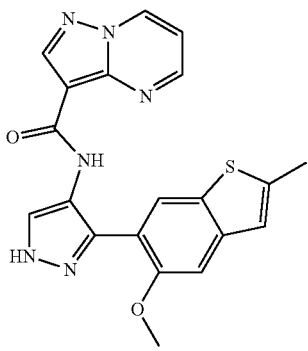 [SMILES: COc1cc2cc(C)sc2cc1-c1n[nH]cc1NC(=O)c1cnn2cccnc12]

N-(3-(5-methoxy-2-methylbenzo[b]thiophen-6-yl)-1H-pyrazol-4-yl)pyrazolo[1,5-a]pyrimidine-3-carboxamide 5-(3-bromo-5-methoxy-2-methylbenzo[b]thiophen-6-yl)-4-nitro-1-((2-(trimethylsilyl)-ethoxy)methyl)-1H-pyrazole was prepared using the same procedure as detailed in General Procedure A using Intermediate 5. LC/MS (Method K, ESI): [M+H]$^+$=498

To a degassed solution of 2-[[5-(3-bromo-5-methoxy-2-methyl-benzothiophen-6-yl)-4-nitro-pyrazol-1-yl]methoxy]ethyl-trimethyl-silane (285 mg, 0.572 mmol) in ethanol (7.62 mL) was added palladium on carbon (0.100 g). On complete addition the reaction mixture was stirred for 16 h at $R_T$. The solid was removed by filtration through celite and the filtrate concentrated under reduced pressure to give 5-(5-methoxy-2-methylbenzo[b]thiophen-6-yl)-1-((2-(trimethylsilyl)ethoxy)methyl)-1H-pyrazol-4-amine (0.251 g, >100%) as a foam. The compound was used without further purification. LC/MS (Method X, ESI): [M+H]$^+$=390.

N-(5-(5-methoxy-2-methylbenzo[b]thiophen-6-yl)-1-((2-(trimethylsilyl)ethoxy)methyl)-1H-pyrazol-4-yl)pyrazolo[1,5-a]pyrimidine-3-carboxamide. The reaction was carried out using the same procedure as General Procedure A. LC/MS (Method K, ESI): [M+H]$^+$=535

N-(3-(5-methoxy-2-methylbenzo[b]thiophen-6-yl)-1H-pyrazol-4-yl)pyrazolo[1,5-a]pyrimidine-3-carboxamide. The reaction was carried out using the same procedure as General Procedure A. LC/MS (Method Y, ESI): [M+H]$^+$=405. $R_T$=4.01 min; $^1$H NMR (400 MHz, DMSO-d$_6$) δ 12.83 (s, 1H), 9.72 (s, 1H), 9.32 (dd, J=7.0, 1.6 Hz, 1H), 8.73 (dd, J=4.3, 1.7 Hz, 1H), 8.64 (s, 1H), 8.17 (s, 1H), 7.85 (s, 1H), 7.54 (s, 1H), 7.27 (dd, J=7.0, 4.3 Hz, 1H), 7.15 (s, 1H), 3.89 (s, 3H), 2.59 (s, 3H).

Example 23 (General Procedure V)

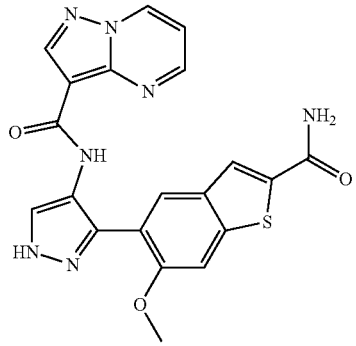 [SMILES: COc1cc2sc(C(N)=O)cc2cc1-c1n[nH]cc1NC(=O)c1cnn2cccnc12]

N-(3-(2-carbamoyl-6-methoxybenzo[b]thiophen-5-yl)-1H-pyrazol-4-yl)pyrazolo[1,5-a]pyrimidine-3-carboxamide To ethyl 6-methoxy-5-(4-(pyrazolo[1,5-a]pyrimidine-3-carboxamido)-1-((2-(trimethylsilyl)ethoxy)methyl)-1H-pyrazol-5-yl)benzo[b]thiophene-2-carboxylate (Prepared following General Procedure A) (150 mg, 0.338 mmol) in a microwave tube was added ethanol (3 mL) and concentrated aq. NH$_4$OH (6 mL). The reaction mixture was sealed and heated to 50° C. overnight. The reaction mixture was cooled to $R_T$ and the precipitated solid was collected by filtration. The solid was washed with water and dried in-vacuo to afford N-(5-(2-carbamoyl-6-methoxybenzo[b]thiophen-5-yl)-1-((2-(trimethylsilyl)ethoxy)methyl)-1H-pyrazol-4-yl)pyrazol[1,5-a]pyrimidine-3-carboxamide (119 mg, 63%) as a white solid, which was used in the next step without further purification. LC/MS (Method K, ESI): [M+H]$^+$=564, $R_T$=2.28 min.

To a solution of N-(5-(2-carbamoyl-6-methoxybenzo[b]thiophen-5-yl)-1-((2-(trimethylsilyl)ethoxy)methyl)-1H-pyrazol-4-yl)pyrazolo[1,5-a]pyrimidine-3-carboxamide (26 mg, 0.0461 mmol) in dioxane (0.5 mL) was added 4N HCl in dioxane (1 mL, 4.00 mmol). The resulting solution was stirred for 18 h at $R_T$. The mixture was concentrated under reduced pressure. The residue was dissolved in ethyl acetate and washed with water and saturated aqueous sodium bicarbonate. The organic extract was combined and washed with brine, dried over magnesium sulfate and concentrated under reduced pressure. The crude residue was further purified by Prep-HPLC (Column: Gemini-NX C18 5 um, 110A, 50×30 mm; mobile phase: Water (0.1% Ammonium Hydroxide) and CH$_3$CN (5% CH$_3$CN to 50% over 10 min); Detector, UV 254 nm) to afford the title compound (2.7 mg, 14%) as a white solid. LC/MS (Method K, ESI): [M+H]$^+$=434, $R_T$=1.38 min. $^1$H NMR (500 MHz, DMSO-d$_6$) δ 12.90 (s, 1H), 9.70 (s, 1H), 9.32 (dd, J=7.0, 1.6 Hz, 1H), 8.75 (dd, J=4.3, 1.7 Hz, 1H), 8.64 (s, 1H), 8.13 (d, J=41.7 Hz, 2H), 8.02 (s, 1H), 7.89 (d, J=9.6 Hz, 2H), 7.55 (s, 1H), 7.28 (dd, J=7.0, 4.2 Hz, 1H), 3.93 (s, 3H).

Example 24 (General Procedure W)

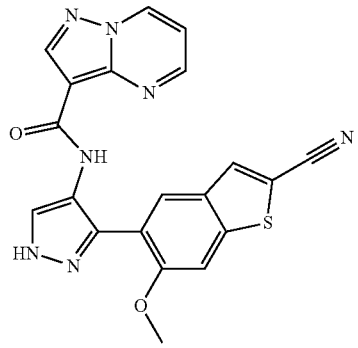 [SMILES: COc1cc2sc(C#N)cc2cc1-c1n[nH]cc1NC(=O)c1cnn2cccnc12]

N-(3-(2-cyano-6-methoxybenzo[b]thiophen-5-yl)-H-pyrazol-4-yl)pyrazolo[1,5-a]pyrimidine-3-carboxamide To a solution of N-(5-(2-carbamoyl-6-methoxybenzo[b]thiophen-5-yl)-1-((2-(trimethylsilyl)ethoxy)methyl)-1H-pyrazol-4-yl)pyrazolo[1,5-a]pyrimidine-3-carboxamide (preparation contained within Example 23) (50 mg, 0.0887 mmol) in N,N-dimethylformamide (0.5 mL) was added cyanuric chloride (8 mg, 0.0443 mmol). The reaction mixture was stirred for 2 h at $R_T$. Another portion of cyanuric chloride (8 mg, 0.0443 mmol) was added and the mixture was stirred for 1 h at $R_T$. The reaction mixture was poured into water (20 mL) and extracted with ethyl acetate (2×100 mL). The combined organic later was washed with brine, dried over magnesium sulfate and concentrated under reduced pressure. To the crude residue was added dioxane (1 mL) and 4N HCl in dioxane (2 mL). The resulting solution was stirred for 16 h at $R_T$. The precipitated solid was collected by filtration. The filtrate was concentrated under reduced pressure to afford an additional crop of product. The solids were combined and washed with saturated aqueous sodium bicarbonate. The crude solid was further purified by Prep-HPLC (Column: Gemini-NX C18 5 um, 110A, 50×30 mm; mobile phase: Water (0.1% Ammonium Hydroxide) and CH$_3$CN (5% CH$_3$CN to 50% over 10 min); Detector, UV 254 nm) to afford N-(3-(2-cyano-6-methoxybenzo[b]thiophen-5-yl)-1H-pyrazol-4-yl)pyrazolo[1,5-a]pyrimidine-3-carboxamide (10.1 mg, 27%) as a white solid. LC/MS (Method K, ESI): [M+H]$^+$=416, $R_T$=1.79 min. $^1$H NMR (400 MHz, DMSO-d$_6$) δ 12.95 (s, 1H), 9.69 (s, 1H), 9.33 (dd, J=7.0, 1.6 Hz, 1H), 8.73 (dd, J=4.3, 1.7 Hz, 1H), 8.64 (s, 1H), 8.35 (s, 1H), 8.24 (s, 1H), 8.05 (m, 2H), 7.28 (dd, J=7.0, 4.2 Hz, 1H), 3.95 (s, 2H).

Example 25

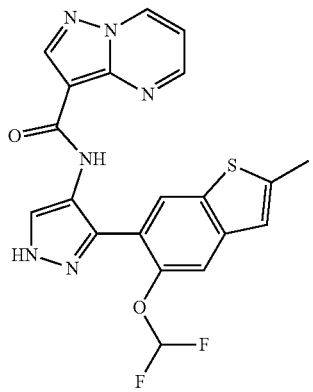 [SMILES: Cc1cc2cc(OC(F)F)c(-c3n[nH]cc3NC(=O)c3cnn4cccnc34)cc2s1]

N-(3-(5-(difluoromethoxy)-2-methylbenzo[b]thiophen-6-yl)-1H-pyrazol-4-yl)pyrazolo[1,5-a]pyrimidine-3-carboxamide A mixture of 5-bromo-2-iodophenol (8.80 g, 29.4 mmol), sodium 2-chloro-2,2-difluoroacetate (11.2 g, 73.6 mmol) and Cs$_2$CO$_3$ (21.1 g, 64.8 mmol) in DMA (150 mL) was heated at 100° C. for 1 h. The mixture was allowed to cool to $R_T$ and partitioned between ethyl acetate (300 mL) and water (300 mL). The organic phase was washed with brine (2×), dried over anhydrous sodium sulfate and concentrated under vacuum. The residue was purified by flash chromatography on silica gel eluting with petroleum ether to give 4-bromo-2-(difluoromethoxy)-1-iodobenzene (8.21 g, 80%) as a white solid.

LiHMDS (27 mL, 1.0 mol/L in THF, 27.0 mmol) dropwise with stirring to a cooled (−70° C.) solution of 4-nitro-1-[[2-(trimethylsilyl)ethoxy]methyl]-1H-pyrazole (5.45 g, 22.4 mmol) in tetrahydrofuran (60 mL) under nitrogen. The resulting solution was stirred for 1 h at −70° C. then ZnCl$_2$ (27 mL, 0.70 mol/L in THF, 18.9 mmol) was added dropwise with stirring. The resulting solution was allowed to warm to $R_T$ and stirred for 1 h. 4-bromo-2-(difluoromethoxy)-1-iodobenzene (8.20 g, 23.5 mmol) and Pd(PPh3)4 (2.59 g, 2.24 mmol) were added and the resultant solution was heated at 70° C. under nitrogen for 18 h. The mixture was allowed to cool to $R_T$, quenched by the addition of 50 mL of water then aqueous 3 N HCl was carefully added until the pH of the solution reached 5. The resulting solution was extracted with ethyl acetate (2×150 mL) and the organic layer combined. The organic phase was washed with water and brine, dried over anhydrous sodium sulfate and concentrated under vacuum. The residue was purified by flash chromatography on silica gel eluting with ethyl acetate/petroleum ether (5/95) to afford 5-[4-bromo-2-(difluoromethoxy)phenyl]-4-nitro-1-[[2-(trimethylsilyl)ethoxy]methyl]-1H-pyrazole (4.71 g, 43%) as a light yellow solid.

A degassed mixture of 5-[4-bromo-2-(difluoromethoxy)phenyl]-4-nitro-1-[[2-(trimethylsilyl)ethoxy]methyl]-1H-pyrazole (4.70 g, 10.1 mmol), 4,4,5,5-tetramethyl-2-(tetramethyl-1,3,2-dioxaborolan-2-yl)-1,3,2-dioxaborolane (3.86 g, 15.2 mmol), Pd(dppf)Cl$_2$.CH$_2$Cl$_2$ (0.830 g, 1.02 mmol) and potassium acetate (2.48 g, 25.3 mmol) in dioxane (50 mL) was heated at 90° C. for 3 h under nitrogen. The resulting mixture was allowed to cool to $R_T$ and concentrated under vacuum. Ethyl acetate (50 mL) was added to the residue and the precipitated solid removed by filtration. The filtrate was concentrated under reduced pressure, THF (30 mL) and H$_2$O$_2$ (3.0 mL, 30% H$_2$O) were added dropwise at 0° C. and the mixture was stirred for 30 minutes at $R_T$. The mixture was diluted with ethyl acetate (150 ml) and washed with water and brine, dried over Na$_2$SO$_4$ and concentrated under vacuum. The residue was purified by flash chromatography on silica gel eluting with petroleum ether and ethyl acetate (95/5). Appropriate fractions were combined and evaporated to afford 3-(difluoromethoxy)-4-(4-nitro-1-[[2-(trimethylsilyl)ethoxy]methyl]-1H-pyrazol-5-yl)phenol (3.86 g, 95%) of as an off-white solid.

A solution of 3-(difluoromethoxy)-4-(4-nitro-1-[[2-(trimethylsilyl)ethoxy]methyl]-1H-pyrazol-5-yl)phenol (2.00 g, 4.98 mmol) and potassium carbonate (1.38 g, 9.99 mmol) in methanol (30 mL) was stirred for 10 minutes at 0° C. NBS (890 mg, 5.00 mmol) was added in portions at 0° C. and the resulting solution was stirred for 1 h. The pH of the solution was adjusted to 5 by the addition of 3 N HCl and extracted with ethyl acetate (100 mL). The organic layer was washed with water (3×50 mL) and brine (3×50 mL), dried over anhydrous sodium sulfate and concentrated under vacuum. The residue was purified by flash chromatography on silica gel eluting with ethyl acetate/petroleum ether (1/5). Appropriate fractions were combined and evaporated to afford 2-bromo-5-(difluoromethoxy)-4-(4-nitro-1-[[2-(trimethylsilyl)ethoxy]methyl]-1H-pyrazol-5-yl)phenol (1.68 g, 70%) as an off-white solid.

To a solution of 2-bromo-5-(difluoromethoxy)-4-(4-nitro-1-[[2-(trimethylsilyl)ethoxy]methyl]-1H-pyrazol-5-yl)phenol (1.68 g, 3.50 mmol) and pyridine (0.330 g, 4.17 mmol) in dichloromethane (20 mL) was added trifluoromethanesulfonic anhydride (Tf$_2$O) (1.18 g, 4.18 mmol) dropwise at 0° C. The resulting solution was stirred for 1 h at 0° C. then quenched by the addition of saturated NH$_4$Cl solution (5 mL) and dichloromethane (50 ml) was added. The organic layer was washed with water (3×30 mL) and brine (2×30 mL), dried over anhydrous sodium sulfate and concentrated under vacuum. The residue was purified by flash chromatography on silica gel eluting with ethyl acetate/petroleum ether (1/10). Appropriate fractions were combined and evaporated to afford 2-bromo-5-(difluoromethoxy)-4-(4-nitro-1-[[2-(trimethylsilyl)ethoxy]methyl]-1H-pyrazol-5-yl)phenyl trifluoromethanesulfonate (1.85 g, 86%) as a white solid.

A degassed mixture of 2-bromo-5-(difluoromethoxy)-4-(4-nitro-1-[[2-(trimethylsilyl)ethoxy]methyl]-1H-pyrazol-5-yl)phenyl trifluoromethanesulfonate (400 mg, 0.653 mmol), bromo(prop-1-yn-1-yl)magnesium (1.3 mL, 0.5 mol/L), Pd(dppf)Cl$_2$ (48 mg, 0.066 mmol), CuI (50.0 mg, 0.263 mmol) in tetrahydrofuran (8.0 mL) was heated at 50° C. for 2 h. The mixture was allowed to cool to R$_T$ and partitioned between ethyl acetate and water. The organic phase was washed with brine, dried over Na$_2$SO$_4$ and concentrated under vacuum. The residue was purified by flash chromatography on silica gel eluting with petroleum ether and ethyl acetate (10/1). Appropriate fractions were combined and evaporated to afford 5-[5-bromo-2-(difluoromethoxy)-4-(prop-1-yn-1-yl)phenyl]-4-nitro-1-[[2-(trimethylsilyl)ethoxy]methyl]-1H-pyrazole (0.157 g, 48%) as a solid. TLC: R$_f$=0.4 (PE/EA=4/1).

Tris(propan-2-yl)silanethiol (77.0 mg, 0.404 mmol) was added dropwise to a suspension of sodium hydride (27 mg, 60% dispersion in mineral oil, 0.667 mmol) in toluene (5 mL) at R$_T$ under nitrogen. The mixture was stirred for 1 h before addition of 5-[5-bromo-2-(difluoromethoxy)-4-(prop-1-yn-1-yl)phenyl]-4-nitro-1-[[2-(trimethylsilyl)ethoxy]methyl]-1H-pyrazole (160 mg, 0.318 mmol), Pd$_2$(dba)$_3$·CHCl$_3$ (16.0 mg, 0.0155 mmol) and XantPhos (18.0 mg, 0.0311 mmol). The resulting solution was heated at 90° C. for 30 min and allowed to cool to R$_T$. A solution of TBAF in THF (0.47 mL, 1M, 0.47 mmol) was added and the mixture was stirred for another 5 minutes. The mixture was partitioned between ethyl acetate (50 mL) and water (50 mL). The organic layer was washed with brine, dried over sodium sulfate and concentrated under vacuum. The residue was purified by flash chromatography on silica gel eluting with ethyl acetate and petroleum ether (1/3). Appropriate fractions were combined and evaporated to afford 5-[5-(difluoromethoxy)-2-methyl-1-benzothiophen-6-yl]-4-nitro-1-[[2-(trimethylsilyl)ethoxy]methyl]-1H-pyrazole (0.135 g, 93%) as a white solid. TLC: R$_f$=0.35 (PE/EA=5/1).

A mixture of 5-[5-(difluoromethoxy)-2-methyl-1-benzothiophen-6-yl]-4-nitro-1-[[2-(trimethylsilyl)ethoxy]methyl]-1H-pyrazole (135 mg, 0.296 mmol), iron powder (165 mg, 2.96 mmol) and NH$_4$Cl (48.0 mg, 0.897 mmol) in ethanol/water (10/1, 5 mL) was heated under reflux for 1 h. The resulting mixture was allowed to cool to R$_T$ and concentrated under vacuum. The residue was partitioned between ethyl acetate (50 mL) and water (50 mL). The organic layer was washed with brine, dried over anhydrous sodium sulfate, and concentrated under vacuum. Appropriate fractions were combined and evaporated to afford 5-[5-(difluoromethoxy)-2-methyl-1-benzothiophen-6-yl]-1-[[2-(trimethylsilyl)ethoxy]methyl]-1H-pyrazol-4-amine (108 mg, 86%) as a solid. TLC: R$_f$=0.1 (PE/EA=2/1).

A mixture of 5-[5-(difluoromethoxy)-2-methyl-1-benzothiophen-6-yl]-1-[[2-(trimethylsilyl)ethoxy]methyl]-1H-pyrazol-4-amine (108 mg, 0.254 mmol), pyrazolo[1,5-a]pyrimidine-3-carboxylic acid (62.0 mg, 0.380 mmol), DIPEA (98.0 mg, 0.758 mmol) and 4-dimethylaminopyridine (3.00 mg, 0.0246 mmol) and PyAOP (198 mg, 0.380 mmol) in DMA (3.0 mL) was stirred at 45° C. for 1 h. The mixture was allowed to cool to R$_T$ and partitioned between ethyl acetate (50 mL) and water (50 mL). The organic layer was dried over anhydrous sodium sulfate and concentrated under vacuum. The residue was purified by flash chromatography on silica gel eluting with ethyl acetate/petroleum ether (1/1). Appropriate fractions were combined and evaporated to afford N-[5-[5-(difluoromethoxy)-2-methyl-1-benzothiophen-6-yl]-1-[[2-(trimethylsilyl)ethoxy]methyl]-1H-pyrazol-4-yl]pyrazolo[1,5-a]pyrimidine-3-carboxamide (87.1 mg, 60%) as a solid. TLC: R$_f$=0.2 (PE/EA=1/1).

N-[5-[5-(difluoromethoxy)-2-methyl-1-benzothiophen-6-yl]-1-[[2-(trimethylsilyl)ethoxy]methyl]-1H-pyrazol-4-yl]pyrazolo[1,5-a]pyrimidine-3-carboxamide (87.0 mg, 0.152 mmol) was added into trifluoroacetic acid (2.0 mL) in several batches. The resulting solution was stirred for 1 h at R$_T$ then concentrated under vacuum. The residue was purified by silica gel column eluting with ethyl acetate/petroleum ether (3/2). Appropriate fractions were combined and evaporated to afford N-[3-[5-(difluoromethoxy)-2-methyl-1-benzothiophen-6-yl]-1H-pyrazol-4-yl]pyrazolo[1,5-a]pyrimidine-3-carboxamide (18.9 mg, 28%) as a solid. LC/MS (Method L, ESI): [M+H]$^+$=441.2, R$_T$=2.90 min. $^1$HNMR (300 MHz, DMSO-d6): δ 12.97 (s, 1H), 9.77 (s, 1H), 9.32 (dd, J=6.9, 1.5 Hz, 1H), 8.66 (s, 1H), 8.58-8.53 (m, 1H), 8.27 (s, 1H), 8.05 (s, 1H), 7.74 (s, 1H), 7.27-7.24 (m, 2H), 7.21 (t, J=73.8 Hz, 1H), 2.62 (s, 3H).

Example 147 (General Procedure X)

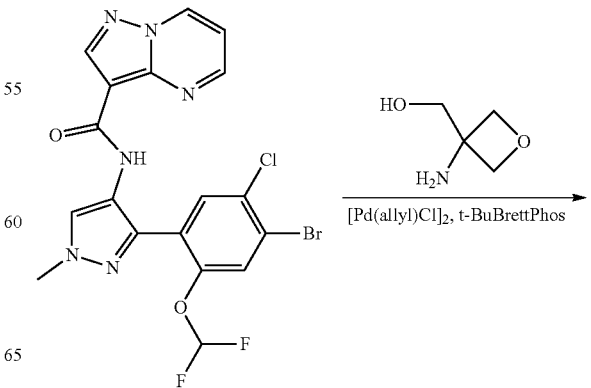

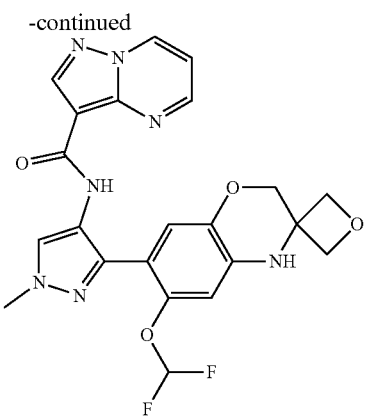

N-(3-(6-(difluoromethoxy)-2,4-dihydrospiro[benzo [b][1,4]oxazine-3,3'-oxetan]-7-yl)-1-methyl-1H-pyrazol-4-yl)pyrazolo[1,5-a]pyrimidine-3-carboxamide A degassed mixture of N-[3-[4-bromo-5-chloro-2-(difluoromethoxy)phenyl]-1-methyl-1H-pyrazol-4-yl]pyrazolo[1,5-a]pyrimidine-3-carboxamide (60.0 mg, 0.121 mmol, Intermediate 19), (3-aminooxetan-3-yl)methanol (25.0 mg, 0.242 mmol), [Pd(allyl)Cl]$_2$ (4.50 mg, 0.0123 mmol), t-BuBrettPhos (12.0 mg, 0.0246 mmol) and Cs$_2$CO$_3$ (79 mg, 0.242 mmol) in toluene (2.0 mL) and dioxane (0.50 mL) was heated at 60° C. for 3 days. The reaction mixture was allowed to cool to room temperature and concentrated under reduced pressure. The residue was purified by flash chromatography on silica gel eluting with dichloromethane/methanol (30/1~20/1). Appropriate fractions were combined and concentrated under reduced pressure. The crude product was further purified by Prep-HPLC with the following conditions: Column, XBridge Shield RP$_{18}$ OBD Column, 5 um, 19*150 mm; mobile phase, Water (0.05% NH$_3$H$_2$O) and CH$_3$CN (15.0% CH$_3$CN up to 35.0% in 7 min); Detector, UV 254/220 nm give 8.3 mg (14%) of N-[3-[7-(difluoromethoxy)-2,4-dihydrospiro[1,4-benzoxazine-3,3-oxetane]-6-yl]-1-methyl-1H-pyrazol-4-yl]pyrazolo[1,5-a]pyrimidine-3-carboxamide as an off-white solid. LC/MS (Method N, ESI): [M+H]$^+$=484.2, R$_T$=1.42 min. $^1$H NMR (400 MHz, DMSO-d$_6$): δ 9.74 (s, 1H), 9.35 (dd, J=6.8, 1.6 Hz, 1H), 8.66 (s, 1H), 8.63 (dd, J=4.4, 1.6 Hz, 1H), 8.22 (s, 1H), 7.31 (dd, J=6.8, 4.4 Hz, 1H), 7.30 (s, 1H), 6.93 (t, J=74.6 Hz, 1H), 6.87 (s, 1H), 6.62 (s, 1H), 4.59 (d, J=6.8 Hz, 2H), 4.51 (d, J=6.4 Hz, 2H), 4.32 (s, 2H), 3.87 (s, 3H).

Example 148 (General Procedure Y)

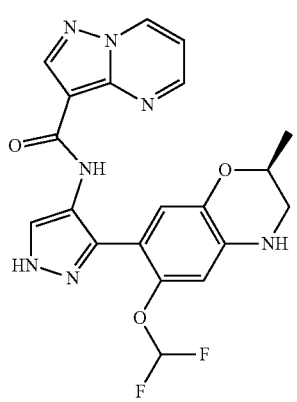 [SMILES: C[C@H]1CNc2cc(OC(F)F)c(-c3n[nH]cc3NC(=O)c3cnn4cccnc34)cc2O1]

(S)—N-(3-(6-(difluoromethoxy)-2-methyl-3,4-dihydro-2H-benzo[b][1,4]oxazin-7-yl)-1H-pyrazol-4-yl)pyrazolo[1,5-a]pyrimidine-3-carboxamide To a degassed mixture of N-[5-[4-bromo-5-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (65.0 mg, 0.106 mmol, intermediate 18), (2S)-1-aminopropan-2-ol (16.0 mg, 0.213 mmol), [Pd(allyl)Cl]$_2$ (4.00 mg, 0.0109 mmol), t-BuBrettPhos (11.0 mg, 0.0225 mmol) and Cs$_2$CO$_3$ (70.0 mg, 0.215 mmol) in toluene (2.0 mL) was added heated at 60° C. for 2 days. [Pd(allyl)Cl]$_2$ (4.00 mg, 0.0109 mmol) and t-BuBrettPhos (11.0 mg, 0.0225 mmol) were added and heating continued for 3 days at 60° C. The reaction mixture was cooled and the resulting mixture was concentrated under reduced pressure. The residue was purified by flash chromatography on silica gel eluting with dichloromethane/methanol (20/1) and the appropriate fractions were combined and concentrated under reduced pressure to afford N-[5-[(2S)-6-(difluoromethoxy)-2-methyl-3,4-dihydro-2H-1,4-benzoxazin-7-yl]-1-[[2-(trimethylsilyl)ethoxy]methyl]-1H-pyrazol-4-yl]pyrazolo[1,5-a]pyrimidine-3-carboxamide (34.0 mg, 56%) as light yellow oil. LC/MS (Method S, ESI): [M+H]$^+$=572.3, R$_T$=1.39 min.

A mixture of N-[5-[(2S)-6-(difluoromethoxy)-2-methyl-3,4-dihydro-2H-1,4-benzoxazin-7-yl]-1-[[2-(trimethylsilyl)ethoxy]methyl]-1H-pyrazol-4-yl]pyrazolo[1,5-a]pyrimidine-3-carboxamide (34.0 mg, 0.059 mmol) and 6M aqueous hydrogen chloride (2.0 mL) in methanol (4.0 mL) was allowed to stir at R$_T$ for 2 h then evaporated. Dichloromethane (5.0 mL) and DIPEA (0.10 mL) were added and the resulting mixture was evaporated. The residue was purified by flash chromatography on silica gel eluting with dichloromethane/methanol (20/1). Appropriate fractions were combined and concentrated under reduced pressure. The crude product was further purified by Prep-HPLC with the following conditions: Column, XBridge BEH130 Prep C18 OBD Column, 19*150 mm 5 um 13 nm; mobile phase, Water (0.05% NH$_3$H$_2$O) and acetonitrile (20.0% CH$_3$CN to 31.0% over 9 min); Detector, UV 254/220 nm. Appropriate fractions were combined and evaporated to afford N-[3-[(2S)-6-(difluoromethoxy)-2-methyl-3,4-dihydro-2H-1,4-benzoxazin-7-yl]-1H-pyrazol-4-yl]pyrazolo[1,5-a]pyrimidine-3-carboxamide (6.1 mg, 23%) as a light yellow solid. LC/MS (Method N, ESI): [M+H]$^+$=442.2, R$_T$=1.47 min. $^1$H NMR (300 MHz, DMSO-d$_6$): δ 12.76 (s, 1H), 9.77 (s, 1H), 9.35 (dd, J=6.9, 1.5 Hz, 1H), 8.67-8.64 (m, 2H), 8.20 (s, 1H), 7.31 (dd, J=6.9, 4.2 Hz, 1H), 6.93 (t, J=74.7 Hz, 1H), 6.82 (s, 1H), 6.59 (s, 1H), 6.32 (br, 1H), 4.16-4.12 (m, 1H), 3.42-3.37 (m, 1H), 3.05-2.98 (m, 1H), 1.31 (d, J=6.3 Hz, 3H).

Example 149

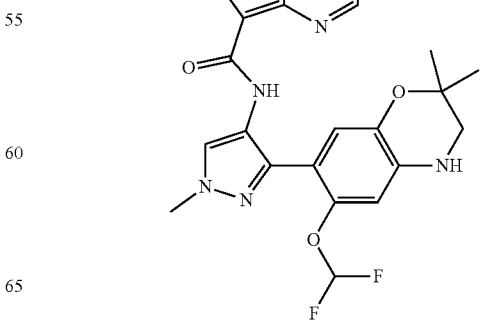

N-(3-(6-(difluoromethoxy)-2,2-dimethyl-3,4-dihydro-2H-benzo[b][1,4]oxazin-7-yl)-1-methyl-1H-pyrazol-4-yl)pyrazolo[1,5-a]pyrimidine-3-carboxamide A degassed solution of N-[3-[4-bromo-5-chloro-2-(difluoromethoxy)phenyl]-1-methyl-1H-pyrazol-4-yl]pyrazolo[1,5-a]pyrimidine-3-carboxamide (50.0 mg, 0.100 mmol, intermediate 19), 1-amino-2-methylpropan-2-ol (11.0 mg, 0.123 mmol), [Pd(allyl)Cl]$_2$ (4.00 mg, 0.0109 mmol), t-Bu-BrettPhos (10.0 mg, 0.0206 mmol) and Cs$_2$CO$_3$ (65.0 mg, 0.199 mmol) in toluene (10 mL) was heated at 60° C. for 7 days. The mixture was allowed to cool to R$_T$ and the solid removed by filtration. The filtrate was concentrated under reduced pressure and the crude product was purified by Prep-HPLC with the following conditions: Column, XBridge Prep C$_{18}$ OBD Column, 19*150 mm 5 um; mobile phase, Water (0.05% NH$_3$.H$_2$O) and CH$_3$CN (30.0% CH$_3$CN to 45.0% over 8 min); Detector, UV 254 and 220 nm. Appropriate fractions were combined and evaporated to afford N-[3-[6-(difluoromethoxy)-2,2-dimethyl-3,4-dihydro-2H-1,4-benzoxazin-7-yl]-1-methyl-1H-pyrazol-4-yl]pyrazolo[1,5-a]pyrimidine-3-carboxamide (1.2 mg, 3%) as a white solid. LC/MS (Method Q, ESI): [M+H]$^+$=470.3, R$_T$=2.22 min. $^1$H NMR (400 MHz, CD$_3$OD): δ 9.10 (dd, J=7.2, 1.6 Hz, 1H), 8.66 (dd, J=4.0, 1.6 Hz, 1H), 8.64 (s, 1H), 8.22 (s, 1H), 7.22 (dd, J=7.0, 4.2 Hz, 1H), 6.85 (s, 1H), 6.65 (s, 1H), 6.52 (t, J=74.8 Hz, 1H), 3.96 (s, 3H), 3.15 (s, 2H), 1.35 (s, 6H).

Example 150

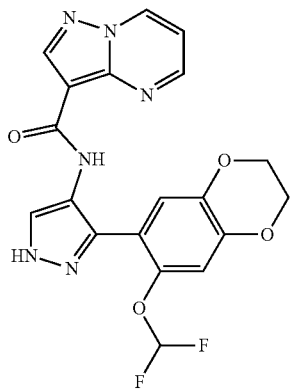

N-(3-(7-(difluoromethoxy)-2,3-dihydrobenzo[b][1,4]dioxin-6-yl)-1H-pyrazol-4-yl)pyrazolo[1,5-a]pyrimidine-3-carboxamide A degassed solution of N-[5-[5-bromo-4-chloro-2-(difluoromethoxy)phenyl]-1-[[2-(trimethylsilyl)ethoxy]methyl]-1H-pyrazol-4-yl]pyrazolo[1,5-a]pyrimidine-3-carboxamide (100 mg, 0.163 mmol, intermediate 12), ethylene glycol (21.0 mg, 0.338 mmol), [PdCl(allyl)]$_2$ (6.00 mg, 0.016 mmol), t-BuBrettPhos (16.0 mg, 0.033 mmol) and Cs$_2$CO$_3$ (107 mg, 0.328 mmol) in toluene (4.0 mL) was heated at 60° C. for 2 days. The resulting mixture was allowed to cool to R$_T$ and concentrated under reduced pressure. The residue was purified by flash chromatography on silica gel eluting with DCM:MeOH (94:6). Appropriate fractions were combined and concentrated under reduced pressure to afford N-[5-[7-(difluoromethoxy)-2,3-dihydro-1,4-benzodioxin-6-yl]-1-[[2-(trimethylsilyl)ethoxy]methyl]-1H-pyrazol-4-yl]pyrazolo[1,5-a]pyrimidine-3-carboxamide (37.2 mg, 41%) as a yellow solid.

To a solution of N-[5-[7-(difluoromethoxy)-2,3-dihydro-1,4-benzodioxin-6-yl]-1-[[2-(trimethylsilyl)ethoxy]methyl]-1H-pyrazol-4-yl]pyrazolo[1,5-a]pyrimidine-3-carboxamide (50 mg, 0.090 mmol) in methanol (10 mL) was added 6 N HCl aqueous solution (2.0 mL). The resulting solution was stirred for 2 h at R$_T$ and concentrated under reduced pressure. DIPEA was added to the residue and then the mixture was concentrated under reduced pressure. The residue was purified by Prep-HPLC with the following conditions: Column, XBridge Prep C$_{18}$ OBD Column, 19*150 mm 5 um; mobile phase, Water (10 mmol/L NH$_4$HCO$_3$) and CH$_3$CN (5.0% CH$_3$CN to 55.0% over 7 min); Detector, uv 254, 220 nm. Appropriate fractions were combined and evaporated to afford N-[3-[7-(difluoromethoxy)-2,3-dihydro-1,4-benzodioxin-6-yl]-1H-pyrazol-4-yl]pyrazolo[1,5-a]pyrimidine-3-carboxamide (10.4 mg, 27%) as a white solid. LC/MS (Method M, ESI): [M+H]$^+$=429.2, R$_T$=1.48 min. $^1$H NMR (400 MHz, CD$_3$OD): δ 9.10 (dd, J=7.2, 1.6 Hz, 1H), 8.67-8.64 (m, 2H), 8.29 (s, 1H), 7.23 (dd, J=7.0, 4.2 Hz, 1H), 7.09 (s, 1H), 6.94 (s, 1H), 6.62 (t, J=74.6 Hz, 1H), 4.37-4.32 (m, 4H).

Example 151 (General Procedure Z)

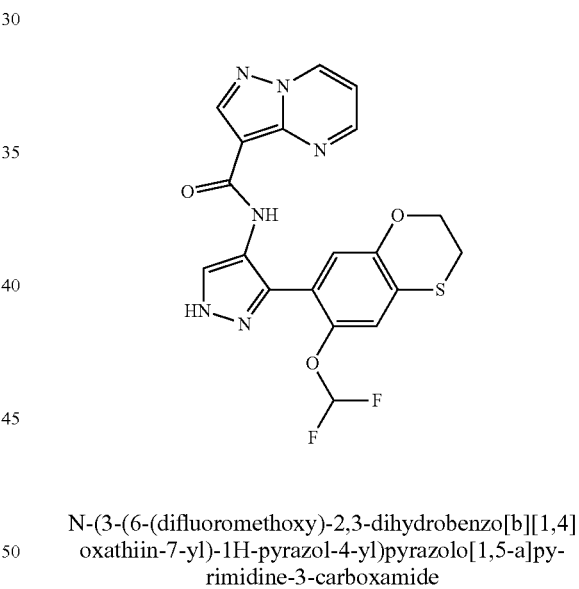

N-(3-(6-(difluoromethoxy)-2,3-dihydrobenzo[b][1,4]oxathiin-7-yl)-1H-pyrazol-4-yl)pyrazolo[1,5-a]pyrimidine-3-carboxamide A degassed solution of N-[5-[4-bromo-5-chloro-2-(difluoromethoxy)phenyl]-1-[[2-(trimethylsilyl)-ethoxy]methyl]-1H-pyrazol-4-yl]pyrazolo[1,5-a]pyrimidine-3-carboxamide (100 mg, 0.163 mmol, intermediate 18), Pd$_2$(dba)$_3$.CHCl$_3$ (16.9 mg, 0.0163 mmol), XantPhos (19 mg, 0.0328 mmol), potassium carbonate (67.0 mg, 0.485 mmol) and 2-sulfanylethan-1-ol (38.2 mg, 0.489 mmol) in toluene (4.0 mL) was heated at 80° C. for 12 h. The mixture was allowed to cool to R$_T$ and the resulting mixture was concentrated under reduced pressure. The residue was purified by flash chromatography on silica gel eluting with ethyl acetate. Appropriate fractions were combined and concentrated under reduced pressure to afford N-[5-[5-chloro-2-(difluoromethoxy)-4-[(2-hydroxyethyl)sulfanyl]phenyl]-1-[[2-(trimethylsilyl)ethoxy]-methyl]-1H-pyrazol-4-yl]

pyrazolo[1,5-a]pyrimidine-3-carboxamide (85 mg, 85%) as yellow oil. LC/MS (Method R, ESI): [M+H]$^+$=611.2, $R_T$=1.96 min.

A degassed solution of N-[5-[5-chloro-2-(difluoromethoxy)-4-[(2-hydroxyethyl)sulfanyl]-phenyl]-1-[[2-(trimethylsilyl)ethoxy]methyl]-1H-pyrazol-4-yl]pyrazolo[1,5-a]pyrimidine-3-carboxamide (85.0 mg, 0.139 mmol), [Pd(allyl)Cl]$_2$ (5.10 mg, 0.0139 mmol), t-BuBrettPhos (13.5 mg, 0.0278 mmol) and Cs$_2$CO$_3$ (90.6 mg, 0.278 mmol) in toluene (3.0 mL) was heated at 80° C. for 12 h. The solution was allowed to cool to $R_T$ and concentrated under reduced pressure. The residue was purified by flash chromatography on silica gel eluting with ethyl acetate/petroleum ether (40/60). Appropriate fractions were combined and concentrated under reduced pressure to afford N-[5-[6-(difluoromethoxy)-2,3-dihydro-1,4-benzoxathiin-7-yl]-1-[[2-(trimethylsilyl)ethoxy]methyl]-1H-pyrazol-4-yl]pyrazolo[1,5-a]pyrimidine-3-carboxamide (37.7 mg, 46%) as yellow oil. LC/MS ((Method R, ESI): [M+H]$^+$=575.2, $R_T$=2.05 min.

To a solution of N-[5-[6-(difluoromethoxy)-2,3-dihydro-1,4-benzoxathiin-7-yl]-1-[[2-(trimethylsilyl)ethoxy]methyl]-1H-pyrazol-4-yl]pyrazolo[1,5-a]pyrimidine-3-carboxamide (37.7 mg, 0.0655 mmol) in dioxane (4.0 mL) was added a solution of HCl in dioxane (10 mL, 4M) dropwise with stirring at 0° C. The resulting solution was stirred for 4 h at $R_T$ and concentrated under reduced pressure. The residue was purified by flash chromatography on silica gel eluting with ethyl acetate/petroleum ether (20/80). Appropriate fractions were collected and concentrated under reduced pressure to afford N-[3-[6-(difluoromethoxy)-2,3-dihydro-1,4-benzoxathiin-7-yl]-1H-pyrazol-4-yl]pyrazolo[1,5-a]pyrimidine-3-carboxamide (7.8 mg, 27%) as a white solid. LC/MS (Method N, ESI): [M+H]$^+$=445.1, $R_T$=1.49 min. $^1$H NMR (400 MHz, DMSO-d6): δ 12.96 (s, 1H), 9.76 (s, 1H), 9.35 (dd, J=7.2, 1.6 Hz, 1H), 8.71-8.66 (m, 2H), 8.25 (s, 1H), 7.30 (dd, J=7.0, 4.2 Hz, 1H), 7.16 (s, 1H), 7.09 (t, J=74.4 Hz, 1H), 7.01 (s, 1H), 4.42 (t, J=4.4 Hz, 2H), 3.28 (t, J=4.4 Hz, 2H).

Example 152 (General Procedure AA)

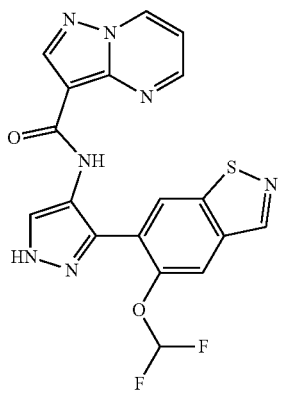 [SMILES: O=C(Nc1c[nH]nc1-c1cc2sncc2cc1OC(F)F)c1cnn2cccnc12]

N-(3-(5-(difluoromethoxy)benzo[d]isothiazol-6-yl)-1H-pyrazol-4-yl)pyrazolo[1,5-a]pyrimidine-3-carboxamide A degassed solution of 5-[4-bromo-5-chloro-2-(difluoromethoxy)phenyl]-4-nitro-1-[[2-(trimethylsilyl)ethoxy]methyl]-1H-pyrazole (1.00 g, 2.01 mmol, Step 3 of intermediate 18), potassium trifluoro(vinyl)borate (536 mg, 4.00 mmol), Pd(dppf)Cl$_2$.CH$_2$Cl$_2$ (326 mg, 0.399 mmol) and Cs$_2$CO$_3$ (1.30 g, 3.99 mmol) in dioxane (10 mL) and water (2.0 mL) was heated under microwave irradiation at 100° C. for 1 h. The resulting mixture was allowed to cool to $R_T$ and concentrated under reduced pressure. The residue was purified by flash chromatography on silica gel eluting with ethyl acetate/petroleum ether (1/9). Appropriate fractions were combined and concentrated under reduced pressure to afford 5-[5-chloro-2-(difluoromethoxy)-4-ethenylphenyl]-4-nitro-1-[[2-(trimethylsilyl)ethoxy]methyl]-1H-pyrazole (880 mg, 98%) as a brown solid.

To a solution of 5-[5-chloro-2-(difluoromethoxy)-4-ethenylphenyl]-4-nitro-1-[[2-(trimethylsilyl)ethoxy]methyl]-1H-pyrazole (880 mg, 1.97 mmol) in tetrahydrofuran (10 mL) and water (5.0 mL) was added OsO$_4$ (998 mg, 3.93 mmol) and NMO (456 mg, 3.89 mmol) and the resulting solution was stirred for 2 h at $R_T$. The reaction mixture was diluted with H$_2$O (20 mL) and quenched by the addition of saturated Na$_2$S$_2$O$_3$ aqueous solution (10 mL). The mixture was extracted with dichloromethane (3×20 mL) and the combined organic layer was concentrated under reduced pressure. The residue was purified by flash chromatography on silica gel eluting with dichloromethane/methanol (9/1). Appropriate fractions were combined and concentrated under reduced pressure to afford 1-[2-chloro-5-(difluoromethoxy)-4-(4-nitro-1-[[2-(trimethylsilyl)ethoxy]methyl]-1H-pyrazol-5-yl)phenyl]ethane-1,2-diol (380 mg, 40%) as a brown solid.

Sodium periodate (465 mg, 2.17 mmol) was added to a solution of 1-[2-chloro-5-(difluoromethoxy)-4-(4-nitro-1-[[2-(trimethylsilyl)ethoxy]methyl]-1H-pyrazol-5-yl)phenyl]ethane-1,2-diol (870 mg, 1.81 mmol) in CH$_3$CN (10 mL) and water (1.0 mL) and the resulting solution was stirred at $R_T$ for 16 h. The mixture was concentrated under reduced pressure and the residue was purified by flash chromatography on silica gel eluting with dichloromethane/methanol (9/1). Appropriate fractions were combined and concentrated under reduced pressure to afford 2-chloro-5-(difluoromethoxy)-4-(4-nitro-1-[[2-(trimethylsilyl)ethoxy]methyl]-1H-pyrazol-5-yl)benzaldehyde (750 mg, 92%) as a white solid.

A mixture of 2-chloro-5-(difluoromethoxy)-4-(4-nitro-1-[[2-(trimethylsilyl)ethoxy]methyl]-1H-pyrazol-5-yl)benzaldehyde (300 mg, 0.670 mmol), K$_2$CO$_3$ (185 mg, 1.34 mmol) and 2-methylpropane-2-thiol (241 mg, 2.67 mmol) in DMF (3.0 mL) was heated at 60° C. for 16 h. The mixture was concentrated under reduced pressure and the residue was purified by flash chromatography on silica gel eluting with ethyl acetate/petroleum ether (1/4). Appropriate fractions were combined and concentrated under reduced pressure to afford 2-(tert-butylsulfanyl)-5-(difluoromethoxy)-4-(4-nitro-1-[[2-(trimethylsilyl)ethoxy]methyl]-1H-pyrazol-5-yl)benzaldehyde (320 mg, 95%) as a yellow solid.

A mixture of 2-(tert-butylsulfanyl)-5-(difluoromethoxy)-4-(4-nitro-1-[[2-(trimethylsilyl)ethoxy]methyl]-1H-pyrazol-5-yl)benzaldehyde (320 mg, 0.638 mmol) and hydroxylamine hydrochloride (88.0 mg, 1.27 mmol) in iso-propanol (4.0 mL) and water (2.0 mL) was heated at 90° C. for 2 h. The resulting mixture was allowed to cool to $R_T$ and concentrated under reduced pressure. The residue was purified by flash chromatography on silica gel eluting with ethyl acetate/petroleum ether (1/4). Appropriate fractions were combined and concentrated under reduced pressure to afford (E)-N-[[2-(tert-butylsulfanyl)-5-(difluoromethoxy)-4-(4-nitro-1-[[2-(trimethylsilyl)ethoxy]methyl]-1H-pyrazol-5-yl)phenyl]methylidene]hydroxylamine (200 mg, 61%) as a yellow solid. LC/MS (Method S, ESI): [M+H]=517.3, $R_T$=1.52 min.

A mixture of (E)-N-[[2-(tert-butylsulfanyl)-5-(difluoromethoxy)-4-(4-nitro-1-[[2-(trimethylsilyl)ethoxy]methyl]-1H-pyrazol-5-yl)phenyl]methylidene]hydroxylamine (180 mg, 0.348 mmol) and 4-methylbenzene-1-sulfonic acid (120 mg, 0.697 mmol) in propanol (5.0 mL) was heated at 100° C. 16 h under nitrogen. The resulting mixture was allowed to cool to $R_T$ and concentrated under reduced pressure. The residue was purified by flash chromatography on silica gel eluting with dichloromethane/methanol (9/1). Appropriate fractions were combined and concentrated under reduced pressure to afford 5-(difluoromethoxy)-6-(4-nitro-1H-pyrazol-3-yl)-1,2-benzothiazole (80 mg, 37%) as a colorless solid. LC/MS (Method S, ESI): [M+H]$^+$=313.1, $R_T$=1.17 min; $^1$H NMR (300 MHz, DMSO-d6): δ 14.24 (s, 1H), 9.22 (s, 1H), 8.97 (s, 1H), 8.47 (s, 1H), 8.11 (s, 1H), 7.22 (t, J=72.9 Hz, 1H).

A mixture of 5-(difluoromethoxy)-6-(4-nitro-1H-pyrazol-3-yl)-1,2-benzothiazole (75.0 mg, 0.240 mmol), iron powder (108 mg, 1.93 mmol) and NH$_4$Cl (102 mg, 1.907 mmol) in propanol (8.0 mL) and water (0.80 mL) was heated at 90° C. for 2 h. The resulting mixture was allowed to cool to $R_T$ and concentrated under reduced pressure. The residue was diluted with H$_2$O (10 mL) and extracted with ethyl acetate (3×10 mL). The combined organic layer was concentrated under reduced pressure to afford 3-[5-(difluoromethoxy)-1,2-benzothiazol-6-yl]-1H-pyrazol-4-amine (70 mg, crude) as a brown solid. LC/MS (Method S, ESI): [M+H]=283.1, $R_T$=0.79 min.

A mixture of pyrazolo[1,5-a]pyrimidine-3-carboxylic acid (18 mg, 0.110 mmol), 4-dimethylaminopyridine (1.00 mg, 0.0078 mmol), DIPEA (27.0 mg, 0.209 mmol), 3H-[1,2,3]triazolo[4,5-b]pyridin-3-yl tris(pyrrolidin-1-yl)phosphinite; hexafluoro-1^[6]-phosphane (73.0 mg, 0.140 mmol) and 3-[5-(difluoromethoxy)-1,2-benzothiazol-6-yl]-1H-pyrazol-4-amine (20.0 mg, 0.0709 mmol) in DMF (2.0 mL) was stirred at $R_T$ for 2 h. The mixture was concentrated under reduced pressure and the crude product was purified by Prep-HPLC using the following conditions: Column, XBridge Shield RP$_{18}$ OBD Column, 5 um, 19*150 mm; mobile phase, Water (0.05% NH$_3$H$_2$O) and acetonitrile (18% acetonitrile to 45% over 7 min); Detector, UV 220 nm. Appropriate fractions were combined and evaporated to afford N-[3-[5-(difluoromethoxy)-1,2-benzothiazol-6-yl]-1H-pyrazol-4-yl]pyrazolo[1,5-a]pyrimidine-3-carboxamide (11.0 mg, 23%) as a yellow solid. LC/MS (Method N, ESI): [M+H]$^+$=428.2, $R_T$=1.40 min. $^1$H NMR (400 MHz, DMSO-d$_6$): δ 13.13 (s, 1H), 9.81 (s, 1H), 9.33 (dd, J=7.2, 1.6 Hz, 1H), 9.22 (s, 1H), 8.66 (s, 1H), 8.55 (dd, J=4.0, 1.6 Hz, 1H), 8.48 (s, 1H), 8.33 (s, 1H), 8.15 (s, 1H), 7.32 (t, J=73.4 Hz, 1H), 7.26 (dd, J=7.2, 4.4 Hz, 1H).

Example 153 (General Procedure AB)

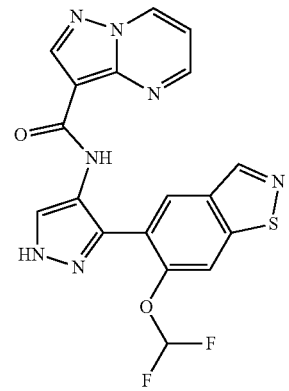 [SMILES: O=C(Nc1c[nH]nc1-c1cc2cnsc2cc1OC(F)F)c1cnn2cccnc12]

N-(3-(6-(difluoromethoxy)benzo[d]isothiazol-5-yl)-1H-pyrazol-4-yl)pyrazolo[1,5-a]pyrimidine-3-carboxamide A degassed mixture of 5-[5-bromo-4-chloro-2-(difluoromethoxy)phenyl]-4-nitro-1-[[2-(trimethylsilyl)ethoxy]methyl]-1H-pyrazole (1.00 g, 2.01 mmol), Cs$_2$CO$_3$ (1.30 g, 3.99 mmol), potassium trifluoro(vinyl)borate (536 mg, 4.00 mmol) and Pd(dppf)Cl$_2$.CH$_2$Cl$_2$ (326 mg, 0.399 mmol) in dioxane (10 mL) and water (2.0 mL) was heated under microwave irradiation at 100° C. for 1.5 h. The resulting mixture was allowed to cool to $R_T$ and concentrated under reduced pressure. The residue was purified by flash chromatography on silica gel eluting with dichloromethane/methanol (9/1). Appropriate fractions were combined and concentrated under reduced pressure to afford 5-[4-chloro-2-(difluoromethoxy)-5-ethenylphenyl]-4-nitro-1-[[2-(trimethylsilyl)ethoxy]methyl]-1H-pyrazole (800 mg, 89%) as a yellow solid.

A solution of 5-[4-chloro-2-(difluoromethoxy)-5-ethenylphenyl]-4-nitro-1-[[2-(trimethylsilyl)ethoxy]methyl]-1H-pyrazole (1.60 g, 3.59 mmol), OsO$_4$ (1.80 g, 7.08 mmol) and NMO (839 mg, 7.16 mmol) in tetrahydrofuran (10 mL) and water (5.0 mL) was stirred at $R_T$ for 2 h. The mixture was diluted with H$_2$O (20 mL), quenched by the addition of saturated Na$_2$S$_2$O$_3$ aqueous solution (20 mL) and extracted with dichloromethane (3×20 mL). The combined organic layer was concentrated under reduced pressure and purified by flash chromatography on silica gel eluting with dichloromethane/methanol (9/1). Appropriate fractions were combined and concentrated under reduced pressure to afford 1-[2-chloro-4-(difluoromethoxy)-5-(4-nitro-1-[[2-(trimethylsilyl)ethoxy]methyl]-1H-pyrazol-5-yl)phenyl]ethane-1,2-diol (1.10 g, 64%) as colorless oil.

A mixture of 1-[2-chloro-4-(difluoromethoxy)-5-(4-nitro-1-[[2-(trimethylsilyl)ethoxy]methyl]-1H-pyrazol-5-yl)phenyl]ethane-1,2-diol (1.10 g, 2.29 mmol) and NaIO4 (567 mg, 2.65 mmol) in CH$_3$CN (10 mL) and water (1.0 mL) was stirred at $R_T$ for 16 h. The resulting mixture was concentrated under reduced pressure and the residue was purified by flash chromatography on silica gel eluting with dichloromethane/methanol (9/1). Appropriate fractions were combined and concentrated under reduced pressure to afford 2-chloro-4-(difluoromethoxy)-5-(4-nitro-1-[[2-(trimethylsilyl)ethoxy]methyl]-1H-pyrazol-5-yl)benzaldehyde (870 mg, 85%) as a yellow solid.

A mixture of 2-chloro-4-(difluoromethoxy)-5-(4-nitro-1-[[2-(trimethylsilyl)ethoxy]methyl]-1H-pyrazol-5-yl)benzaldehyde (870 mg, 1.942 mmol), 2-methylpropane-2-thiol (699 mg, 7.75 mmol) and potassium carbonate (535 mg, 3.87 mmol) in DMF (10 mL) was heated at 60° C. for 16 h. The mixture was allowed to cool to $R_T$ and concentrated under reduced pressure. The residue was purified by flash chromatography on silica gel eluting with ethyl acetate/petroleum ether (1/4). Appropriate fractions were combined and concentrated under reduced pressure to afford 2-(tert-butylsulfanyl)-4-(difluoromethoxy)-5-(4-nitro-1-[[2-(trimethylsilyl)ethoxy]-methyl]-1H-pyrazol-5-yl)benzaldehyde (240 mg, 25%) as colorless oil.

A mixture of 2-(tert-butylsulfanyl)-4-(difluoromethoxy)-5-(4-nitro-1-[[2-(trimethylsilyl)ethoxy]methyl]-1H-pyrazol-5-yl)benzaldehyde (240 mg, 0.478 mmol) and hydroxylamine hydrochloride (66.0 mg, 0.950 mmol) in iso-propanol (4.0 mL) and water (2.0 mL) was heated at 90° C. for 2 h. The mixture was allowed to cool to $R_T$ and concentrated under reduced pressure. The residue was purified by flash chromatography on silica gel eluting with ethyl acetate/petroleum ether (1/4). Appropriate fractions were combined and concentrated under reduced pressure to afford (E)-N-[[2-(tert-butylsulfanyl)-4-(difluoromethoxy)-5-(4-nitro-1-[[2-(trimethylsilyl)ethoxy]methyl]-1H-pyrazol-5-yl)phenyl]methylidene]hydroxylamine (180 mg, 73%) as yellow oil.

A mixture of (E)-N-[[2-(tert-butylsulfanyl)-4-(difluoromethoxy)-5-(4-nitro-1-[[2-(trimethylsilyl)ethoxy]methyl]-1H-pyrazol-5-yl)phenyl]methylidene]hydroxylamine (180 mg, 0.348 mmol) and 4-methylbenzene-1-sulfonic acid (120 mg, 0.697 mmol) in propanol (4.0 mL) was heated at 100° C. for 16 h under nitrogen. The resulting mixture was allowed to cool to $R_T$ and concentrated under reduced pressure. The residue was purified by flash chromatography on silica gel eluting with ethyl acetate/petroleum ether (1/1). Appropriate fractions were combined and concentrated under reduced pressure to afford 6-(difluoromethoxy)-5-(4-nitro-1H-pyrazol-3-yl)-1,2-benzothiazole (100 mg, 46%) as a white solid. LC/MS (Method S, ESI): [M+H]$^+$=313.1, $R_T$=1.17 min.

A mixture of 6-(difluoromethoxy)-5-(4-nitro-1H-pyrazol-3-yl)-1,2-benzothiazole (109 mg, 0.349 mmol), iron powder (157 mg, 2.81 mmol) and NH$_4$Cl (148 mg, 2.77 mmol) in propanol (5.0 mL) and water (0.50 mL) was heated at 90° C. for 2 h. The mixture was allowed cool to $R_T$, partitioned between water (20 mL) and dichloromethane (20 mL). The aqueous phase was extracted with dichloromethane (2×) and the combined organic layer was washed with brine, dried over sodium sulfate and concentrated under reduced pressure to afford 3-[6-(difluoromethoxy)-1,2-benzothiazol-5-yl]-1H-pyrazol-4-amine (100 mg, crude) as a brown solid. LC/MS (Method S, ESI): [M+H]$^+$=283.1, $R_T$=0.81 min.

A mixture of pyrazolo[1,5-a]pyrimidine-3-carboxylic acid (86.0 mg, 0.527 mmol), 4-dimethylaminopyridine (5.00 mg, 0.0410 mmol), DIPEA (135 mg, 1.05 mmol), 3H-[1,2,3]triazolo[4,5-b]pyridin-3-yl tris(pyrrolidin-1-yl)phosphinite; hexafluoro-1^[6]-phosphane (365 mg, 0.700 mmol) and 3-[6-(difluoromethoxy)-1,2-benzothiazol-5-yl]-1H-pyrazol-4-amine (100 mg, 0.354 mmol) in N,N-dimethylformamide (2.0 mL) was heated at 60° C. for 2 h. The mixture allowed to cool to $R_T$ and concentrated under reduced pressure. The crude product (20 mg) was purified by prep-HPLC with the following conditions: Column, SunFire Prep C18 OBD Column, 19*150 mm, 5 um; mobile phase, Water (0.1% formic acid) and acetonitrile (15% acetonitrile to 53% over 7 min); Detector, UV 254/220 nm to afford N-[3-[6-(difluoromethoxy)-1,2-benzothiazol-5-yl]-1H-pyrazol-4-yl]pyrazolo[1,5-a]pyrimidine-3-carboxamide; formic acid (5.7 mg, 3%) as a white solid. LC/MS (Method P, ESI): [M+H]$^+$=428.2, $R_T$=2.18 min. $^1$H NMR (300 MHz, DMSO-d$_6$): δ 13.07 (s, 1H), 9.76 (s, 1H), 9.33 (dd, J=6.9, 1.5 Hz, 1H), 9.17 (s, 1H), 8.65 (s, 1H), 8.49 (dd, J=4.2, 1.5 Hz, 1H), 8.40 (s, 1H), 8.33-8.30 (m, 2H), 7.35 (t, J=73.2 Hz, 1H), 7.26 (dd, J=7.1, 4.4 Hz, 1H).

Example 154 (General Procedure AC)

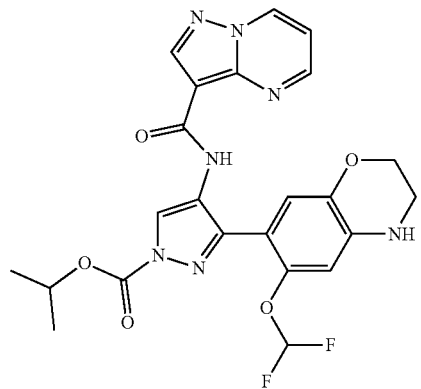 [SMILES: CC(C)OC(=O)n1cc(NC(=O)c2cnn3cccnc23)c(-c2cc3c(cc2OC(F)F)NCCO3)n1]

Propan-2-yl 3-[6-(difluoromethoxy)-3,4-dihydro-2H-1,4-benzoxazin-7-yl]-4-[pyrazolo[1,5-a]pyrimidine-3-amido]-1H-pyrazole-1-carboxylate To a solution of N-[3-[6-(difluoromethoxy)-3,4-dihydro-2H-1,4-benzoxazin-7-yl]-1H-pyrazol-4-yl]pyrazolo[1,5-a]pyrimidine-3-carboxamide (50.0 mg, 0.117 mmol) in dichloromethane (2.0 mL) was added DIPEA (45.0 mg, 0.348 mmol), followed by isopropyl chloroformate (21.4 mg, 0.175 mmol) at 0° C. The resulting solution was stir overnight at $R_T$, concentrated under reduced pressure and the crude product was purified by Prep-HPLC under the following conditions: Column, XBridge Prep C18 OBD Column, 19*150 mm 5 um; mobile phase, Water (10 mmol/L NH$_4$HCO$_3$) and acetonitrile (35.0% acetonitrile to 50.0% in 10 min); Detector, UV 254/220 nm. Appropriate fractions were combined and evaporated to afford propan-2-yl 3-[6-(difluoromethoxy)-3,4-dihydro-2H-1,4-benzoxazin-7-yl]-4-[pyrazolo[1,5-a]pyrimidine-3-amido]-1H-pyrazole-1-carboxylate (1.6 mg, 3%) as a white solid. LC/MS (Method O, ESI): [M+H]$^+$=514.2, $R_T$=1.29 min. $^1$H NMR (300 MHz, DMSO-d$_6$): δ 9.94 (s, 1H), 9.37 (dd, J=7.1, 1.7 Hz, 1H), 8.70 (s, 1H), 8.67 (s, 1H), 8.62 (dd, J=4.1, 1.7 Hz, 1H), 7.32 (dd, J=7.1, 4.2 Hz, 1H), 6.95 (t, J=74.3 Hz, 1H), 6.86 (s, 1H), 6.65 (s, 1H), 6.54 (s, 1H), 5.21-5.14 (m, 1H), 4.18 (t, J=4.5 Hz, 1H), 3.39-3.35 (m, 2H), 1.40 (d, J=6.3 Hz, 6H).

The examples in the following Table 2 were prepared. Absolute stereochemistry of each compound below may not be depicted: therefore, structures may appear more than once, each representing a single stereoisomer.

TABLE 2

| Example No. | Intermediate Reference | General Procedure | Product Structure | m/z |
|---|---|---|---|---|
| 1 | 10 | A | | 421 |
| 2 | Example 1 | B | | 479 |
| 3 | Example 2 | C | | 645 |

TABLE 2-continued

| Example No. | Intermediate Reference | General Procedure | Product Structure | m/z |
|---|---|---|---|---|
| 4 | Example 1 | D | | 435 |
| 5 | Example 1 | E | | 504 |
| 6 | Example 11 | F | | 553 |
| 7 | 14, 17 | G | | 485 |

TABLE 2-continued

| Example No. | Intermediate Reference | General Procedure | Product Structure | m/z |
|---|---|---|---|---|
| 8 | 1, 15 | H | | 499 |
| 9 | 3 | I | | 639 |
| 10 | Example 7 | J | | 539 |
| 11 | 12 | K | | 428 |

TABLE 2-continued
| Example No. | Intermediate Reference | General Procedure | Product Structure | m/z |
|---|---|---|---|---|
| 12 | 12 | L | 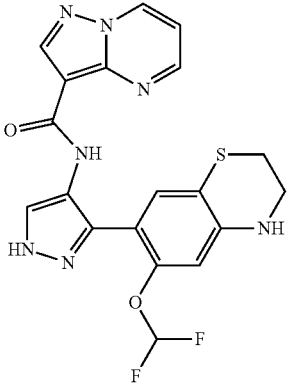 [SMILES: O=C(Nc1c[nH]nc1-c1cc2c(cc1OC(F)F)NCCS2)c1cnn2cccnc12] | 444.2 |
| 13 | 12 | M | 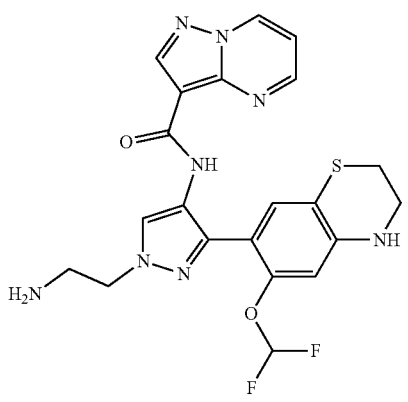 [SMILES: NCCn1cc(NC(=O)c2cnn3cccnc23)c(-c2cc3c(cc2OC(F)F)NCCS3)n1] | 487 |
| 14 | 12 | N | 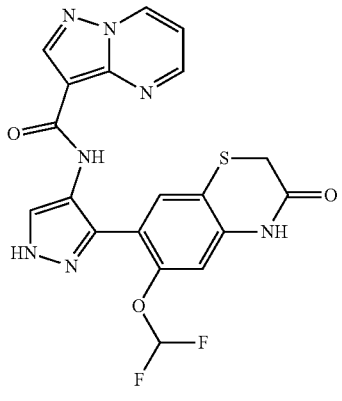 [SMILES: O=C1CSc2cc(-c3n[nH]cc3NC(=O)c3cnn4cccnc34)c(OC(F)F)cc2N1] | 458 |
| 15 | 18 | O | 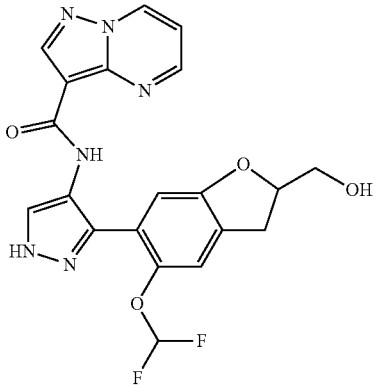 [SMILES: O=C(Nc1c[nH]nc1-c1cc2c(cc1OC(F)F)CC(CO)O2)c1cnn2cccnc12] | |

TABLE 2-continued

| Example No. | Intermediate Reference | General Procedure | Product Structure | m/z |
|---|---|---|---|---|
| 16 | 18 | P | | 413 |
| 17 | 18 | Q | | 427 |
| 18 | Example 21 | | | 636 |
| 19 | Example 92 | R | | 524 |

TABLE 2-continued

| Example No. | Intermediate Reference | General Procedure | Product Structure | m/z |
|---|---|---|---|---|
| 20 | 3, 16 | S | | 653 |
| 21 | 9 | T | | 411 |
| 22 | 5 | U | | 405 |
| 23 | | V | | 434 |

TABLE 2-continued

| Example No. | Intermediate Reference | General Procedure | Product Structure | m/z |
|---|---|---|---|---|
| 24 | Example 23 | W | | 416 |
| 25 | | | | 441.2 |
| 26 | 8 | A | | 410.4 |
| 27 | | A | | 374.4 |

TABLE 2-continued

| Example No. | Intermediate Reference | General Procedure | Product Structure | m/z |
|---|---|---|---|---|
| 28 | | A | | 384.4 |
| 29 | | A | | 385.4 |
| 30 | 11 | T | | 374.4 |
| 31 | | A | | 374.4 |

TABLE 2-continued

| Example No. | Intermediate Reference | General Procedure | Product Structure | m/z |
|---|---|---|---|---|
| 32 | 7 | A | | 391.4 |
| 33 | | A | | 391.4 |
| 34 | | A | | 390.4 |
| 35 | | A | | 390.4 |

TABLE 2-continued
| Example No. | Intermediate Reference | General Procedure | Product Structure | m/z |
|---|---|---|---|---|
| 36 | 6 | A | 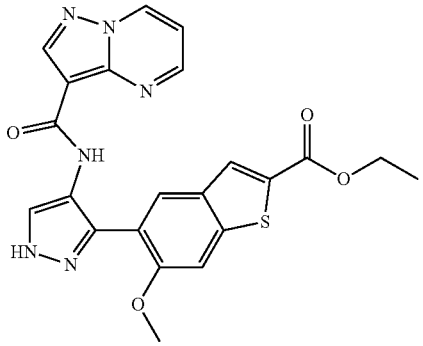 [SMILES: CCOC(=O)c1cc2cc(-c3n[nH]cc3NC(=O)c3cnn4cccnc34)c(OC)cc2s1] | 462.5 |
| 37 | 12 | L | 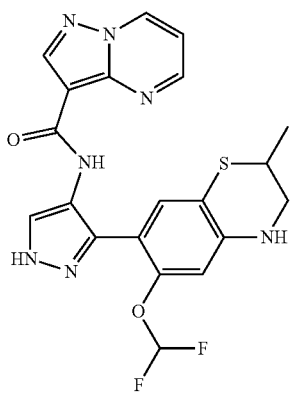 [SMILES: CC1CNc2cc(OC(F)F)c(-c3n[nH]cc3NC(=O)c3cnn4cccnc34)cc2S1] | 457.5 |
| 38 | 12 | L | 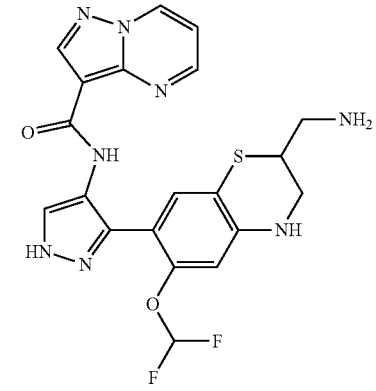 [SMILES: NCC1CNc2cc(OC(F)F)c(-c3n[nH]cc3NC(=O)c3cnn4cccnc34)cc2S1] | 472.5 |
| 39 | 12 | N | 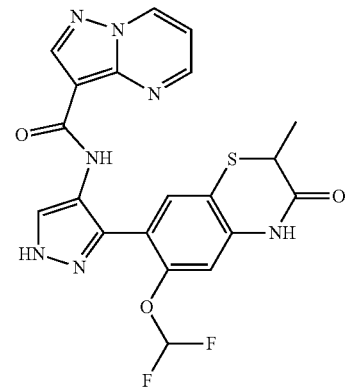 [SMILES: CC1Sc2cc(-c3n[nH]cc3NC(=O)c3cnn4cccnc34)c(OC(F)F)cc2NC1=O] | 471.4 |

TABLE 2-continued
| Example No. | Intermediate Reference | General Procedure | Product Structure | m/z |
|---|---|---|---|---|
| 40 | 12 | N | 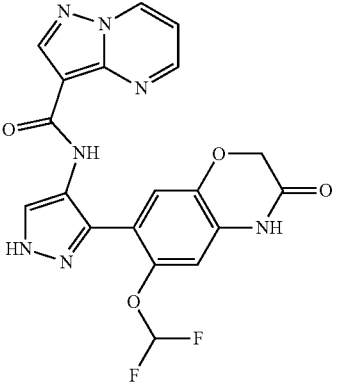 | 441.3 |
| 41 | 12 | L | 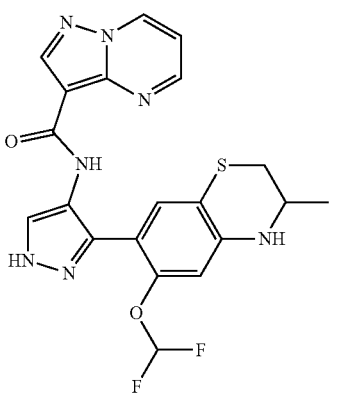 [SMILES: CC1CSc2cc(-c3n[nH]cc3NC(=O)c3cnn4cccnc34)c(OC(F)F)cc2N1] | 457.5 |
| 42 | 12 | K | 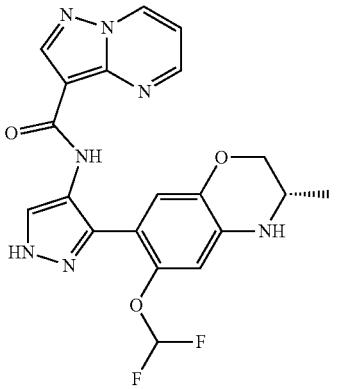 [SMILES: C[C@H]1COc2cc(-c3n[nH]cc3NC(=O)c3cnn4cccnc34)c(OC(F)F)cc2N1] | 441.4 |
| 43 | 12 | K | 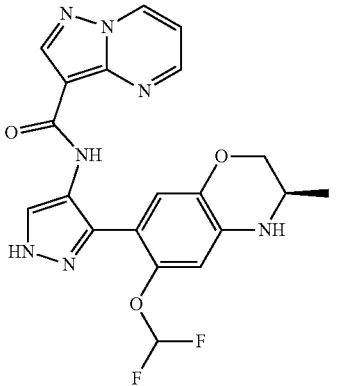 [SMILES: C[C@@H]1COc2cc(-c3n[nH]cc3NC(=O)c3cnn4cccnc34)c(OC(F)F)cc2N1] | 441.4 |

TABLE 2-continued
| Example No. | Intermediate Reference | General Procedure | Product Structure | m/z |
|---|---|---|---|---|
| 44 | 12 | K, F | 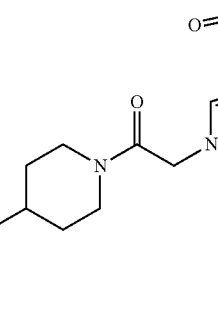 | 651.7 |
| 45 | 12 | L, F | 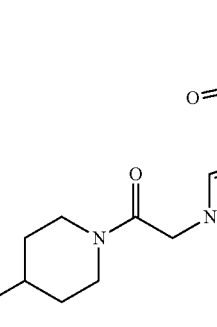 | 681.8 |
| 46 | 12 | L, F | 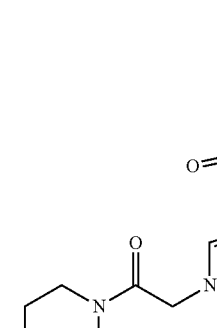 | 681.8 |
| 47 | 12 | K, E | 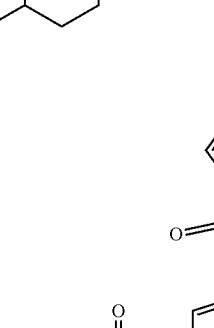 | 637.6 |

TABLE 2-continued

| Example No. | Intermediate Reference | General Procedure | Product Structure | m/z |
|---|---|---|---|---|
| 48 | 12 | K, F | | 568.5 |
| 49 | 12 | K, F | | 550.5 |
| 50 | 12 | L, F | | 566.6 |
| 51 | 12 | L, F | | 568.6 |

TABLE 2-continued
| Example No. | Intermediate Reference | General Procedure | Product Structure | m/z |
|---|---|---|---|---|
| 52 | 12 | L, F | 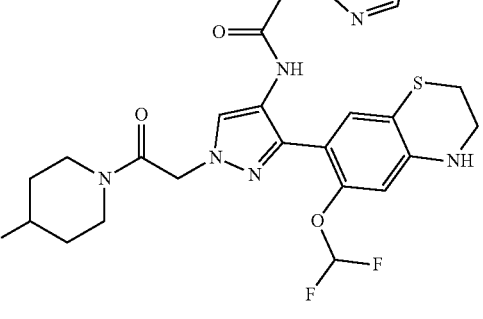 | 584.6 |
| 53 | 9 | T, F | 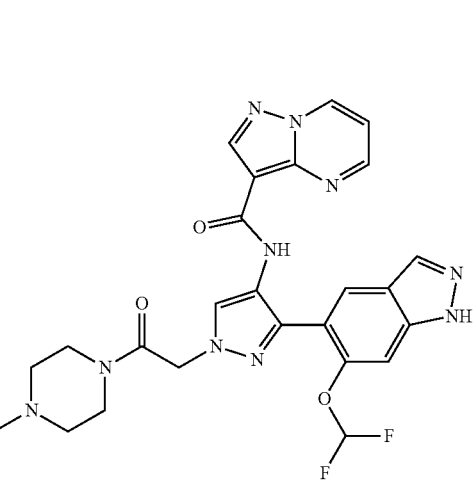 | 564.5 |
| 54 | | A, F | 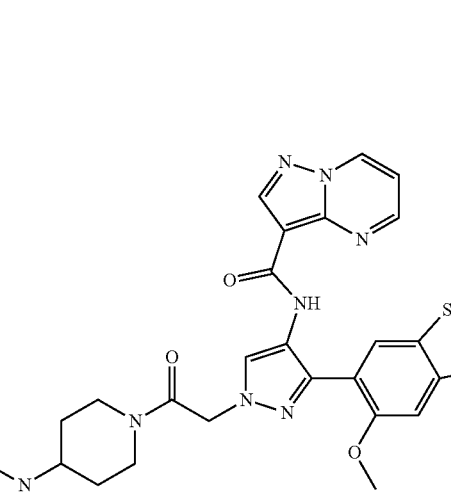 | 600.7 |

TABLE 2-continued

| Example No. | Intermediate Reference | General Procedure | Product Structure | m/z |
|---|---|---|---|---|
| 55 | 2 | A, W, F | | 661.7 |
| 56 | 2 | A, V, F | | 679.7 |
| 57 | 10 | A, F | | 630.6 |

TABLE 2-continued

| Example No. | Intermediate Reference | General Procedure | Product Structure | m/z |
|---|---|---|---|---|
| 58 | 12 | L, F | | 653.7 |
| 59 | 12 | L, F | | 667.7 |
| 60 | 2 | A, W, F | | 675.7 |
| 61 | 2 | A, V, F | | 693.7 |

TABLE 2-continued
| Example No. | Intermediate Reference | General Procedure | Product Structure | m/z |
|---|---|---|---|---|
| 62 | 2 | A, V, F | 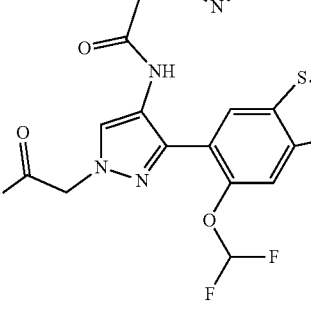 | 608.6 |
| 63 | 10 | A, F | 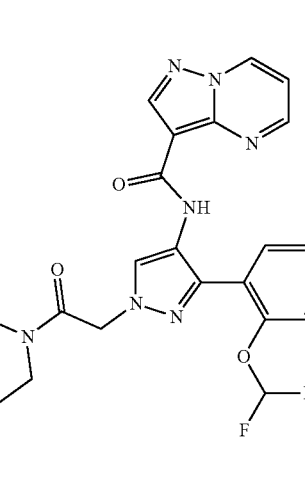 | 627.6 |
| 64 | 2 | V, F | 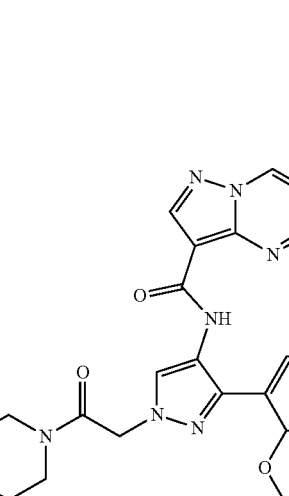 | 688.7 |

TABLE 2-continued

| Example No. | Intermediate Reference | General Procedure | Product Structure | m/z |
|---|---|---|---|---|
| 65 | 1 | A, F | | 650.7 |
| 66 | 1 | A, F | | 636.7 |
| 67 | 10 | A, B, C | | 574.6 |

TABLE 2-continued

| Example No. | Intermediate Reference | General Procedure | Product Structure | m/z |
|---|---|---|---|---|
| 68 | 10 | A, B, C | | 574.5 |
| 69 | 10 | A, B, C | | 631.6 |
| 70 | 10 | A, B, C | | 646.6 |

TABLE 2-continued

| Example No. | Intermediate Reference | General Procedure | Product Structure | m/z |
|---|---|---|---|---|
| 71 | 10 | A, B, C, J | | 546.5 |
| 72 | 12 | L, E | | 540.6 |
| 73 | 12 | N, E | | 554.6 |
| 74 | 9 | T, E | | 507.5 |

TABLE 2-continued
| Example No. | Intermediate Reference | General Procedure | Product Structure | m/z |
|---|---|---|---|---|
| 75 | 9 | T, E | 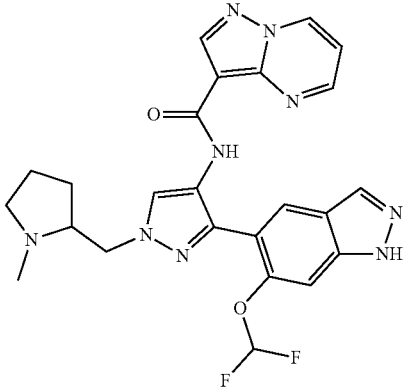 [SMILES: CN1CCCC1Cn1cc(NC(=O)c2cnn3cccnc23)c(-c2cc3cn[nH]c3cc2OC(F)F)n1] | 507.5 |
| 76 | 9 | T, E | 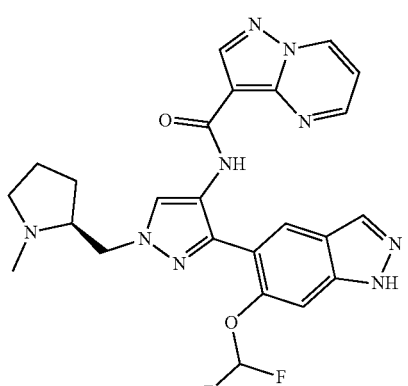 | 507.5 |
| 77 | 9 | T, E | 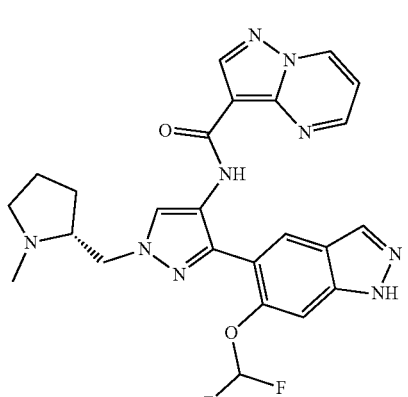 | 507.5 |
| 78 | 12 | L, E | 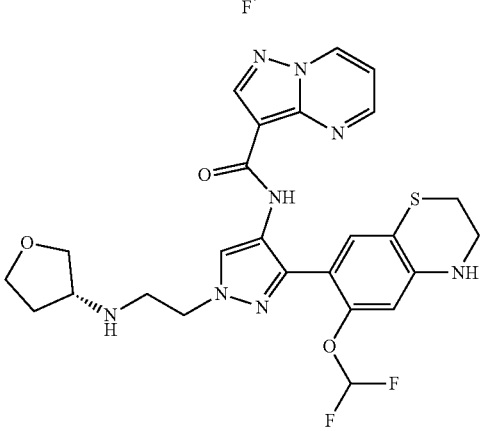 | 556.6 |

TABLE 2-continued

| Example No. | Intermediate Reference | General Procedure | Product Structure | m/z |
|---|---|---|---|---|
| 79 | 12 | N, E | | 514.5 |
| 80 | 12 | L, E | | 500.5 |
| 81 | 12 | L, E | | 500.5 |
| 82 | 12 | L, E | | 514.6 |

TABLE 2-continued

| Example No. | Intermediate Reference | General Procedure | Product Structure | m/z |
|---|---|---|---|---|
| 83 | 12 | N, E | | 528.5 |
| 84 | 12 | M | | 483.4 |
| 85 | 10 | E | | 533.5 |
| 86 | 10 | E | | 531.6 |

TABLE 2-continued

| Example No. | Intermediate Reference | General Procedure | Product Structure | m/z |
|---|---|---|---|---|
| 87 | 10 | A, D | | 448.4 |
| 88 | 13 | L, D | | 457.5 |
| 89 | 13 | K, D | | 441.4 |
| 90 | 13 | N | | 471.4 |

TABLE 2-continued
| Example No. | Intermediate Reference | General Procedure | Product Structure | m/z |
|---|---|---|---|---|
| 91 | 2 | S, J | 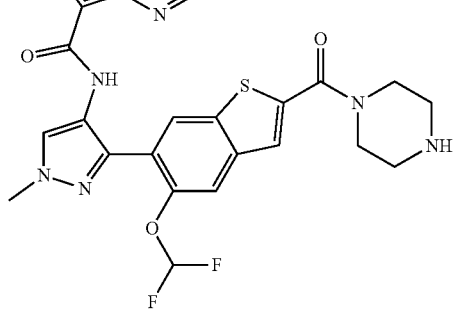 | 552.6 |
| 92 | 2 | H | 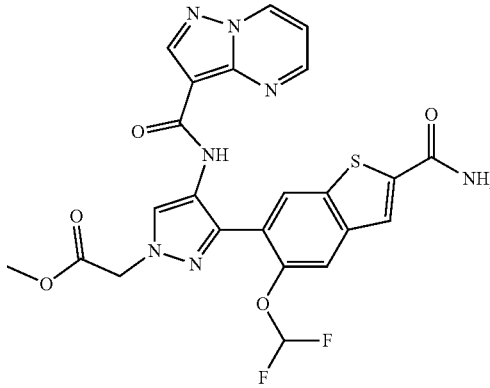 | 541.5 |
| 93 | 12 | L | 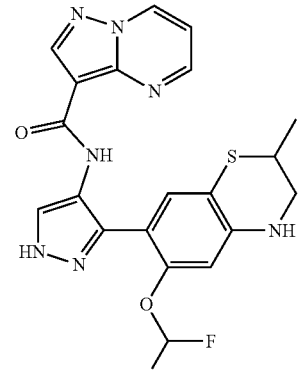<br>Isomer 1 | 458.2 |

TABLE 2-continued
| Example No. | Intermediate Reference | General Procedure | Product Structure | m/z |
|---|---|---|---|---|
| 94 | 12 | L | 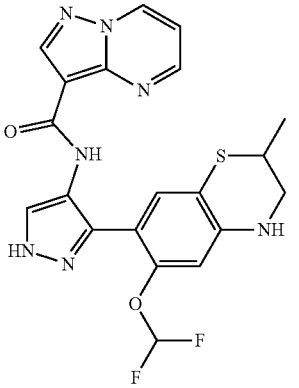<br>Isomer 2 | 458.2 |
| 95 | 12 | N | 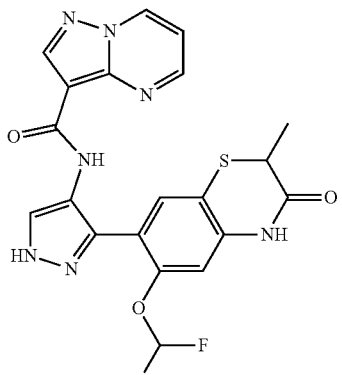<br>Isomer 1 | 472.2 |
| 96 | 12 | N | 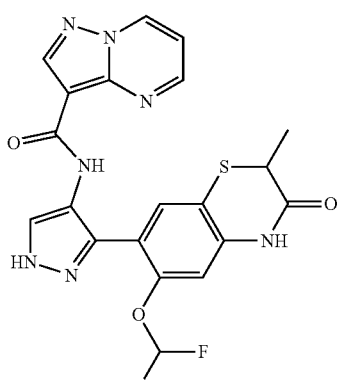<br>Isomer 2 | 472.2 |

TABLE 2-continued
| Example No. | Intermediate Reference | General Procedure | Product Structure | m/z |
|---|---|---|---|---|
| 97 | 13 | N | 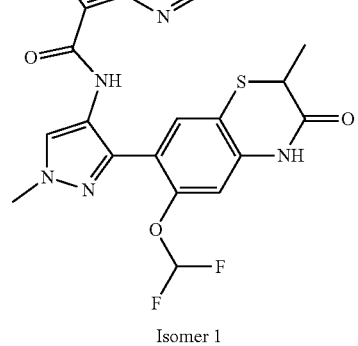 Isomer 1 | 486.2 |
| 98 | 13 | N | 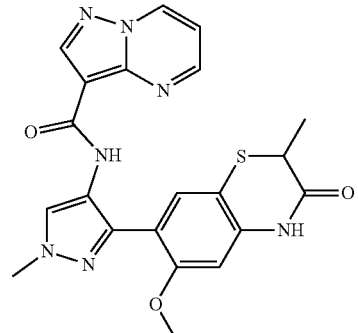 Isomer 2 | 486.2 |
| 99 | 12 | L, F | 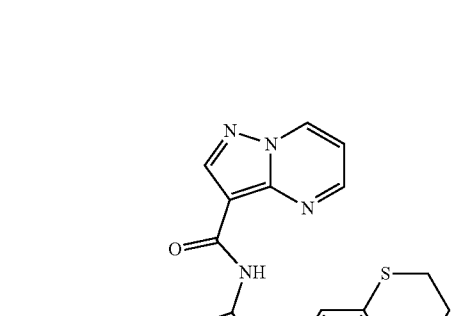 | 529.3 |

TABLE 2-continued
| Example No. | Intermediate Reference | General Procedure | Product Structure | m/z |
|---|---|---|---|---|
| 100 | 12 | K, F | 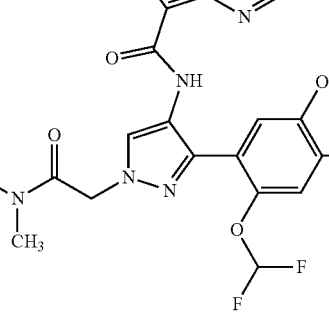 | 513.3 |
| 101 | 12 | L, F | 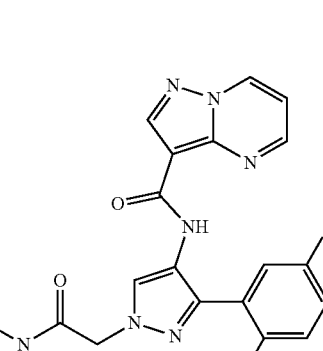<br>Isomer 1 | 583.4 |
| 102 | 12 | L, F | 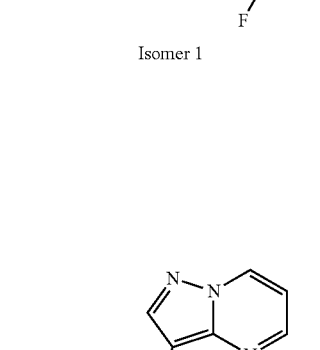<br>Isomer 2 | 583.3 |

TABLE 2-continued
| Example No. | Intermediate Reference | General Procedure | Product Structure | m/z |
|---|---|---|---|---|
| 103 | 12 | L, F | 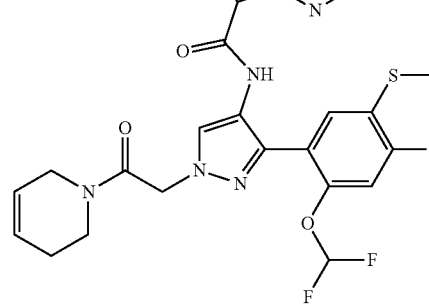<br>Isomer 1 | 581.3 |
| 104 | 12 | L, F | 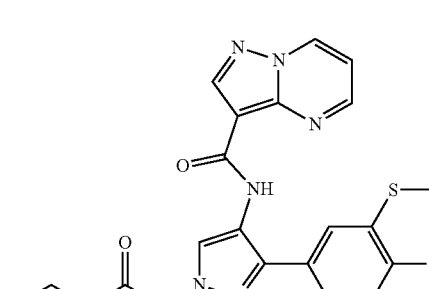<br>Isomer 2 | 581.3 |
| 105 | 12 | L, F | 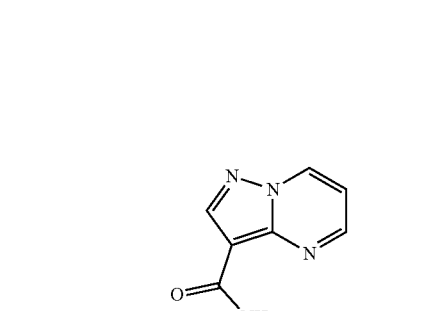<br>Isomer 1 | 543.3 |

TABLE 2-continued
| Example No. | Intermediate Reference | General Procedure | Product Structure | m/z |
|---|---|---|---|---|
| 106 | 12 | L, F | 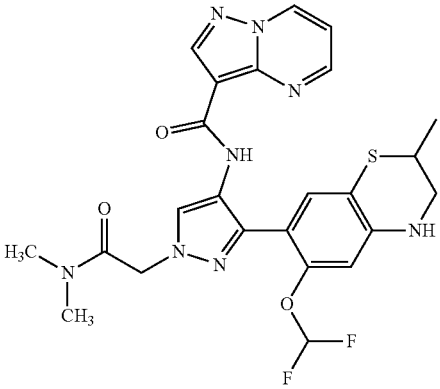<br>Isomer 2 | 543.3 |
| 107 | 12 | L, F | 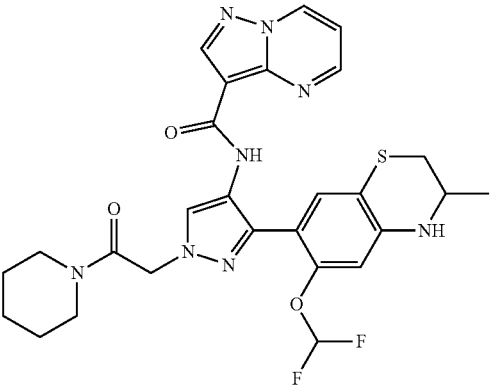<br>Isomer 1 | 583.3 |
| 108 | 12 | L, F | 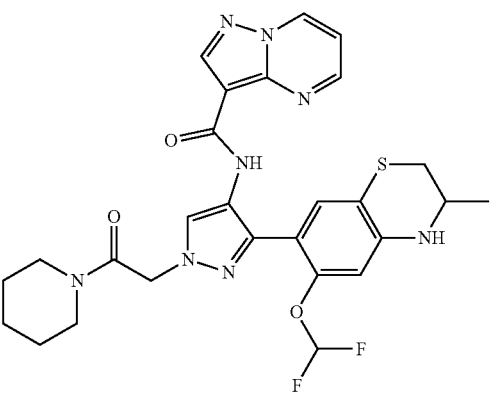<br>Isomer 2 | 583.3 |

TABLE 2-continued
| Example No. | Intermediate Reference | General Procedure | Product Structure | m/z |
|---|---|---|---|---|
| 109 | 12 | P, F | 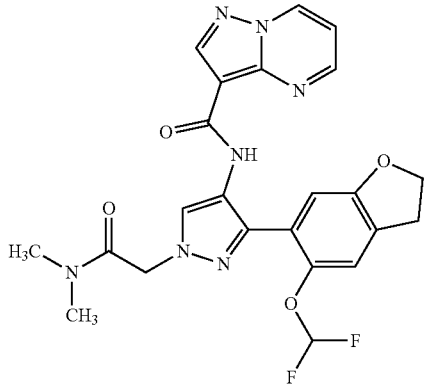 [SMILES: CN(C)C(=O)Cn1cc(NC(=O)c2cnn3cccnc23)c(-c2cc3c(cc2OC(F)F)CCO3)n1] | 498.2 |
| 110 | 12 | L | 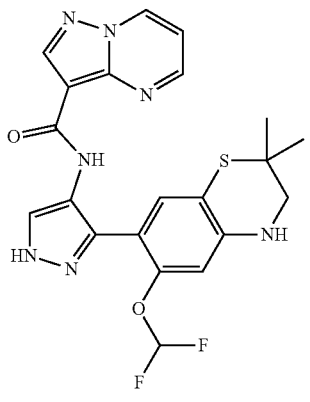 [SMILES: CC1(C)CNc2cc(OC(F)F)c(-c3n[nH]cc3NC(=O)c3cnn4cccnc34)cc2S1] | 472.2 |
| 111 | 12 | L, F | 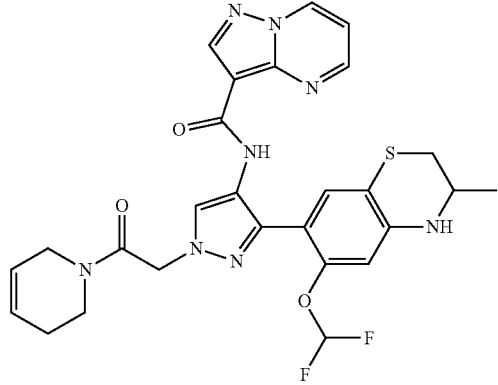\\ Isomer 1 | 581.3 |

TABLE 2-continued
| Example No. | Intermediate Reference | General Procedure | Product Structure | m/z |
|---|---|---|---|---|
| 112 | 12 | L, F | 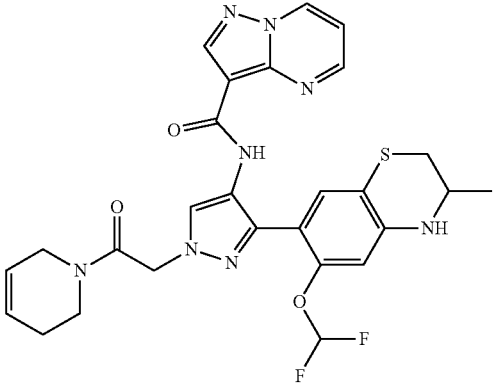<br>Isomer 2 | 581.3 |
| 113 | 12 | L, F | 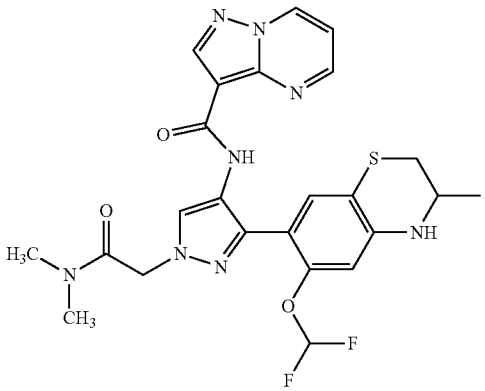<br>Isomer 1 | 543.3 |
| 114 | 12 | L, F | 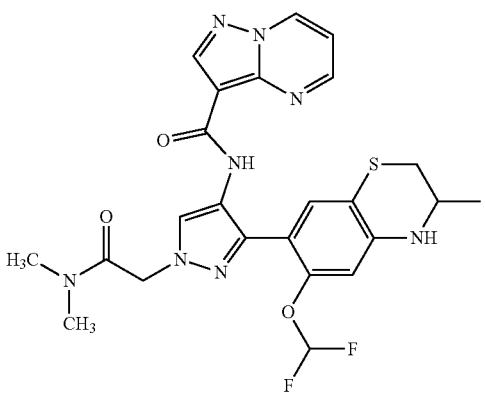<br>Isomer 2 | 543.3 |

TABLE 2-continued

| Example No. | Intermediate Reference | General Procedure | Product Structure | m/z |
|---|---|---|---|---|
| 115 | 20 | A | | 469.2 |
| 116 | 12 | K, F | | 499.2 |
| 117 | 12 | L, F | | 515.2 |
| 118 | 18 | Y | | 442.2 |

TABLE 2-continued

| Example No. | Intermediate Reference | General Procedure | Product Structure | m/z |
|---|---|---|---|---|
| 119 | 18 | Z, F | | 516.2 |
| 120 | 18 | Z, F | | 530.2 |
| 121 | 12 | K, E | | 500.3 |
| 122 | 12 | K, E | | 500.3 |

TABLE 2-continued
| Example No. | Intermediate Reference | General Procedure | Product Structure | m/z |
|---|---|---|---|---|
| 123 | 12 | K, E | 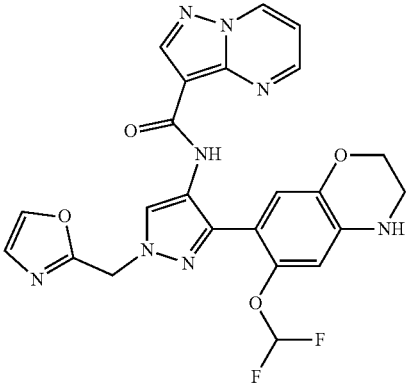 | 509.2 |
| 124 | 12 | L, E | 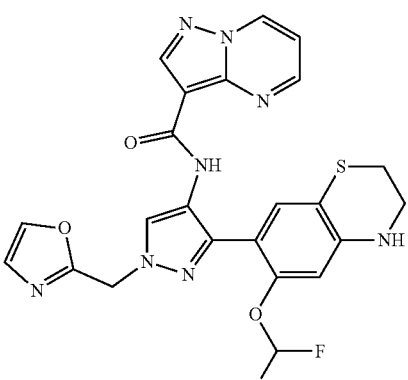 | 525.2 |
| 125 | 12 | L, F | 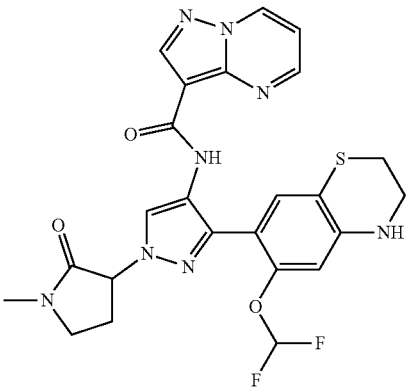 [SMILES: CN1CCC(n2cc(NC(=O)c3cnn4cccnc34)c(-c3cc4c(cc3OC(F)F)NCCS4)n2)C1=O] | 541.3 |
| 126 | 12 | L, F | 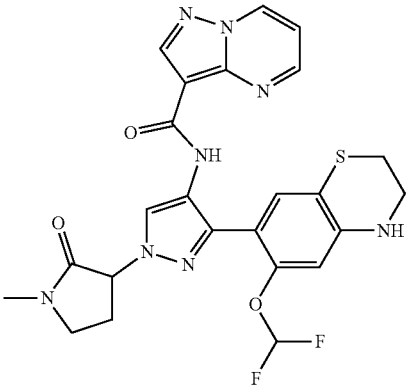 [SMILES: CN1CCC(n2cc(NC(=O)c3cnn4cccnc34)c(-c3cc4c(cc3OC(F)F)NCCS4)n2)C1=O] | 541.2 |

TABLE 2-continued
| Example No. | Intermediate Reference | General Procedure | Product Structure | m/z |
|---|---|---|---|---|
| 127 | 12 | L, E | 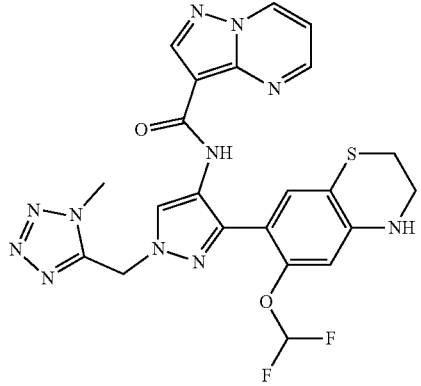 | 540.2 |
| 128 | 12 | L, E | 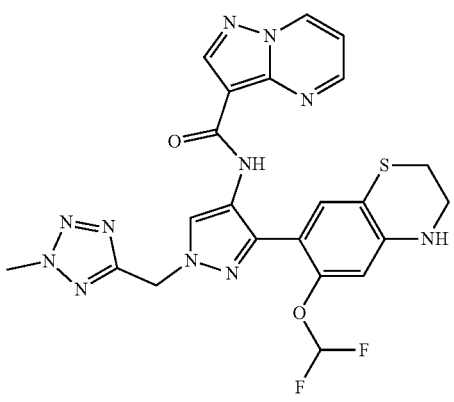 | 540.2 |
| 129 |  | AA, F | 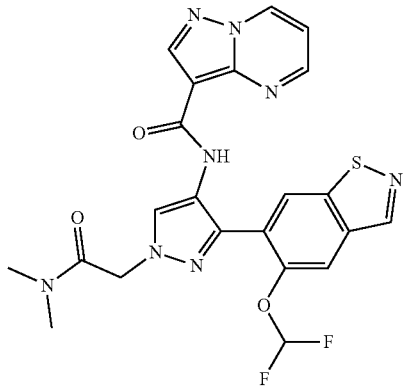 [SMILES: CN(C)C(=O)Cn1cc(NC(=O)c2cnn3cccnc23)c(-c2cc3sncc3cc2OC(F)F)n1] | 513.2 |
| 130 | 12 | K, F | 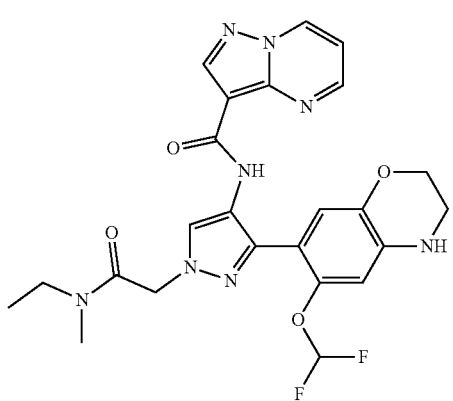 [SMILES: CCN(C)C(=O)Cn1cc(NC(=O)c2cnn3cccnc23)c(-c2cc3c(cc2OC(F)F)NCCO3)n1] | 527.3 |

TABLE 2-continued

| Example No. | Intermediate Reference | General Procedure | Product Structure | m/z |
|---|---|---|---|---|
| 131 | 12 | L, E | | 539.3 |
| 132 | 12 | K, F | | 575.3 |
| 133 | 12 | K, E | | 523.3 |
| 134 | 12 | K, E | | 542.3 |

TABLE 2-continued

| Example No. | Intermediate Reference | General Procedure | Product Structure | m/z |
|---|---|---|---|---|
| 135 | 12 | K, E | | 524.3 |
| 136 | 12 | K, E | | 524.3 |
| 137 | 13 | N | | 456.2 |
| 138 | 12 | K, F | | 561.3 |

TABLE 2-continued
| Example No. | Intermediate Reference | General Procedure | Product Structure | m/z |
|---|---|---|---|---|
| 139 | | AA, E | 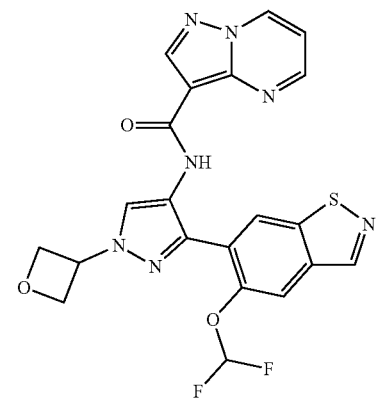 [SMILES: O=C(Nc1cn(C2COC2)nc1-c1cc2sncc2cc1OC(F)F)c1cnn2cccnc12] | 484.2 |
| 140 | 12 | L, E | 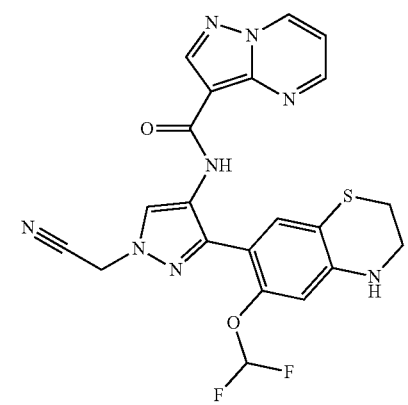 [SMILES: N#CCn1cc(NC(=O)c2cnn3cccnc23)c(-c2cc3c(cc2OC(F)F)NCCS3)n1] | 483.1 |
| 141 | 12 | L, E | 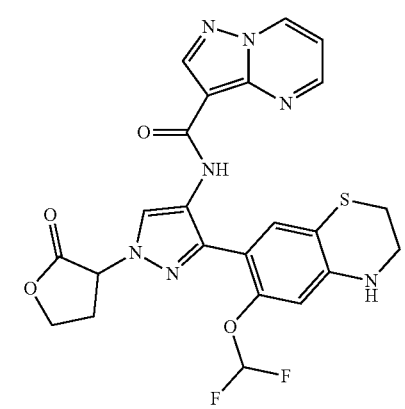 [SMILES: O=C(Nc1cn(C2CCOC2=O)nc1-c1cc2c(cc1OC(F)F)NCCS2)c1cnn2cccnc12] | 528.2 |

TABLE 2-continued
| Example No. | Intermediate Reference | General Procedure | Product Structure | m/z |
|---|---|---|---|---|
| 142 | 12 | L, E | 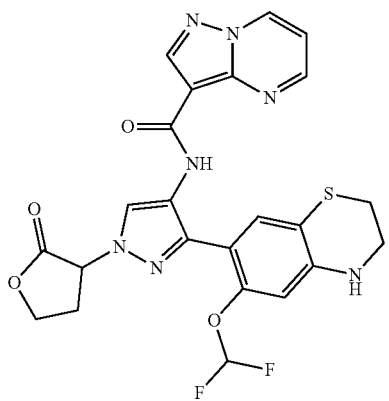 [SMILES: O=C(Nc1cn(C2CCOC2=O)nc1-c1cc2c(cc1OC(F)F)NCCS2)c1cnn2cccnc12] | 528.2 |
| 143 |  | AB, F | 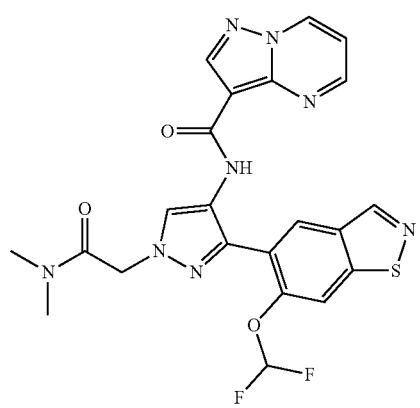 [SMILES: CN(C)C(=O)Cn1cc(NC(=O)c2cnn3cccnc23)c(-c2cc3cnsc3cc2OC(F)F)n1] | 513.2 |
| 144 | 12 | K, E | 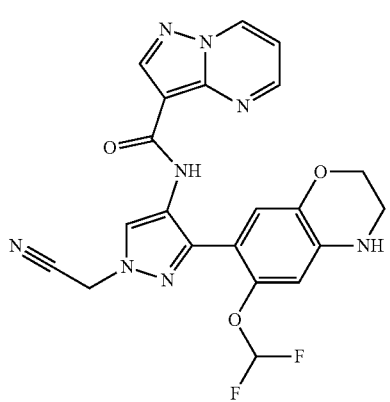 [SMILES: N#CCn1cc(NC(=O)c2cnn3cccnc23)c(-c2cc3c(cc2OC(F)F)NCCO3)n1] | 467.2 |

TABLE 2-continued
| Example No. | Intermediate Reference | General Procedure | Product Structure | m/z |
|---|---|---|---|---|
| 145 | 12 | K, E | 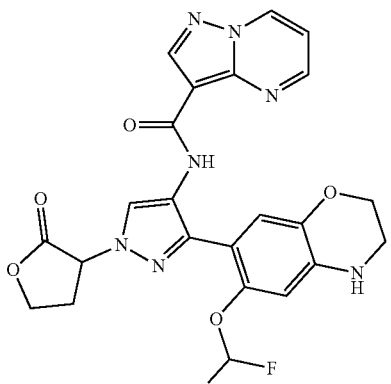 Isomer 1 | 512.2 |
| 146 | 12 | K, E | 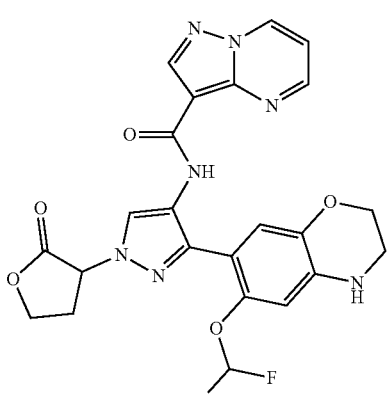 Isomer 2 | 512.2 |
| 147 | 19 | X | 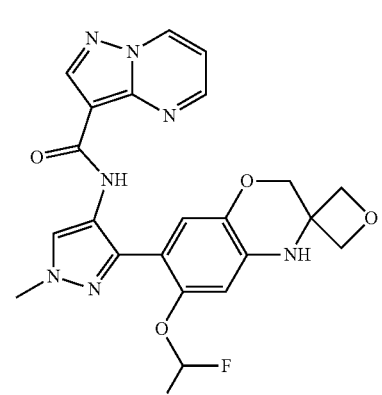 | 484.2 |

TABLE 2-continued
| Example No. | Intermediate Reference | General Procedure | Product Structure | m/z |
|---|---|---|---|---|
| 148 | 18 | Y | 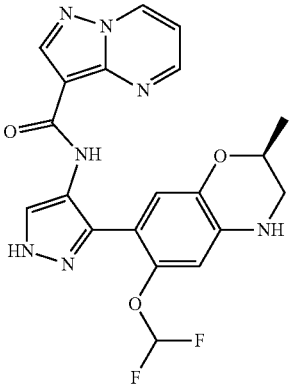 [SMILES: C[C@H]1CNc2cc(OC(F)F)c(-c3n[nH]cc3NC(=O)c3cnn4cccnc34)cc2O1] | 442.2 |
| 149 | 19 | Y | 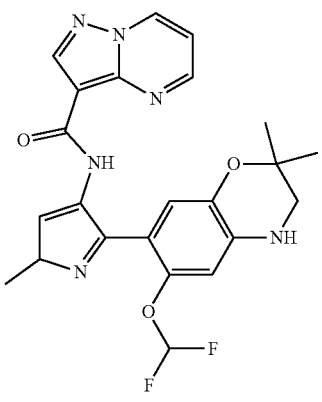 | 470.3 |
| 150 | 12 | Y | 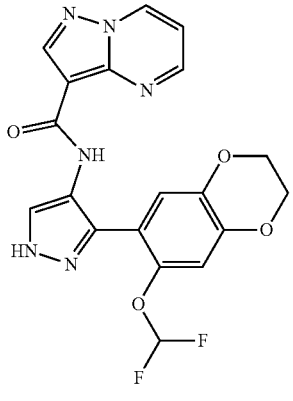 | 429.2 |
| 151 | 18 | Z | 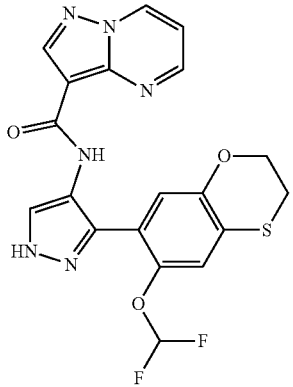 | 445.1 |

TABLE 2-continued

| Example No. | Intermediate Reference | General Procedure | Product Structure | m/z |
|---|---|---|---|---|
| 152 | | AA | | 428.2 |
| 153 | | AB | | 428.2 |
| 154 | | K, AC | | 514.2 |

Enzymatic Assays

JAK Enzyme Assays were Carried Out as Follows:

The activity of the isolated recombinant JAK1 and JAK2 kinase domain was measured by monitoring phosphorylation of a peptide derived from JAK3 (Val-Ala-Leu-Val-Asp-Gly-Tyr-Phe-Arg-Leu-Thr-Thr, fluorescently labeled on the N-terminus with 5-carboxyfluorescein) using the Caliper LabChip R technology (Caliper Life Sciences, Hopkinton, Mass.). To determine inhibition constants ($K_i$), compounds were diluted serially in DMSO and added to 50 μL kinase reactions containing purified enzyme (1.5 nM JAK1, or 0.2 nM JAK2), 100 mM HEPES buffer (pH 7.2), 0.015% Brij-35, 1.5 μM peptide substrate, ATP (25 μM), 10 mM $MgCl_2$, 4 mM DTT at a final DMSO concentration of 2%. Reactions were incubated at 22° C. in 384-well polypropylene microtiter plates for 30 minutes and then stopped by addition of 25 μL of an EDTA containing solution (100 mM HEPES buffer (pH 7.2), 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip R 3000 according to the manufacturer's specifications. K values were then determined using the Morrison tight binding model (Morrison, J. F., Biochim. Biophys. Acta. 185:269-296 (1969); William, J. W. and Morrison, J. F., Meth. Enzymol., 63:437-

467 (1979)) modified for ATP-competitive inhibition [$K_i=K_{i,app}/(1+[ATP]/K_{m,app})$].

JAK1 Pathway Assay in Cell Lines was Carried Out as Follows:

Inhibitor potency ($EC_{50}$) was determined in cell-based assays designed to measure JAK1 dependent STAT phosphorylation. As noted above, inhibition of IL-4, IL-13, and IL-9 signalling by blocking the Jak/Stat signaling pathway can alleviate asthmatic symptoms in pre-clinical lung inflammation models (Mathew et al., 2001, J Exp Med 193(9): 1087-1096; Kudlacz et. al., 2008, Eur J. Pharmacol 582(1-3): 154-161).

In one assay approach, TF-1 human erythroleukemia cells obtained from the American Type Culture Collection (ATCC; Manassas, Va.) were used to measure JAK1-dependent STAT6 phosphorylation downstream of IL-13 stimulation. Prior to use in the assays, TF-1 cells were starved of GM-CSF overnight in OptiMEM medium (Life Technologies, Grand Island, N.Y.) supplemented with 0.5% charcoal/dextran stripped fetal bovine serum (FBS), 0.1 mM non-essential amino acids (NEAA), and 1 mM sodium pyruvate. The assays were run in 384-well plates in serum-free OptiMEM medium using 300,000 cells per well. In a second assay approach, BEAS-2B human bronchial epithelial cells obtained from ATCC were plated at 100,000 cells per well of a 96-well plate one day prior to the experiment. The BEAS-2B assay was run in complete growth medium (bronchial epithelial basal medium plus bulletkit; Lonza; Basel, Switzerland).

Test compounds were serially diluted 1:2 in DMSO and then diluted 1:50 in medium just before use. Diluted compounds were added to the cells, for a final DMSO concentration of 0.2%, and incubated for 30 min (for the TF-1 assay) or 1 hr (for the BEAS-2B assay) at 37° C. Then, cells were stimulated with human recombinant cytokine at their respective $EC_{90}$ concentrations, as previously determined for each individual lot. Cells were stimulated with IL-13 (R&D Systems, Minneapolis, Minn.) for 15 min at 37° C. The TF-1 cell reactions were stopped by the direct addition of 10× lysis buffer (Cell Signaling Technologies, Danvers, Mass.), whereas the BEAS-2B cell incubations were halted by the removal of medium and addition of 1× lysis buffer. The resultant samples were frozen in the plates at −80° C. Compound mediated inhibition of STAT6 phosphorylation was measured in the cell lysates using MesoScale Discovery (MSD) technology (Gaithersburg, Md.). $EC_{50}$ values were determined as the concentration of compound required for 50% inhibition of STAT phosphorylation relative to that measured for the DMSO control.

Table 3 provides JAK1 $K_i$, JAK2 $K_i$, and IL-13-pSTAT6 $IC_{50}$ information for the noted Examples of the indicated Tables.

TABLE 3

| Example | JAK1 $K_i$ (uM) | JAK2 $K_i$ (uM) | IL-13 p-STAT6 BEAS-2B $IC_{50}$ (uM) |
|---|---|---|---|
| 1 | 0.00031 | 0.00014 | 0.006 |
| 2 | 0.00064 | 0.00022 | 0.128 |
| 3 | 0.00038 | 0.00097 | 0.008 |
| 4 | 0.00022 | 0.00012 | 0.022 |
| 5 | 0.00121 | 0.00078 | 0.031 |
| 6 | 0.00020 | 0.00031 | 0.017 |
| 7 | 0.00017 | 0.00011 | 0.006 |
| 8 | 0.00032 | 0.00029 | 0.010 |
| 9 | 0.00399 | 0.00285 | 0.153 |
| 10 | 0.00454 | 0.00199 | >1 |
| 11 | 0.00010 | 0.00008 | 0.004 |
| 12 | 0.00009 | 0.00006 | 0.006 |
| 13 | 0.00018 | 0.00013 | 0.020 |
| 14 | 0.00005 | 0.00004 | 0.027 |
| 15 | 0.00069 | 0.00024 | 0.143 |
| 16 | 0.00021 | 0.00009 | 0.005 |
| 17 | 0.00032 | 0.00014 | 0.014 |
| 18 | 0.00802 | 0.00259 | |
| 19 | 0.00030 | 0.00033 | 0.021 |
| 20 | 0.00557 | 0.00448 | 0.186 |
| 21 | 0.00007 | 0.00005 | 0.037 |
| 22 | 0.00019 | 0.00012 | 0.006 |
| 23 | 0.00927 | 0.00601 | |
| 24 | 0.00041 | 0.00027 | 0.014 |
| 25 | 0.00011 | 0.00006 | 0.005 |
| 26 | 0.00019 | 0.00008 | 0.008 |
| 27 | 0.00089 | 0.00034 | 0.006 |
| 28 | 0.00067 | 0.00033 | 0.014 |
| 29 | 0.00084 | 0.00049 | 0.085 |
| 30 | 0.00030 | 0.00020 | 0.369 |
| 31 | 0.00209 | 0.00090 | 6.910 |
| 32 | 0.00016 | 0.00011 | 0.002 |
| 33 | 0.00091 | 0.00040 | 0.021 |
| 34 | 0.00060 | 0.00019 | 0.010 |
| 35 | 0.00028 | 0.00011 | 0.003 |
| 36 | 0.00065 | 0.00049 | 0.032 |
| 37 | 0.00007 | 0.00005 | 0.005 |
| 38 | 0.00033 | 0.00029 | >1 |
| 39 | 0.00006 | 0.00005 | 0.071 |
| 40 | 0.00009 | 0.00006 | 0.067 |
| 41 | 0.00008 | 0.00006 | 0.004 |
| 42 | 0.00044 | 0.00025 | 0.034 |
| 43 | 0.00025 | 0.00017 | 0.012 |
| 44 | 0.00034 | 0.00051 | 0.045 |
| 45 | 0.00022 | 0.00024 | 0.029 |
| 46 | 0.00025 | 0.00031 | 0.031 |
| 47 | 0.00031 | 0.00045 | 0.106 |
| 48 | 0.00030 | 0.00051 | >1 |
| 49 | 0.00023 | 0.00029 | 0.019 |
| 50 | 0.00011 | 0.00010 | 0.010 |
| 51 | 0.00013 | 0.00010 | 0.011 |
| 52 | 0.00016 | 0.00014 | 0.285 |
| 53 | 0.00025 | 0.00039 | 0.088 |
| 54 | 0.00092 | 0.00210 | 0.046 |
| 55 | 0.00041 | 0.00041 | 0.020 |
| 56 | 0.00039 | 0.00037 | >0.333 |
| 57 | 0.00056 | 0.00087 | 0.017 |
| 58 | 0.00019 | 0.00022 | 0.054 |
| 59 | 0.00022 | 0.00023 | 0.025 |
| 60 | 0.00036 | 0.00035 | 0.012 |
| 61 | 0.00064 | 0.00078 | >0.333 |
| 62 | 0.00038 | 0.00024 | >0.333 |
| 63 | 0.00040 | 0.00058 | 0.014 |
| 64 | 0.00029 | 0.00035 | >1 |
| 65 | 0.00041 | 0.00060 | 0.013 |
| 66 | 0.00030 | 0.00049 | 0.021 |
| 67 | 0.00211 | 0.00407 | 0.053 |
| 68 | 0.00088 | 0.00162 | 0.035 |
| 69 | 0.00044 | 0.00094 | 0.152 |
| 70 | 0.00035 | 0.00116 | 0.025 |
| 71 | 0.00086 | 0.00160 | 0.078 |
| 72 | 0.00022 | 0.00022 | 0.010 |
| 73 | 0.00020 | 0.00019 | 0.009 |
| 74 | 0.00163 | 0.00098 | 0.018 |
| 75 | 0.00031 | 0.00026 | 0.011 |
| 76 | 0.00048 | 0.00053 | 0.017 |
| 77 | 0.00028 | 0.00043 | 0.009 |
| 78 | 0.00019 | 0.00010 | 0.013 |
| 79 | 0.00018 | 0.00013 | 0.097 |
| 80 | 0.00016 | 0.00017 | 0.013 |
| 81 | 0.00012 | 0.00011 | 0.007 |
| 82 | 0.00023 | 0.00016 | 0.007 |
| 83 | 0.00023 | 0.00014 | 0.014 |
| 84 | 0.00019 | 0.00012 | 0.008 |
| 85 | 0.00132 | 0.00169 | 0.034 |

TABLE 3-continued

| Example | JAK1 K$_i$ (uM) | JAK2 K$_i$ (uM) | IL-13 p-STAT6 BEAS-2B IC$_{50}$ (uM) |
|---|---|---|---|
| 86 | 0.00153 | 0.00102 | 0.031 |
| 87 | 0.00062 | 0.00042 | 0.015 |
| 88 | 0.00008 | 0.00010 | 0.005 |
| 89 | 0.00012 | 0.00010 | 0.007 |
| 90 | 0.00007 | 0.00007 | 0.005 |
| 91 | 0.00403 | 0.00185 | 0.308 |
| 92 | 0.00022 | 0.00020 | 0.092 |
| 93 | 0.00007 | 0.00003 | 0.006 |
| 94 | 0.00007 | 0.00005 | 0.007 |
| 95 | 0.00006 | 0.00003 | 0.06 |
| 96 | 0.00007 | 0.00005 | 0.07 |
| 97 | 0.00013 | 0.00009 | 0.007 |
| 98 | 0.00011 | 0.00007 | 0.006 |
| 99 | 0.00012 | 0.00012 | 0.024 |
| 100 | 0.00018 | 0.00034 | 0.039 |
| 101 | 0.00023 | 0.00016 | 0.013 |
| 102 | 0.0002 | 0.00019 | 0.012 |
| 103 | 0.0002 | 0.00014 | 0.012 |
| 104 | 0.00015 | 0.00016 | 0.011 |
| 105 | 0.00019 | 0.00013 | 0.024 |
| 106 | 0.00017 | 0.00019 | 0.027 |
| 107 | 0.0002 | 0.00023 | 0.011 |
| 108 | 0.00019 | 0.00023 | 0.012 |
| 109 | 0.00022 | 0.00042 | 0.022 |
| 110 | 0.00008 | 0.00005 | 0.01 |
| 111 | 0.0002 | 0.00021 | 0.015 |
| 112 | 0.00015 | 0.00018 | 0.01 |
| 113 | 0.00022 | 0.00027 | 0.022 |
| 114 | 0.00021 | 0.00024 | 0.015 |
| 115 | 0.00091 | 0.00036 | 0.055 |
| 116 | 0.00025 | 0.0004 | 0.042 |
| 117 | 0.0001 | 0.0001 | 0.024 |
| 118 | 0.00068 | 0.00023 | 0.037 |
| 119 | 0.00101 | 0.00193 | 0.04 |
| 120 | 0.00063 | 0.00254 | 0.046 |
| 121 | 0.00041 | 0.00045 | 0.038 |
| 122 | 0.00028 | 0.00025 | 0.032 |
| 123 | 0.00036 | 0.00028 | 0.024 |
| 124 | 0.00025 | 0.00015 | 0.02 |
| 125 | 0.00015 | 0.00011 | 0.081 |
| 126 | 0.00088 | 0.00043 | 0.286 |
| 127 | 0.00012 | 0.00006 | 0.014 |
| 128 | 0.00014 | 0.00009 | 0.007 |
| 129 | 0.0002 | 0.00047 | 0.011 |
| 130 | 0.00031 | 0.00047 | 0.059 |
| 131 | 0.00012 | 0.00008 | 0.03 |
| 132 | 0.00036 | 0.0004 | 0.031 |
| 133 | 0.00026 | 0.00021 | 0.017 |
| 134 | 0.0004 | 0.00047 | 0.023 |
| 135 | 0.00019 | 0.00014 | 0.026 |
| 136 | 0.00023 | 0.00017 | 0.021 |
| 137 | 0.00009 | 0.00008 | 0.008 |
| 138 | 0.00026 | 0.00032 | 0.036 |
| 139 | 0.00033 | 0.00021 | 0.01 |
| 140 | 0.00009 | 0.00006 | 0.004 |
| 141 | 0.00017 | 0.00009 | 0.011 |
| 142 | 0.00009 | 0.00006 | 0.015 |
| 143 | 0.00022 | 0.00097 | 0.013 |
| 144 | 0.00014 | 0.00011 | 0.007 |
| 145 | 0.0006 | 0.00042 | 0.036 |
| 146 | 0.00032 | 0.00029 | 0.074 |
| 147 | 0.00034 | 0.00032 | 0.014 |
| 148 | 0.00051 | 0.00017 | 0.055 |
| 149 | 0.00133 | 0.00064 | 0.043 |
| 150 | 0.00165 | 0.00061 | 0.061 |
| 151 | 0.00077 | 0.00025 | 0.03 |
| 152 | 0.0001 | 0.00006 | 0.004 |
| 153 | 0.00015 | 0.00008 | 0.005 |
| 154 | 0.0004 | 0.00038 | 0.022 |

Blank = not determined

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually.

What is claimed is:

1. A compound having the general structure (IA):

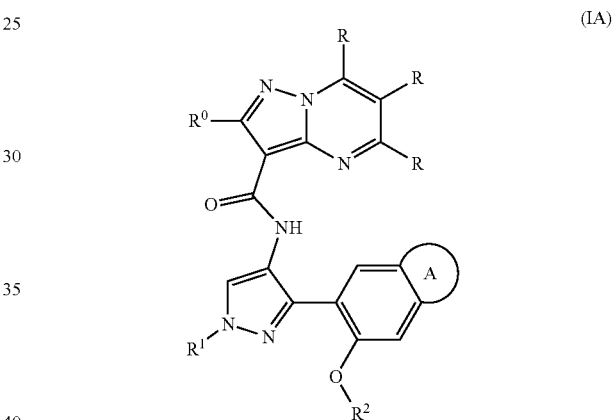

or a pharmaceutically acceptable salt thereof;
wherein:
A is a fused ring selected from the group consisting of a 6-membered aromatic group; a 5-membered or 6-membered heterocyclic group; and a 5-membered or 6-membered cycloalkyl group; wherein fused ring A is optionally substituted by 1-5 $R^n$;
R is hydrogen
$R^0$ is hydrogen;
$R^1$ is selected from the group consisting of hydrogen, $C_2$-$C_6$alkenyl, $C_2$-$C_6$alkynyl, —($C_0$-$C_3$alkyl)CN, —($C_0$-$C_4$alkyl)OR$^a$, —($C_0$-$C_3$alkyl)R$^a$, —($C_0$-$C_3$alkyl)SR$^a$, —($C_0$-$C_6$alkyl)NR$^a$R$^b$, —($C_0$-$C_3$alkyl)OCF$_3$, —($C_0$-$C_3$alkyl)CF$_3$, —($C_0$-$C_3$alkyl)NO$_2$, —($C_0$-$C_6$alkyl)C(O)R$^a$, —($C_0$-$C_6$alkyl)C(O)OR$^a$, —($C_0$-$C_3$alkyl)C(O)NR$^a$R$^b$, —($C_0$-$C_3$alkyl)NR$^a$C(O)R$^b$, —($C_0$-$C_3$alkyl)S(O)$_{1-2}$R$^a$, —($C_0$-$C_3$alkyl)NR$^a$S(O)$_{1-2}$R$^b$, —($C_0$-$C_3$alkyl)S(O)$_{1-2}$NR$^a$R$^b$, —($C_0$-$C_6$alkyl)(5-6-membered heteroaryl group), or —($C_0$-$C_6$alkyl)phenyl, wherein when $R^1$ is not hydrogen, $R^1$ is optionally substituted by one or more groups independently selected from the group consisting of halogen, $C_1$-$C_6$alkyl, oxo, —CF$_3$, —($C_0$-$C_3$alkyl)OR$^c$, and —($C_0$-$C_3$alkyl)NR$^c$R$^d$;
$R^2$ is —C(R$^3$)$_3$, wherein $R^3$ is independently selected from the group consisting of hydrogen and halogen;

$R^a$ is independently hydrogen, hydroxy, $C_1$-$C_6$alkyl, $C_3$-$C_6$ cycloalkyl group, 3-10 membered heterocyclic group, —C(O)$R^c$, —C(O)O$R^c$, —C(O)N$R^c R^d$, —N$R^c$C(O)$R^d$, —S(O)$_{1-2}R^c$, —N$R^c$S(O)$_{1-2}R^d$ or —S(O)$_{1-2}$N$R^c R^d$, wherein any $C_1$-$C_6$alkyl, $C_3$-$C_6$ cycloalkyl group, and 3-10 membered heterocyclic group of $R^a$ is optionally substituted with one or more groups $R^e$;

$R^b$ is independently hydrogen or $C_1$-$C_3$alkyl, wherein said alkyl is optionally substituted by one or more groups independently selected from the group consisting of halogen and oxo;

$R^c$ and $R^d$ are independently selected from the group consisting of hydrogen, 3-6 membered heterocyclic group, $C_3$-$C_6$ cycloalkyl group, and $C_1$-$C_3$alkyl, wherein any 3-6 membered heterocyclic group, $C_3$-$C_6$ cycloalkyl group, and $C_1$-$C_3$alkyl of $R^c$ and $R^d$ is optionally substituted by one or more groups independently selected from the group consisting of halogen and oxo; or $R^c$ and $R^d$ are taken together with the atom to which they are attached to form a 3-6-membered heterocyclic group, optionally substituted by one or more groups independently selected from the group consisting of halogen, oxo, —CF$_3$, and $C_1$-$C_3$alkyl;

each $R^e$ is independently selected from the group consisting of oxo, —O$R^f$, —N$R^f R^g$, —C(O)O$R^f$, —C(O)$R^f$, halogen, 3-10 membered heterocyclic group, $C_3$-$C_6$ cycloalkyl group, and $C_1$-$C_6$alkyl, wherein any $C_3$-$C_6$ cycloalkyl group and $C_1$-$C_6$alkyl of $R^e$ is optionally substituted by one or more groups independently selected from the group consisting of —O$R^f$, —N$R^f R^g$, —C(O)O$R^f$, —C(O)N$R^f R^g$, halogen, 3-10 membered heterocyclic group, oxo, and cyano, and wherein any 3-10 membered heterocyclic group of $R^e$ and any 3-10 membered heterocyclic group substituted on a $C_3$-$C_6$ cycloalkyl group or $C_1$-$C_6$alkyl of $R^e$ is optionally substituted by one or more groups independently selected from the group consisting of halogen, oxo, cyano, —CF$_3$, —N$R^h R^k$, 3-6 membered heterocyclic group, and $C_1$-$C_3$alkyl that is optionally substituted by one or more groups independently selected from the group consisting of halogen, oxo, —O$R^f$, and —N$R^h R^k$;

$R^f$ and $R^g$ are each independently selected from the group consisting of hydrogen, $C_1$-$C_6$alkyl, 3-6 membered heterocyclic group, and $C_3$-$C_6$ cycloalkyl group, wherein any $C_1$-$C_6$alkyl, 3-6 membered heterocyclic group, and $C_3$-$C_6$ cycloalkyl group of $R^f$ and $R^g$ is optionally substituted by one or more $R^m$;

$R^h$ and $R^k$ are each independently selected from the group consisting of hydrogen and $C_1$-$C_6$alkyl that is optionally substituted by one or more groups independently selected from the group consisting of halogen, cyano, 3-6 membered heterocyclic group, and oxo; or $R^h$ and $R^k$ are taken together with the atom to which they are attached to form a 3-6-membered heterocyclic group that is optionally substituted by one or more groups independently selected from the group consisting of halogen, cyano, oxo, —CF$_3$ and $C_1$-$C_3$alkyl that is optionally substituted by one or more groups independently selected from the group consisting of halogen and oxo;

each $R^m$ is independently selected from the group consisting of halogen, cyano, oxo, $C_3$-$C_6$cycloalkyl group, hydroxy, and N$R^h R^k$, wherein any $C_3$-$C_6$cycloalkyl group of $R^m$ is optionally substituted with one or more groups independently selected from the group consisting of halogen, oxo, cyano, and $C_1$-$C_3$alkyl:

each $R^n$ is independently $C_1$-$C_6$ alkyl, $C_2$-$C_6$ alkenyl, $C_2$-$C_6$ alkynyl, oxo, halogen, —($C_0$-$C_3$ alkyl)CN, —($C_0$-$C_6$ alkyl)O$R^o$, —($C_0$-$C_3$ alkyl)S$R^o$, —($C_0$-$C_6$ alkyl)N$R^o R^p$, —($C_0$-$C_3$ alkyl)OCF$_3$, —($C_0$-$C_3$ alkyl)CF$_3$, —($C_0$-$C_3$ alkyl)NO$_2$, —($C_0$-$C_6$ alkyl)C(O)$R^o$, —($C_0$-$C_6$ alkyl)C(O)O$R^o$, —($C_0$-$C_6$ alkyl)C(O)N$R^o R^p$, —($C_0$-$C_3$ alkyl)N$R^o$C(O)$R^p$, —($C_0$-$C_3$ alkyl)S(O)$_{1-2}R^o$, —($C_0$-$C_3$ alkyl)N$R^o$S(O)$_{1-2}R^p$, —($C_0$-$C_3$ alkyl)S(O)$_{1-2}$N$R^o R^p$, —($C_0$-$C_3$ alkyl)($C_3$-$C_6$ cycloalkyl), —($C_0$-$C_6$ alkyl)(3-6-membered heterocyclic group), —($C_0$-$C_3$ alkyl)C(O)(3-6-membered heterocyclic group), or —($C_0$-$C_3$ alkyl)phenyl, wherein each $R^n$ is independently optionally substituted by halogen, $C_1$-$C_3$ alkyl, oxo, —CF$_3$, —($C_0$-$C_3$ alkyl)O$R^r$, —($C_0$-$C_3$ alkyl)N$R^r R^s$: or two $R^n$ are taken together to form —O(CH$_2$)$_{1-3}$O— or —(CH$_2$)$_{1-3}$—O—(CH$_2$)$_{1-3}$—;

$R^o$ is independently hydrogen, $C_1$-$C_6$ alkyl, $C_2$-$C_6$alkenyl, $C_2$-$C_6$alkynyl, $C_3$-$C_6$ cycloalkyl group, 3-6 membered heterocyclic group, —($C_3$-$C_6$ cycloalkyl group)$C_1$-$C_6$alkyl, -(3-6-membered heterocyclic group)$C_1$-$C_6$alkyl, —C(O)($C_3$-$C_6$ cycloalkyl group), —C(O)(3-6-membered heterocyclic group), —C(O)$R^r$, —C(O)O$R^r$, —N$R^r R^s$, —C(O)N$R^r R^s$, —N$R^r$C(O)$R^s$, —S(O)$_{1-2}R^r$, —N$R^r$S(O)$_{1-2}R^s$ or —S(O)$_{1-2}$N$R^r R^s$, wherein said alkyl, cycloalkyl group, and heterocyclic group are independently optionally substituted by oxo, $C_1$-$C_3$ alkyl, —O$R^r$, N$R^r R^s$, —C(O)O$R^r$, or halogen;

$R^p$ is independently hydrogen or $C_1$-$C_3$ alkyl, wherein said alkyl is independently optionally substituted by halogen or oxo;

or $R^o$ and $R^p$ are taken together with the atom to which they are attached to form a 3-6-membered heterocyclic group, optionally substituted by halogen, oxo, or $C_1$-$C_3$ alkyl optionally substituted by halogen;

$R^r$ and $R^s$ are independently hydrogen or $C_1$-$C_6$ alkyl optionally substituted by halogen or oxo; or $R^r$ and $R^s$ are taken together with the atom to which they are attached to form a 3-6-membered heterocyclic group, optionally substituted by halogen, oxo, or $C_1$-$C_3$ alkyl optionally substituted by halogen; and $R^t$ is hydrogen, $C_1$-$C_6$ alkyl, $C_2$-$C_6$ alkenyl, $C_2$-$C_6$ alkynyl, or —($C_0$-$C_3$ alkyl)phenyl.

2. The compound of claim 1, or a pharmaceutically acceptable salt thereof, wherein A is substituted with 1-5 $R^n$, wherein each $R^n$ is independently selected from the group consisting of: oxo; cyano; $C_1$-$C_6$ alkyl; —($C_0$-$C_6$ alkyl)C(O)$R^o$, wherein $R^o$ is selected from the group consisting of hydrogen, $C_1$-$C_6$ alkyl, or a 6-membered heterocyclic group, optionally substituted with —($C_0$-$C_3$ alkyl)C(O)O$R^r$, wherein $R^r$ is $C_1$-$C_6$ alkyl; —($C_1$-$C_6$ alkyl)O$R^o$, wherein $R^o$ is hydrogen or $C_1$-$C_6$ alkyl; —($C_0$-$C_6$ alkyl)C(O)O$R^o$, wherein $R^o$ is hydrogen or $C_1$-$C_6$ alkyl; —($C_0$-$C_6$ alkyl)N$R^o R^p$, wherein each $R^o$ and $R^p$ is independently hydrogen or $C_1$-$C_3$ alkyl; and —($C_0$-$C_6$ alkyl)C(O)N$R^o R^p$, wherein each $R^o$ and $R^p$ is independently hydrogen or $C_1$-$C_3$ alkyl.

3. The compound of claim 1, or a pharmaceutically acceptable salt thereof, wherein A is the 6-membered aromatic group.

4. The compound of claim 1, or a pharmaceutically acceptable salt thereof, wherein A is the 5-membered heterocyclic group.

5. The compound of claim 4, or a pharmaceutically acceptable salt thereof, wherein the 5-membered heterocyclic group is a 5-membered heteroaryl group.

6. The compound of claim 5, or a pharmaceutically acceptable salt thereof, wherein the 5-membered heteroaryl group is substituted with 1-5 R″, wherein R″ is selected from the group consisting of cyano; unsubstituted $C_1$-$C_6$ alkyl; —($C_0$-$C_6$ alkyl)C(O)OR°, wherein R° is hydrogen or $C_1$-$C_6$ alkyl; —($C_0$-$C_6$ alkyl)C(O)R°, wherein R° is selected from the group consisting of hydrogen, $C_1$-$C_6$ alkyl, or a 6-membered heterocyclic group, optionally substituted with —($C_0$-$C_3$ alkyl)C(O)OR″, wherein R″ is $C_1$-$C_6$ alkyl; and —($C_0$-$C_6$ alkyl)C(O)NR°R$^p$, wherein each R° and R$^p$ is independently hydrogen or $C_1$-$C_3$ alkyl.

7. The compound of claim 1, or a pharmaceutically acceptable salt thereof, wherein A is the 6-membered heterocyclic group.

8. The compound of claim 7, or a pharmaceutically acceptable salt thereof, wherein the 6-membered heterocyclic group is substituted with 1-5 R″, wherein R″ is selected from the group consisting of: oxo; unsubstituted $C_1$-$C_6$ alkyl; and —($C_1$-$C_6$ alkyl)NR°R$^p$, wherein each R° and R$^p$ are hydrogen; or two R″ are taken together to form —$(CH_2)_{1-3}$—O—$(CH_2)_{1-3}$—.

9. The compound of claim 7, or a pharmaceutically acceptable salt thereof, wherein the 6-membered heterocyclic group is a 6-membered heteroaryl group.

10. The compound of claim 1, or a pharmaceutically acceptable salt thereof, wherein A is a fused ring selected from the group consisting of phenyl, morpholinyl, thiophenyl, thiomorpholinyl, tetrahydrofuranyl, tetrahydro-2H-pyranyl, 1H-pyrazolyl, cyclopentanyl, pyridinyl, 1H-imidazolyl, and isothiazolyl, oxathiinyl, and dioxinyl each of which is optionally substituted with 1-5 R″.

11. The compound of claim 10, or a pharmaceutically acceptable salt thereof, wherein each R″ is independently selected from the group consisting of —$CH_3$, =O, —$CH_2OH$, —$CH_2NH_2$, — and any combination thereof.

12. The compound of claim 1, or a pharmaceutically acceptable salt thereof, wherein R° is hydrogen.

13. The compound of claim 1, or a pharmaceutically acceptable salt thereof, wherein $R^1$ is hydrogen or —($C_0$-$C_3$alkyl)$R^a$ wherein $R^a$ is $C_1$-$C_6$alkyl, which is optionally substituted.

14. The compound of claim 1, or a pharmaceutically acceptable salt thereof, wherein $R^1$ is selected form the group consisting of hydrogen, methyl, ethyl, —$CH_2CN$,

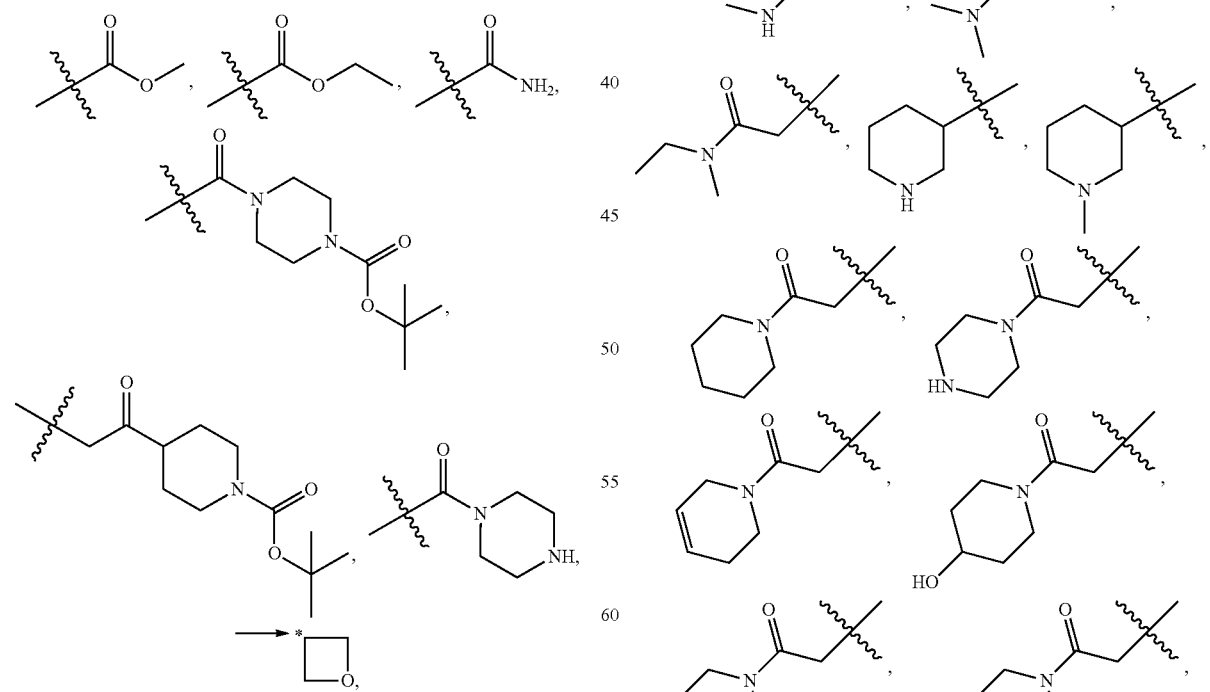

-continued

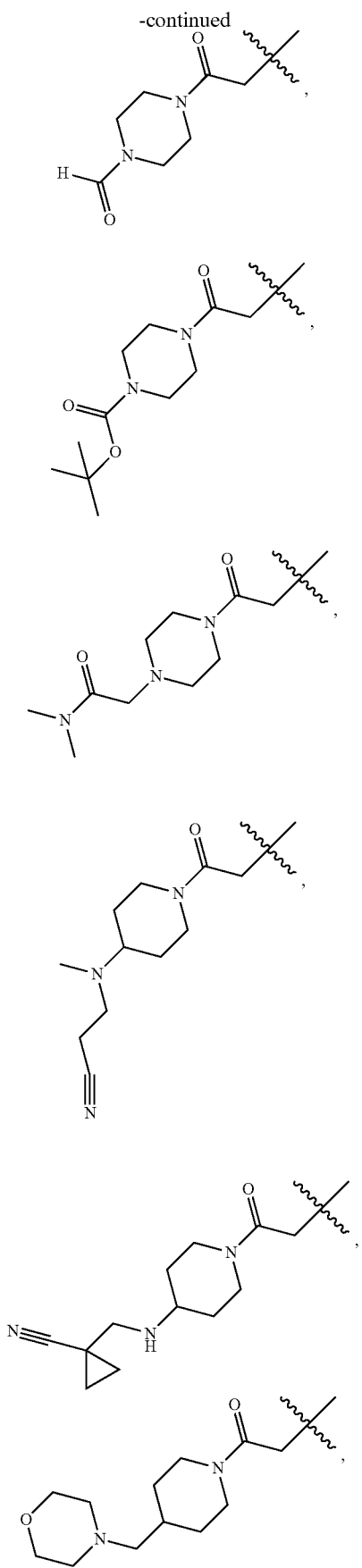

-continued

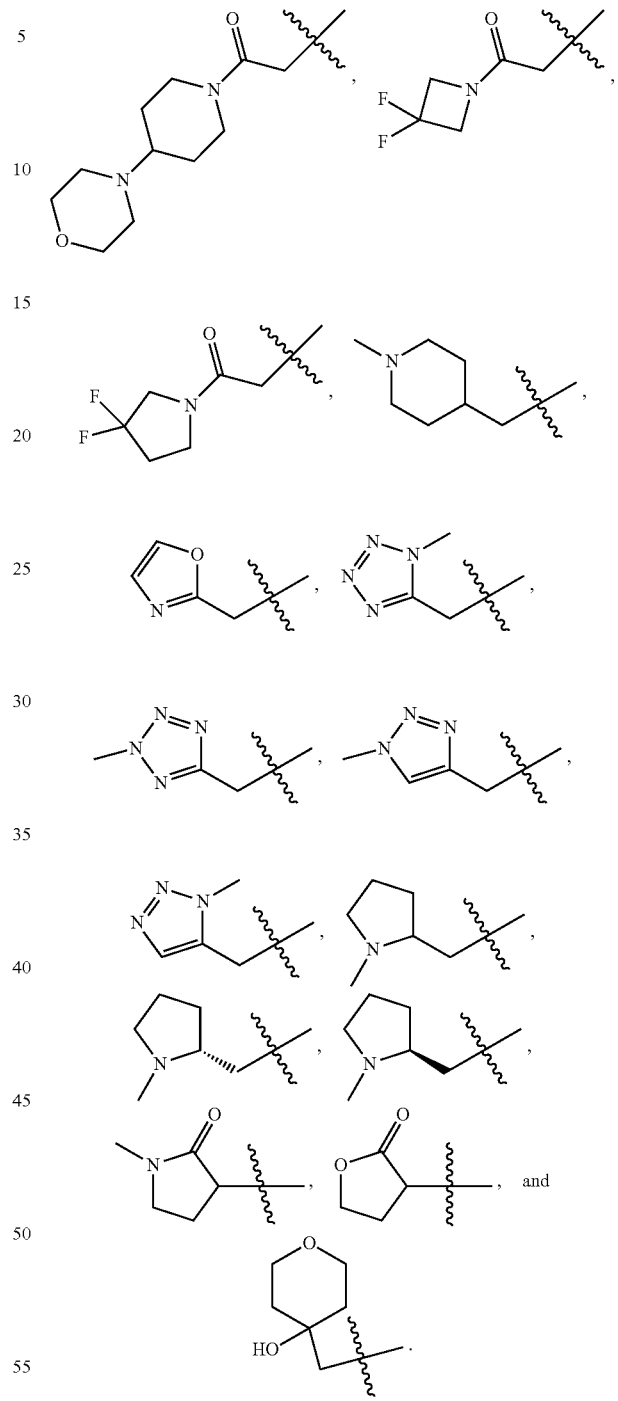

15. The compound of claim 1, or a pharmaceutically acceptable salt thereof, wherein $R^1$ is hydrogen.

16. The compound of claim 1, or a pharmaceutically acceptable salt thereof, wherein $R^2$ is —$CH_3$ or —$CHF_2$.

17. The compound of claim 1, or a pharmaceutically acceptable salt thereof, wherein each R is hydrogen.

18. A compound, or a pharmaceutically acceptable salt thereof, selected from the group consisting of:

353
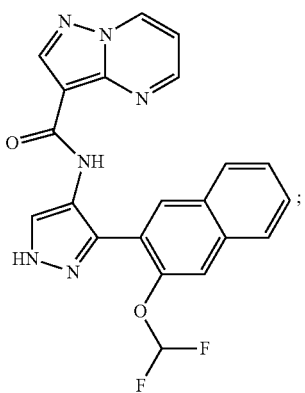
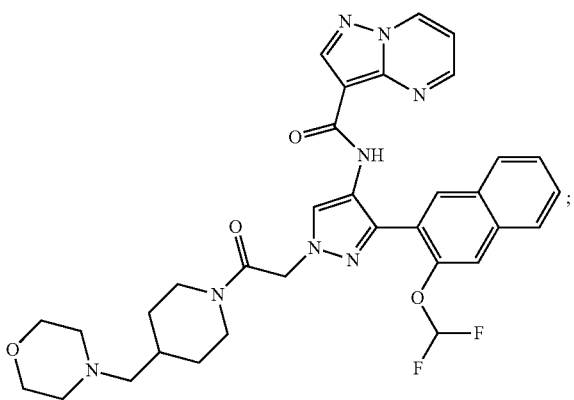
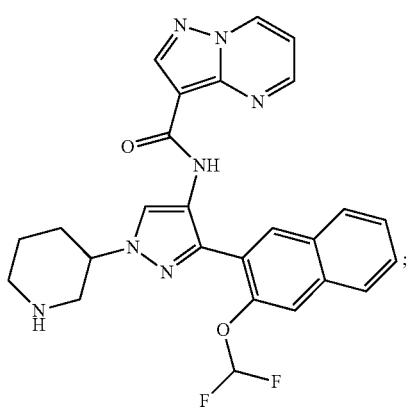
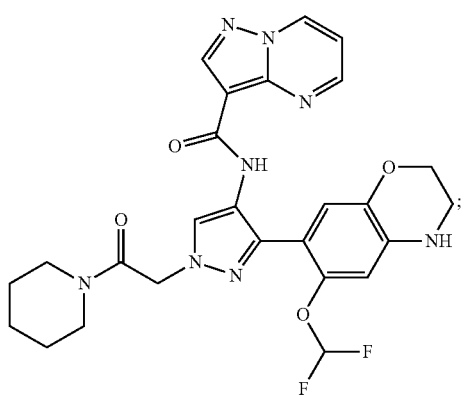
354
-continued
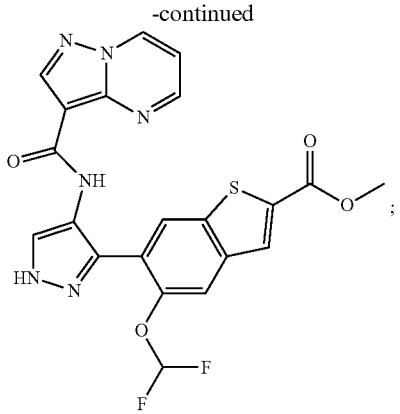
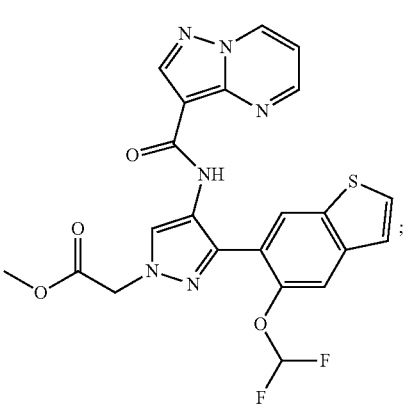
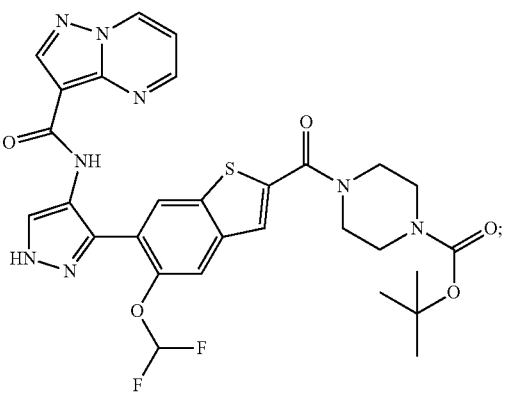
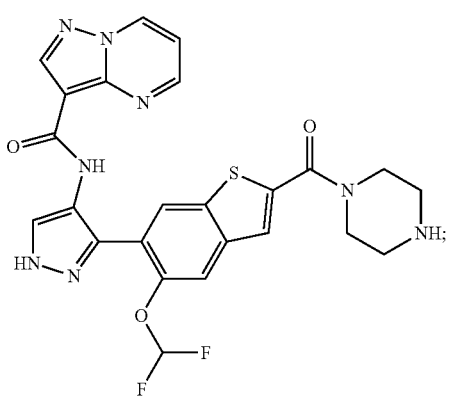

355
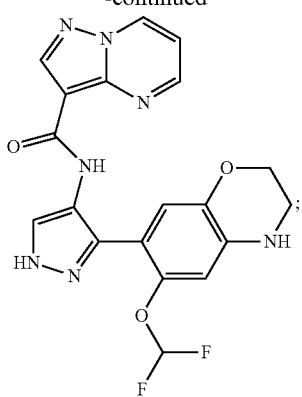
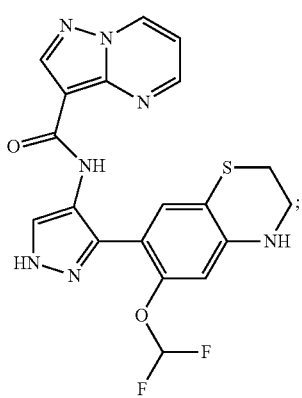
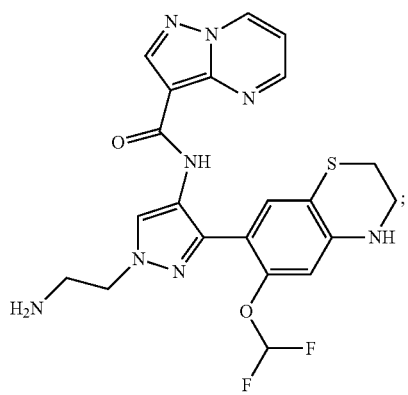
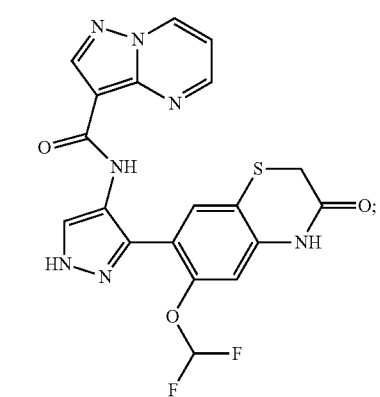
356
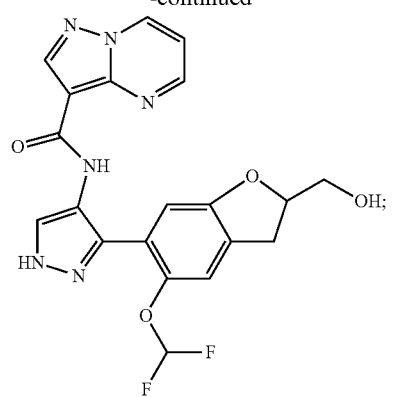
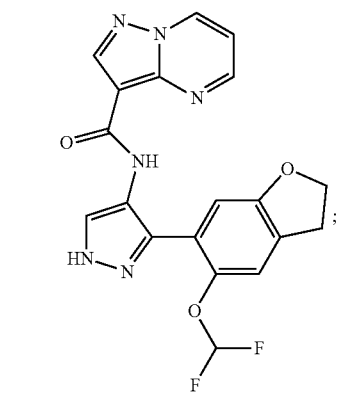
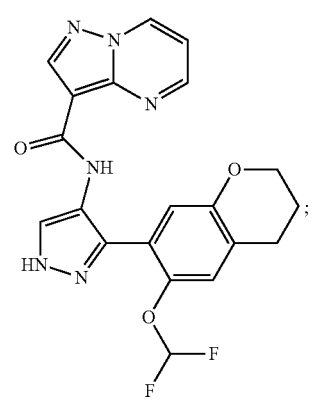
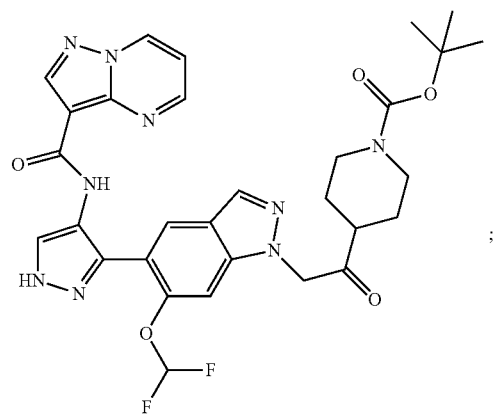

357
-continued
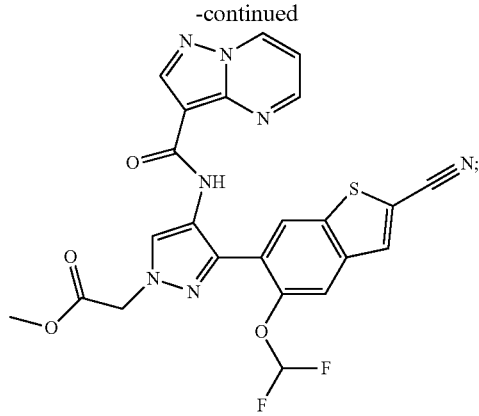
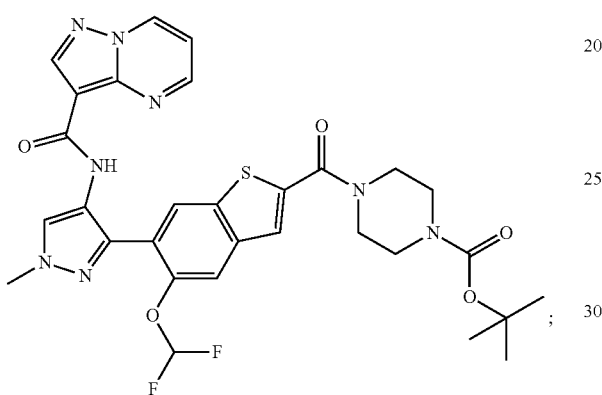
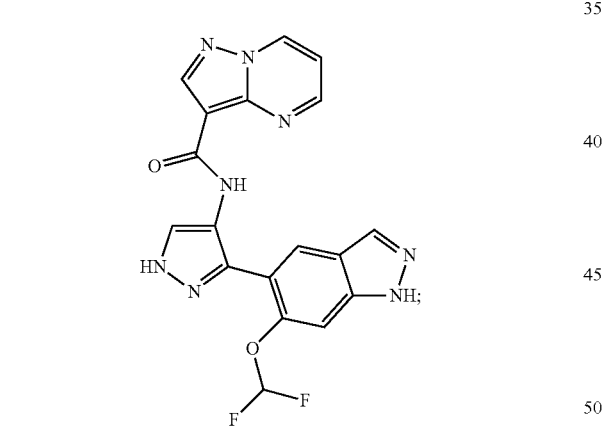
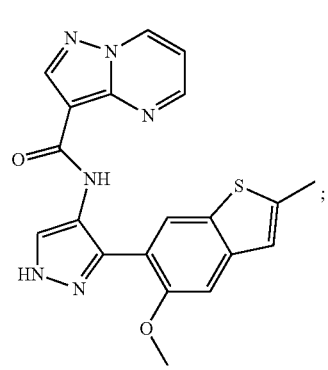
358
-continued
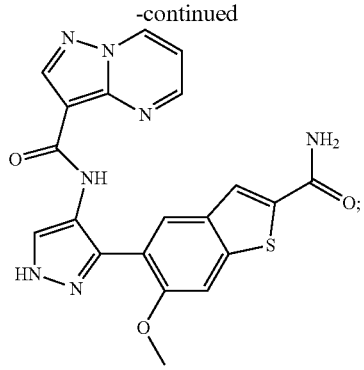
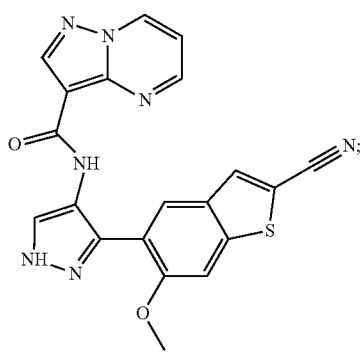
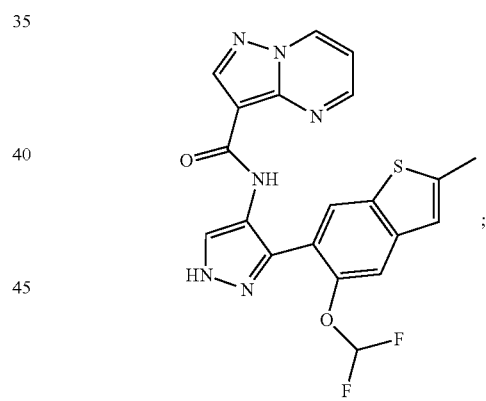
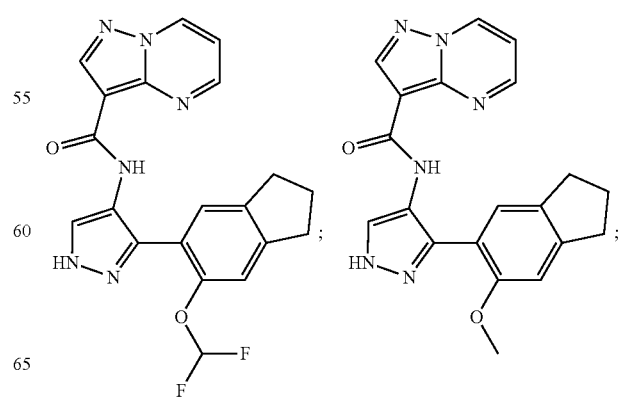

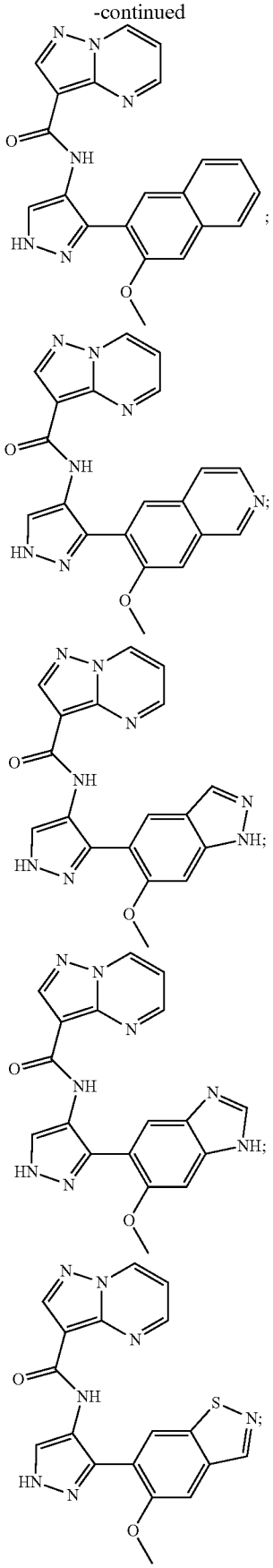
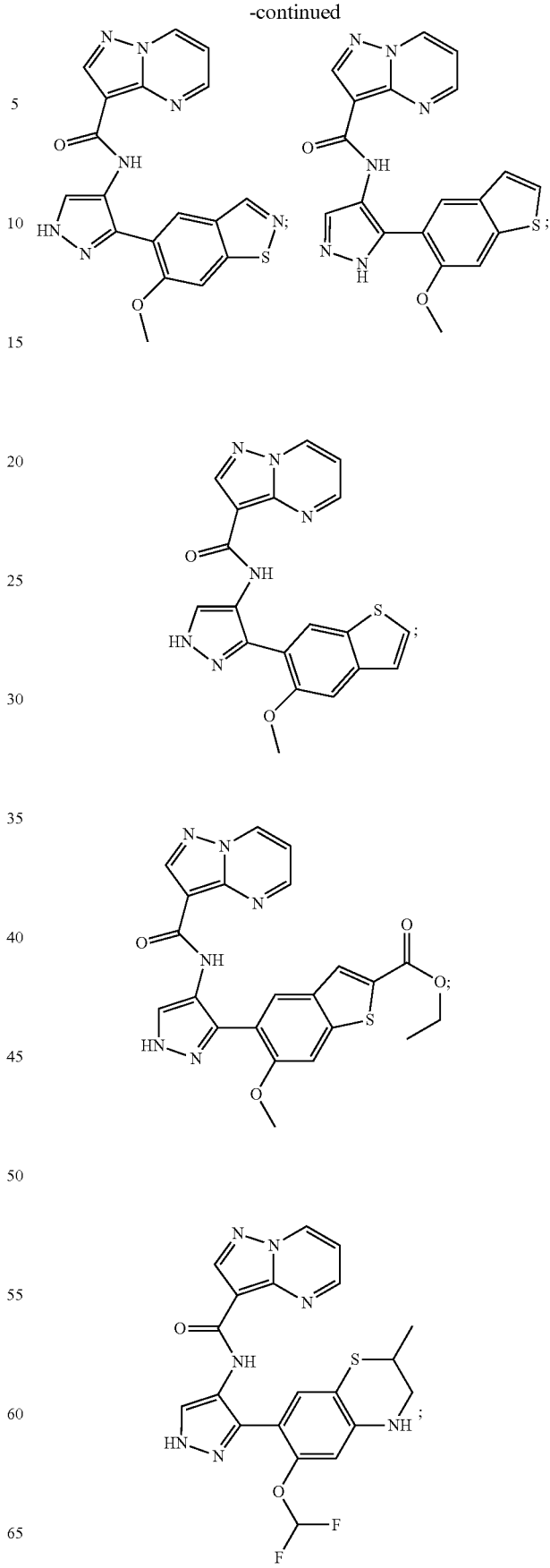

361
-continued
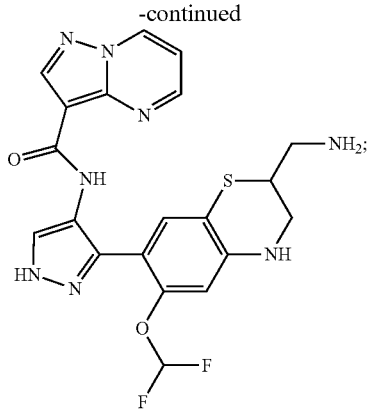
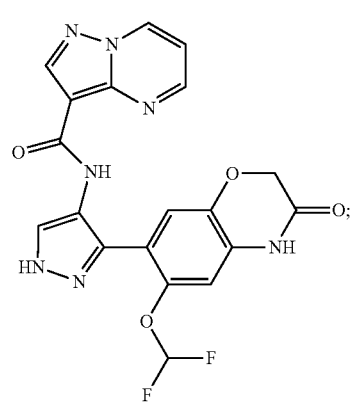
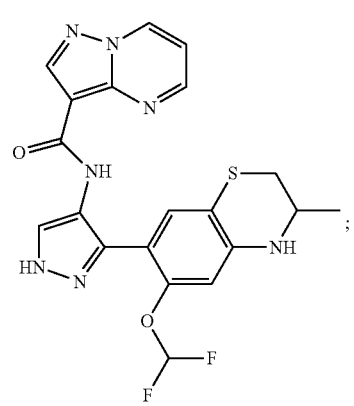
362
-continued
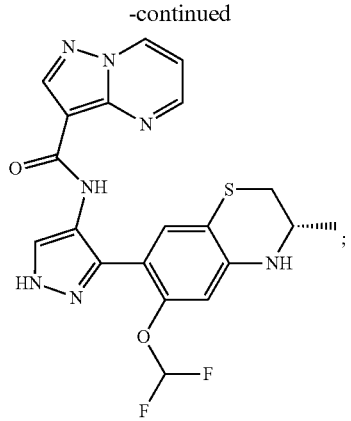
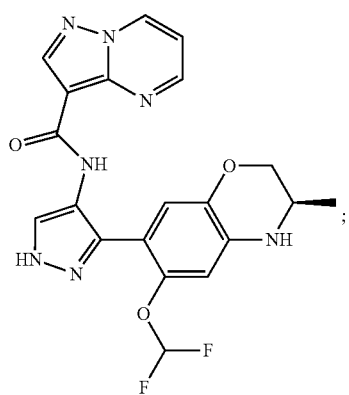

363
-continued
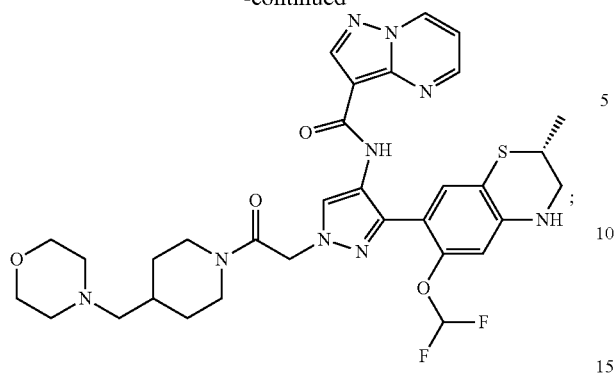
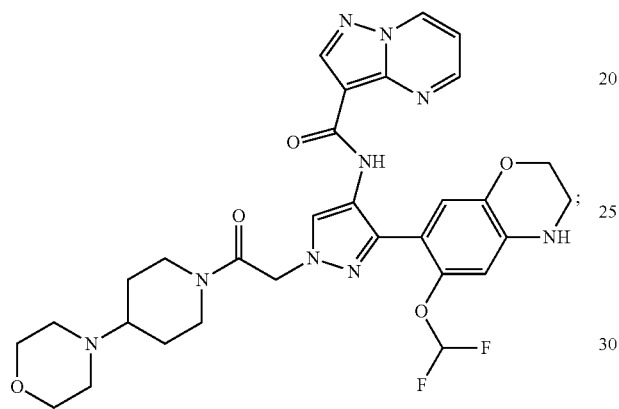
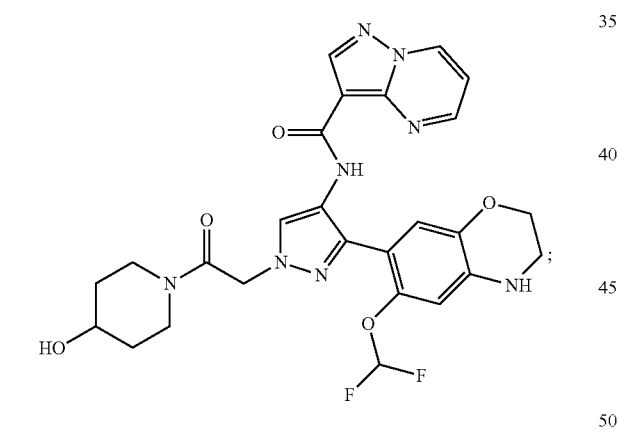
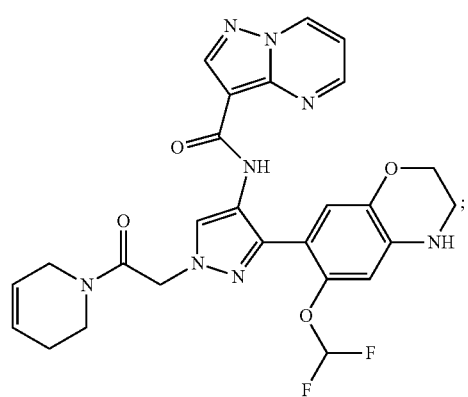
364
-continued
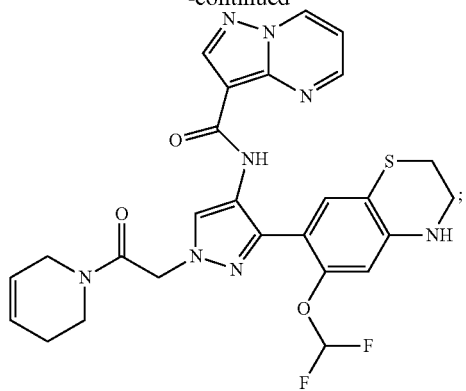
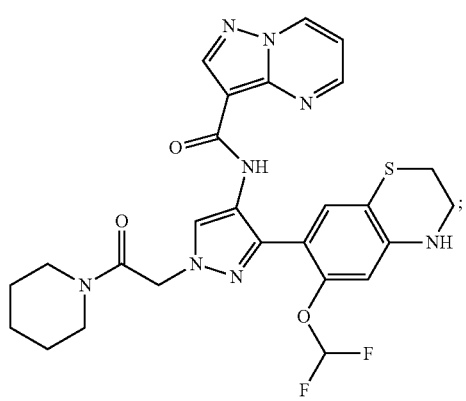
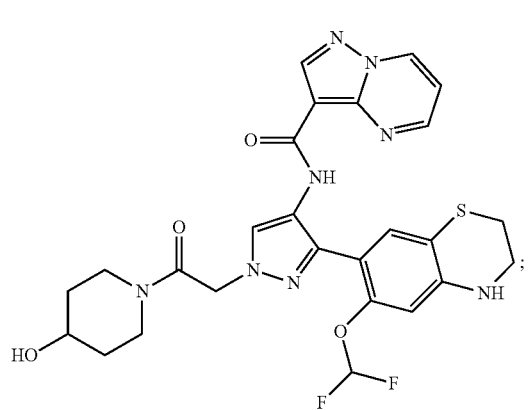
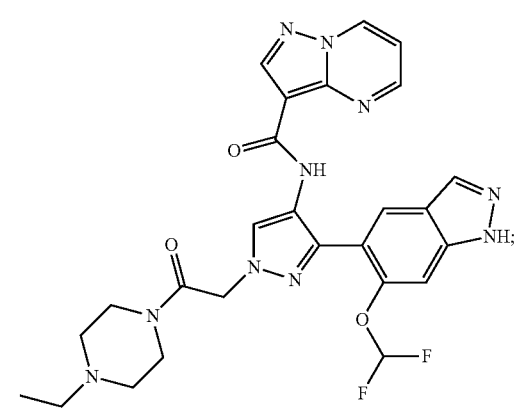

365
-continued
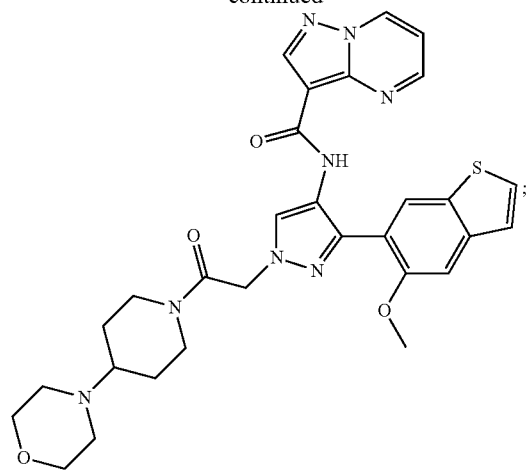
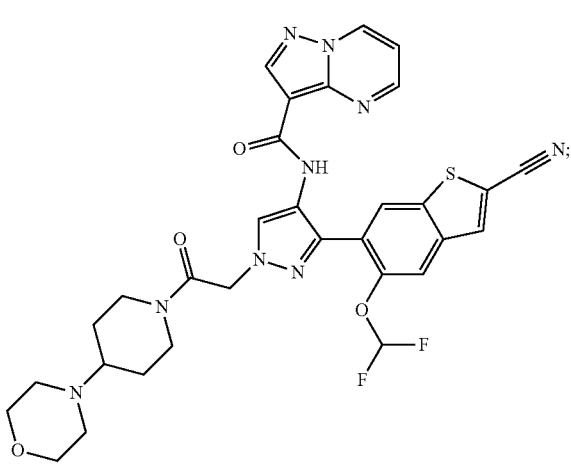
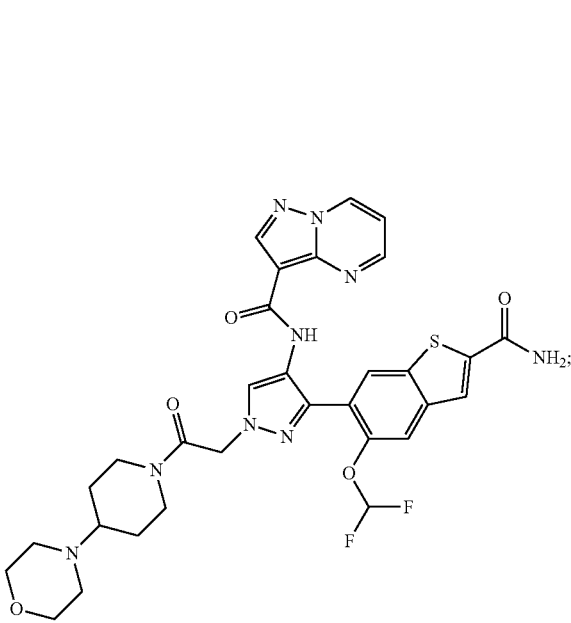
366
-continued
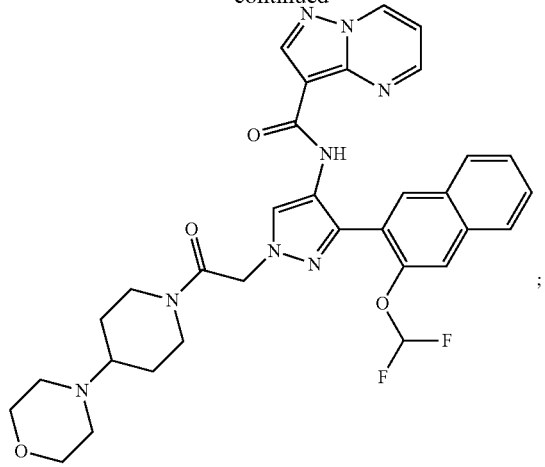
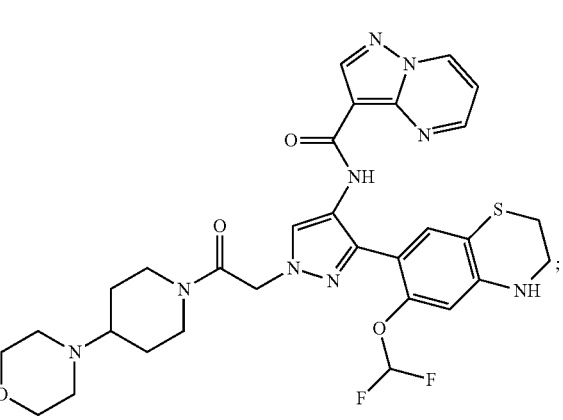
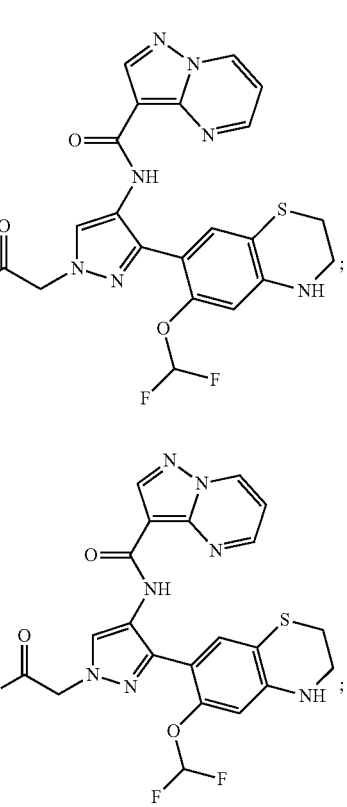
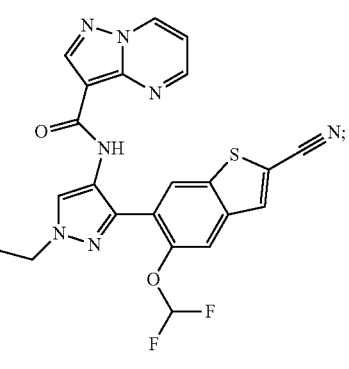

367
-continued
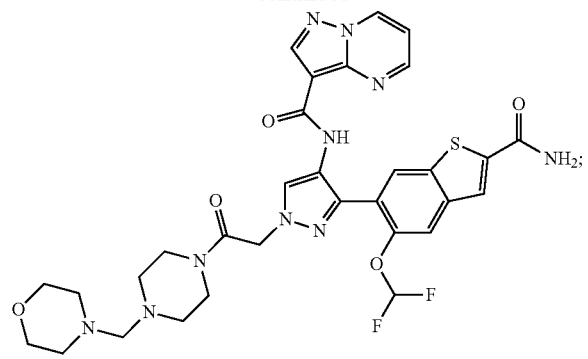
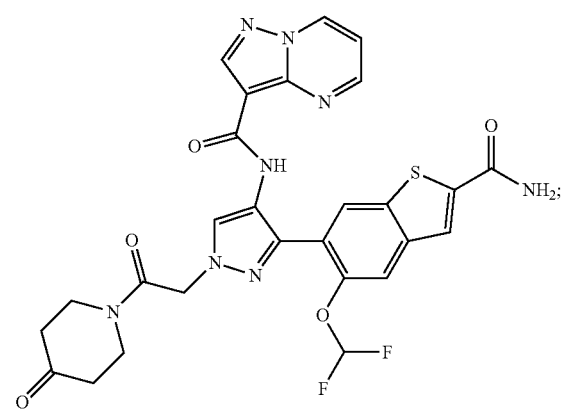
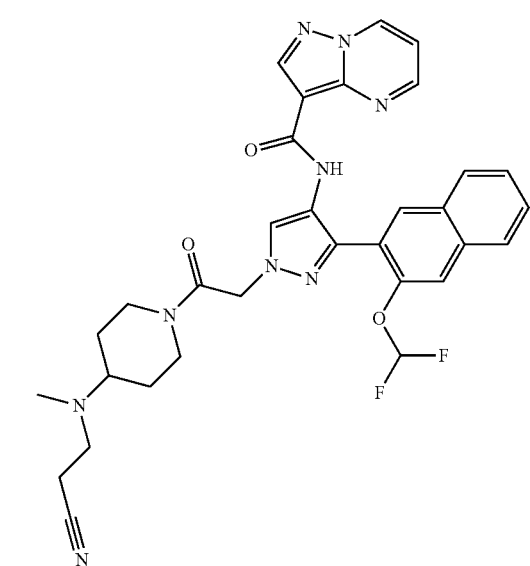
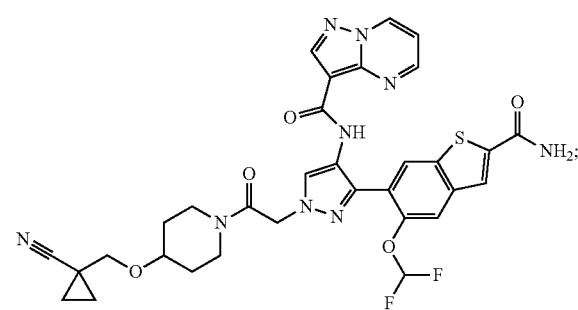
368
-continued
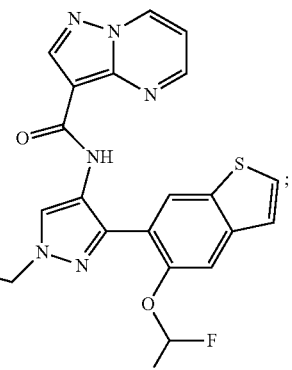
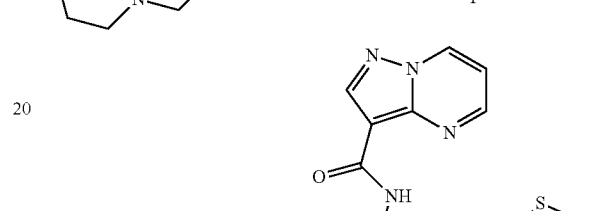
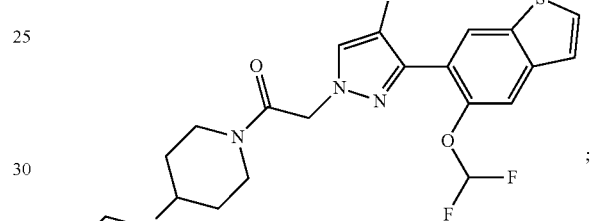
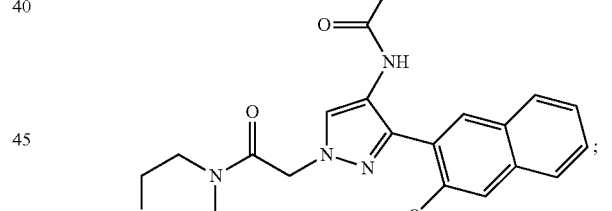
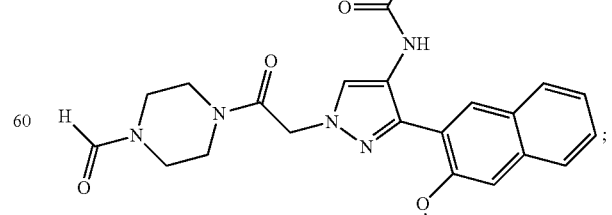

369
-continued
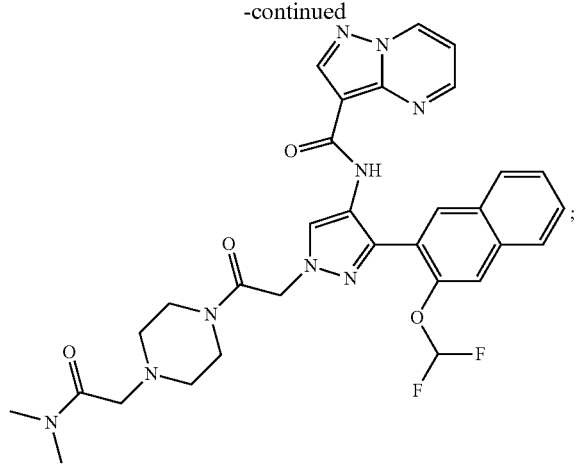
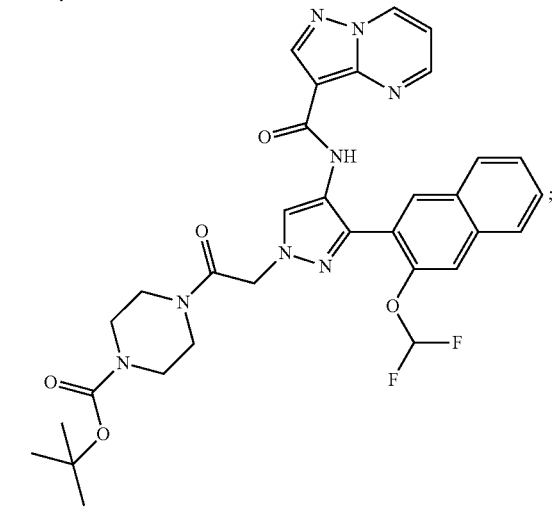
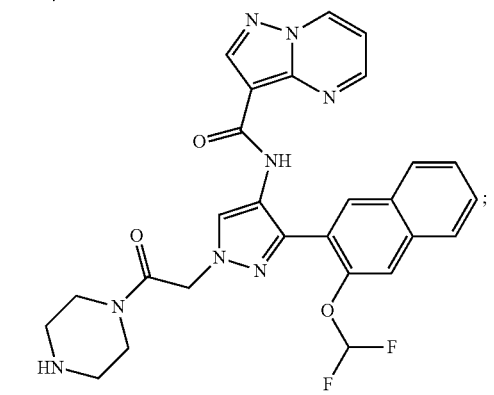
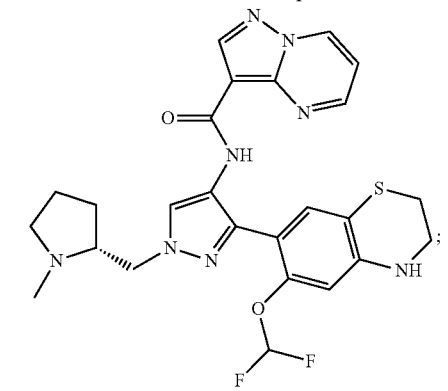
370
-continued
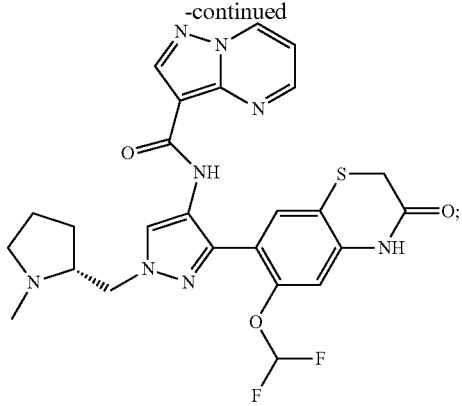
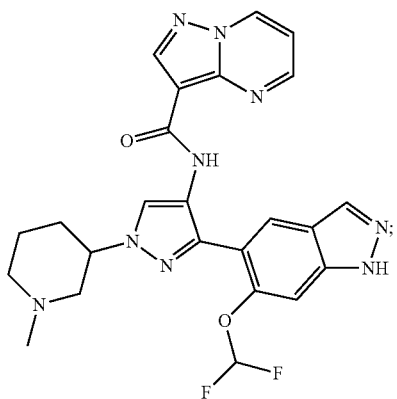
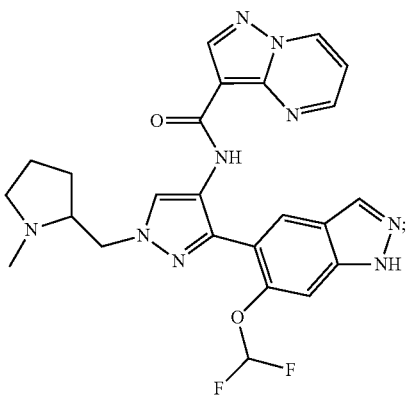
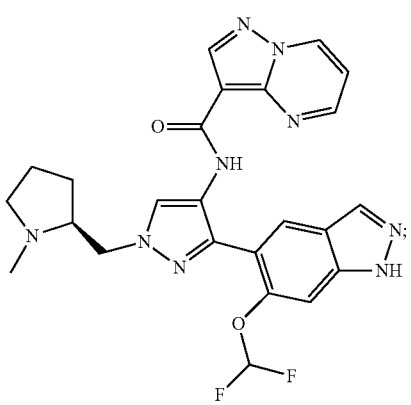

371
-continued
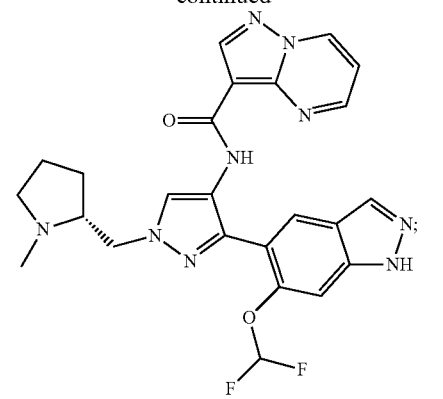
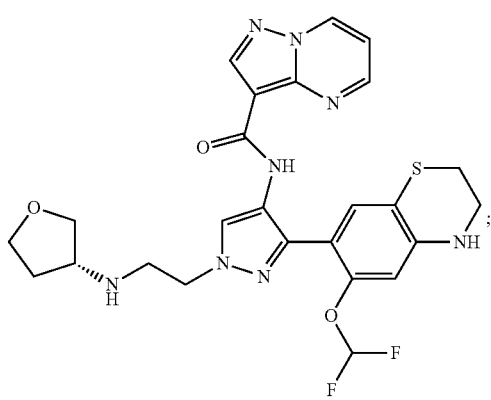
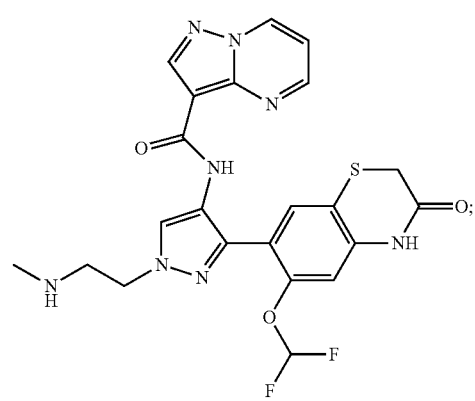
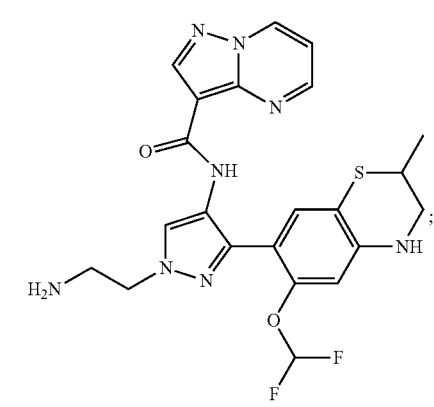
372
-continued
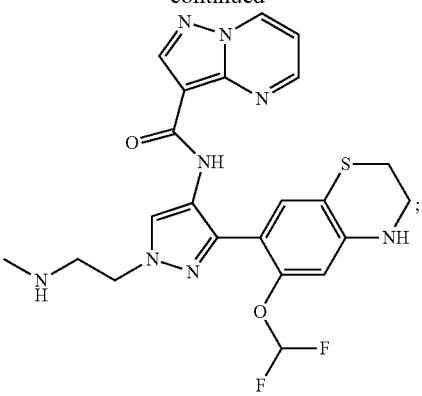
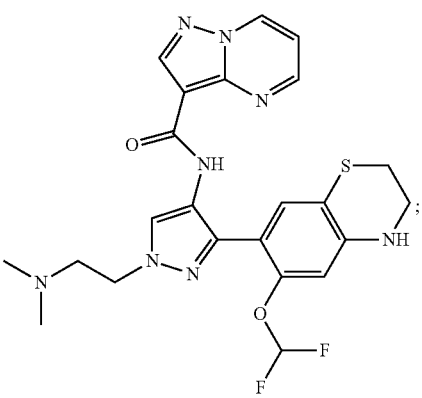
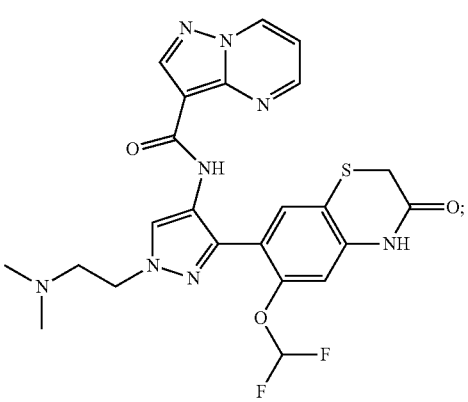
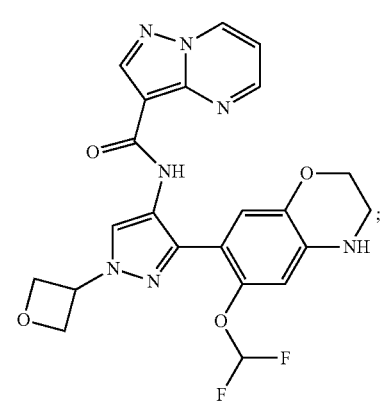

373
-continued
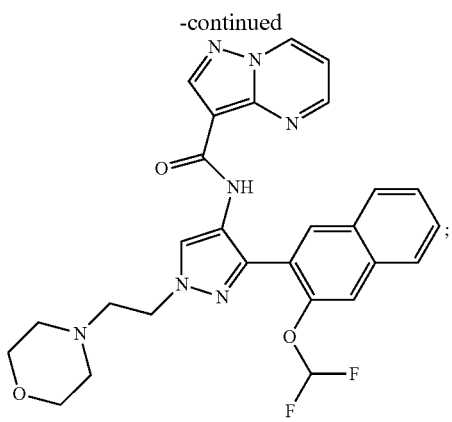
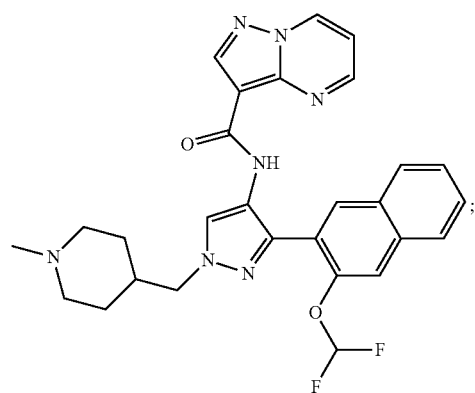
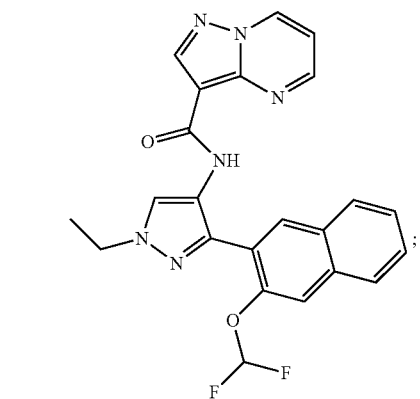
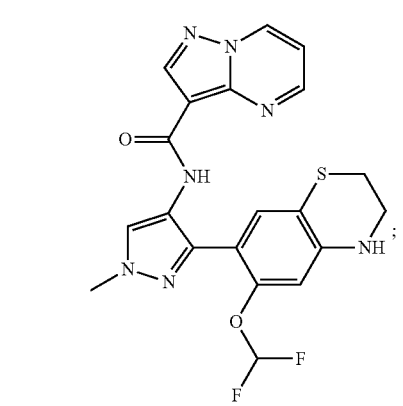
374
-continued
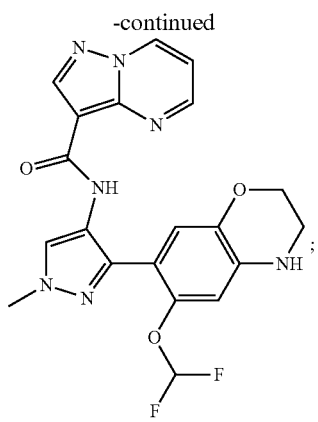
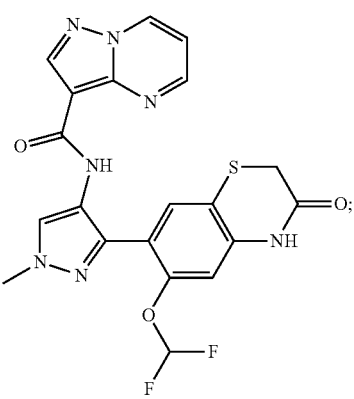
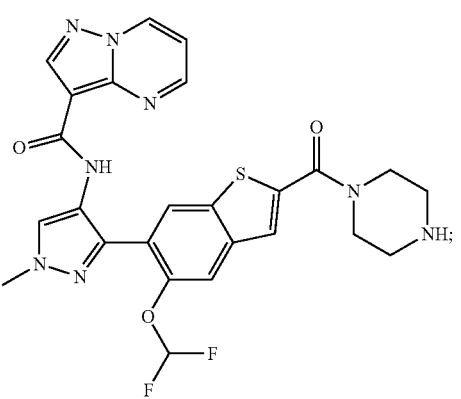
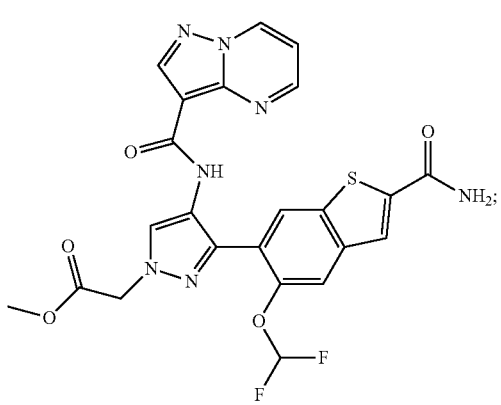

375
-continued
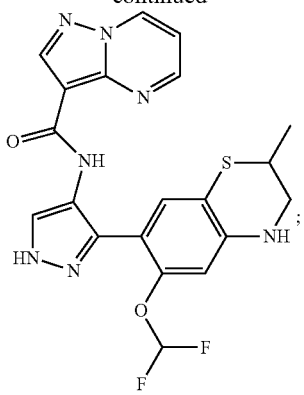
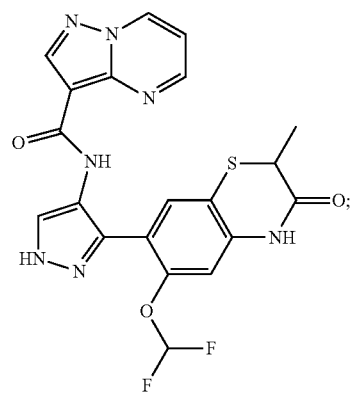
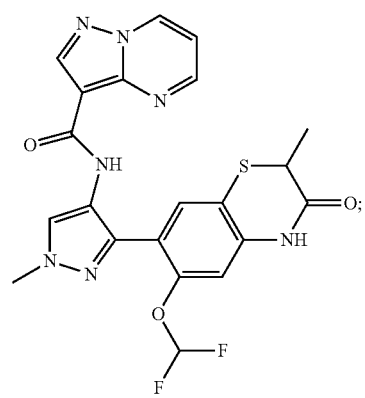
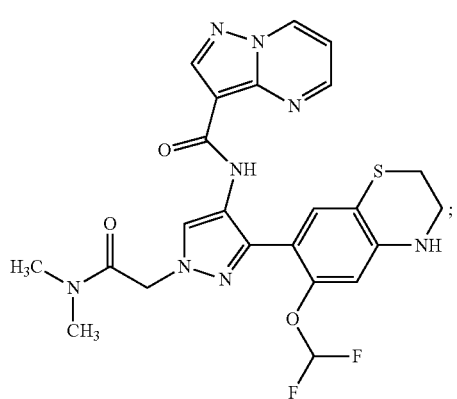
376
-continued
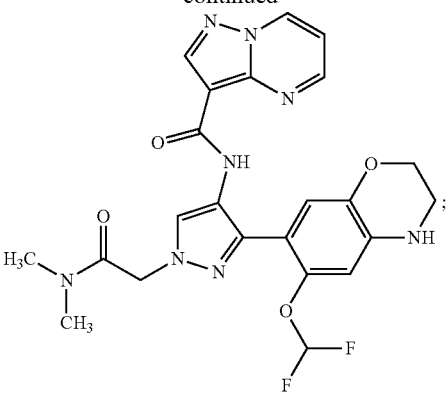
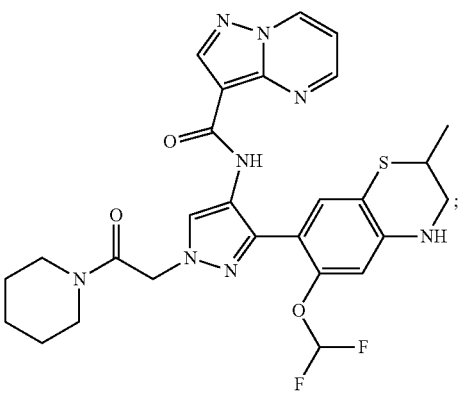
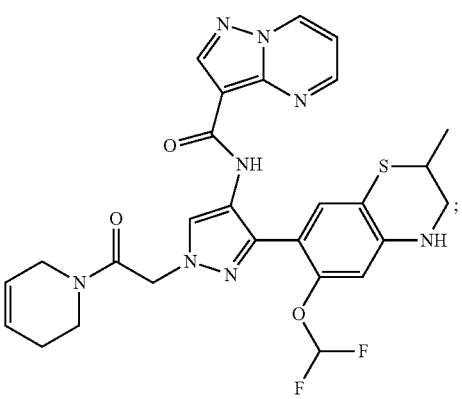
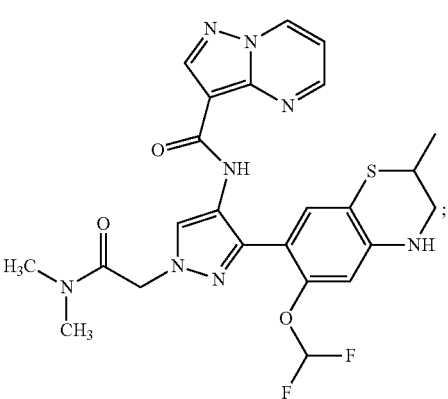

377
-continued
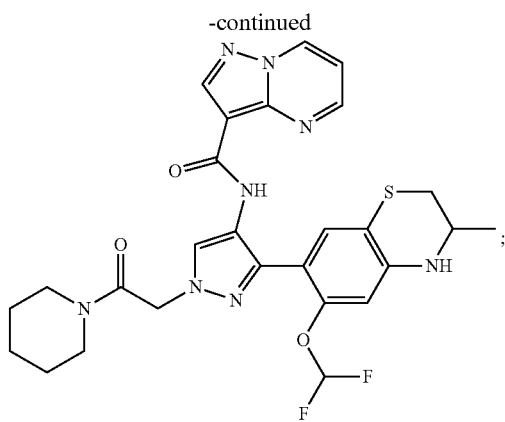
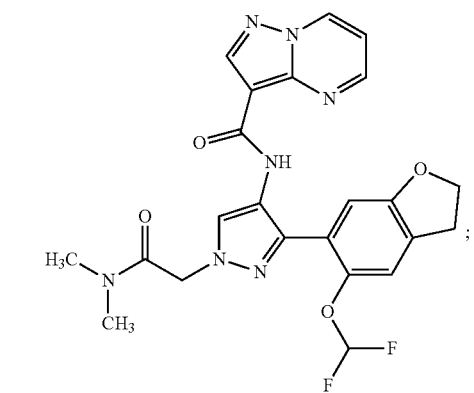
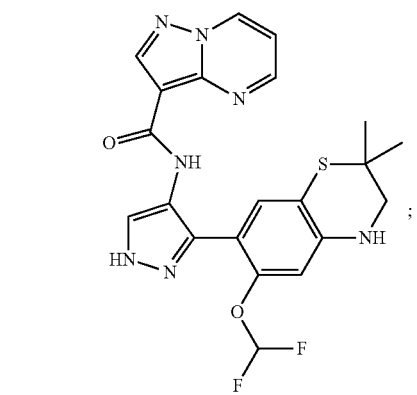
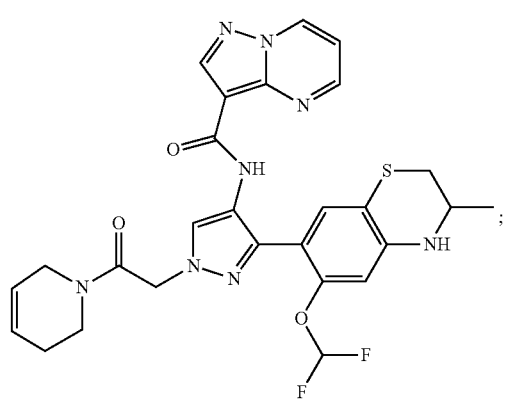
378
-continued
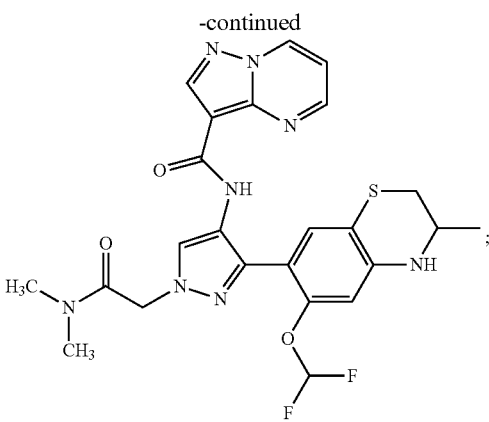
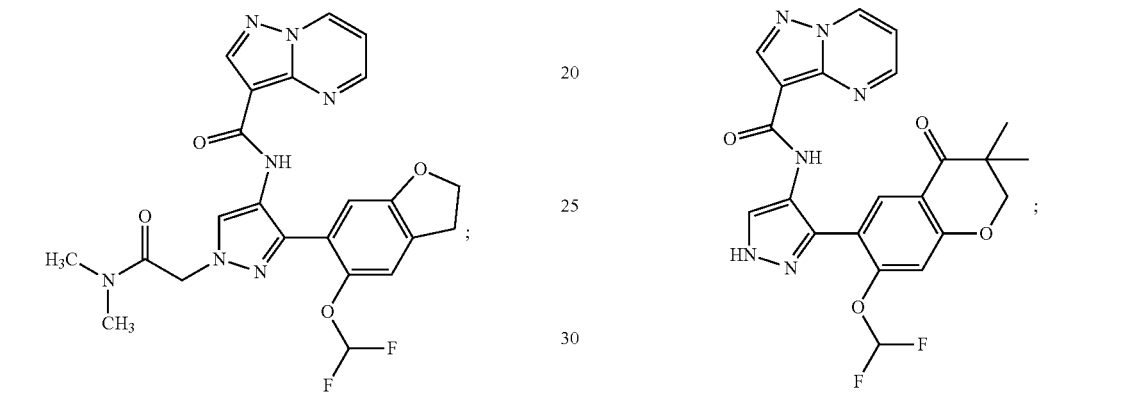
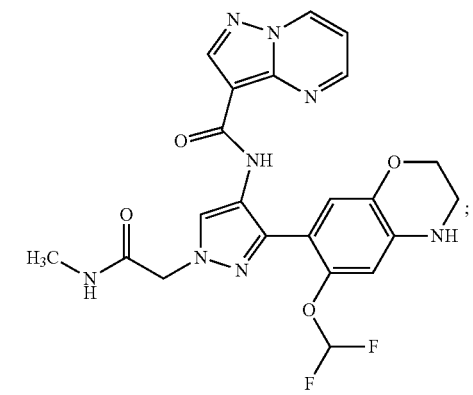
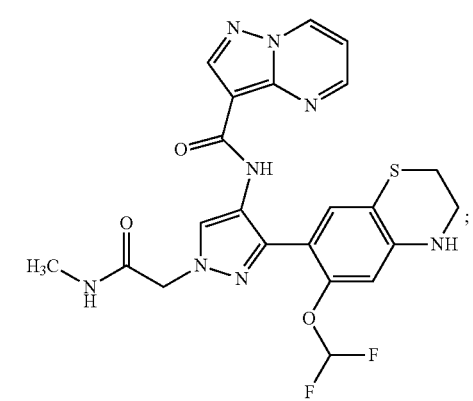

379
-continued
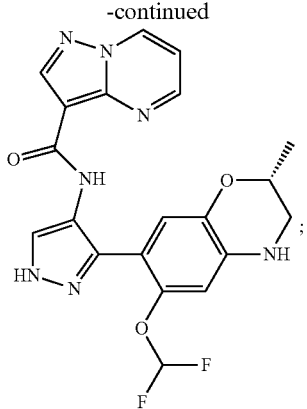
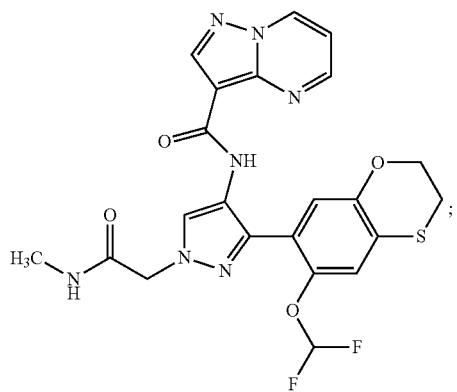
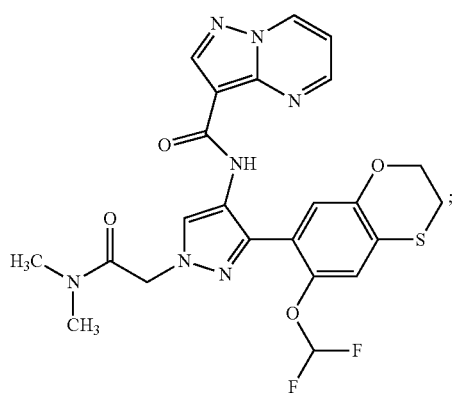
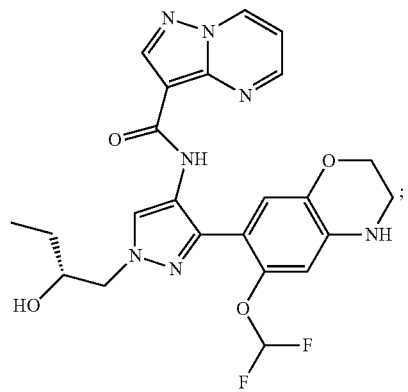
380
-continued
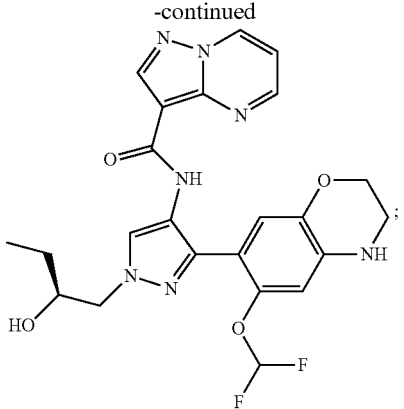
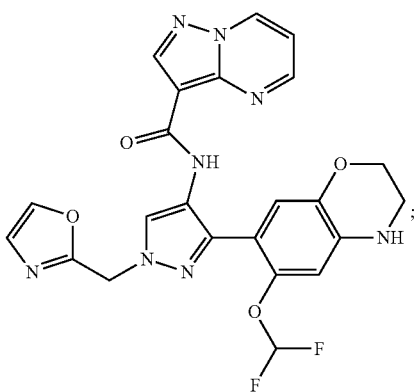
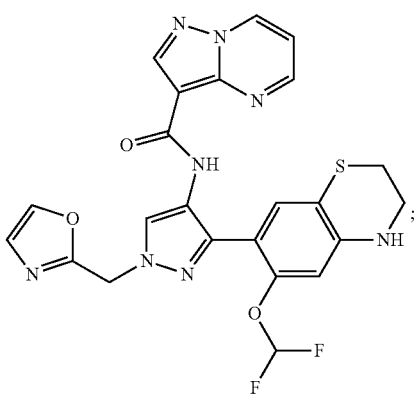
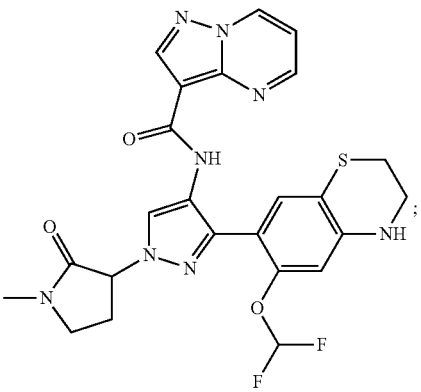

381
-continued
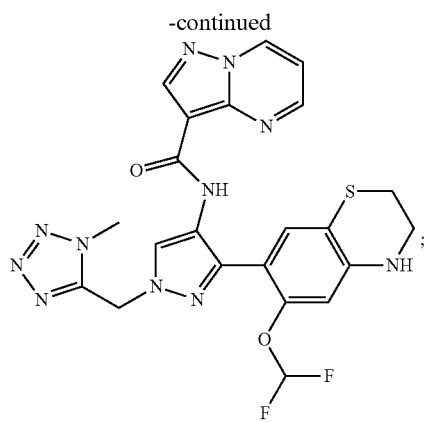
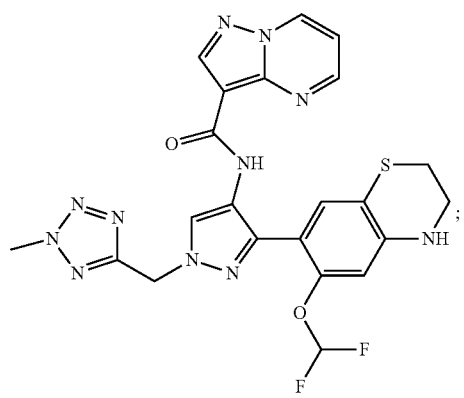
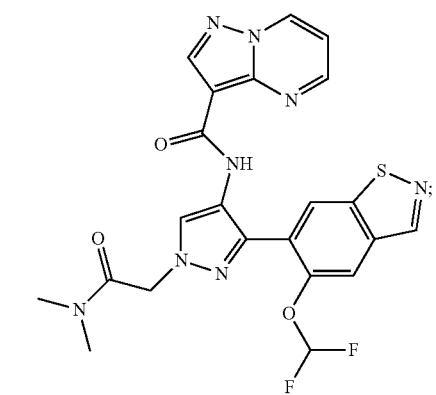
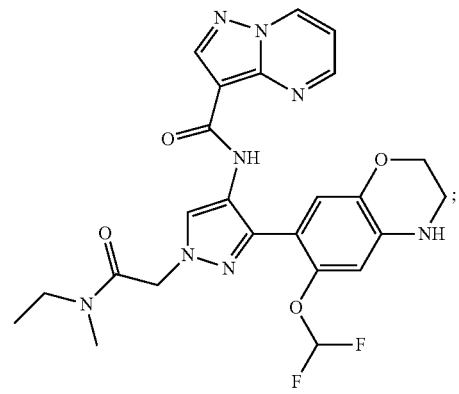
382
-continued
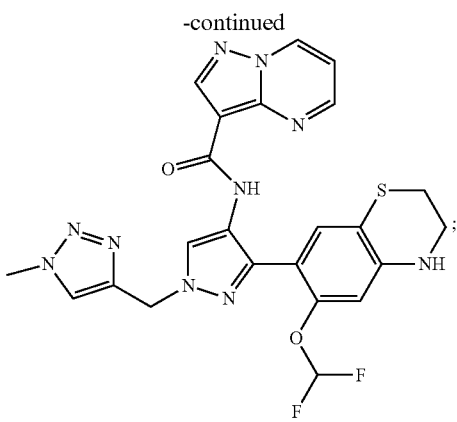
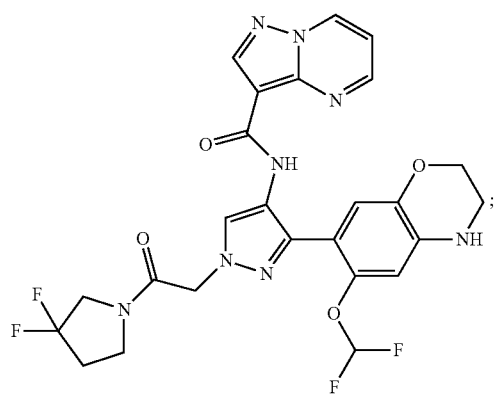
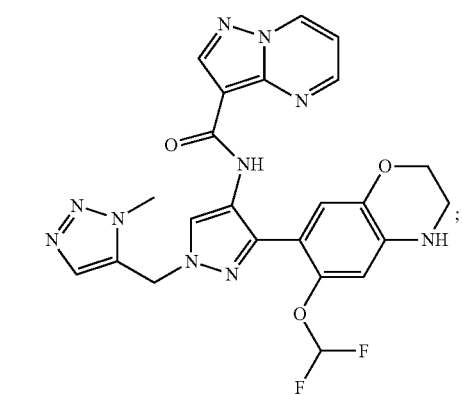
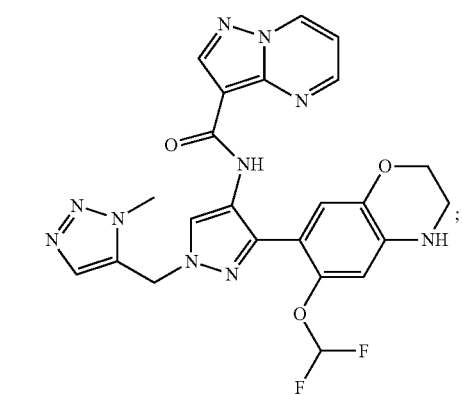

383
-continued
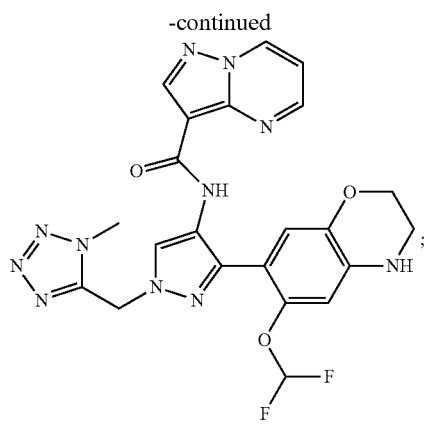
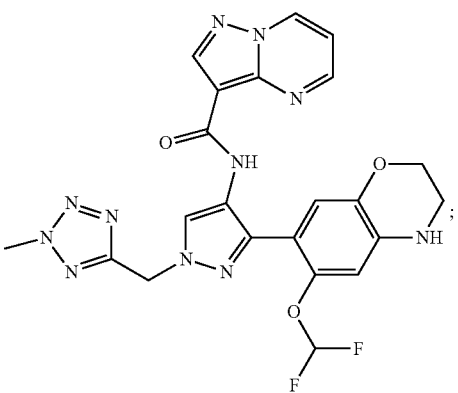
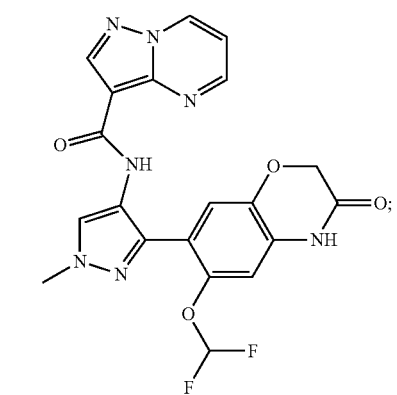
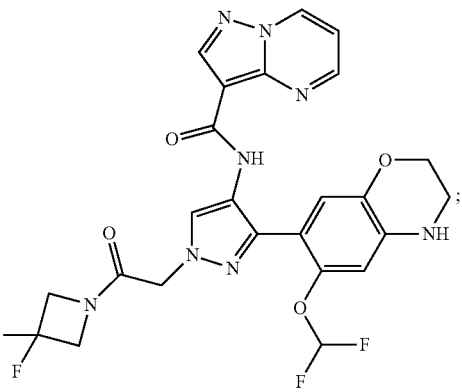
384
-continued
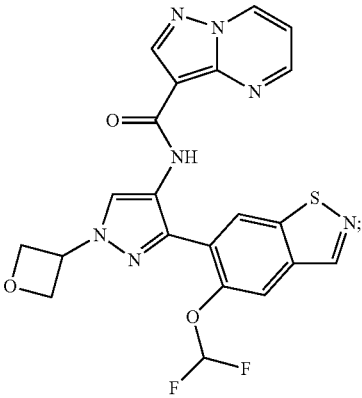
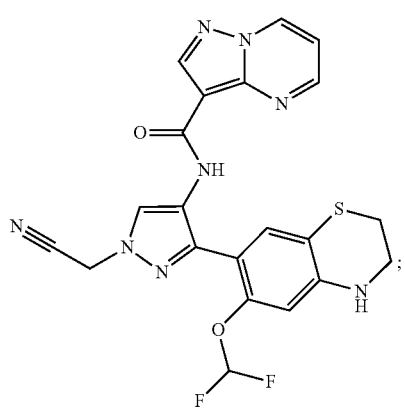
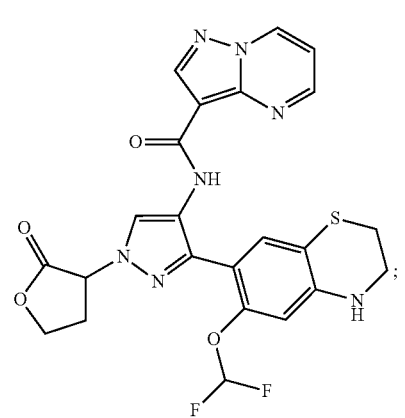
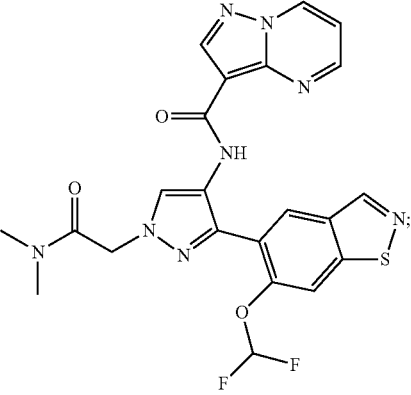

385
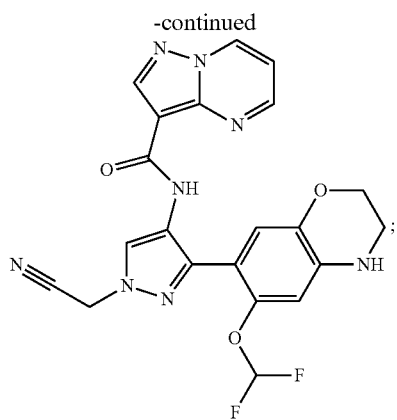
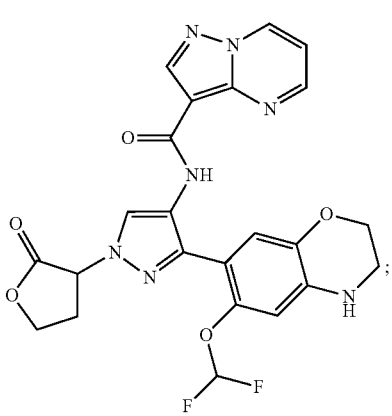
386
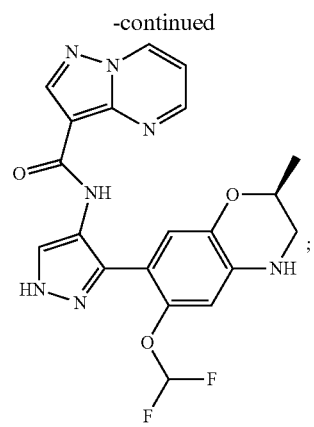
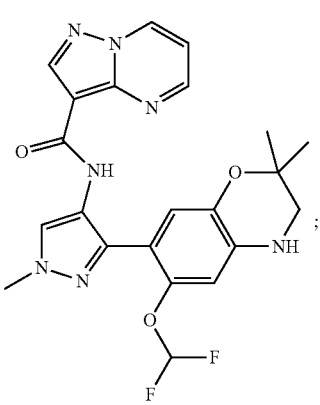
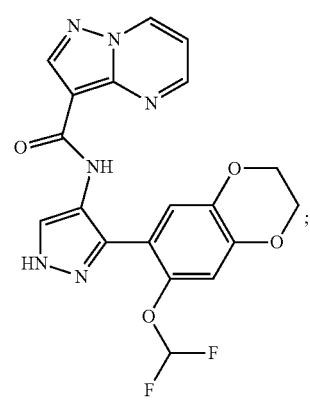

387
-continued
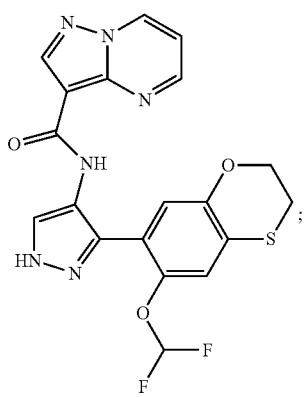
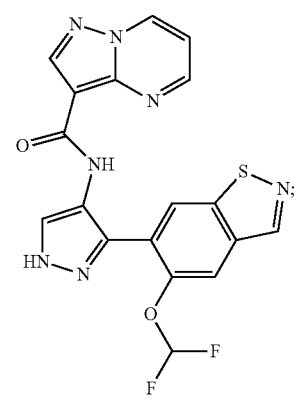
388
-continued
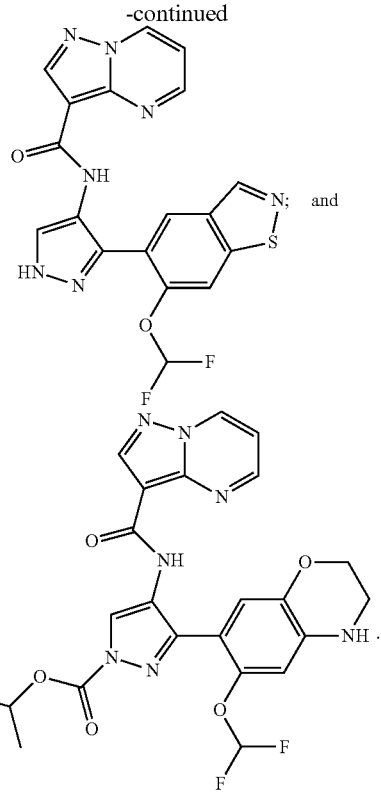
19. A pharmaceutical composition comprising a compound of claim 1, or a pharmaceutically acceptable salt thereof, and a pharmaceutically acceptable carrier, diluent or excipient.
* * * * *